US007247472B2

(12) United States Patent
Wilson et al.

(10) Patent No.: US 7,247,472 B2
(45) Date of Patent: Jul. 24, 2007

(54) SIMIAN ADENOVIRUS NUCLEIC ACID AND AMINO ACID SEQUENCES, VECTORS CONTAINING SAME, AND METHODS OF USE

(75) Inventors: James M. Wilson, Gladwyne, PA (US); Guangping Gao, Rosemont, PA (US); Soumitra Roy, Wayne, PA (US)

(73) Assignee: The Trustees of the University of Pennsylavania, Philadelphia, PA (US)

( * ) Notice: Subject to any disclaimer, the term of this patent is extended or adjusted under 35 U.S.C. 154(b) by 421 days.

(21) Appl. No.: 10/494,364

(22) PCT Filed: Nov. 20, 2002

(86) PCT No.: PCT/US02/33645

§ 371 (c)(1),
(2), (4) Date: May 12, 2004

(87) PCT Pub. No.: WO03/046124

PCT Pub. Date: Jun. 5, 2003

(65) Prior Publication Data

US 2005/0069866 A1 Mar. 31, 2005

Related U.S. Application Data

(60) Provisional application No. 60/366,798, filed on Mar. 22, 2002, provisional application No. 60/331,951, filed on Nov. 21, 2001.

(51) Int. Cl.
*C12N 15/861* (2006.01)

(52) U.S. Cl. .................. 435/320.1; 424/93.2; 435/456

(58) Field of Classification Search .................... None
See application file for complete search history.

(56) References Cited

U.S. PATENT DOCUMENTS

| | | | | |
|---|---|---|---|---|
| 5,698,202 | A | 12/1997 | Ertl et al. | |
| 5,770,442 | A * | 6/1998 | Wickham et al. | 435/320.1 |
| 5,922,315 | A * | 7/1999 | Roy | 424/93.2 |
| 5,972,596 | A | 10/1999 | Pavlakis et al. | |
| 6,001,557 | A | 12/1999 | Wilson et al. | |
| 6,019,978 | A | 2/2000 | Ertl et al. | |
| 6,083,716 | A | 7/2000 | Wilson et al. | |
| 6,127,525 | A | 10/2000 | Crystal et al. | |
| 6,203,975 | B1 | 3/2001 | Wilson et al. | |
| 6,210,663 | B1 | 4/2001 | Ertl | |
| 6,287,571 | B1 | 9/2001 | Ertl et al. | |
| 2004/0171807 | A1* | 9/2004 | Gao et al. | 530/350 |

FOREIGN PATENT DOCUMENTS

| | | | |
|---|---|---|---|
| EP | 0 787 200 | B1 | 4/2005 |
| WO | WO 96/13597 | A3 | 5/1996 |
| WO | WO 99/16884 | A1 | 4/1999 |
| WO | WO 00/11140 | A1 | 3/2000 |
| WO | WO 01/02607 | A1 | 1/2001 |
| WO | WO 01/54719 | A3 | 8/2001 |
| WO | WO 03/000283 | | 1/2003 |
| WO | WO 03/000851 | A2 | 1/2003 |

OTHER PUBLICATIONS

Amara et al, Control of a Mucosal Challenge and Prevention of AIDS by a Multiprotein DNA/MVA Vaccine, Science, vol. 292, pp. 69-74 (Apr. 6, 2001).

Babiuk et al, Adenoviruses as Vectors for Delivering Vaccines to Mucosal Surfaces, Journal of Biotechnology, 83, pp. 105-113, (Sep. 29, 2000).

Cohen et al, Chimpanzee Adenovirus CV-68 Adapted as a Gene Delivery Vector Interacts with the Coxsackievirus and Adenovirus Receptor, Journal of General Virology, 83, pp. 151-155, (Jan. 2002).

Ertl et al, Mucosal Vaccine to HIV-1 Gag, (Apr. 15, 2001) Abstract.

Holmgren et al, Mucosal Immunity: Implications for Vaccine Development, Immunobiol, vol. 184, pp. 157-179, (Feb. 1992).

Lubeck et al, Immunogenicity of Recombinant Adenovirus-human Immunodeficiency Virus Vaccines in Chimpanzees following Inrranasal Administration, AIDS Res Hum Retroviruses, 10(11):1443-9, (Nov. 1994), abstract only.

Qiu et al, Evaluation of Novel Human Immunodeficiency Virus Type 1 Gag DNA Vaccines for Protein Expression in Mammalian Cells And Induction of Immune Responses, Journal of Virology, vol. 73, No. 11, pp. 9145-9152, (Nov. 1999).

Santra et al, Recombinant canarypox Vaccine-Elicited CTL Specific for dominant and Subdominant Simian Immunodeficiency Virus Epitopes in Rhesus Monkeys, The Journal of Immunology, 168:pp. 1847-1853 (Feb. 15, 2002).

Schneider et al, Inactibation of the Human Immunodeficiency Virus Type 1 Inhibitory Elements Allows Rev-Independent Expression of Gag and Gag/Protease and Particle Formation, Journal of Virology, vol. 71, No. 7, pp. 4892-4903, (Jul. 1997).

Toes et al, Protective Anti-tumor Immunity Induced by Vaccination with Recombinant Adenoviruses Encoding Multiple Tumor-Associated Cytotoxic T Lymphocyte Epitopes in a String-of-Beads Fashion, Proc Natl. Acad. Sci. vol. 94, pp. 14660-14665, (Dec. 1997).

Van Olphen et al, Development and Characterization of bovine X Human Hybrid Cell Loines that Efficiently Support the Replication of Both Wild-type Bovine and Human Adenoviruses and Those with E1 Deleted, Journal of Virology, vol. 76, No. 12, pp. 5882-5892, (Jun. 2002).

Xiang et al, Novel Chimpanzee Serotype 68-Based Adenoviral Vaccine Carrier for Induction of Antibodies to a Transgene Product, Journal of Virology, vol. 76, No. 6, pp. 2667-2675 (Mar. 2002).

Zolla-Pazner et al, Induction of Neutralizing Antibodies to T-Cell Line Adapted and Primary Human Immunodeficiency Virus Type 1 Isolates with a Prime-Boost Vaccine Regimen in Chimpanzees, Journal of Virology, vol. 72, No. 2, pp. 1052-1059, (Feb. 1998).

(Continued)

*Primary Examiner*—Scott D. Priebe
(74) *Attorney, Agent, or Firm*—Howson & Howson LLP

(57) ABSTRACT

A recombinant vector comprising capsid proteins derived from simian adenovirus Pan5, Pan6, Pan7, SV1, SV25 or SV39 sequences are described. These vectors contain a heterologous gene under the control of regulatory sequences packaged in the capsid. A cell line which expresses simian adenovirus gene(s) is also disclosed. Methods of using the vectors and cell lines are provided.

13 Claims, 2 Drawing Sheets

OTHER PUBLICATIONS

Roy et al, Characterization of a Family of Chimpanzee Adenoviruses and Development of Molecular Clones for Gene Transfer Vectors, Human Gene Therapy, 15:519-530 (May 2004).

Fitzgerald et al, A Simian Replication-Defective Adenoviral Recombinant Vaccine to HIV-1 Gag[1], The Journal of Immunology, 170(3):1416-1422, (Feb. 1, 2003).

Russell et al, Update on Adenovirus and its Vectors, Journal of General Virology, 81, pp. 2573-2604, (Nov. 2000).

Farina et al, Replication-Defective Vector Based on a Chimpanzee Adenovirus, Journal of Virology, vol. 75, No. 23, pp. 11603-11613, (Dec. 2001).

Crawford-Miksza et al, Analysis of 15 Adenovirus Hexon Proteins Reveals the Location and Structure of Seven Hypervariable Regions Containing Serotype-Specific Residues, Journal of Virology, vol. 70, No. 3, pp. 1836-1844, (Mar. 1996).

Hashimoto et al, Induction of Protective Immunity to Anthrax Lethal Toxin with a Chimpanzee Adenovirus-Based Vaccine Carrier in the Presence of Pre-Existing Anti-Human Adenovirus Immunity, Abstract 1015, 7th Annual Meeting of the American Society of Gene Therapy [Jun. 2-6, 2004] Minneapolis, Minnesota, (e-published-May 2, 2004).

Zhi et al, Comparison of Antigen-Specifc Immune Responses Elicited by Recombinant Simian Adenoviral Vectors with Deletions in Either E1, or E1/E3, or E1/E4 Regions, Abstract 568, 7th Annual Meeting of the American Society of Gene Therapy [Jun. 2-6, 2004] Minneapolis, Minnesota, (e-published-May 2, 2004).

Gao et al, Autoimmune Anemia in Macaques Following Erythropoietin Gene Therapy, Abstract 341, 7th Annual Meeting of the American Society of Gene Therapy [Jun. 2-6, 2004] Minneapolis, Minnesota, (e-published-May 2, 2004).

Kobinger et al, Pseudotyping HIV Vector with the Spike Envelope Protein of SARS-CoV for Studying Viral Tropism, Immunology and Gene Therapy Applications, Abstract 368, 7th Annual Meeting of the American Society of Gene Therapy [Jun. 2-6, 2004] Minneapolis, Minnesota, (e-published-May 2, 2004).

Kobinger et al, Simian Adenoviral Vector Based-Vaccine Fully Protect Against Ebola Virus Even in the Presence of Pre-Existing Immunity to Human Adenovirus, Abstract 373, 7th Annual Meeting of the American Society of Gene Therapy [Jun. 2-6, 2004] Minneapolis, Minnesota, (e-published-May 2, 2004).

Kobinger et al, Pharmacologically Regulated Regeneration of Functional Human Pancreatic Islets, Abstract 1053, 7th Annual Meeting of the American Society of Gene Therapy [Jun. 2-6, 2004] Minneapolis, Minnesota, (e-published-May 2, 2004).

Roy et al, Use of Chimeric Adenoviral Vectors to Assess Capsid Neutralization Determinants, Abstract 128, 7th Annual Meeting of the American Society of Gene Therapy [Jun. 2-6, 2004] Minneapolis, Minnesota, (e-published-May 2, 2004).

Lebherz et al, Nonhuman Primate Models for Retinal and Choroidal Neovascularization using AAV2-Mediated Overexpression of Vascular Endothelial Growth Factor, Abstract 218, 7th Annual Meeting of the American Society of Gene Therapy [Jun. 2-6, 2004] Minneapolis, Minnesota, (e-published-May 2, 2004).

Roy et al, Complete Nucleotide Sequences and Genome Organization of Four Chimpanzee Adenoviruses, Virology, 324, pp. 361-372, (May 2004).

Stevens, D, American Type Culture Collection Catalogue of Strains II 4th Edition, Viruses and Antisera, p. 226, (1983), XP002392467.

Bruce et al, Replication-deficient Recombinanat Adenoviruses Expressing the Human Immunodeficiency Virus Env Antigen can Induce Both Humoral and CTL Immune Responses in Mice, Journal of General Virology, 80, pp. 2621-2628, (Oct. 1999).

Wigand et al, Chimpanzee Adenoviruses are Related to Four Subgenera of Human Adenoviruses, Intervirology, 30:1-9, (Jan. 1989) XP002052837.

* cited by examiner

FIGURE 1

| | |
|---|---|
| Hu5 | APKGAPNPCEWDEAATALEINLEEEDDDNEDEVDEQAEQQKTHVFGQAPYSGINITKEGIQIGVEGQT-- |
| Pan-6 | APKGAPNSSQWEQAKTG------------------NGGTMETHTYGVAPMGGENITKDGLQIGTDVTANQ |
| Pan-5 | APKGAPNTCQWTYKADG------------------DTGTEKTYTYGNAPVQGISITKDGIQLGTDTDD-- |
| Pan-7 | APKGAPNTCQWTYKAG-------------------DTDTEKTYTYGNAPVQGISITKDGIQLGTDSDG-- |
| Pan-9 | APKGAPNTCQWTYKADG------------------ETATEKTYTYGNAPVQGINITKDGIQLGTDTDD-- |
| | |
| Hu5 | --PKYADKTFQPEPQIGESQWYETEIN--HAAGRVLKKTTPMKPCYGSYAKPTNENGGQGILVKQQN--G |
| Pan-6 | NKPIYADKTFQPEPQVGEENWQETEN---FYGGRALKKDTNMKPCYGSYARPTNEKGGQAKLKVGDDGVP |
| Pan-5 | -QPIYADKTYQPEPQVGDAEWHDITGTDEKYGGRALKPDTKMKPCYGSFAKPTNKEGGQANVKTETG--G |
| Pan-7 | -QAIYADETYQPEPQVGDAEWHDITGTDEKYGGRALKPDTKMKPCYGSFAKPTNKEGGQANVKTETG--G |
| Pan-9 | -QPIYADKTYQPEPQVGDAEWHDITGTDEKYGGRALKPDTKMKPCYGSFAKPTNKEGGQANVKTGTG--T |
| | |
| Hu5 | KLESQVEMQFFSTTEATAGNGDNLTPKVVLYSEDVDIETPDTHISYMPTIKEGNSRELMGQQSMPNRPNY |
| Pan-6 | TKEFDIDLAFFDTPGGTVNGQDEYKADIVMYTENTYLETPDTHVVYKPGKDDASSEINLVQQSMPNRPNY |
| Pan-5 | TKEYDIDMAFFDNRSAAAAG---LAPEIVLYTENVDLETPDTHIVYKAGTDDSSSSINLGQQSMPNRPNY |
| Pan-7 | TKEYDIDMAFFDNRSAAAAG---LAPEIVLYTENVDLETPDTHIVYKAGTDDSSSSINLGQQSMPNRPNY |
| Pan-9 | TKEYDIDMAFFDNRSAAAAG---LAPEIVLYTENVDLETPDTHIVYKAGTDDSSSSINLGQQAMPNRPNY |
| | |
| Hu5 | IAFRDNFIGLMYYNSTGNMGVLAGQASQLNAVVDLQDRNTELSYQLLLDSIGDRTRYFSMWNQAVDSYDP |
| Pan-6 | IGFRDNFIGLMYYNSTGNMGVLAGQASQLNAVVDLQDRNTELSYQLLLDSLGDRTRYFSMWNQAVDSYDP |
| Pan-5 | IGFRDNFIGLMYYNSTGNMGVLAGQASQLNAVVDLQDRNTELSYQLLLDSLGDRTRYFSMWNQAVDSYDP |
| Pan-7 | IGFRDNFIGLMYYNSTGNMGVLAGQASQLNAVVDLQDRNTELSYQLLLDSLGDRTRYFSMWNQAVDSYDP |
| Pan-9 | IGFRDNFIGLMYYNSTGNMGVLAGQASQLNAVVDLQDRNTELSYQLLLDSLGDRTRYFSMWNQAVDSYDP |
| | |
| Hu5 | DVRIIENHGTEDELPNYCFPLGGVINTETLTKVKPKTG----QENGWEKDATEFSDKNEIRVGNNFAMEI |
| Pan-6 | DVRIIENHGVEDELPNYCFPLDGSGTNAAYQGVKVKDGQDGDVESEWENDDTVA-ARNQLCKGNIFAMEI |
| Pan-5 | DVRIIENHGVEDELPNYCFPLDAVGRTDTYQGIKAN----GADQTTWTKDDTVN-DANELGKGNPFAMEI |
| Pan-7 | DVRIIENHGVEDELPNYCFPLDAVGRTDTYQGIKAN----GDNQTTWTKDDTVN-DANELGKGNPFAMEI |
| Pan-9 | DVRIIENHGVEDELPNYCFPLDAVGRTDTYQGIKAN----GTDQTTWTKDDSVN-DANEIGKGNPFAMEI |

Fig. 2

```
Pan-9 fiber knob    (1) TLWTTPDPSPNCQILAENDAKLTLCLTKCGSQILATVSVLVVGSG-NLNP
Pan-6 fiber knob    (1) TLWTTPDPSPNCQLLSDRDAKFTLCLTKCGSQILGTVAVAAVTVGSALNP
 Ad 2 fiber knob    (1) TLWTTPDPSPNCRIHSDNDCKFTLVLTKCGSQVLATVAALAVSG--DLSS
 Ad 5 fiber knob    (1) TLWTTPAPSPNCRLNAEKDAKLTLVLTKCGSQILATVSVLAVKG--SLAP
Pan-7 fiber knob    (1) TLWTTADPSPNCKIYSEKDAKLTLCLTKCGSQILGTVTVLAVNNG-SLNP
Pan-5 fiber knob    (1) TLWTTADPSPNCHIYSEKDAKLTLCLTKCGSQILGTVSLIAVDTG-SLNP

Pan-9 fiber knob   (50) ITGTVSSAQVFLRFDANGVLLTEHSTLKKYWGYRQGDSIDGTPYTNAVGF
Pan-6 fiber knob   (51) INDTVKSAIVFLRFDSDGVLMSNSSMVGDYWNFREGQTTQSVAYTNAVGF
 Ad 2 fiber knob   (49) MTGTVASVSIFLRFDQNGVLMENSSLKKHYWNFRNGNSTNANPYTNAVGF
 Ad 5 fiber knob   (49) ISGTVQSAHLIIRFDENGVLLNNSFLDPEYWNFRNGDLTEGTAYTNAVGF
Pan-7 fiber knob   (50) ITNTVSTALVSLKFDASGVLLSSSTLDKEYWNFRKGDVTPAEPYTNAIGF
Pan-5 fiber knob   (50) ITGTVTTALVSLKFDANGVLQSSSTLDSDYWNFRQGDVTPAEAYTNAIGF

Pan-9 fiber knob  (100) MPNLKAYPKSQSSTTKNNIVGQVYMNGDVSKPMLLTITLNGTDDS-----
Pan-6 fiber knob  (101) MPNIGAYPKTQSKTPKNSIVSQVYLTGETTMPMTLTITFNGTDEK-DTTP
 Ad 2 fiber knob   (99) MPNLLAYPKTQSQTAKNNIVSQVYLHGDKTKPMILTITLNGTSESTETSE
 Ad 5 fiber knob   (99) MPNLSAYPKSHGKTAKSNIVSQVYLNGDKTKPVTLTITLNGTQET-GDTT
Pan-7 fiber knob  (100) MPNIKAYPKNTSAASKSHIVSQVYLNGDEAKPLMLIITFNETEDAT----
Pan-5 fiber knob  (100) MPNLKAYPKNTSGAAKSHIVGKVYLHGDTGKPLDLIITFNETSDES----

Pan-9 fiber knob  (145) NSTYSMSFSYTWT-NGSYVGATFGANSYTFSYIAQE
Pan-6 fiber knob  (150) VSTYSMTFTWQWTGDYKDKNITFATNSFSFSYIAQE
 Ad 2 fiber knob  (149) VSTYSMSFTWSWE-SGKYTTETFATNSYTFSYIAQE
 Ad 5 fiber knob  (148) PSAYSMSFSWDWS-GHNYINEIFATSSYTFSYIAQE
Pan-7 fiber knob  (146) -CTYSITFQWKWD-STKYTGETLATSSFTFSYIAQE
Pan-5 fiber knob  (146) -CTYCINFQWQWG-ADQYKNETLAVSSFTFSYIAKE
```

SIMIAN ADENOVIRUS NUCLEIC ACID AND AMINO ACID SEQUENCES, VECTORS CONTAINING SAME, AND METHODS OF USE

CROSS-REFERENCE TO RELATED APPLICATIONS

This is a national stage application under 35 U.S.C. 371 of PCT/US02/33645, filed Nov. 20, 2002, which claims the benefit under 35 USC 119(e) of the priority of U.S. patent application Ser. No. 60/331,951, filed Nov. 21, 2001, and U.S. patent application Ser. No. 60/336,798, filed Mar. 22, 2002.

BACKGROUND OF THE INVENTION

Adenovirus is a double-stranded DNA virus with a genome size of about 36 kilobases (kb), which has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.*, 81:2573-2604 (November 2000)]. The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Recombinant adenoviruses have been described for delivery of molecules to host cells. See, U.S. Pat. No. 6,083,716, which describes the genome of two chimpanzee adenoviruses.

What is needed in the art are more effective vectors which avoid the effect of pre-existing immunity to selected adenovirus serotypes in the population and/or which are useful for repeat administration and for titer boosting by second vaccination, if required.

SUMMARY OF THE INVENTION

The present invention provides the isolated nucleic acid sequences and amino acid sequences of six simian adenoviruses, vectors containing these sequences, and cell lines expressing simian adenovirus genes. Also provided are a number of methods for using the vectors and cells of the invention.

The methods of the invention involve delivering one or more selected heterologous gene(s) to a mammalian patient by administering a vector of the invention. Because the various vector constructs are derived from simian rather than from human adenoviruses, the immune system of the non-simian human or veterinary patient is not primed to respond immediately to the vector as a foreign antigen. Use of the compositions of this invention thus permits a more stable expression of the selected transgene when administered to a non-simian patient. Use of the compositions of this invention for vaccination permits presentation of a selected antigen for the elicitation of protective immune responses. Without wishing to be bound by theory, the ability of the adenoviruses of the invention to transduce human dendritic cells is at least partially responsible for the ability of the recombinant constructs of the invention to induce an immune response. The recombinant simian adenoviruses of this invention may also be used for producing heterologous gene products in vitro. Such gene products are themselves useful in a variety for a variety of purposes such as are described herein.

These and other embodiments and advantages of the invention are described in more detail below.

BRIEF DESCRIPTION OF THE DRAWINGS

FIG. 1 provides an alignment of the amino acid sequences of the L1 and a portion of the L2 loops of the capsid protein hexon of the human adenovirus 5 [SEQ ID NO: 40], chimpanzee adenovirus C68 (Pan-9) [SEQ ID NO:14], and the novel Pan5 [SEQ ID NO:15], Pan6 [SEQ ID NO:16] and Pan7 [SEQ ID NO:17] chimpanzee adenovirus sequences of the invention. The intervening conserved region is part of the pedestal domain conserved between adenovirus serotypes.

FIG. 2 provides an alignment of the amino acid sequences of the fiber knob domains of chimpanzee C68 (Pan-9) [SEQ ID NO:18], Pan-6 [SEQ ID NO:19], Pan-7 [SEQ ID NO:20], and Pan-5 [SEQ ID NO:21] and the human adenoviruses serotypes 2 [SEQ ID NO:22] and 5 [SEQ ID NO:23].

DETAILED DESCRIPTION OF THE INVENTION

The invention provides novel nucleic acid and amino acid sequences from Ad Pan5 [SEQ ID NO:1-4, 15 and 21], Ad Pan6 [SEQ ID NO: 5-8, 16, 19], and Ad serotype Pan7 [SEQ ID NO: 9-12, 17, 20], which were originally isolated from chimpanzee lymph nodes. In several instances throughout the specification, these adenoviruses are alternatively termed herein C5, C6 and C7, respectively. Also provided are sequences from adenovirus SV1 [SEQ ID NO: 24-28], which was originally isolated from the kidney cells of cynomolgus monkey. The invention also provides sequences of adenoviruses SV-25 [SEQ ID NO:29-33] and SV-39 [SEQ ID NO: 34-37], which were originally isolated from rhesus monkey kidney cells.

The present invention provides novel adenovirus vectors and packaging cell lines to produce those vectors for use in the in vitro production of recombinant proteins or fragments or other reagents. The invention further provides compositions for use in delivering a heterologous molecule for therapeutic or vaccine purposes. Such therapeutic or vaccine compositions contain the adenoviral vectors carrying an inserted heterologous molecule. In addition, novel sequences of the invention are useful in providing the essential helper functions required for production of recombinant adeno-associated viral (AAV) vectors. Thus, the invention provides helper constructs, methods and cell lines which use these sequences in such production methods.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the aligned sequences.

The term "substantial homology" or "substantial similarity," when referring to amino acids or fragments thereof, indicates that, when optimally aligned with appropriate amino acid insertions or deletions with another amino acid (or its complementary strand), there is amino acid sequence identity in at least about 95 to 99% of the aligned sequences. Preferably, the homology is over full-length sequence, or a protein thereof, or a fragment thereof which is at least 8 amino acids, or more desirably, at least 15 amino acids in length. Examples of suitable fragments are described herein.

The term "percent sequence identity" or "identical" in the context of nucleic acid sequences refers to the residues in the two sequences that are the same when aligned for maximum correspondence. The length of sequence identity comparison may be over the full-length of the genome (e.g., about 36 kbp), the full-length of an open reading frame of a gene, protein, subunit, or enzyme [see, e.g., the tables providing the adenoviral coding regions], or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired. Similarly, "percent sequence identity" may be readily determined for amino acid sequences, over the full-length of a protein, or a fragment thereof. Suitably, a fragment is at least about 8 amino acids in length, and may be up to about 700 amino acids. Examples of suitable fragments are described herein.

Identity is readily determined using such algorithms and computer programs as are defined herein at default settings. Preferably, such identity is over the full length of the protein, enzyme, subunit, or over a fragment of at least about 8 amino acids in length. However, identity may be based upon shorter regions, where suited to the use to which the identical gene product is being put.

As described herein, alignments are performed using any of a variety of publicly or commercially available Multiple Sequence Alignment Programs, such as "Clustal W", accessible through Web Servers on the internet. Alternatively, Vector NTI utilities are also used. There are also a number of algorithms known in the art that can be used to measure nucleotide sequence identity, including those contained in the programs described above. As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Similarly programs are available for performing amino acid alignments. Generally, these programs are used at default settings, although one of skill in the art can alter these settings as needed. Alternatively, one of skill in the art can utilize another algorithm or computer program that provides at least the level of identity or alignment as that provided by the referenced algorithms and programs.

As used throughout this specification and the claims, the term "comprise" and its variants including, "comprises", "comprising", among other variants, is inclusive of other components, elements, integers, steps and the like. The term "consists of" or "consisting of" are exclusive of other components, elements, integers, steps and the like.

I. The Simian Adenovirus Sequences

The invention provides nucleic acid sequences and amino acid sequences of Pan5, Pan6, Pan7, SV1, SV25 and SV39, which are isolated from the other viral material with which they are associated in nature.

A. Nucleic Acid Sequences

The Pan5 nucleic acid sequences of the invention include nucleotides 1 to 36462 of SEQ ID NO:1. The Pan6 nucleic acid sequences of the invention include nucleotides 1 to 36604 of SEQ ID NO: 5. The Pan7 nucleic acid sequences of the invention include nucleotides 1 to 36535 of SEQ ID NO: 9. The SV1 nucleic acid sequences of the invention include nucleotides 1 to 34264 of SEQ ID NO: 24. The SV25 nucleic acid sequences of the invention include nucleotides 1 to 31044 of SEQ ID NO: 29. The SV39 nucleic acid sequences of the invention include nucleotides 1 to 34115 of SEQ ID NO: 34. See, Sequence Listing, Which is incorporated by reference herein.

The nucleic acid sequences of the invention further encompass the strand which is complementary to the sequences of SEQ ID NO: 5, 9, 24, 29 and 34, as well as the RNA and cDNA sequences corresponding to the sequences of these sequences figures and their complementary strands. Further included in this invention are nucleic acid sequences which are greater than 95 to 98%, and more preferably about 99 to 99.9% homologous or identical to the Sequence Listing. Also included in the nucleic acid sequences of the invention are natural variants and engineered modifications of the sequences provided in SEQ ID NO: 5, 9, 24, 29 and 34 and their complementary strands. Such modifications include, for example, labels that are known in the art, methylation, and substitution of one or more of the naturally occurring nucleotides with a degenerate nucleotide.

The invention further encompasses fragments of the sequences of Pan5, Pan6, Pan7, SV1, SV25 and SV39, their complementary strand, cDNA and RNA complementary thereto. Suitable fragments are at least 15 nucleotides in length, and encompass functional fragments, i.e., fragments which are of biological interest. For example, a functional fragment can express a desired adenoviral product or may be useful in production of recombinant viral vectors. Such fragments include the gene sequences and fragments listed in the tables below.

The following tables provide the transcript regions and open reading frames in the simian adenovirus sequences of the invention. For certain genes, the transcripts and open reading frames (ORFs) are located on the strand complementary to that presented in SEQ ID NO: 5, 9, 24, 29 and 34. See, e.g., E2b, E4 and E2a. The calculated molecular weights of the encoded proteins are also shown. Note that the E1a open reading frame Pan5 [nt 576-1436 of SEQ ID NO:1], Pan6 [nt 576 to 1437 of SEQ ID NO: 5] and Pan7 [nt 576 to 1437 of SEQ ID NO: 9] contain internal splice sites. These splice sites are noted in the following tables.

Ad Pan-5 [SEQ ID NO: 1]

| | Regions | Start (nt) | End (nt) | M.W. (Daltons) |
|---|---|---|---|---|
| ITR | | 1 | 120 | — |
| E1a | Transcript | 478 | | — |
| | 13S | 576–664, 1233–1436 | | 28120 |

-continued

Ad Pan-5 [SEQ ID NO: 1]

| | Regions | Start (nt) | End (nt) | M.W. (Daltons) |
|---|---|---|---|---|
| | 12S | 576–1046, 1233–1436 | | 24389 |
| | 9S | 576–644, 1233–1436 | | 9962 |
| | Transcript | | 1516 | — |
| E1b | Transcript | 1552 | | — |
| | Small T | 1599 | 2171 | 22317 |
| | Large T | 1904 | 3412 | 55595 |
| | IX | 3492 | 3920 | 14427 |
| | Transcript | | 3959 | — |
| E2b | Transcript | 10349 | | — |
| | PTP | 10349 | 8451 | 72930 |
| | Polymerase | 8448 | 5083 | 127237 |
| | IVa2 | 5604 | 3980 | 50466 |
| | Transcript | | 3960 | |
| 28.1 kD | | 5155 | 5979 | 28141 |
| Agnoprotein | | 7864 | 8580 | 25755 |
| L1 | Transcript | 10849 | | — |
| | 52/55D | 10851 | 12025 | |
| | IIIa | 12050 | 13819 | 65669 |
| | Transcript | | 13832 | — |
| | Transcript | 13894 | | — |
| L2 | Penton | 13898 | 15490 | 59292 |
| | VII | 15494 | 16078 | 21478 |
| | V | 16123 | 17166 | 39568 |
| | Mu | 17189 | 17422 | 8524 |
| | transcript | | 17442 | — |
| | Transcript | 17488 | | — |
| L3 | VI | 17491 | 18222 | 26192 |
| | Hexon | 18315 | 21116 | 104874 |
| | Endoprotease | 20989 | 21783 | 28304 |
| | transcript | | 21811 | — |
| E2a | Transcript | 26782 | | — |
| | DBP | 23386 | 21845 | 57358 |
| | transcript | | 21788 | — |
| L4 | Transcript | 23406 | | — |
| | 100 kD | 23412 | 25805 | 88223 |
| | 33 kD homolog | 25525 | 26356 | 24538 |
| | VIII | 26428 | 27111 | 24768 |
| | transcript | | 27421 | — |
| E3 | Transcript | 26788 | | — |
| | Orf #1 | 27112 | 27432 | 12098 |
| | Orf #2 | 27386 | 28012 | 23040 |
| | Orf #3 | 27994 | 28527 | 19525 |
| | Orf #4 | 28557 | 29156 | 22567 |
| | Orf #5 | 29169 | 29783 | 22267 |
| | Orf #6 | 29798 | 30673 | 31458 |
| | Orf #7 | 30681 | 30956 | 10477 |
| | Orf #8 | 30962 | 31396 | 16523 |
| | Orf #9 | 31389 | 31796 | 15236 |
| | transcript | | 31837 | — |
| L5 | Transcript | 32032 | | — |
| | Fiber | 32035 | 33372 | 47670 |
| | transcript | | 33443 | — |
| E4 | Transcript | 36135 | | — |
| | Orf 7 | 33710 | 33462 | 9191 |
| | Orf 6 | 34615 | 33710 | 35005 |
| | Orf 4 | 34886 | 34521 | 13878 |
| | Orf 3 | 35249 | 34896 | 13641 |
| | Orf 2 | 35635 | 35246 | 14584 |
| | Orf 1 | 36050 | 35676 | 13772 |
| | Transcript | | 33437 | — |
| ITR | | 36343 | 36462 | — |

Ad Pan-6 [SEQ ID NO: 5]

| | Regions | Start (nt) | End (nt) | M.W. (Daltons) |
|---|---|---|---|---|
| ITR | | 1 | 123 | — |
| E1a | transcript | 478 | | — |
| | 13S | 576–1143, 1229–1437 | | 28291 |
| | 12S | 576–1050, 1229–1437 | | 24634 |
| | 9S | 576–645, 1229–1437 | | 10102 |
| | transcript | | 1516 | — |
| E1b | transcript | 1553 | | — |
| | Small T | 1600 | 2172 | 22315 |
| | LargeT | 1905 | 3413 | 55594 |
| | IX | 3498 | 3926 | 14427 |
| | transcript | | 3965 | — |
| E2b | transcript | 10341 | | — |
| | PTP | 10340 | 8451 | 72570 |
| | Polymerase | 8445 | 5089 | 126907 |
| | IVa2 | 5610 | 3986 | 50452 |
| | transcript | | 3966 | — |
| L1 | transcript | 10838 | | — |
| | 52/55 kD | 10840 | 12012 | 44205 |
| | IIIa | 12036 | 13799 | 65460 |
| | Transcript | | 13812 | — |
| 28.1 kd | | 5161 | 5985 | 28012 |
| Agnoprotein | | 7870 | 8580 | 25382 |
| L2 | transcript | 13874 | | — |
| | Penton | 13878 | 15467 | 59314 |
| | VII | 15471 | 16055 | 21508 |
| | V | 16100 | 17137 | 39388 |
| | Mu | 17160 | 17393 | 8506 |
| | transcript | | 17415 | — |
| L3 | transcript | 17466 | | — |
| | VI | 17469 | 18188 | 25860 |
| | Hexon | 18284 | 21112 | 106132 |
| | Endoprotease | 21134 | 21754 | 23445 |
| | transcript | | 21803 | — |
| E2a | transcript | 26780 | | — |
| | DBP | 23375 | 21837 | 57299 |
| | transcript | | 21780 | — |
| L4 | Transcript | 23398 | | — |
| | 100 kD | 23404 | 25806 | 88577 |
| | 33 kD homolog | 25523 | 26357 | 24609 |
| | VIII | 26426 | 27109 | 24749 |
| | transcript | | 27419 | — |
| E3 | transcript | 26786 | | — |
| | Orf #1 | 27110 | 27430 | 12098 |
| | Orf #2 | 27384 | 28007 | 22880 |
| | Orf #3 | 27989 | 28519 | 19460 |
| | Orf #4 | 28553 | 29236 | 25403 |
| | Orf #5 | 29249 | 29860 | 22350 |
| | Orf #6 | 29875 | 30741 | 31028 |
| | Orf #7 | 30749 | 31024 | 10469 |
| | Orf #8 | 31030 | 31464 | 16540 |
| | Orf #9 | 31457 | 31864 | 15264 |
| | transcript | | 31907 | — |
| L5 | transcript | 32159 | | |
| | Fiber | 32162 | 33493 | 47364 |
| | transcript | | 33574 | — |
| E4 | transcript | 36276 | | — |
| | Orf 7 | 33841 | 33593 | 9177 |
| | Orf 6 | 34746 | 33841 | 35094 |
| | Orf 4 | 35017 | 34652 | 13937 |
| | Orf 3 | 35380 | 35027 | 13627 |
| | Orf 2 | 35766 | 35377 | 14727 |
| | Orf 1 | 36181 | 35807 | 13739 |
| | transcript | | 33558 | — |
| ITR | | 36482 | 36604 | — |

| Regions | | Start (nt) | End (nt) | M.W. (Daltons) |
|---|---|---|---|---|
| | | Ad Pan-7 [SEQ ID NO: 9] | | |
| ITR | | 1 | 132 | — |
| E1a | transcript | 478 | | — |
| | 13S | 576–1143, 1229–1437 | | 28218 |
| | 12S | 576–1050, 1229–1437 | | 24561 |
| | 9S | 576–645, 1229–1437 | | 10102 |
| | transcript | | 1516 | — |
| E1b | transcript | 1553 | | — |
| | Small T | 1600 | 2178 | 22559 |
| | LargeT | 1905 | 3419 | 55698 |
| | IVa2 | 3992 | 5616 | 50210 |
| | transcript | | 3971 | — |
| E2b | transcript | 10341 | | — |
| | PTP | 10340 | 8457 | 72297 |
| | Polymerase | 8451 | 5095 | 126994 |
| | IX | 3504 | 3932 | 14441 |
| | transcript | | 3972 | — |
| 28.1 kD | | 5167 | 5991 | 28028 |
| Agnoprotein | | 7876 | 8586 | 25424 |
| L1 | transcript | 10834 | | |
| | 52/55 kD | 10836 | 12011 | 44302 |
| | IIIa | 12035 | 13795 | 65339 |
| | transcript | | 13808 | — |
| L2 | transcript | 13870 | | — |
| | Penton | 13874 | 15469 | 59494 |
| | VII | 15473 | 16057 | 21339 |
| | V | 16102 | 17139 | 39414 |
| | Mu | 17167 | 17400 | 8506 |
| | transcript | | 17420 | — |
| L3 | transcript | 17467 | | — |
| | VI | 17470 | 18198 | 26105 |
| | Hexon | 18288 | 21086 | 104763 |
| | Endoprotease | 21106 | 21732 | 23620 |
| | transcript | | 21781 | — |
| E2a | transcript | 26764 | | — |
| | DBP | 23353 | 21815 | 57199 |
| | transcript | | 21755 | — |
| L4 | transcript | 23370 | | — |
| | 100 kD | 23376 | 25781 | 88520 |
| | 33 kD homolog | 25489 | 26338 | 25155 |
| | VIII | 26410 | 27093 | 24749 |
| | transcript | | 27403 | — |
| E3 | transcript | 26770 | | — |
| | Orf #1 | 27094 | 27414 | 12056 |
| | Orf #2 | 27368 | 27988 | 22667 |
| | Orf #3 | 27970 | 28500 | 19462 |
| | Orf #4 | 28530 | 29150 | 22999 |
| | Orf #5 | 29163 | 29777 | 22224 |
| | Orf #6 | 29792 | 30679 | 32153 |
| | Orf #7 | 30687 | 30962 | 10511 |
| | Orf #8 | 30968 | 31399 | 16388 |
| | Orf #9 | 31392 | 31799 | 15205 |
| | transcript | | 31842 | — |
| L5 | transcript | 32091 | | — |
| | Fiber | 32094 | 33425 | 47344 |
| | transcript | | 33517 | — |
| E4 | transcript | 36208 | | — |
| | Orf 7 | 33784 | 33536 | 9191 |
| | Orf 6 | 34689 | 33784 | 35063 |
| | Orf 4 | 34960 | 34595 | 13879 |
| | Orf 3 | 35323 | 34970 | 13641 |
| | Orf 2 | 35709 | 35320 | 14644 |
| | Orf 1 | 36123 | 35749 | 13746 |
| | transcript | | 33501 | — |
| ITR | | 36404 | 36535 | — |

| | Ad SV-1 [SEQ ID NO: 24] | | Ad SV-25 [SEQ ID N0: 29] | | Ad SV-39 [SEQ ID NO: 34] | |
|---|---|---|---|---|---|---|
| Region | Start | End | Start | End | Start | End |
| ITR | 1 | 106 | 1 | 133 | 1 | 150 |
| E1a | 352 | 1120 | — | — | 404 | 1409 |
| E1b | 1301 | 2891 | 359 | 2273 | 1518 | 3877 |
| E2b | 9257 | 2882 | 9087 | 2754 | 10143 | 3868 |
| E2a | 24415 | 20281 | 24034 | 20086 | 25381 | 21228 |
| E3 | 24974 | 27886 | 24791 | 25792 | 25790 | 29335 |
| E4 | 33498 | 30881 | 30696 | 28163 | 33896 | 31157 |
| ITR | 34145 | 34264 | 30912 | 31044 | 33966 | 34115 |
| ITR | 1 | 106 | 1 | 133 | 1 | 150 |
| L1 | 9513 | 12376 | 9343 | 12206 | 10416 | 13383 |
| L2 | 12453 | 15858 | 12283 | 15696 | 13444 | 16877 |
| L3 | 15910 | 20270 | 15748 | 20080 | 17783 | 21192 |
| L4 | 21715 | 25603 | 21526 | 25420 | 22659 | 26427 |
| L5 | 28059 | 30899 | 25320 | 28172 | 29513 | 31170 |
| ITR | 34145 | 34264 | 30912 | 31044 | 33966 | 34115 |

| | | Ad SV-1, SEQ ID NO: 24 | | |
|---|---|---|---|---|
| | protein | Start | End | M.W. |
| ITR | | 1 | 106 | — |
| E1a | 13S | 459 | 953 | 18039 |
| | 12S | | | |
| E1b | Small T | | | |
| | LargeT | 1301 | 2413 | 42293 |
| | IX | 2391 | 2885 | 16882 |
| E2b | IVa2 | 4354 | 2924 | 54087 |
| | Polymerase | 6750 | 4027 | 102883 |
| | PTP | 9257 | 7371 | 72413 |
| | Agno-protein | 6850 | 7455 | 20984 |
| L1 | 52/55 kD | 9515 | 10642 | 42675 |
| | IIIa | 10663 | 12372 | 636568 |
| L2 | Penton | 12454 | 13965 | 56725 |
| | VII | 13968 | 14531 | 20397 |
| | V | 14588 | 15625 | 39374 |
| | Mu | 15645 | 15857 | 7568 |
| L3 | VI | 15911 | 16753 | 30418 |
| | Hexon | 16841 | 19636 | 104494 |
| | Endoprotease | 19645 | 20262 | 23407 |
| 2a | DBP | 21700 | 20312 | 52107 |
| L4 | 100 kD | 21721 | 24009 | 85508 |
| | VIII | 24591 | 25292 | 25390 |
| E3 | Orf #1 | 25292 | 25609 | 11950 |
| | Orf #2 | 25563 | 26081 | 18940 |
| | Orf #3 | 26084 | 26893 | 30452 |
| | Orf #4 | 26908 | 27180 | 10232 |
| | Orf #5 | 27177 | 17512 | 12640 |
| | Orf #6 | 27505 | 27873 | 13639 |
| L5 | Fiber #2 | 28059 | 29150 | 39472 |
| | Fiber #1 | 29183 | 30867 | 61128 |
| E4 | Orf 7 | 31098 | 30892 | 7837 |
| | Orf 6 | 31982 | 31122 | 33921 |
| | Orf 4 | 32277 | 31915 | 14338 |
| | Orf 3 | 32629 | 32279 | 13386 |
| | Orf 2 | 33018 | 32626 | 14753 |
| | Orf 1 | 33423 | 33043 | 14301 |
| ITR | | 34145 | 34264 | |

| | protein | Ad SV-25, SEQ ID NO: 29 Start | End | M.W. | Ad SV-39, SEQ ID NO: 34 Start | End | M.W. |
|---|---|---|---|---|---|---|---|
| ITR | | 1 | 133 | — | 1 | 150 | — |
| E1a | 13S | | | | 492 | 1355 | 28585 |
| | 12S | | | | 492 | 1355 | 25003 |
| E1b | Small T | 478 | 1030 | 20274 | 1518 | 2075 | 21652 |
| | Large T | 829 | 2244 | 52310 | 1823 | 3349 | 55534 |
| | IX | 2306 | 2716 | 13854 | 3434 | 3844 | 14075 |
| E2b | IVa2 | 4208 | 2755 | 54675 | 3912 | 5141 | 46164 |
| | Polymerase | 6581 | 3858 | 102839 | 7753 | 5033 | 103988 |
| | PTP | 9087 | 7207 | 71326 | 10143 | 8335 | 69274 |
| | Agnoprotein | 6681 | 7139 | 16025 | — | — | — |
| L1 | 52/55 kD | 9345 | 10472 | 42703 | 10418 | 11608 | 44232 |
| | IIIa | 10493 | 12202 | 63598 | 11574 | 13364 | 66078 |
| L2 | Penton | 12284 | 13801 | 56949 | 13448 | 14959 | 56292 |
| | VII | 13806 | 14369 | 20369 | 14960 | 15517 | 20374 |
| | V | 14426 | 15463 | 39289 | 15567 | 16628 | 39676 |
| | Mu | 15483 | 15695 | 7598 | 16650 | 16871 | 7497 |
| L3 | VI | 15749 | 16591 | 30347 | 16925 | 17695 | 28043 |
| | Hexon | 16681 | 19446 | 104035 | 17785 | 20538 | 102579 |
| | Endoprotease | 19455 | 20072 | 23338 | 20573 | 21181 | 22716 |
| 2a | DBP | 21511 | 20123 | 52189 | 22631 | 21231 | 53160 |
| L4 | 100 kD | 21532 | 23829 | 85970 | 22659 | 25355 | 100362 |
| | VIII | 24408 | 25109 | 25347 | 25410 | 26108 | 25229 |
| E3 | Orf #1 | 25109 | 25426 | 11890 | 26375 | 27484 | 42257 |
| | Orf #2 | | | | 27580 | 28357 | 29785 |
| | Orf #3 | | | | 28370 | 28645 | 10514 |
| | Orf #4 | | | | 28863 | 29333 | 18835 |
| | Orf #5 | | | | | | |
| | Orf #6 | | | | | | |
| L5 | Fiber #2 | 25380 | 26423 | 37529 | | | |
| | Fiber #1 | 26457 | 28136 | 60707 | 29515 | 31116 | 56382 |
| E4 | Orf 7 | | | | 31441 | 31118 | 11856 |
| | Orf 6 | 29255 | 28395 | 33905 | 32292 | 31438 | 33437 |
| | Orf 4 | 29550 | 29188 | 14399 | 32587 | 32222 | 13997 |
| | Orf 3 | 29902 | 29552 | 13284 | 32954 | 32607 | 13353 |
| | Orf 2 | 30291 | 29899 | 14853 | 33348 | 32959 | 14821 |
| | Orf 1 | 30316 | 30696 | 14301 | 33764 | 33378 | 14235 |
| ITR | | 30912 | 31044 | | 33966 | 34115 | |

The Pan5, Pan6, Pan7, SV1, SV25 and SV39 adenoviral nucleic acid sequences are useful as therapeutic agents and in construction of a variety of vector systems and host cells. As used herein, a vector includes any suitable nucleic acid molecule including, naked DNA, a plasmid, a virus, a cosmid, or an episome. These sequences and products may be used alone or in combination with other adenoviral sequences or fragments, or in combination with elements from other adenoviral or non-adenoviral sequences. The adenoviral sequences of the invention are also useful as antisense delivery vectors, genie therapy vectors, or vaccine vectors. Thus, the invention further provides nucleic acid molecules, gene delivery vectors, and host cells which contain the Ad sequences of the invention.

For example, the invention encompasses a nucleic acid molecule containing simian Ad ITR sequences of the invention. In another example, the invention provides a nucleic acid molecule containing simian Ad sequences of the invention encoding a desired Ad gene product. Still other nucleic acid molecule constructed using the sequences of the invention will be readily apparent to one of skill in the art, in view of the information provided herein.

In one embodiment, the simian Ad gene regions identified herein may be used in a variety of vectors for delivery of a heterologous molecule to a cell. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E4ORF6 region.

In addition, the adenoviral gene sequences and fragments thereof are useful for providing the helper functions necessary for production of helper-dependent viruses (e.g., adenoviral vectors deleted of essential functions or adeno-associated viruses (AAV)). For such production methods, the simian adenoviral sequences of the invention are utilized in such a method in a manner similar to those described for the human Ad. However, due to the differences in sequences between the simian adenoviral sequences of the invention and those of human Ad, the use of the sequences of the invention essentially eliminate the possibility of homologous recombination with helper functions in a host cell carrying human Ad E1 functions, e.g., 293 cells, which may produce infectious adenoviral contaminants during rAAV production.

Methods of producing rAAV using adenoviral helper functions have been described at length in the literature with human adenoviral serotypes. See, e.g., U.S. Pat. No. 6,258,595 and the references cited therein. See, also, U.S. Pat. No. 5,871,982; WO 99/14354; WO 99/15685; WO 99/47691. These methods may also be used in production of non-human serotype AAV, including non-human primate AAV serotypes. The simian adenoviral gene sequences of the invention which provide the necessary helper functions (e.g., E1a, E1b, E2a and/or E4 ORF6) can be particularly useful in providing the necessary adenoviral function while minimizing or eliminating the possibility of recombination with any other adenoviruses present in the rAAV-packaging cell which are typically of human origin. Thus, selected genes or open reading frames of the adenoviral sequences of the invention may be utilized in these rAAV production methods.

Alternatively, recombinant adenoviral simian vectors of the invention may be utilized in these methods. Such recombinant adenoviral simian vectors may include, e.g., a hybrid chimp Ad/AAV in which chimp Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or gene sequences of the invention will be useful for production of rAAV and other viruses dependent upon adenoviral helper.

In still another embodiment, nucleic acid molecules are designed for delivery and expression of selected adenoviral gene products in a host cell to achieve a desired physiologic effect. For example, a nucleic acid molecule containing sequences encoding an adenovirus E1a protein of the invention may be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, the Pan5, Pan6, Pan7, SV1, SV25 and/or SV39 simian Ad genomes of the invention can be utilized in a variety of rAd and non-rAd vector systems. Such vectors systems may include, e.g., plasmids, lentiviruses, retroviruses, poxviruses, vaccinia viruses, and adeno-associated viral systems, among others. Selection of these vector systems is not a limitation of the present invention.

The invention further provides molecules useful for production of the simian and simian-derived proteins of the invention. Such molecules which carry polynucleotides including the simian Ad DNA sequences of the invention can be in the form of naked DNA, a plasmid, a virus or any other genetic element.

B. Simian Adenoviral Proteins of the Invention

The invention further provides gene products of the above adenoviruses, such as proteins, enzymes, and fragments thereof, which are encoded by the adenoviral nucleic acids of the invention. The invention further encompasses Pan5, Pan6 and Pan7, SV1, SV25 and SV39 proteins, enzymes, and fragments thereof, having the amino acid sequences encoded by these nucleic acid sequences which are generated by other methods. Such proteins include those encoded by the open reading frames identified in the tables above, in FIGS. 1 and 2, and fragments thereof.

Thus, in one aspect, the invention provides unique simian adenoviral proteins which are substantially pure, i.e., are free of other viral and proteinaceous proteins. Preferably, these proteins are at least 10% homogeneous, more preferably 60% homogeneous, and most preferably 95% homogeneous.

In one embodiment, the invention provides unique simian-derived capsid proteins. As used herein, a simian-derived capsid protein includes any adenoviral capsid protein that contains a Pan5, Pan6, Pan7, S1, SV25 or SV39 capsid protein or a fragment thereof, as defined above, including, without limitation, chimeric capsid proteins, fusion proteins, artificial capsid proteins, synthetic capsid proteins, and recombinantly capsid proteins, without limitation to means of generating these proteins.

Suitably, these simian-derived capsid proteins contain one or more Pan5, Pan6, Pan7, SV1, SV25 or SV39 regions or fragments thereof (e.g., a hexon, penton, fiber or fragment thereof) in combination with capsid regions or fragments thereof of different adenoviral serotypes, or modified simian capsid proteins or fragments, as described herein. A "modification of a capsid protein associated with altered tropism" as used herein includes an altered capsid protein, i.e, a penton, hexon or fiber protein region, or fragment thereof, such as the knob domain of the fiber region, or a polynucleotide encoding same, such that specificity is altered. The simian-derived capsid may be constructed with one or more of the simian Ad of the invention or another Ad serotypes which may be of human or non-human origin. Such Ad may be obtained from a variety of sources including the ATCC, commercial and academic sources, or the sequences of the Ad may be obtained from GenBank or other suitable sources.

The amino acid sequences of the simian adenoviruses penton proteins of the invention are provided herein. The AdPan5 penton protein is provided in SEQ ID NO:2. The AdPan7 penton is provided in SEQ ID NO:6. The AdPan6 penton is provided in SEQ ID NO:10. The SV1 penton is provided in SEQ ID NO:25. The SV25 penton protein is provided in SEQ ID NO:30. The SV39 penton is provided in SEQ ID NO:35. Suitably, any of these penton proteins, or unique fragments thereof, may be utilized for a variety of purposes. Examples of suitable fragments include the penton having N-terminal and/or C-terminal truncations of about 50, 100, 150, or 200 amino acids, based upon the amino acid numbering provided above and in SEQ ID NO:2; SEQ ID NO:6; SEQ ID NO:25; SEQ ID NO:30; or SEQ ID NO:35. Other suitable fragments include shorter internal, C-terminal, or N-terminal fragments. Further, the penton protein may be modified for a variety of purposes known to those of skill in the art.

The invention further provides the amino acid sequences of the hexon protein of Pan5 [SEQ ID NO:3], Pan6 [SEQ ID NO:7], Pan 7 [SEQ ID NO:11], SV1 [SEQ ID NO:26], SV25 [SEQ ID NO:31], and/or SV39 [SEQ ID NO:36]. Suitably, this hexon protein, or unique fragments thereof, may be utilized for a variety of purposes. Examples of suitable fragments include the hexon having N-triennial and/or C-terminal truncations of about 50, 100, 150, 200, 300, 400, or 500 amino acids, based upon the amino acid numbering provided above and in SEQ ID NO: 3, 7, 11, 26, 31 and 36. Other suitable fragments include shorter internal, C-terminal, or N-terminal fragments. For example, one suitable fragment the loop region (domain) of the hexon protein, designated DE1 and FG1, or a hypervariable region thereof. Such fragments include the regions spanning amino acid residues about 125 to 443; about 138 to 441, or smaller fragments, such as those spanning about residue 138 to residue 163; about 170 to about 176; about 195 to about 203; about 233 to about 246; about 253 to about 264; about 287 to about 297; and about 404 to about 430 of the simian hexon proteins, with reference to SEQ ID NO: 3, 7, 11, 26, 31 or 36. Other suitable fragments may be readily identified by one of skill in the art. Further, the hexon protein may be modified for a variety of purposes known to those of skill in the art. Because the hexon protein is the determinant for serotype of an adenovirus, such artificial hexon proteins Would result in adenoviruses having artificial serotypes. Other artificial capsid proteins can also be constructed using the chimp Ad penton sequences and/or fiber sequences of the invention and/or fragments thereof.

In one example, it may be desirable to generate an adenovirus having an altered hexon protein utilizing the sequences of a hexon protein of the invention. One suitable method for altering hexon proteins is described in U.S. Pat. No. 5,922,315, which is incorporated by reference. In this method, at least one loop region of the adenovirus hexon is changed with at least one loop region of another adenovirus serotype. Thus, at least one loop region of such an altered adenovirus hexon protein is a simian Ad hexon loop region of the invention (e.g. Pan7). In one embodiment, a loop region of the Pan7 hexon protein is replaced by a loop region from another adenovirus serotype. In another embodiment, the loop region of the Pan7 hexon is used to replace a loop region from another adenovirus serotype. Suitable adenovirus serotypes may be readily selected from among human and non-human serotypes, as described herein. Pan7 is selected for purposes of illustration only; the other simian Ad hexon proteins of the invention may be similarly altered, or used to alter another Ad hexon. The selection of a suitable serotype is not a limitation of the present invention. Still other uses for the hexon protein sequences of the invention will be readily apparent to those of skill in the art.

The invention further encompasses the fiber proteins of the simian adenoviruses of the invention. The fiber-protein of AdPan 5 has the amino acid sequence of SEQ ID NO:4. The fiber protein AdPan6 has the amino acid sequence of SEQ ID NO: 8. The fiber protein of AdPan7 has the amino acid sequence of SEQ ID NO: 12. SV-1 has two fiber proteins; fiber 2 has the amino acid sequence of SEQ ID NO:27 and fiber 1 has the amino acid sequence of SEQ ID NO:28. SV-25 also has two fiber proteins; fiber 2 has the amino acid sequence of SEQ ID NO:32 and fiber 1 has the amino acid sequence of SEQ ID NO:33. The fiber protein of SV-39 has the amino acid sequence of SEQ ID NO:37.

Suitably, this fiber protein, or unique fragments thereof, may be utilized for a variety of purposes. One suitable fragment is the fiber knob, which spans about amino acids 247 to 425 of SEQ ID NO: 4, 8, 12, 28, 32, 33 and 37. See FIG. 2. Examples of other suitable fragments include the fiber having N-terminal and/or C-terminal truncations of about 50, 100, 150, or 200 amino acids, based upon the amino acid numbering provided above and in SEQ ID NO: 4, 8, 12, 28, 32, 33 and 37. Still other suitable fragments include internal fragments. Further, the fiber protein may be modified using a variety of techniques known to those of skill in the art.

The invention further encompasses unique fragments of the proteins of the invention which are at least 8 amino acids in length. However, fragments of other desired lengths can be readily utilized. In addition, the invention encompasses such modifications as may be introduced to enhance yield and/or expression of a Pan5, Pan6, Pan7, SV1, SV25 or SV39 gene product, e.g., construction of a fusion molecule in which all or a fragment of the Pan5, Pan6, Pan7, SV1, SV25 or SV39 gene product is fused (either directly or via a linker) with a fusion partner to enhance. Other suitable modifications include, without limitation, truncation of a coding region (e.g., a protein or enzyme) to eliminate a pre- or pro-protein ordinarily cleaved and to provide the mature protein or enzyme and/or mutation of a coding region to provide a secretable gene product. Still other modifications will be readily apparent to one of skill in the art. The invention further encompasses proteins having at least about 95% to 99% identity to the Pan5, Pan6, Pan7, SV1, SV25 or SV39 proteins provided herein.

As described herein, vectors of the invention containing the adenoviral capsid proteins of the invention are particularly well suited for use in applications in which the neutralizing antibodies diminish the effectiveness of other Ad serotype based vectors, as well as other viral vectors. The rAd vectors of the invention are particularly advantageous in readiministration for repeat gene therapy or for boosting immune response (vaccine titers).

Under certain circumstances, it may be desirable to use one or more of the Pan5, Pan6, Pan7, SV1, SV25 and/or SV39 gene products (e.g., a capsid protein or a fragment thereof) to generate an antibody. The term "an antibody," as used herein, refers to an immunoglobulin molecule which is able to specifically bind to an epitope. Thus, the antibodies of the invention bind, preferably specifically and without cross-reactivity, to a Pan5, Pan6, Pan7, SV1, SV25 or SV39 epitope. The antibodies in the present invention exist in a variety of forms including, for example, high affinity polyclonal antibodies, monoclonal antibodies, synthetic antibodies, chimeric antibodies, recombinant antibodies and humanized antibodies. Such antibodies originate from immunoglobulin classes IgG, IgM, IgA, IgD and IgE.

Such antibodies may be generated using any of a number of methods known in the art. Suitable antibodies may be generated by well-known conventional techniques, e.g. Kohler and Milstein and the many known modifications thereof. Similarly desirable high titer antibodies are generated by applying known recombinant techniques to the monoclonal or polyclonal antibodies developed to these antigens [see, e.g., PCT Patent Application No. PCT/GB85/00392; British Patent Application Publication No. GB2188638A; Amit et al., 1986 *Science*, 233:747-753; Queen et al., 1989 *Proc. Nat'l. Acad. Sci. USA*, 86:10029-10033; PCT Patent Application No. PCT/WO9007861; and Riechmann et al., *Nature*, 332:323-327 (1988); Huse et al, 1988a *Science*, 246:1275-1281]. Alternatively, antibodies can be produced by manipulating the complementary determining regions of animal or human antibodies to the antigen of this invention. See, e.g., E. Mark and Padlin, "Humanization of Monoclonal Antibodies", Chapter 4, The Handbook of Experimental Pharmacology, Vol. 113, The Pharmacology of Monoclonal Antibodies, Springer-Verlag (June, 1994); Harlow et al., 1999, Using Antibodies: A Laboratory Manual, Cold Spring Harbor Laboratory Press, N.Y.; Harlow et al., 1989, Antibodies: A Laboratory Manual, Cold Spring Harbor, New York; Houston et al., 1988, *Proc. Natl. Acad. Sci. USA* 85:5879-5883; and Bird et al., 1988, *Science* 242:423-426. Further provided by the present invention are anti-idiotype antibodies (Ab2) and anti-anti-idiotype antibodies (Ab3). See, e.g., M. Wettendorff et al., "Modulation of anti-tumor immunity by anti-idiotypic antibodies." In Idiotypic Network and Diseases, ed. by J. Cerny and J. Hiernaux, 1990 *J. Am. Soc. Microbiol.*, Washington D.C.: pp. 203-229]. These anti-idiotype and anti-anti-idiotype antibodies are produced using techniques well known to those of skill in the art. These antibodies may be used for a variety of purposes, including diagnostic and clinical methods and kits.

Under certain circumstances, it may be desirable to introduce a detectable label or a tag onto a Pan5, Pan6, Pan7, SV1, SV25 or SV39 gene product, antibody or other construct of the invention. As used herein, a detectable label is a molecule which is capable, alone or upon interaction with another molecule, of providing a detectable signal. Most desirably, the label is detectable visually, e.g. by fluorescence, for ready use in immunohistochemical analyses or immunofluorescent microscopy. For example, suitable labels include fluorescein isothiocyanlate (FITC), phycoerythrin (PE), allophlycocyanin (APC), coriphosphine-O (CPO) or tandem dyes, PE-cyanin-5 (PC5), and PE-Texas Red (ECD). All of these fluorescent dyes are commercially available, and their uses known to the art. Other useful labels include a colloidal gold label. Still other useful labels include radioactive compounds or elements. Additionally, labels include a variety of enzyme systems that operate to reveal a colorimetric signal in an assay, e.g., glucose oxidase (which uses glucose as a substrate) releases peroxide as a product which in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase which reacts with ATP, glucose, and NAD+ to yield, among other products, NADH that is detected as increased absorbance at 340 nm wavelength.

Other label systems that are utilized in the methods of this invention are detectable by other means, e.g., colored latex microparticles [Bangs Laboratories, Indiana] in which a dye is embedded are used in place of enzymes to form conjugates with the target sequences provide a visual signal indicative of the presence of the resulting complex in applicable assays.

Methods for coupling or associating the label with a desired molecule are similarly conventional and known to those of skill in the art. Known methods of label attachment are described [see, for example, Handbook of Fluorescent probes and Research Chemicals, 6th Ed., R. P. M. Haugland, Molecular Probes, Inc., Eugene, Oreg., 1996; Pierce Catalog and Handbook, Life Science and Analytical Research Products, Pierce Chemical Company, Rockford, Ill., 1994/1995]. Thus, selection of the label and coupling methods do not limit this invention.

The sequences, proteins, and fragments of the invention may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well known solid phase peptide synthesis methods (Merrifield, *J. Am. Chem. Soc*., 85:2149 (1962); Stewart and Young, Solid Phase Peptide Synthesis (Freeman, San Francisco, 1969) pp. 27-62). These and other suitable production methods are within the knowledge of those of skill in the art and are not a limitation of the present invention.

In addition, one of skill in the art will readily understand that the Ad sequences of the invention can be readily adapted for use for a variety of viral and non-viral vector systems for in vitro, ex vivo or in vivo delivery of therapeutic and immunogenic molecules. For example, in one embodiment, the simian Ad capsid proteins and other simian adenovirus proteins described herein are used for non-viral, protein-based delivery of genes, proteins, and other desirable diagnostic, therapeutic and immunogenic molecules. In one such embodiment, a protein of the invention is linked, directly or indirectly, to a molecule for targeting to cells with a receptor for adenoviruses. Preferably, a capsid protein such as a hexon, penton, fiber or a fragment thereof having a ligand for a cell surface receptor is selected for such targeting. Suitable molecules for delivery are selected from among the therapeutic molecules described herein and their gene products. A variety of linkers including, lipids, polyLys, and the like may be utilized as linkers. For example, the simian penton protein may be readily utilized for such a purpose by production of a fusion protein using the simian penton sequences in a manner analogous to that described in Medina-Kauwe LK, et al, *Gene Ther*. 2001 May; 8(10):795-803 and Medina-Kauwe LK, et al, *Gene Ther*. 2001 December; 8(23): 1753-1761. Alternatively, the amino acid sequences of simian Ad protein IX may be utilized for targeting vectors to a cell surface receptor, as described in U.S. patent application Ser. No. 20010047081. Suitable ligands include a CD40 antigen, an RGD-containing or polylysine-containing sequence, and the like. Still other simian Ad proteins, including, e.g., the hexon protein and/or the fiber protein, may be used for used for these and similar purposes.

Still other adenoviral proteins of the invention may be used as alone, or in combination with other adenoviral protein, for a variety of purposes which will be readily apparent to one of skill in the art. In addition, still other uses for the adenoviral proteins of the invention will be readily apparent to one of skill in the art.

II. Recombinant Adenoviral Vectors

The compositions of this invention include vectors that deliver a heterologous molecule to cells, either for therapeutic or vaccine purposes. As used herein, a vector may include any genetic element including, without limitation, naked DNA, a phage, transposon, cosmid, episome, plasmid, or a virus. Such vectors contain simian adenovirus DNA of Pan5, Pan6, Pan7, SV1, SV25 and/or SV39 and a minigene. By “minigene” is meant the combination of a selected heterologous gene and the other regulatory elements necessary to drive translation, transcription and/or expression of the gene product in a host cell.

Typically, an adenoviral vector of the invention is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of such as the site of a functional E1 deletion or functional E3 deletion, among others that may be selected. The term “functionally deleted” or “functional deletion” means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' inverted terminal repeat (ITR) sequences (which functions as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene is located between the 5' and 3' adenoviral sequences. Any adenoviral vector of the invention may also contain additional adenoviral sequences.

Suitably, these adenoviral vectors of the invention contain one or more adenoviral elements derived from an adenoviral genome of the invention. In one embodiment, the vectors contain adenoviral ITRs from Pan5, Pan6, Pan7, SV1, SV25 or SV39 and additional adenoviral sequences from the same adenoviral serotype. In another embodiment, the vectors contain adenoviral sequences that are derived from a different adenoviral serotype than that which provides the ITRs. As defined herein, a pseudotyped adenovirus refers to an adenovirus in which the capsid protein of the adenovirus is from a different serotype than the serotype which provides the ITRs. The selection of the serotype of the ITRs and the serotype of any other adenoviral sequences present in vector is not a limitation of the present invention. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other simian or from human adenoviruses are described in the published literature [see, for example, U.S. Pat. No. 5,240,846]. The DNA sequences of a number of adenovirus types are available from GenBank, including type Ad5 [GenBank Accession No. M73260]. The adenovirus sequences may be obtained from any known adenovirus serotype, such as serotypes 2, 3, 4, 7, 12 and 40, and further including any of the presently identified human types. Similarly adenoviruses known to infect non-human animals (e.g., simians) may also be employed in the vector Constructs of this invention. See, e.g., U.S. Pat. No. 6,083,716.

The viral sequences, helper viruses, if needed, and recombinant viral particles, and other vector components and sequences employed in the construction of the vectors described herein are obtained as described above. The DNA sequences of the Pan5, Pan6, Pan7, SV1, SV25 and/or SV39 simian adenovirus sequences of the invention are employed to construct vectors and cell lines useful in the preparation of such vectors.

Modifications of the nucleic acid sequences forming the vectors of this invention, including sequence deletions, insertions, and other mutations may be generated using standard molecular biological techniques and are within the scope of this invention.

A. The “Minigene”

The methods employed for the selection of the transgene, the cloning and construction of the “minigene” and its insertion into the viral vector are within the skill in the art given the teachings provided herein.

1. The Transgene

The transgene is a nucleic acid sequence, heterologous to the vector sequences flanking the transgene, which encodes a polypeptide, protein, or other product, of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, one type of transgene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry. For example, where the marker sequence is the LacZ gene, the presence of the vector carrying the signal is detected by assays for beta-galactosidase activity. Where the transgene is GFP or luciferase, the vector carrying the signal may be measured visually by color or light production in a luminometer.

However, desirably, the transgene is a non-marker sequence encoding a product which is useful in biology and medicine, such as proteins, peptides, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a molecule (e.g., a gene product) to induce a T cell and/or a humoral immune response to the molecule. The invention further includes using multiple transgenes, e.g., to correct or ameliorate a condition caused by a multi-subunit protein. In certain situations, a different transgene may be used to encode each subunit of a protein, or to encode different peptides or proteins. This is desirable when the size of the DNA encoding the protein subunit is large, e.g., for an immunoglobulin, the platelet-derived growth factor, or a dystrophin protein. In order for the cell to produce the multi-subunit protein, a cell is infected with the recombinant virus containing each of the different subunits. Alternatively, different subunits of a protein may be encoded by the same transgene. In this case, a single transgene includes the DNA encoding each of the subunits, with the DNA for each subunit separated by an internal ribozyme entry site (IRES). This is desirable when the size of the DNA encoding each of the subunits is small, e.g., the total size of the DNA encoding the subunits and the IRES is less than five kilobases. As an alternative to an IRES, the DNA may be separated by sequences encoding a 2A peptide, which self-cleaves in a post-translational event. See, e.g., M. L. Donnelly, et al, *J. Gen. Virol.*, 78(Pt 1):13-21 (January 1997); Furler, S., et al, *Gene Ther.*, 8(11):864-873 (June 2001); Klump H., et al., *Gene Ther.*, 8(10):811-817 (May 2001). This 2A peptide is significantly smaller than an IRES, making it well suited for use when space is a limiting factor.

However, the selected transgene may encode any biologically active product or other product, e.g., a product desirable for study.

Suitable transgenes may be readily selected by one of skill in the art. The selection of the transgene is not considered to be a limitation of this invention.

2. Regulatory Elements

In addition to the major elements identified above for the minigene, the vector also includes conventional control elements necessary which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1α promoter [Invitrogen].

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system [WO 98/10088]; the ecdysone insect promoter [No et al, *Proc. Natl. Acad. Sci. USA*, 93:3346-3351 (1996)], the tetracycline-repressible system [Gossen et al, *Proc. Natl. Acad. Sci. USA*, 89:5547-5551 (1992)], the tetracycline-inducible system [Gossen et al, *Science*, 268:1766-1769 (1995), see also Harvey et al, *Curr. Opin. Chem. Biol*., 2:512-518 (1998)]. Other systems include the FK506 dimer, VP16 or p65 using castradiol, diphenol murislerone, the RU486-inducible system [Wang et al, *Nat. Biotech*., 15:239-243 (1997) and Wang et al, *Gene Ther*., 4:432-441 (1997)] and the rapamycin-inducible system [Magari et al, *J. Clin. Invest*., 100:2865-2872 (1997)]. The effectiveness of some inducible promoters increases over time. In such cases one can enhance the effectiveness of such systems by inserting multiple repressors in tandem, e.g., TetR linked to a TetR by an IRES. Alternatively, one can wait at least 3 days before screening for the desired function. One can enhance expression of desired proteins by known means to enhance the effectiveness of this system. For example, using the Woodchuck Hepatitis Virus Posttranscriptional Regulatory Element (WPRE).

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylationi sites or Kozak consensus sequences may also be used to mimic the native expression.

Another embodiment of tie transgene includes a transgene operably linked to a tissue-specific promoter. For instance, if expression in skeletal muscle is desired, a promoter active in muscle should be used. These include the promoters from genes encoding skeletal β-actin, myosin light chain 2A, dystrophin, muscle creative kinase, as well as synthetic muscle promoters with activities higher than naturally occurring promoters (see Li et al., *Nat. Biotech*., 17:241-245 (1999)). Examples of promoters that are tissue-specific are known for liver (albumin, Miyatake et al., *J. Virol*., 71:5124-32 (1997); hepatitis B virus core promoter, Sandig et al., *Gene Ther*., 3:1002-9 (1996); alpha-fetoprotein (AFP), Arbuthnot et al., *Hum. Gene Ther*., 7:1503-14 (1996)), bone osteocalcin (Stein et al., *Mol. Biol. Rep*., 24:185-96 (1997)); bone sialoprotein (Chen et al., *J. Bone Miner. Res*., 11:654-64 (1996)), lymphocytes (CD2, Hansal et al., *J. Immunol*., 161:1063-8 (1998); immunoglobulin heavy chain; T cell receptor chain), neuronal such as neuron-specific enolase (NSE) promoter (Andersen et al., *Cell Mol. Neurobiol*., 13:503-15 (1993)), neurofilament light-chain gene (Piccioli et al., *Proc. Natl. Acad. Sci. USA*, 88:5611-5 (1991)), and the neuron-specific vgf gene (Piccioli et al., *Neuron*. 15:373-84 (I1995)), among others.

Optionally, vectors carrying transgenes encoding therapeutically useful or immunogenic products may also include selectable markers or reporter genes may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication. Selection of these and other promoters and vector elements are conventional and many such sequences are available [see, e.g., Sambrook et al, and references cited therein].

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

III. Production of the Recombinant Viral Particle

In one embodiment, the simian adenoviral plasmids (or other vectors) are used to produce recombinant adenoviral particles. In one embodiment, the recombinant adenoviruses are functionally deleted in the E1a or E1b genes, and optionally bearing other mutations, e.g., temperature-sensitive mutations or deletions in other genes. In other embodiments, it is desirable to retain an intact E1a and/or E1b region in the recombinant adenoviruses. Such an intact E1 region may be located in its native location in the adenoviral genome or placed in the site of a deletion in the native adenoviral genome (e.g., in the E3 region).

In the construction of useful simian adenovirus vectors for delivery of a gene to the human (or other mammalian) cell, a range of adenovirus nucleic acid sequences can be employed in the vectors. For example, all or a portion of the adenovirus delayed early gene E3 may be eliminated from the simian adenovirus sequence which forms a part of the recombinant virus. The function of simian E3 is believed to be irrelevant to the function and production of the recombinant virus particle. Simian adenovirus vectors may also be constructed having a deletion of at least the ORF6 region of the E4 gene, and more desirably because of the redundancy in the function of this region, the entire E4 region. Still another vector of this invention contains a deletion in the delayed early gene E2a. Deletions may also be made in any of the late genes L1 through L5 of the simian adenovirus genome. Similarly, deletions in the intermediate genes IX and $IVa_2$ may be useful for some purposes. Other deletions may be made in the other structural or non-structural adenovirus genes. The above discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2a and E3 genes, or of the E1 and E3 genes, or of E1, E2a and E4 genes, with or without deletion of E3, and so on. As discussed above, such deletions may be used in combination with other mutations, such as temperature-sensitive mutations, to achieve a desired result.

An adenoviral vector lacking any essential adenoviral sequences (e.g., E1a, E1b, E2a, E2b, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application WO96/13597, published May 9, 1996, and incorporated herein by reference.

1. Helper Viruses

Thus, depending upon the simian adenovirus gene content of the viral vectors employed to carry the minigene, a helper adenovirus or non-replicating virus fragment may be necessary to provide sufficient simian adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helped virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 7., 264:16985-16987 (1989); K. J. Fisher and J. M. Wilson, *Biochem. J.*, 299:49 (Apr. 1, 1994). Helper virus may optionally contain a second reporter minigene. A number of such reporter genes are known to the art. The presence of a reporter gene on the helper virus which is different from the transgene on the adenovirus vector allows both the Ad vector and the helper virus to be independently monitored. This second reporter is used to enable separation between the resulting recombinant virus and the helper virus upon purification.

2. Complementation Cell Lines

To generate recombinant simian adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene from Pan5, Pan6, Pan7, SV1, SV25 or SV39 under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired AdPan5, Pan6, Pan7, SV1, SV25 or SV39 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant simian adenovirus E1 deleted vectors. Additionally, or alternatively, the invention provides cell lines that express one or more simian adenoviral gene products, e.g., E1a, E1b, E2a, and/or E4 ORF6, can be constructed using essentially the same procedures for use in the generation of recombinant simian viral vectors. Such cell lines can be utilized to transcomplement adenovirus vectors deleted in the essential genes that encode those products, or to provide helper functions necessary for packaging of a helper-dependent virus (e.g., adeno-associated virus). The preparation of a host cell according to this invention involves techniques such as assembly of selected DNA sequences. This assembly may be accomplished utilizing conventional techniques. Such techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, FJ et al, (1998), *Hum Gene Ther*, 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast hepatocyte, tumor cell, etc.

3. Assembly of Viral Particle and Transfection of a Cell Line

Generally, when delivering the vector comprising the minigene by transfection, the vector is delivered in an amount from about 5 μg to about 100 μg DNA, and preferably about 10 to about 50 μg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently. Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaguing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant simian adenoviruses are useful in transferring a selected transgene to a selected cell. In in vivo experiments with the recombinant virus grown in the packaging cell lines, the E1-deleted recombinant simian adenoviral vectors of the invention demonstrate utility in transferring a transgene to a non-simian, preferably a human, cell.

IV. Use of the Recombinant Adenovirus Vectors

The recombinant simian adenovirus vectors of the invention are useful for gene transfer to a human or non-simian veterinary patient in vitro, ex vivo, and in vivo.

The recombinant adenovirus vectors described herein can be used as expression vectors for the production of the products encoded by the heterologous genes in vitro. For example, the recombinant adenoviruses containing a gene inserted into the location of an E1 deletion may be transfected into an E1-expressing cell line as described above. Alternatively, replication-competent adenoviruses may be used in another selected cell line. The transfected cells are then cultured in the conventional manner, allowing the recombinant adenovirus to express the gene product from the promoter. The gene product may then be recovered from the culture medium by known conventional methods of protein isolation and recovery from culture.

A Pan5, Pan6, Pan7, SV1, SV25 or SV39-derived recombinant simian adenoviral vector of the invention provides an efficient gene transfer vehicle that can deliver a selected transgene to a selected host cell in vivo or ex vivo even where the organism has neutralizing antibodies to one or more AAV serotypes. In one embodiment, the rAAV and the cells are mixed ex vivo; the infected cells are cultured using conventional methodologies; and the transduced cells are re-infused into the patient. These compositions are particularly well suited to gene delivery for therapeutic purposes and for immunization, including inducing protective immunity.

More commonly, the Pan 5, Pan6, Pan7, SV1, SV25, or SV39 recombinant adenoviral vectors of the invention will be utilized for delivery of therapeutic or immunogenic molecules, as described below. It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g., one, two, three, four or more). Thus, a regimen may involve delivery of a rAd with a first simian capsid, delivery with a rAd with a second simian capsid, and delivery with a third simian capsid. A variety of other regimens which use the Ad capsids of the invention alone, in combination with one another, or in combination with other Ad serotypes will be apparent to those of skill in the art. Optionally, such a regimen may involve administration of rAd with capsids of other non-human primate adenoviruses, human adenoviruses, or artificial serotypes such as are described herein. Each phase of the regimen may involve administration of a series of injections (or other delivery routes) with a single Ad serotype capsid followed by a series with another Ad serotype capsid. Alternatively, the recombinant Ad vectors of the invention may be utilized in regimens involving other non-adenoviral-mediated delivery systems, including other viral systems, non-viral delivery systems, protein, peptides, and other biologically active molecules.

The following sections will focus on exemplary molecules which may be delivered via the adenoviral vectors of the invention.

A. Ad-Mediated Delivery of Therapeutic Molecules

In one embodiment, the above-described recombinant vectors are administered to humans according to published methods for gene therapy. A simian viral vector bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The simian adenoviral vectors are administered in sufficient amounts to transduce the target cells and to provide sufficient levels of gene transfer and expression to provide a therapeutic benefit without undue adverse or with medically acceptable physiological effects, which can be determined by those skilled in the medical arts. Conventional and pharmaceutically acceptable routes of administration include, but are not limited to, direct delivery to the retina and other intraocular delivery methods, direct delivery to the liver, inhalation, intranasal, intravenous, intramuscular, intratracheal, subcutaneous, intradermal, rectal, oral and other parenteral routes of administration. Routes of administration may be combined, if desired, or adjusted depending upon the transgene or the condition. The route of administration primarily will depend on the nature of the condition being treated.

Dosages of the viral vector will depend primarily on factors such as the condition being treated, the age, weight and health of the patient, and may thus vary among patients. For example, a therapeutically effective adult human or veterinary dosage of the viral vector is generally in the range of from about 100 μL to about 100 mL of a carrier containing concentrations of from about $1\times10^6$ to about $1\times10^{15}$ particles, about $1\times10^{11}$ to $1\times10^{13}$ particles, or about $1\times10^9$ to $1\times10^{12}$ particles virus. Dosages will range depending upon the size of the animal and the route of administration. For example, a suitable human or veterinary dosage (for about an 80 kg animal) for intramuscular injection is in the range of about $1\times10^9$ to about $5\times10^{12}$ particles per mL, for a single site. Optionally, multiple sites of administration may be delivered. In another example, a suitable human or veterinary dosage may be in the range of about $1\times10^{11}$ to about $1\times10^{15}$ particles for an oral formulation. One of skill in the art may adjust these doses, depending the route of administration, and the therapeutic or vaccinal application for which the recombinant vector is employed. The levels of expression of the transgene, or for an immunogen, the level of circulating antibody, can be monitored to determine the frequency of dosage administration. Yet other methods for determining the timing of frequency of administration will be readily apparent to one of skill in the art.

An optional method step involves the co-administration to the patient, either concurrently with, or before or after administration of the viral vector, of a suitable amount of a short acting immune modulator. The selected immune modulator is defined herein as an agent capable of inhibiting the formation of neutralizing antibodies directed against the recombinant vector of this invention or capable of inhibiting cytologic T lymphocyte (CTL) elimination of the vector. The immune modulator may interfere with the interactions between the T helper subsets ($T_{H1}$ or $T_{H2}$) and B cells to inhibit neutralizing antibody formation. Alternatively, the immune modulator may inhibit the interaction between $T_{H1}$ cells and CTLs to reduce the occurrence of CTL elimination of the vector. A variety of useful immune modulators and dosages for use of same are disclosed, for example, in Yang et al., *J. Virol.*, 70(9) (September, 1996); International Patent Application No. WO96/12406, published May 2, 1996; and International Patent Application No.PCT/US96/03035, all incorporated herein by reference.

1. Therapeutic Transgenes

Useful therapeutic products encoded by the transgene include hormones and growth and differentiation factors including, without limitation, insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor (TGF), platelet-derived growth factor (PDGF), insulin growth factors I and II (IGF-I and IGF-II), any one of the transforming growth factor superfamily, including TGF, activins, inhibins, or any of the bone morphogenic proteins (BMP) BMPs 1-15, any one of the heregluin/neuregulin/ARIA/neu differentiation factor (NDF) family of growth factors, nerve growth factor (NGF), brain-derived neurotrophic factor (BDNF), neurotrophins NT-3 and NT-4/5, ciliary neurotrophic factor (CNTF), glial cell line derived neurotrophic factor (GDNF), neurturin, agrin, any one of the family of semaphorins/collapsins, netrin-1 and netrin-2, hepatocyte growth factor (HGF), ephrins, noggin, sonic hedgehog and tyrosine hydroxylase.

Other useful transgene products include proteins that regulate the immune system including, without limitation, cytokines and lymphokines such as thrombopoietin (TPO), interleukins (IL) IL-1 through IL-25 (including, e.g., IL-2, IL-4, IL-12 and IL-18), monocyte chemoattactant protein, leukemia inhibitory factor, granulocyte-macrophage colony stimulating factor, Fas ligand, tumor necrosis factors and, interferons, and, stem cell factor, flk-2/flt3 ligand. Gene products produced by the immune system are also useful in the invention. These include, without limitation, immunoglobulins IgG, IgM, IgA, IgD and IgE, chimeric immunoglobulins, humanized antibodies, single chain antibodies, T cell receptors, chimeric T cell receptors, single chain T cell receptors, class I and class II MHC molecules, as well as engineered immunoglobulins and MHC molecules. Useful gene products also include complement regulatory proteins such as complement regulatory proteins, membrane cofactor protein (MCP), decay accelerating factor (DAF), CR1, CF2 and CD59.

Still other useful gene products include any one of the receptors for the hormones, growth factors, cytokines, lymphokines, regulatory proteins and immune system proteins. The invention encompasses receptors for cholesterol regulation, including the low density lipoprotein (LDL) receptor, high density lipoprotein (HDL) receptor, the very low density lipoprotein (VLDL) receptor, and the scavenger receptor. The invention also encompasses gene products such as members of the steroid hormone receptor superfamily including glucocorticoid receptors and estrogen receptors, Vitamin D receptors and other nuclear receptors. In addition, useful gene products include transcription factors such as jun, fos, max, mad, serum response factor (SRF), AP-1, AP2, myb, MyoD and myogenin, ETS-box containing proteins, TFE3, E2F, ATF1, ATF2, ATF3, ATF4, ZF5, NFAT, CREB, HNF-4, C/EBP, SP1, CCAAT-box binding proteins, interferon regulation factor (IRF-1), Wilms tumor protein, ETS-binding protein, STAT, GATA-box binding proteins, e.g., GATA-3, and the forkhead family of winged helix proteins.

Other useful gene products include, carbamoyl synthetase I, ornithine transcarbamylase, arginosuccinate synthetase, arginosuccinate lyase, arginase, fumarylacetacetate hydrolase, phenylalanine hydroxylase, alpha-1 antitrypsin, glucose-6-phosphatase, porphobilinogen deaminase, factor VIII, factor IX, cystathione beta-synthase, branched chain ketoacid decarboxylase, albumin, isovaleryl-coA dehydrogenase, propionyl CoA carboxylase, methyl malonyl CoA mutase, glutaryl CoA dehydrogenase, insulin, beta-glucosidase, pyruvate carboxylate, hepatic phosphorylase, phosphorylase kinase, glycine decarboxylase, H-protein, T-protein, a cystic fibrosis transmembrane regulator (CFTR) sequence, and a dystrophin cDNA sequence.

Other useful gene products include non-naturally occurring polypeptides, such as chimeric or hybrid polypeptides having a non-naturally occurring amino acid sequence containing insertions, deletions or amino acid substitutions. For example, single-chain engineered immunoglobulins could be useful in certain immunocompromised patients. Other types of non-naturally occurring gene sequences include antisense molecules and catalytic nucleic acids, such as ribozymes, which could be used to reduce overexpression of a target.

Reduction and/or modulation of expression of a gene are particularly desirable for treatment of hyperproliferative conditions characterized by hyperproliferating cells, as are cancers and psoriasis. Target polypeptides include those polypeptides which are produced exclusively or at higher levels in hyperproliferative cells as compared to normal cells. Target antigens include polypeptides encoded by oncogenes such as myb, myc, fyn, and the translocation gene bcr/abl, ras, src, P53, neu, trk and EGRF. In addition to oncogene products as target antigens, target polypeptides for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated polypeptides can be used as target polypeptides such as polypeptides which are found at higher levels in tumor cells including the polypeptide recognized by monoclonal antibody 17-1A and folate binding polypeptides.

Other suitable therapeutic polypeptides and proteins include those which may be useful for treating individuals suffering from autoimmune diseases and disorders by conferring a broad based protective immune response against targets that are associated with autoimmunity including cell receptors and cells which produce self-directed antibodies. T cell mediated autoimmune diseases include Rheumatoid arthritis (RA), multiple sclerosis (MS), Sjögren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors (TCRs) that bind to endogenous antigens and initiate the inflammatory cascade associated with autoimmune diseases.

The simian adenoviral vectors of the invention are particularly well suited for therapeutic regimens in which multiple adenoviral-mediated deliveries of transgenes is desired, e.g., in regimens involving redelivery of the same transgene or in combination regimens involving delivery of other transgenes. Such regimens may involve administration of a Pan5, Pan6, Pan7, SV1, SV25 or SV39 simian adenoviral vector, followed by re-administration with a vector from the same serotype adenovirus. Particularly desirable regimens involve administration of a Pan5, Pan6, Pan7, SV1, SV25 or SV39 simian adenoviral vector of the invention, in which the serotype of the viral vector delivered in the first administration differs from the serotype of the viral vector utilized in one or more of the subsequent administrations. For example, a therapeutic regimen involves administration of a Pan5, Pan6, Pan7, SV1, SV25 or SV39 vector and repeat administration with one or more adenoviral vectors of the same or different serotypes. In another example, a therapeutic regimen involves administration of an adenoviral vector followed by repeat administration with a Pan5, Pan6, Pan7, SV1, SV25 or SV39 vector of the invention which differs from the serotype of the first delivered adenoviral vector, and optionally further administration with another vector which is the same or, preferably, differs from the serotype of the vector in the prior administration steps. These regimens are not limited to delivery of adenoviral vectors constructed using the Pan5, Pan6, Pan7, SV1, SV25 or SV39 simian serotypes of the invention. Rather, these regimens can readily utilize vectors other adenoviral serotypes, including, without limitation, other simian adenoviral serotypes (e.g., Pan9 or C68, C1, etc), other non-human primate adenoviral serotypes, or human adenoviral serotypes, in combination with one or more of the Pan5, Pan6, Pan7, SV1, SV25 or SV39 vectors of the invention. Examples of such simian, other non-human primate and human adenoviral serotypes are discussed elsewhere in this document. Further, these therapeutic regimens may involve either simultaneous or sequential delivery of Pan 5, Pan6, Pan7, SV1, SV25, and/or SV39 adenoviral vectors of the invention in combination with non-adenoviral vectors, non-viral vectors, and/or a variety of other therapeutically useful compounds or molecules. The present invention is not limited to these therapeutic regimens, a variety of which will be readily apparent to one of skill in the art.

B. Ad-Mediated Delivery of Immunogenic Transgenes

The recombinant simian adenoviruses may also be employed as immunogenic compositions. As used herein, an immunogenic composition is a composition to which a humoral (e.g., antibody) or cellular (e.g., a cytotoxic T cell) response is mounted to a transgene product delivered by the immunogenic composition following delivery to a mammal, and preferably a primate. The present invention provides a recombinant simian Ad that can contain in any of its adenovirus sequence deletions a gene encoding a desired immunogen. The simian adenovirus is likely to be better suited for use as a live recombinant virus vaccine in different animal species compared to an adenovirus of human origin, but is not limited to such a use. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a vaccinal composition of tic invention may be formulated to contain other components, including, e.g. adjuvants, stabilizers, pH adjusters, preservatives and the like. Such components are well known to those of skill in the vaccine art. Examples of suitable adjuvants include, without limitation, liposomes, alum, monophosphoryl lipid A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming DNA vaccine encoding an antigen to enhance the antigen-specific immune response compared with the immune response generated upon priming with a DNA vaccine encoding the antigen only.

The recombinant adenoviruses are administered in a "an immunogenic amount", that is, an amount of recombinant adenovirus that is effective in a route of administration to transfect the desired cells and provide sufficient levels of expression of the selected gene to induce an immune response. Where protective immunity is provided, the recombinant adenoviruses are considered to be vaccine compositions useful in preventing infection and/or recurrent disease.

Alternatively, or in addition, the vectors of the invention may contain a transgene encoding a peptide, polypeptide or protein which induces an immune response to a selected immunogen. The recombinant adenoviruses of this invention are expected to be highly efficacious at inducing cytolytic T cells and antibodies to the inserted heterologous antigenic protein expressed by the vector.

For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the pivornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, Ross-River virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses. Other target antigens may be generated from the Hepatitis C or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus. The influenza virus is classified within the family orthomyxovirus and is a suitable source of antigen (e.g., the HA protein, the N1 protein). The bunyavirus family includes the genera bunyavirus (*California encephalitis*, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick; fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency Virus (HIV), simian immunodeficiency virus (SIV), feline immunodeficiency virus (FIV), equine infectious anemia virus, and spumavirinal). Among the lentiviruses, many suitable antigens have been described and can readily be selected. Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981. ] See, also, the HIV and SIV proteins described in D. H. Barouch et al, J. Virol., 75(5):2462-2467 (March 2001), and R. R. Amara, et al, *Science*, 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in WO 01/54719, published Aug. 2, 2001, and WO 99/16884, published Apr. 8, 1999. The invention is not limited to the HIV and/or SIV immunogenic proteins or peptides described herein. In addition, a variety of modifications to these proteins have been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (HCMV, muromegalovirus) and the sub-family gammaherpesvirinae, which includes the genera lymphocryptovirus, EBV (Burkitts lymphoma), infectious rhinotrachetis, Marek's disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass immunogens which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include meningococcus; gonococcus. Pathogenic enteric gram-negative bacilli include *enterobacteriaceae; pseudomonas, acinetobacteria* and *eikenella; melioidosis; salmonella; shigella; haemophilus; moraxella; H. ducreyi* (which causes chiancroid); brucella; *Franisella tularensis* (which causes tularemia); *yersinia* (pasteurella); *streptobacillus moniliformis* and *spirillum*; Gram-positive bacilli include *listeria monocytogenes; erysipelothrix rhusiopathiae; Corynebacterium diphtheria* (diphtheria); cholera; *B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria. Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of mycoplasma and chlamydial infections include: mycoplasma pneumoniae; lymphogranuloma venereum; psittacosis; and perinatal chlamydial infections. Pathogenic eukaryotes encompass pathogenic protozoans and helminths and infections produced thereby include: amebiasis; malaria; leishmaniasis; trypanosomiasis; toxoplasmosis; *Pneumocystis carinii; Trichans; Toxoplasma gondii*; babesiosis; giardiasis; trichinosis; filariasis; schistosomiasis; nematodes; trematodes or flukes; and cestode (tapeworm) infections.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); Brucella species (brucellosis), *Burkholderia mallei* (glanders), *Burkholderia pseudomallei* (meloidosis), *Ricinus communis* is and its toxin (ricin toxin), *Clostridium perfringens* and its toxin (epsilon toxin), *Staphylococus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, nay be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors of the invention to deliver immunogens against the variable region of the T cells elicit an immune response including CTLs to eliminate those T cells. In RA, several specific variable regions of TCRs which are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In MS, several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a recombinant simian adenovirus that encodes at least one of these polypeptides will elicit an immune response that will target T cells involved in scleroderma.

C. Ad-Mediated Delivery Methods

The therapeutic levels, or levels of immunity, of the selected gene can be monitored to determine the need, if any, for boosters. Following an assessment of CD8+ T cell response, or optionally, antibody titers, in the serum, optional booster immunizations may be desired. Optionally, the recombinant simian adenoviral vectors of the invention may be delivered in a single administration or in various combination regimens, e.g., in combination with a regimen or course of treatment involving other active ingredients or in a prime-boost regimen. A variety of such regimens have been described in the art and may be readily selected.

For example, prime-boost regimens may involve the administration of a DNA (e.g., plasmid) based vector to prime the immune system to second, booster, administration with a traditional antigen, such as a protein or a recombinant virus carrying the sequences encoding such an antigen. See, e.g., WO 00/11140, published Mar. 2, 2000, incorporated by reference. Alternatively, an immunization regimen may involve the administration of a recombinant simian adenoviral vector of the invention to boost the immune response to a vector (either viral or DNA-based) carrying an antigen, or a protein. In still another alternative, an immunization regimen involves administration of a protein followed by booster with a vector encoding the antigen.

In one embodiment, the invention provides a method of priming and boosting an immune response to a selected antigen by delivering a plasmid DNA vector carrying said antigen, followed by boosting with a recombinant simian adenoviral vector of the invention. In one embodiment, the prime-boost regimen involves the expression of multiproteins from the prime and/or the boost vehicle. See, e.g., R. R. Amara, *Science*, 292:69-74 (6 Apr. 2001) which describes a multiprotein regimen for expression of protein subunits useful for generating an immune response against HIV and SIV. For example, a DNA prime may deliver the Gag, Pol, Vif, VPX and Vpr and Env, Tat, and Rev from a single transcript. Alternatively, the SIV Gag, Pol and HIV-1 Env is delivered in a recombinant adenovirus construct of the invention. Still other regimens are described in WO 99/16884 and WO 01/54719.

However, the prime-boost regimens are not limited to immunization for HIV or to delivery of these antigens. For example, priming may involve delivering with a first chimp vector of the invention followed by boosting with a second chimp vector, or with a composition containing the antigen itself in protein form. In one example, the prime-boost regimen can provide a protective immune response to the virus, bacteria or other organism from which the antigen is derived. In another desired embodiment, the prime-boost regimen provides a therapeutic effect that can be measured using convention assays for detection of the presence of the condition for which therapy is being administered.

The priming composition may be administered at various sites in the body in a dose dependent manner, which depends on the antigen to which the desired immune response is being targeted. The invention is not limited to the amount or situs of injection(s) or to the pharmaceutical carrier. Rather, the regimen may involve a priming and/or boosting step, each of which may include a single dose or dosage that is administered hourly, daily, weekly or monthly, or yearly. As an example, the mammals may receive one or two doses containing between about 10 μg to about 50 μg of plasmid in carrier. A desirable amount of a DNA composition ranges between about 1 μg to about 10,000 μg of the DNA vector. Dosages may vary from about 1 μg to 1000 μg DNA per kg of subject body weight. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Preferably, a boosting composition is administered about 2 to about 27 weeks after administering the priming composition to the mammalian subject. The administration of the boosting composition is accomplished using an effective amount of a boosting composition containing or capable of delivering the same antigen as administered by the priming DNA vaccine. The boosting composition may be composed of a recombinant viral vector derived from the same viral source (e.g., adenoviral sequences of the invention) or from another source. Alternatively, the "boosting composition" can be a composition containing the same antigen as encoded in the priming DNA vaccine, but in the form of a protein or peptide, which composition induces an immune response in the host. In another embodiment, the boosting composition contains a DNA sequence encoding the antigen under the control of a regulatory sequence directing its expression in a mammalian cell, e.g., vectors such as well-known bacterial or viral vectors. The primary requirements of the boosting composition are that the antigen of the composition is the same antigen, or a cross-reactive antigen, as that encoded by the priming composition.

In another embodiment, the simian adenoviral erectors of the invention are also well suited for use in a variety of other immunization and therapeutic regimens. Such regimens may involve delivery of simian adenoviral vectors of the invention simultaneously or sequentially with Ad vectors of different serotype capsids, regimens in which adenoviral vectors of the invention are delivered simultaneously or sequentially with non-Ad vectors, regimens in which the adenoviral vectors of the invention are delivered simultaneously or sequentially with proteins, peptides, and/or other biologically useful therapeutic or immunogenic compounds. Such uses will be readily apparent to one of skill in the art.

The following examples illustrate the cloning of the simian adenoviruses and the construction of exemplary recombinant adenovirus vectors of the present invention. These examples are illustrative only, and do not limit the scope of the present invention.

EXAMPLE 1

Viral Propagation

The Pan5 [ATCC Accession No. VR-591], Pan6 [ATCC Accession No. VR-592], and Pan7 [ATCC Accession No. VR-593] viruses, originally isolated from lymph nodes from chimpanzees, were propagated in 293 cells [ATCC CRL1573]. Typically, these cells are cultured in Dulbecco's Modified Eagles Medium (DMEM; Sigma, St. Louis, Mo.) supplemented with 10% fetal calf serum (FCS) [Sigma or Hyclone, Logan, Utah] and 1% Penicillin-Streptomycin (Sigma). Infection of 293 cells is carried out in DMEM supplemented with 2% FCS for the first 24 hours, after which FCS is added to bring the final concentration to 10%. Infected cells are harvested when 100% of the cells exhibit virus-iniduced cytopathic effect (CPE), and are then collected, and concentrated by centrifugation. Cell pellets are resuspended in 10 mM Tris (pH 8.0), and lysed by 3 cycles of freezing and thawing. Virus preparations are obtained following two ultra centrifugation steps on cesium chloride density gradients and stocks of virus are diluted to 1 to $5\times10^{12}$ particles/ml in 10 mM Tris/100 mM NaCl/50% glycerol and stored at −70° C.

The ability of 293 cells to propagate these adenoviruses exceeded expectations which were based on knowledge of other non-human adenovirus serotypes.

| Virus | Yield (virus particles produced in $8 \times 10^8$ cells) |
|---|---|
| Pan5 | $8.8 \times 10^{13}$ |
| Pan6 | $1.6 \times 10^{14}$ |
| Pan7 | $8.8 \times 10^{13}$ |

Example 2

Characterization of Spiral Genomic DNA

Genomic DNA was isolated from the purified virus preparations of Example 1 and digested with HindIII or BamHI restriction enzymes following the manufacturers' recommendations. The results (not shown) revealed that that the Pan5, Pan6, Pan7 genomes of the invention and the published Pan 9 (C68) genome show different restriction patterns, and thus, are distinct from each other.

The nucleotide sequences of Pan5, Pan6 and Pan7 were determined. The nucleotide sequence of the top strand of Pan5 DNA is reported in SEQ ID NO: 1. The nucleotide sequence of the top strand of Pan6 DNA is reported in SEQ ID NO: 5. The nucleotide sequence of the top strand of Pan7 DNA is reported in SEQ ID NO: 9.

Regulatory and coding regions in the viral DNA sequences were identified by homology to known adenoviral sequences using the "Clustal W" program described above at conventional settings. See the tables above providing the adenoviral sequences. Open reading frames were translated and the predicted amino acid sequences examined for homology to previously described adenoviral protein sequences, Ad4, Ad5, Ad7, Ad12, and Ad40.

Analysis of the sequence revealed a genome organization that is similar to that present in human adenoviruses, With the greatest similarity to human Ad4. However, substantial differences in the hexon hypervariable regions were noted between the chimpanzee adenoviruses and other known adenoviruses, including AdHu4. These differences fit well with the serological cross-reactivity data that has been obtained (see below).

An alignment of a portion of the hexon sequences is shown in FIG. 1. The portion shown is from the region of the hexon that corresponds to the outwardly disposed extended loops DE1 and FG1 where the most variability between serotypes is observed. An intervening portion that contributes to the base of the hexon (corresponding to residues 308-368 of the published AdC68 sequence; U.S. Pat. No. 6,083,716), and is highly conserved between serotypes, is also present. The following table summarizes the pair-wise comparisons of the amino acids in the hexon proteins.

| Comparison | | Hexon amino-acid |
|---|---|---|
| #1 | #2 | Similarity (%) |
| AdC5 | AdC7 | 99.0 |
| AdC5 | AdC68 | 98.3 |
| AdC5 | AdC6 | 88.0 |
| AdC5 | AdC1 | 84.9 |
| AdC6 | AdC7 | 87.7 |
| AdC6 | AdC68 | 87.3 |
| AdC6 | AdC1 | 84.9 |
| AdC7 | AdC68 | 97.5 |
| AdC7 | AdC1 | 84.8 |
| AdC68 | AdC1 | 84.9 |

Analysis of the fiber knob domain (which is responsible for receptor binding) of the chimpanzee adenoviruses shows an overall similarity in structure (FIG. 2).

The degree of sequence similarity between the E1 proteins of huAd5 and C68 (see Tables below) is similar to that between huAd5 and Pan-5, Pan-6, and Pan-7.

| Comparison | | E1a (13S) amino-acid |
|---|---|---|
| #1 | #2 | identity (%) |
| AdHu5 | AdC5 | 36.6 |
| AdHu5 | AdC6 | 28.5 |
| AdHu5 | AdC7 | 34.9 |
| AdHu5 | AdC68 | 35.6 |
| AdHu5 | AdC1 | 35.6 |
| AdC5 | AdC6 | 68.3 |
| AdC5 | AdC7 | 96.9 |
| AdC5 | AdC68 | 80.4 |
| AdC5 | AdC1 | 51.3 |
| AdC6 | AdC7 | 69.3 |
| AdC6 | AdC68 | 59.4 |
| AdC6 | AdC1 | 37.7 |
| AdC7 | AdC68 | 81.5 |
| AdC7 | AdC1 | 51.0 |
| AdC68 | AdC1 | 54.9 |

| | Sequence Identity with human Ad5 | |
|---|---|---|
| | E1b Small T Protein | E1b Large T Protein |
| C68 | 47.3% | 55.8% |
| Pan-5 | 43.2% | 54.5% |
| Pan-6 | 45.3% | 54.5% |
| Pan-7 | 46.4% | 53.8% |

Replication-defective versions of AdC5, AdC6 and AdC7 were created by molecular cloning methods described in the following examples in which minigene cassettes were inserted into the place of the E1a and E1b genes. The molecular clones of the recombinant viruses were rescued and grown up in 293 cells for large-scale purification using the published CsCl sedimentation method [K. Fisher et al., J. Virol., 70:520 (1996)]. Vector yields were based on 50 plate (150 mm) preps in which approximately $1\times10^9$ 293 cells were infected with the corresponding viruses. Yields were determined by measuring viral particle concentrations spectrophotometrically. After having constructed E1-deleted vectors, it was determined that HEK 293 cells (which express human adenovirus serotype 5 E1 functions) trans-complement the E1 deletions of the novel viral vectors and allow for the production of high titer stocks. Examples of virus yields for a few of these recombinant viruses are shown in the table below.

The transgenes for these vectors, β-galactosidase (LacZ), green fluorescent protein (GFP), alpha-1-anti-trypsin (A1AT), ebola glycoprotein (ebo), a soluble ebola glycoprotein variant lacking the transmembrane and cytoplasmic domains (sEbo), and three deletion mutants of the ebola glycoprotein (EboΔ2, EboΔ3, and EboΔ4), were expressed by the cytomegalovirus promoter (CMV). In the following table, ND indicates that the study has not yet been done.

| | Viral backbone/Vector yield (Viral particles x $10^{13}$) | | | |
|---|---|---|---|---|
| Transgene | AdHu5 | AdC7 | AdC68 | AdC6 |
| CMVLacZ | 1.5 | 1.4 | 3.3 | 6.1 |
| CMVGFP | 2.5 | 3.6 | 8 | 10 |
| CMVA1AT | 3.7 | 6 | 10 | ND |
| CMVEbo | 1.1 | 4.3 | ND | ND |
| CMVsEbo | 4.9 | 5.4 | ND | ND |
| CMVEboΔ2 | 1 | 9.3 | ND | ND |
| CMVEboΔ3 | 0.8 | 9.5 | ND | ND |
| CMVEboΔ4 | 1.4 | 6.2 | ND | ND |

The ability of human adenovirus E1 to trans-complement the E1-deleted chimpanzee viruses of the invention is highly advantageous, as it permits the production of E1-deleted chimpanzee adenoviral vectors of the invention, while reducing or eliminating the risk of homologous recombination due to the differences in sequences between human Ad and the chimpanzee adenoviruses described herein.

Example 3

Serological Studies of Pan 5, 6, and 7 Viruses

Because of the differences in the hexon hypervariable region, it was anticipated that the C5, C6, and C7 viruses would be serologically distinct from human adenoviruses, including AdHu4.

1. Cross-Reactivity of Wild-type Viruses

For screening of wild-type viruses in order to make a determination of antibody cross-reactivity, the replication competent viruses were used and inhibition of cytopathic effects (CPE) was measured. Briefly, preparations of adenoviruses (Adhu5, Pan-5, Pan-6, Pan-7 and AdC68) stored at $5\times10^{12}$ particles/ml were diluted 1/600 for the assays. This concentration of virus was selected since it results in 100% CPE within 48 hours in the absence of neutralization. Prior to adding the virus to 293 cells ($4\times10^4$ cells/well in a 96 well dish), 1:20 dilutions of sera were added. The assay is read as the presence or absence of CPE; full neutralization would read as no cytopathic effect. The results are summarized in the Table below. The fact that 9/36 human sera neutralized Adhu5 induced CPE is consistent with previous estimates of neutralizing antibodies in the human population. The numbers indicate the total individuals who showed neutralization (numerator) versus the total number screened (denominator). ND=not determined.

| | Neutralization by 1/20 diln of serum | | |
|---|---|---|---|
| | Human (N = 36) | Rhesus (N = 52) | Chimpanzee (N = 20) |
| Adhu5 | 9/36 | ND | ND |
| AdC68 | 1/36 | 0/52 | 12/20 |
| Pan 5 | 0/36 | 0/52 | 10/20 |
| Pan 6 | 0/36 | 0/52 | 9/20 |
| Pan 7 | 0/36 | 0/52 | 12/20 |

Of all human sera screened, 35/36 were negative for neutralization to AdC68 while 36/36 were negative for neutralization to Pan-5, Pan-6 and Pan-7. Of 52 rhesus monkeys screened, none showed neutralization to any chimpanzee adenovirus; rhesus monkey is the preferred pie-clinical model for evaluating HIV vaccines. Between 9 to 12 out of 20 chimpanzees had substantial neutralization to one or another of the chimpanzee adenoviruses consistent with the fact these are indeed endemic chimpanzee-specific pathogens. Interestingly, there are chimpanzees with neutralizing antibodies only to Pan-5, Pan-6 or AdC68 supporting the hypothesis that several of these chimpanzee adenoviral vectors will not cross neutralize each other and are distinct serotypes.

The same assay was carried out for 20 chimpanzee serum samples. Fifty percent (50%) of the samples reacted serologically, in different degrees to Pan5; 40% to Pan6; 55% to Pan7 and 60% to C68. Among the positive serum samples, one of them had strong neutralizing activity to all foul chimp viruses.

2. Cross-Neutralization with Recombinant Viruses

High-titer polyclonal antibodies were obtained to each of the simian adenoviruses in order to more precisely gauge the degree of cross-neutralization among the different serotypes. This was done by intramuscular immunization of rabbits using a recombinant virus containing GFP based on previously the described C68 chimpanzee adenovirus as an adjuvant. The serum was then used to assay for neutralizing activity against each of the three chimpanzee adenoviruses of the invention, AdC5, AdC6 and AdC7. A rabbit was injected with $5\times10^{12}$ viral particle per kg of C68CMVGFP vector intramuscularly and boosted 5 weeks later using the same dose. A bleed collected at the 9 week time point revealed extremely potent neutralizing activity against C68 as well as Pan-5 and Pan-7 but not against Pan-6 (see Table below), indicating that the administration of a C68 (or Pan-5 and Pan-7) based vaccine could be effectively followed by a boost using a vector based on Pan-6. However, it has been found that this level of inter-relatedness does not necessarily prevent with re-administration in a setting where antiviral antibody titers were not as high as was achieved in this rabbit. In the following table, + indicates 33% CPE; ++ indicates 66% CPE; +++ indicates 100% CPE.

| Infection on 293 cells with virus: | | | | | |
|---|---|---|---|---|---|
| Pan5 | Pan6 | Pan7 | Pan9(C68) | C68 GFP | Serum Dilution |
| – | +++ | – | – | – | 1/20 |
| – | +++ | – | – | – | 1/40 |
| – | +++ | – | – | – | 1/80 |
| – | +++ | – | – | – | 1/160 |

-continued

| Infection on 293 cells with virus: | | | | | |
|---|---|---|---|---|---|
| Pan5 | Pan6 | Pan7 | Pan9(C68) | C68 GFP | Serum Dilution |
| – | +++ | – | – | – | 1/320 |
| – | +++ | – | – | – | 1/640 |
| – | +++ | – | – | – | 1/1,280 |
| – | +++ | – | – | – | 1/2,560 |
| – | +++ | – | – | – | 1/5,120 |
| + | +++ | – | – | – | 1/10,240 |
| + | +++ | ++ | – | – | 1/20,480 |
| ++ | +++ | +++ | – | – | 1/40,960 |
| ++ | +++ | +++ | + | + | 1/81,920 |
| +++ | +++ | +++ | ++ | ++ | 1/163,840 |
| +++ | +++ | +++ | +++ | +++ | 1/327,680 |
| +++ | +++ | +++ | +++ | +++ | 1/665,360 |
| +++ | +++ | +++ | +++ | +++ | 1/1,310,720 |
| +++ | +++ | +++ | +++ | +++ | 1/2,621,440 |

3. Quantitative Assay for Detection of Neutralizing Antibody

The result was validated by a more quantitative-based assay for detecting neutralizing antibody, which is based on transduction of a GFP vector. Briefly, groups of C57BL/6 mice were immunized intramuscularly or intravenously with $5.0\times10^{10}$ particles/ml Pan5, Pan6, Pan7 or C68. Sera from day 28 bleeds were tested for cross-neutralizing activity against C68CMVEGFP at dilutions of 1/20 and 1/80. In summary, when a pharmaceutical preparation of human immunoglobulin was tested for serological reactions to Pan 5, 6, and 7, and C68, some low levels of neutralizing activities against Pan 7 and C68 were detected. No neutralizing activity against Pan5 or Pan6 was detected. Serum samples from 36 human subjects were run for the same assay. Serum samples were tested at a 1/20 dilution. The results indicated that only one individual has clear neutralizing activity to C68. No neutralizing activity to Pan5, Pan6 or Pan7 was detected.

4. In Vitro Cross-Neutralization

Cross-neutralization of the simian adenoviruses by high-titer rabbit polyclonal antibodies raised against each of the adenoviruses Pan-5, Pan-6, Pan-7, and C68 was tested.

Rabbits were immunized with intra-muscular injections of $10^{13}$ particles of each of the chimpanzee adenoviruses and boosted 40 days later with the same dose with incomplete Freud's adjuvant. Sera were analyzed or the presence of neutralizing antibodies by incubating serial two-fold dilutions with $10^9$ genome copies of each of the appropriate chimpanzee adenovirus vector expressing GFP and testing for the attenuation of GFP expression when applied to 293 cells. The serum dilution which produced a 50% reduction of GFP expression was scored as the neutralizing antibody titer against that particular virus.

The results are shown in the Table. The data are consistent with the expectation from sequence analysis of the hexon amino-acid sequences, which indicated that Ad Pan-6 was likely to be the most serologically distinct compared to the other chimpanzee adenoviruses.

| Serum from rabbit immunized | Infection of 293 cells with $10^9$ genome copies of | | | |
|---|---|---|---|---|
| with: | Ad Pan-5 | Ad Pan-6 | Ad Pan-7 | Ad C68 |
| Ad Pan-5 | 1/5120 | <1/20 | 1/2560 | 1/2560 |
| Ad Pan-6 | No neutralization | 1/20,480 | <1/20 | <1/20 |
| Ad Pan-7 | 1/2560 | 1/160 | 1/163,840 | 1/2560 |
| Ad C68 | No neutralization | <1/20 | <1/20 | 1/5120 |

In order to determine whether antibodies cross-reacting with the simian adenoviruses were likely to be of low prevalence in humans, simian adenoviruses SV1, SV39, and SV25 were tested for their ability to withstand neutralization when incubated with commercially available pooled human immunoglobulins (Ig). The same assay was also performed with Adhu5 and the chimpanzee adenoviruses Pan-5, Pan-6, Pan-7, and C68. In a further study, sera from mice has been immunized with one of the chimpanzee adenoviruses C5, C6, C7, and C68 and their ability to cross-neutralize the simian adenoviruses SV-15, SV-23, SA-17, and Baboon Adenovirus has been tested. No cross-reactivity was observed in any case.

Example 4

Generation of Recombinant E1-Deleted Pan5 Vector

A modified pX plasmid was prepared by destroying the FspI site in the bla gene region of pX (Clontech) by site-directed mutagenesis. The resulting modified plasmid, termed pX', is a circular plasmid of 3000 bp which contains an f1 ori and an ampicillin resistance gene (AmpR-cds).

A. Production of Pan-5 Adenovirus Plasmid

A polylinker for sequential cloning of the Pan5 DNA fragments into pX' is created. The polylinker is substituted for the existing pX' polylinker following digestion with MIUI and EcoRI. The blunt-FseI fragment of the Pan 5 is inserted into the SmaI and FseI sites of the polylinker. This fragment contains the 5' end of the adenoviral genome (bp 1 to 3606, SEQ ID NO:1). The SnaBI-FspI fragment of Pan 5 (bp 455 to 3484, SEQ ID NO:1) is replaced with a short sequence flanked by I-Ceu and PI-Sce sites from pShuttle (Clontech), to eliminate the E1 region of the adenoviral genome. The EcoRI-blunt fragment of Pan5 (bp 28658 to 36462, SEQ ID NO:1) is inserted into the EcoRI and EcoRV sites of the polylinker (to provide the 3' end of the adenoviral genome); the FseI-MluI fragment (bp 3606 to 15135, SEQ ID NO:1) is inserted into the polylinker; and the MluI-EcoRI fragment is inserted into the polylinker (bp 15135 to 28658, SEQ ID NO:1). Optionally, a desired transgene is inserted into I-CeuI and PI-SceI sites of the newly created pX'Pan5ΔE1 vector.

B. Alternative Method of Generating pX'Pan5ΔE1.

The initial plasmid pX is derived from pAdX adenovirus plasmid available from Clontech, as described above. Thereafter, a PacI-XhoI region of pX' was deleted and the blunt-ended Pan5 polylinker was inserted into the FspI site to generate pX'PLNK (2994 bp). The 5'end-FseI region of Pan 5 (bp 1-3607, SEQ ID NO:1) was inserted into SmaI and FseI sites of pX'LNK to generate the pX'Pan5-5' plasmid (6591 bp). The SnaBi-NdeI region of pX'Pan5-5' was excised and replaced with the Ceu/Sce cassette, which had been PCR amplified from pRCS to create pX'Pan5-5'ΔE1 (4374 bp). Briefly, a sequence containing I-CeuI and PI-SceI rare cutter sites was PCR amplified from pRCS (3113 bp). The 3' PCR primer was introduced an NdeI site into the PCR product.

To extend the Pan5 DNA in pX'Pan5-5'ΔE1 (4374 bp), the FseI-MluI region of Pan 5 (bp 3607-15135, SEQ ID NO:1) is added, to create pX'Pan5-5'Mlu (15900 bp). The remaining MluI-3' end of the Pan5 sequence (bp 15135-36462, SEQ ID NO:1) is added to the vector between the MluI and EcoRV sites of the vector polylinker to form pX'Pan5ΔE1 which contains the full-length Pan5 sequence containing a deletion in the E1 region.

C. Generation of Recombinant Viruses

To generate the recombinant adenoviruses from pX'Pan5ΔE1, the plasmid is co-transfected with a helper expressing E1, or from an E1-expressing packaging cell line, such as 293 cell line or a cell line prepared as described herein. The expression of E1 in the packaging cell permits the replication and packaging of the Pan5ΔE1 into a virion capsid. In another embodiment, the packaging cell transfected with pX'Pan5ΔE1 is transfected with an adenovirus vector as described above bearing the transgene of interest. Homologous recombination occurs between the helper and the plasmid, which permits the adenovirus-transgene sequences in the vector to be replicated and packaged into virion capsids, resulting in the recombinant adenovirus.

Transfection is followed by an agar overlay for 2 weeks, after which the viruses are plagued, expanded and screened for expression of the transgene. Several additional rounds of plaque purification are followed by another expansion of the cultures. Finally the cells are harvested, a virus extract prepared and the recombinant chimpanzee adenovirus containing the desired transgene is purified by buoyant density ultracentrifugation in a CsCl gradient or by alternative means known to those of skill in the art.

Example 5

Generation of Recombinant E1-Deleted Pan6 Vector

A. Strategy for Construction of Pan-6 Adenoviral Plasmid

1. Cloning of Terminal Fragments

Pan 6 Virus is deproteinated by pronase and proteanase K treatment and phenol extraction. Synthetic 12 bp Pme I linkers are ligated onto the viral DNA as described by Berkner and Sharp, *Nucleic Acids Research*, 11: 6003 (1983). The viral DNA is then digested with Xba I to isolate a 5' terminal fragment (6043 bp). The Ad6 XbaI 5' fragment is then ligated into pX link at Sma I and Xba I sites to form pX-AdPan6-0-16.5. The viral DNA with Pme I linkers is also digested with Pac I to isolate the 6475 bp 3' terminal fragment and cloned into pX link at Pac I and Sma I sites, resulting in pXAdPan6-82-100.

2. Deletion of E1 From the 5' Clone

To delete E1 (m.u.1.2-9), the BsiWi-Xba I fragment in pX-AdPan6-0-16.5 is replaced with a PCR fragment spanning m.u.9-16.7 fragment treated with BsiWi and Xba I, leading to pX-Ad-Pan6 m.u.0-1, 9-16.5.

3. Fusion of 5' and 3' Clones and to Create an Anchor Site to Accept the Middle Hind III fragment First, the 5' clone, pX-Ad-Pan6 m.u.0-1, 9-16.5, is further expanded by inserting the 2nd Xba I fragment (4350 bp, m.u.16.5-28) from Pan 6 genome into the Xba I site in the pX-Ad-Pan6 m.u.0-1, 9-16.5. This construct is named pXAd-Pan6-mu 0-1, 9-28.

Second, the 3' clone is also expanded by inserting the 15026 bp Mlu I/Pac I fragment covering m.u.41-82 from Pan 6 genome into the Mlu I/Pac I sites of pXAdPan6-82-100, generating pXAdPan6-m.u.41-100.

Then, a 8167 bp Hind III/Eco 47III Pan 6 fragment is isolated from pXAd-Pan6-mu 0-1, 9-28 and subcloned into pXAdPan6-m.u.41-100 at Hind III and Xba I blunt sites. This 5' and 3' fusion clone is called pXAdPan6mu0-1, 9-19.5, 64-100.

4. Drop of the Middle Fragment of the Genome into the Fusion Clone

A 16335 bp Hind III fragment (m.u.19.5-64) from Pan 6 is inserted into Hind III site of pXAdPan6mu0-1, 9-19.5, 64-100 to form pXAdPan6-0-1, 9-100.

5. Introduction of a PKGFP Selective Maker into the Final Construct for Direct Cloning the Gene of Interest and Green/White Selection of Recombinant Transformants A minigene cassette that expresses GFP under a lac promoter and is flanked with recognition sites of rare intron encoding restriction enzymes, PI-Sce I and I-Ceu I, was isolated from pShuttle-pkGFP (bare) by Sap I and Dra III digestions followed by filling-in reaction. The pShuttle-pkGFP (bare) plasmid is 4126 bp in length, and contains a ColE1-Ori, a kanamycin resistance gene, plac, a LacZ promoter-GFPmut3-1 cds (Clontech), and a GFPmut3-1 cds (Clontech). This cassette is subcloned into Srf I cut and blunted pXAdPan6-0-1, 9-100. This final construct is called pX-Pan6-pkGFP m.u.0-1, 9-100, which is useful for generating recombinant E1-deleted Pan 6 molecular clones carrying genes of interest by direct ligation and green/white selection in combination with the generic pShuttlepkGFP vectors.

B. Alternative Strategy for Generation of Pan-6 Plasmid

1. Cloning of 5' Terminal Fragment

The Pan 6 virus is deproteinated by pronase and proteanase K treatment and phenol extraction as described above and synthetic 12 bp Pme I linkers are ligated onto the viral DNA as described. The AdPan6 5' XbaI fragment is isolated and ligated into pX to form pX-AdPan6-0-16.5 (9022 bp) as described in Part A above.

2. Deletion of E1 from the 5' Clone

To delete E1 (m.u. 1.2-9), pX-AdPan6-0-16.5 is digested with SnaBI and NdeI to remove the regions encoding the E1a and E1b proteins (3442-6310 bp). This vector is subsequently digested with BsiWI in preparation for blunting with the minigene cassette carrying a selective marker.

3. Introduction of a Selective Marker

A minigene cassette that expressed GFP under a lac promoter and which is flanked with recognition sites of rare intron encoding restriction enzymes, PI-XceI and I-CeuI, was isolated from pShuttle-pkGFP as described above. The DraIII-SapI fragment is then ligated with the digested pX-AdPan6-0-16.5 to form pX-AdPan6 MU 0-16.5ΔE1 (7749 bp).

4. Extension of Pan-6 Adenoviral Sequences pX-AdPan6 MU 0-16.5ΔE1 was subjected to XbaI digestion to permit insertion of an XbaI-RsrII linker. An XbaI/RsrII digestion fragment from the AdPan6 genome was isolated (mu 28-100, 26240 bp) and ligated into the Xba/RsrII-digested pX-AdPan6 MU 0-16.5ΔE1 to provide pX-AdPan6 MU 0-1, 9-16.5, 28-100. A second XbaI fragment from the Pan6 genome (mu 16.5-28, 4350 bp) is then ligated into this plasmid to form pX-AdPan6 MU 0-1, 9-100 (38551 bp).

C. Generation of Recombinant Adenoviruses

To generate the recombinant adenoviruses from a E1-deleted Pan6 plasmid prepared as described in Parts A or b, the plasmid is co-transfected with a helper expressing E1, or from an E1-expressing packaging cell line, such as 293 cell line or a cell line prepared as described herein. The expression of E1 in the packaging cell permits the replication and packaging of the Pan6-pkGFP mu.0-1, 9-100 into a virion capsid. Alternatively, the packaging cell transfected with pX-Pan6-pkGFP mu.0-1, 9-100 is transfected with an adenovirus vector as described above bearing another transgene of interest.

Example 6

Generation of Recombinant E1-Deleted Pan7 Vector

A. Generation of Pan7 Plasmids

A synthetic linker containing the restriction sites PacI-SmaI-FseI-MluI-EcoRV-PacI was cloned into pBR322 that was cut with EcoRI and NdeI. The left end (bp 1 to 3618) of Ad Pan7 was cloned into the linker between the SmaI and FseI sites. The adenovirus E1 was then excised from the cloned left end by cutting with SnaBI and NdeI and inserting an I-CeuI-GFP-PI-SceI cassette from pShuttle (Clontech) in its place. The resulting plasmid was cut with FseI and MluI and Ad Pan7 fragment FseI (bp 3618) to MluI (bp 155114 was inserted to extend the left end. The Construct (pPan7pGFP) was completed by inserting the 21421 bp Ad Pan7 right end fragment from the MluI site (bp 15114) into the above plasmid between MluI and EcoRV to generate a complete molecular clone of E1 deleted adenovirus Pan7 suitable for the generation of recombinant adenoviruses. Optionally, a desired transgene is inserted into the I-CeuI and PI-SceI sites of the newly created pPan7 vector plasmid.

B. Construction of E1-Deleted Pan 7 Viral Vectors

To generate the recombinant adenoviruses from pPan7ΔE1, the plasmid is co-transfected with a helper expressing E1, or from an E1-expressing packaging cell line, such as 293 cell line or a cell line prepared as described herein. The expression of E1 in the packaging cell permits the replication and packaging of the Pan7ΔE1 into a virion capsid. In another embodiment, the packaging cell transfected with pX'Pan7 ΔE1 is transfected with an adenovirus vector as described above bearing the transgene of interest. Homologous recombination occurs between the helper and the plasmid, which permits the adenovirus-transgene sequences in the vector to be replicated and packaged into virion capsids, resulting in the recombinant adenovirus. Transfection and purification is as described above.

Example 7

Generation of Plasmid Vectors Expressing the E1 Genes

Plasmid vectors are constructed which encode the Pan5 E1 region gene, and these plasmids are used to generate stable cell lines expressing viral E1 proteins.

The E1 region of Pan5 is cloned into pX', essentially as described in Example 4 above, prior to replacement of this region with the fragment from pShuttle (Clontech). The expression plasmid contains the Pan5 adenoviral genome sequence spanning at least bp 1 to 3959 in the Pan5 genomic sequence. Thus, the expression plasmid contains the sequence encoding E1a and E1b of chimpanzee Ad Pan5 under the control of a heterologous promoter. Similar expression plasmids can be generated using the Ad Pan6 and AdPan 7 E1 regions, identified in the tables above.

Example 8

Generation of Cell Lines Expressing Chimpanzee Adenovirus E1 Proteins

Cell lines expressing viral E1 proteins are generated by transfecting HeLa (ATCC Acc. No. CCL2) with the plasmid of Example 6. These cell lines are useful for the production of E1-deleted recombinant chimpanzee adenoviruses by co-transfection of genomic viral DNA and the expression plasmids described above. Transfection of these cell lines, as well as isolation and purification of recombinant chimpanzee adenoviruses therefrom are performed by methods conventional for other adenoviruses, i.e., human adenoviruses [see, e.g., Horwitz, cited above and other standard texts].

A. Cell Lines Expressing Pan5 E1 Proteins

HeLa cells in 10 cm dishes are transfected with 10 μg of pX-Pan51-E1 DNA using a Cellphect™ kit (Pharmacia, Uppsala, Sweden) and following the manufacturer's protocol. 22 hours post-transfection, the cells are subjected to a three minute glycerol shock (15% glycerol in Hepes Buffered Saline, pH 7.5) washed once in DMEM (HeLa) or F12K (A549; Life Technologies, Inc., Grand Island, N.Y.) media supplemented with 10% FCS, 1% Pen-Strep, then incubated for six hours at 37° C. in the above described media. The transfected cells are then split into duplicate 15 cm plates at ratios of 1:20, 1:40, 1:80, 1:160, and 1:320. Following incubation at37° C. overnight, the media is supplemented with G418 (Life Technologies, Inc.) at a concentration of 1 μg/ml. The media is replaced every 5 days and clones are isolated 20 days post-transfection.

HeLa E1 cell clones are isolated and assayed for their ability to augment adeno-associated virus (AAV) infection and expression of recombinant LacZ protein as described below.

B. AAV Augmentation Assay for Screening E1 Expressing Cell Lines

AAV requires adenovirus-encoded proteins in order to complete its life cycle. The adenoviral E1 proteins as well as the E4 region-encoded ORF6 protein are necessary for the augmentation of AAV infection. An assay for E1 expression based on AAV augmentation is used. Briefly, the method for identifying adenoviral E1-expressing cells comprises the steps of infecting in separate cultures a putative adenovirus E1-expressing cell and a cell containing no adenovirus sequence, with both an adeno-associated virus (AAV) expressing a marker gene and an AAV expressing the ORF6 of the E4 gene of human adenovirus, for a suitable time. The marker gene activity in the resulting cells is measured and those cells with significantly greater measurable marker activity than the control cells are selected as confirmed E1-expressing cells. In the following experiment, the marker gene is a lacZ gene and the marker activity is the appearance of blue stain.

For example, the cell lines described above, as well as untransfected control cells (HeLa) are infected with 100 genomes per cell of an AAV vector bearing a marker gene, e.g., AV.LacZ [K(. Fisher et al., J. Virol., 70:520 (1996)] and an AAV vector expressing the ORF6 region of human 5 (AV.orf6). The DNA sequence of the plasmid generates a novel recombinant adeno-associated virus (rAAV) containing the LacZ transgene and the Ad E4 ORF 6, which is an open reading frame whose expression product facilitates single-stranded (ss) to double-stranded (ds) conversion of rAAV genomic DNA. These vectors are incubated in medium containing 2% FCS and 1% Pen-Strep at 37° C. for 4 hours, at which point an equal volume of medium containing 10% FCS is added. It should be understood by one of skill in the art that any marker gene (or reporter gene) may be employed in the first AAV vector of this assay, e.g., alkaline phosphatase, luciferase, and others. An antibody-enzyme assay can also be used to quantitate levels of antigen, where the marker expresses an antigen. The assay is not limited by the identity of the marker gene. Twenty to twenty-four hours post-infection, the cells are stained for LacZ activity using standard methods. After 4 hours the cells are observed microscopically and cell lines with significantly more blue cells than the A549 or HeLa cell controls are scored as positive.

Example 9

Delivery of Transgene to Host Cell

The resulting recombinant chimpanzee adenovirus described in Example 4, 5 or 6 above is then employed to deliver the transgene to a mammalian, preferably human, cell. For example, following purification of the recombinant virus, human embryonic kidney 293 cells are infected at an MOI of 50 particles per cell. GFP expression was documented 24 hours post-infection.

A. Gene Transfer in Mouse Models via Pan-6, Pan-7, and Pan-9 Vectors

Gene transfer efficiencies and toxicological profile of recombinant chimpanzee adenoviruses were compared in mouse liver directed gene transfer, mouse lung directed gene transfer, and mouse muscle directed gene transfer.

E1-deleted adenoviral vectors containing LacZ under the control of the CMV promoter were constructed using the techniques herein for human Ad5, chimpanzee Pan 6, chimpanzee Pan 7 and chimpanzee Pan 9 (C68). The vectors were delivered to immune-deficient NCR nude mice (80 for each study) as follows. For the liver study, 100 μl ($1\times10^{11}$ particles) were injected into the tail vein. For the lung study, 50 μl ($5\times10^{10}$ particles) were delivered intratracheally. For the muscle study, 25 μl ($5\times10^{10}$ particles) were injected into tibialis anterior. The mice were sacrificed on days 3, 7, 14 and 28 post-vector injection (5 animals per group at each time point). At each necropsy, the liver/lung/Muscle tissue was harvested and prepared for cryoblocks and paraffin embedding. The cryoblocks were sectioned for X-gal staining and the paraffin sections are H&E stained for histopathic analysis. At each time point, terminal bleeding, was performed. Serum samples were subjected to liver function tests.

It was observed in this experiment the chimpanzee adenoviruses Pan-6, Pan-7, and Pan-9 were less efficient than huAd5 in gene transfer to the liver and to the lung. However, this may be desirable in certain circumstances, to reduce liver toxicity observed for huAd5. The gene transfer efficiency in muscle varied less between serotypes.

B. Mouse Study to Feasibility of Re-administration of Adenovirus Vectors by Serotype Switching Between Adhu5, Pan-6, Pan-7, and Pan-9 Vectors Mice were administered (C57/B16; 4/group) LacZ vectors based on huAd5, Pan-6, Pan-7, and Pan-9 (H5.040CMVLacZ, Pan6.000CMVLacZ, Pan7.000CMVLacZ, Pan9.000CMVLacZ; $10^{11}$ particles/injection) by tail vein. Thirty days later the mice were re-administered adenovirus vectors expressing α1-antitrypsin (H5.040CMVhA1AT, Pan6.000CMVhA1AT, $1\times10^{11}$ particles, Pan7.000CMVhA1AT, Pan9.000CMVhA1AT, $10^{11}$ particles/injection). Successful transduction by the re-administered vector is monitored by measuring serum α1-antitrypsin on days 3 and 7, following re-administration.

The ability of adenovirus vectors based on huAd5, Pan-6, Pan-7, and Pan-9 respectively to transduce the livers of mice in the presence of neutralizing antibodies to the other serotypes was determined. The results are tabulated here.

| 1st injection | 2nd injection | Cross-neutralization |
|---|---|---|
| Adhu5 | Adhu5 | Yes (+ve control) |
| | Pan-6 | No |
| | Pan-7 | No |
| | Pan-9 (C68) | No |
| Pan-6 | Adhu5 | No |
| | Pan-6 | Yes (+ve control) |
| | Pan-7 | Yes |
| | Pan-9 (C68) | No |
| Pan-7 | Adhu5 | No |
| | Pan-6 | Yes |
| | Pan-7 | Yes (+ve control) |
| | Pan-9 (C68) | Yes |
| Pan-9 (C68) | Adhu5 | No |
| | Pan-6 | No |
| | Pan-7 | Yes |
| | Pan-9 (C68) | Yes (+ve control) |

Ability of vectors to transduce immune liver in the presence of neutralizing antibodies to other serotypes.

Thus, immunization with huAd5 does not prevent re-administration with either of the chimpanzee adenovirus vectors Pan-6, Pan-7, or Pan-9 (C68). This experiment also appears to indicate that Pan-7 is between Pan-6 and Pan-9 in the spectrum of antigenic relatedness and cross-reacts with both; however Pan-6 and Pan-9 do not neutralize each other. This is a surprising result based on homology comparisons, which indicates that Pan-6 is quite distinct from Pan-7 and Pan-9. Evaluation of antisera generated against Pan-9 indicated no cross-neutralization against Pan-6 but some neutralization against Pan-7, arguing that Pan-6 is distinct from the others.

Example 10

Generation of Recombinant E1-Deleted SV-25 Vector

A plasmid was constructed containing the complete SV-25 genome except for an engineered E1 deletion. At the site of the E1 deletion recognition sites for the restriction enzymes I-CeuI and PI-SceI which would allow insertion of transgene from a shuttle plasmid where the transgene expression cassette is flanked by these two enzyme recognition sites were inserted.

A synthetic linker containing the restriction sites SwaI-SnaBI-SpeI-AflII-EcoRV-SwaI was cloned into pBR322 that was cut with EcoRI and NdeI. This was done by annealing together two synthetic oligomers SV25T (5'-AAT TTA AAT ACG TAG CGC ACT AGT CGC GCT AAG CGC GGA TAT CAT TTA AA-3', SEQ ID NO: 38) and SV25B (5'-TAT TTA AAT GAT ATC CGC GCT TAA GCG CGA CTA GTG CGC TAC GTA TTT A-3', SEQ ID NO:39) and inserting it into pBR322 digested with EcoRI and NdeI. The left end (bp 1 to 1057, SEQ ID NO:29) of Ad SV25 was cloned into the above linker between the SnaBI and SpeI sites. The right end (bp28059 to 31042, SEQ ID NO: 29) of Ad SV25 was cloned into the linker between the AflII and EcoRV sites. The adenovirus E1 was then excised between the EcoRI site (bp 547) to XhoI (bp 2031) from the cloned left end as follows. A PCR generated I-CeuI-PI-SceI cassette from pShuttle (Clontech) was inserted between the EcoRI and SpeI sites. The 10154 bp XhoI fragment of Ad SV-25 (bp2031 to 12185, SEQ ID NO:29) was then inserted into the SpeI site. The resulting plasmid was digested with HindIII and the construct (pSV25) was completed by inserting the 18344 bp Ad SV-25 HindIII fragment (bp11984 to 30328, SEQ ID NO:29) to generate a complete molecular clone of E1 deleted adenovirus SV25 suitable for the generation of recombinant adenoviruses. Optionally, a desired transgene is inserted into the I-CeuI and PI-SceI sites of the newly created pSV25 vector plasmid.

To generate an AdSV25 carrying a marker gene, a GFP (green fluorescent protein) expression cassette previously cloned in the plasmid pShuttle (Clontech) was excised with the restriction enzymes I-CeuI and PI-SceI and ligated into pSV25 (or another of the Ad chimp plasmids described herein) digested with the same enzymes. The resulting plasmid (pSV25GFP) was digested with SwaI to separate the bacterial plasmid backbone and transfected into the E1 complementing cell line HEK 293. About 10 days later, a cytopathic effect was observed indicating the presence of replicative virus. The successful generation of an Ad SV25 based adenoviral vector expressing GFP was confirmed by applying the supernatant from the transfected culture on to fresh cell cultures. The presence of secondarily infected cells was determined by observation of green fluorescence in a population of the cells.

Example 11

Construction of E3 Deleted Pan-5, Pan-6, Pan-7 and C68 Vectors

In order to enhance the cloning capacity of the adenoviral vectors, the E3 region can be deleted because this region encodes genes that are not required for the propagation of the virus in culture. Towards this end, E3-deleted versions of Pan-5, Pan-6, Pan-7, and C68 have been made (a 3.5 kb Nru-AvrII fragment containing E31-9 is deleted).

A. E3 Deleted Pan5 Based Vector

E1-deleted pPan5-pkGFP plasmid was treated with Avr II endonuclease to isolate a 5.8 kb fragment containing the E3 region and re-circulate pPan5-pkGFP with Avr II deletion to form construct pPan5-pkGFP-E3-Avr II. Subsequently, the 5.8 kb Avr II fragment was subcloned into pSL-Pan5-E3-Avr II for a further deletion of E3 region by Nru I digestion. This led to a plasmid pSL-Pan5-E3-deletion. The final construct pPan5-E3-pkGFP was produced by removing a 4.3 kb Avr II/Spe I fragment from pSL-Pan5-E3-deletion plasmid and inserting into pPan5-pkGFP-E3-Avr II at Avr II site. In this final construct, a 3.1 kb deletion in E3 region was accomplished.

B. E3 Deletion in Pan6 Based Vector

E1-deleted pPan6-pkGFP molecular clone was digested with Sbf I and Not I to isolate 19.3 kb fragment and ligated back at Sbf I site. The resulting construct pPan6-Sbf I-E3 was treated with Eco 47 III and Swa I, generating pPan6-E3. Finally, 21 kb Sbf I fragment from Sbf I digestion of pPan6-pkGFP was subcloned into pPan6-E3 to create pPan6-E3-pkGFP with a 4 kb deletion in E3.

C. E3 Deleted Pan7 and Pan9 Vectors

The same strategy was used to achieve E3 deletions in both vectors. First, a 5.8 kb Avr II fragment spanning the E3 region was subcloned pSL-1180, followed by deletion of E3 by Nru I digestion. The resulting plasmids were treated with Spe I and Avr II to obtain 4.4 kb fragments and clone into pPan7-pkGFP and pPan9-pkGFP at Avr II sites to replace the original E3 containing Avr II fragments, respectively. The final pPan7-E3-pkGFP and pPan9-E3-pkGFP constructs have 3.5 kb E3-deletions.

Example 12

Construction of E3- and E4-deleted Pan-7 Vector

Although the deletion of the E1 region of adenoviruses (first generation adenovirus vectors) renders them replication-incompetent, expression of the adenoviral vector backbone genes is not fully abolished. Deletion of the E4 region considerably attenuates this residual gene expression and may confer a safety advantage. An E4-deleted Pan-7 vector containing a 2.5 kb deletion (a PvuII-AgeI fragment containing E4ORF1-ORF7 is deleted) has been constructed. High titer stocks of this virus were generated using a HEK 293-based cell line, which in addition to E1, expresses an essential E4 gene (orf 6).

1. E4 Deletion in the Molecular Clone of Pan7

A 19 kb Xba I fragment was deleted from pPan7-pkGFP to create pPan7-Xba I from which a 2.5 kb E4 fragment was deleted by Age I and Pvu II partial digestion, resulting in pPan7-Xba I-E4. pPan7-E4-pkGFP plasmid was generated from pPan7-Xba I-E4 in two sequential cloning steps, adding 19 kb Xba I and 15 kb I-Ceu I/Mlu I fragments, both of which came from pPan7-pkGFP construct.

2. Introduction of E3 and E4 Deletions in Pan9 Vector

A 11 kb plasmid, pPan9-EcoRI, containing E4 region was created by retrieving 11 kb EcoRI fragment from pPan9 pkGFP after EcoRI digestion and self-ligation. E4 region was deleted from this construct by Age I digestion/filled in and Pvu II partial digestion and self-ligation to generate pPan9-EcoR I-E4. A 23 kb EcoR I fragment was isolated from pPan9-pkGFP and inserted into pPan9-EcoR I-E4 at EcoR I site, followed by adding 5.8 kb Avr II fragment from pPan9-pkGFP, to form the final product pPan9-E3-E4-pkGF.

Compared to the genome size of wild type Pan9, this E1-E3-E4-deleted vector could have a transgene capacity up to 8 kb.

3. Introduction of Minigene Cassettes with Genes of Interest Including Reporter Genes, Glyco- and Nuclear Proteins of Ebo into Molecular Clones of Pan Vectors A highly efficient direct cloning and green/white selection procedure was employed for creating molecular clones of recombinant viruses. Briefly, genes of interest were cloned into pShuttlepkGFP by screening white colonies for recombinants. Subsequently, the minigene cassettes were transferred into chimpanzee adenovirus backbone plasmids, pPanX-pkGFP with various deletions, easily by swapping with pkGFP cassette at I-Ceu I and PI-Sce I sites and screening a few white colonies for correct recombinants.

4. Rescue of Molecular Clones of Pan Vectors with Multiple Deletions in Early Regions and Virus Propagation For rescue of E1-E3-deleted molecular clones of chimpanzee adenovirus vectors, the clones were linearized with appropriate restriction enzymes and transfected into regular 293 cells. Once a full cytopathic effect (CPE) observed in the transfected cells, crude lysate was harvested and expanded in 293 cells to large-scale infections. The viruses were purified by CsCl sedimentation method.

For E1-E4 and E1-E3-E4-deleted Pan vectors, 10-3 cells, a 293-based E1-E4-complementing cell line, were used for rescue and propagation of vectors. E4 ORF6 gene expression in 10-3 cells was induced by addition of 150 μM $ZnSO^4$ to the culture medium.

Example 13

Vaccination with Adenovirus Vectors Expressing Wild Type and Variant EboZ GP.

AdHu5 or AdC7 vectors expressing Ebola envelope chimeras were produced for in vivo immunization experiments in C57BL/6 mice. Recombinant viruses with different viral backbones were created by molecular cloning method in which the minigene cassettes were inserted into the place of E1-deletions. The molecular clones of all recombinant viruses were rescued and grown up in 293 cells for large-scale purification using CsCl sedimentation method. Five EboZ variants encoded by AdHu5 or AdPan7 (C7) were selected and produced to evaluate their relative immunogenicity following an intramuscular Ad injection. The wt Ebo, a soluble Ebo variant, EboΔ1, EboΔ2, EboΔ3, EboΔ4, EboAΔ5S, EboΔ6S, EboΔ7S and EboΔ8S were evaluated in the initial vaccine studies. For the data summarized in the following table, the number of viral particles (per ml or total) produced and amplified from infected 293 cells was established by spectrophotometry reading.

Table: Production of Adhu5 or AdC7 Adenoviral vector encoding EboZ variant.

| | HuAd5 | | AdC7 | |
|---|---|---|---|---|
| Gene | Titer (VP × $10^{12}$/ml) | Total yield (VP × $10^{12}$) | Titer (VP × $10^{12}$/ml) | Total yield (VP × $10^{12}$) |
| Ebo wt | 2.6 | 12 | 4.3 | 43 |
| EboS | 4.9 | 49 | 4.6 | 55 |
| EboΔ2 | 2.1 | 9 | 5.8 | 93 |

-continued

| | HuAd5 | | AdC7 | |
|---|---|---|---|---|
| Gene | Titer (VP × $10^{12}$/ml) | Total yield (VP × $10^{12}$) | Titer (VP × $10^{12}$/ml) | Total yield (VP × $10^{12}$) |
| EboΔ3 | 1.7 | 8 | 5.3 | 95 |
| EboΔ4 | 3 | 12 | 4.1 | 62 |

Vector was administered intramuscularly ($10^{11}$ genome copies/cell) in C57BL/6 mice and the presence of virus neutralizing antibody (VNA0 was evaluated 28 days later as a first measure of an immune response generated against the Ebola envelope glycoprotein. VNA is defined here as serum antibody able to inhibit transduction of HeLa cells mediated by HIV-based vector pseudotyped with the wild-type Ebola envelope.

VNA to the EboZ pseudotypes was detected with AdPan7 (C7) yielding higher titers than AdHu5. The EboZΔ3 elicited the highest VNA in terms of the transgene targets. For the data summarized in the following table, neutralizing antibody titers to HIV-EboZ-GFP pseudotypes (reciprocal dilution) are provided (N=5 animals/group).

| | VNA Titers EboZ wildtype | EboZs | EboZΔ3 |
|---|---|---|---|
| AdHu5 | 12 | 16 | 12 |
| AdC7 | 44 | 12 | 140 |

Example 14

Pan7-mediated Expression of Ebola Proteins

Mouse studies to evaluate Pan-7 vectors expressing Ebola envelope proteins and the Ebola nuclear antigen have been initiated. These are directed towards evaluation of neutralizing antibodies in C57B1/6 mice injected intramuscularly (IM) with Adhu5 or Pan-7 expressing each of 4 Ebola env constructs.

A. Evaluation of CTL from C57B1/6 Mice Injected IM with Adhu5 or Pan-7 Expressing the Ebola Env Constructs.

1. Challenge Experiment in Mice with Ebola Virus.

Neutralizing antibody (NAB) responses to the Ebola envelope were analyzed by looking at immunized mouse sera mediated neutralization of a lentiviral (HIV) vector pseudotyped with the several constructs (eEbo, NTD2, NTD3, NTD4) of the Ebola envelope glycoprotein. C57BL/6 or BALB/c mice received a single intramuscular injection of $5\times10^{10}$ particles per mouse of C7 (Ad Pan-7) encoding Ebola envelope variant. Neutralizing antibody was evaluated 30 days post-vaccination. Briefly, Ebola Zaire pseudotyped HIV vector encoding for β-galactosidase (EboZ-HIV-LacZ) was incubated for 2 hr at 37° C. with different dilution of heat inactivated mouse serum. Following the incubation with serum, EboZ-HIV-LacZ was then used to infect HeLa cells for 16 hr at 37° C. Infectivity was revealed by X-gal staining of transduced HeLa cells positive for β-galactosidase. Neutralizing titer represent the serum reciprocal dilution where a 50% decrease in the number of β-galactosidase positive blue cells was observed. Sera were collected 30 days post-immunization, which consisted in a single intramuscular (I.M.) administration of $5\times10^{10}$ particles/animal. Neutralizing antibody to Ebola pseudotyped HIV could be detected from all groups with antibody titers ranging from 20 for Ad-EboZ (Adhu5 expressing EboZ), Ad-NTD3 (Adhu5 expressing NTD3) and C7-sEbo (Ad Pan-7 expressing soluble EboZ) to over 130 for C7-NTD3 (Ad Pan-7 expressing soluble NTD3) and C7-NTD4 (Ad Pan-7 expressing soluble NTD3). The same immunization strategy in BALB/c mice resulted in lower neutralizing antibody titers for Ad- and C7-NTD2, and NTD4.

B. Cellular Immune Response

The cellular immune response to the Ebola envelope in C57BL/6 mice was evaluated 8 days after a single I.M. administration of $5\times10^{10}$ particles of C7-LacZ or C7-Ebola envelope variant per animal. Mice were vaccinated I.M. with $5\times10^{10}$ particles of C7 encoding LacZ or Ebola envelope variant. Splenic lymphocytes from immunized mice were collected 8 days post vaccination and stimulated in vitro with feeder cells (splenic lymphocytes from untreated mice infected with human Adenovirus serotype 5 encoding for the wild-type Ebola envelope and irradiated). Standard 5-hr CTL assays were performed using $^{51}$Cr-labeled syngenic C57 cells transfected with an expressor of EboZ.

A positive MHC-restricted cytotoxic T lymphocyte (CTL) response was observed from all AdPan-7 encoding for Ebola envelope variants with a higher response from NTD2, NTD3 or NTD4 immunized mice. Indeed, effector cells from C7 encoding Ebola envelope variant immunized mice recognized EboZ transfected target cells and gave recall CTL responses up to 30% specific lysis. Less than 5% lysis was seen with effector cells from naïve or LacZ immunized control mice confirming that lysis was specific for Ebola envelope antigens.

C. Protection Studies

The most direct means of evaluating C7 (Ad Pan-7) encoding for the EboZ variants as a successful vaccine in mice was to assess protection against weight loss and death following lethal challenge with mouse adapted Ebola Zaire virus. BALB/c mice were immunized with a single dose of$5\times10^{10}$ particles per animal as performed previously and vaccinated animals were challenged with 200 $LD_{50}$ of mouse adapted Ebola Zaire 21 days later. All control mice (vehicle and C7-LacZ) died between day 5 to day 9 post-challenge. In contrast, all vaccinated mice but one, (from the C7-sEbo group), survived the challenge with Ebola Zaire.

Weight loss was observed from mice vaccinated with C7-sEbo from day 4 to day 7. Signs of illness Such as pilo-erection and from light to severe lethargy were also noted from mice vaccinated with C7-sEbo, NTD2 and NTD3 between day 4 to day 7. Mice immunized with C7-EboZ and C7-NTD4 did not show sign of illness. Overall, a single dose of C7-EboZ and C7-NTD4 completely protected immunized mice from illness and death possibly due to a significant T cell mediated immunity.

All documents recited above are incorporated herein by reference. Numerous modifications and variations of the present invention are included in the scope of the above-identified specification and are expected to be obvious to one of skill in the art. Such modifications and alterations to the compositions and processes of the present invention, such as selections of different minigenes or selection or dosage of the vectors or immune modulators are believed to be within the scope of the claims appended hereto.

What is claimed is:

1. An adenovirus having an artificial adenovirus capsid comprising a hexon protein of Pan7 having the sequence of SEQ ID NO:11 and a heterologous adenovirus capsid protein sequence.

2. A recombinant adenovirus having a capsid comprising an AdPan7 hexon protein having the amino acid sequence of SEQ ID NO:11 and a nucleic acid sequence heterologous to AdPan7.

3. The recombinant adenovirus according to claim 2, wherein the capsid further comprises an AdPan7 fiber protein.

4. The recombinant adenovirus according to claim 2, wherein the capsid further comprises an AdPan7 penton protein.

5. The recombinant adenovirus according to claim 2, wherein said recombinant adenovirus vector is a pseudotyped adenovirus comprising 5' and 3' adenovirus cis-elements necessary for replication and encapsidation, said cis-elements comprising an adenovirus 5' inverted terminal repeat and an adenovirus 3' inverted terminal repeat.

6. The recombinant adenovirus according to claim 2, wherein the adenovirus comprises a nucleic acid sequence encoding a product operatively linked to sequences which direct expression of said product in a host cell.

7. The recombinant adenovirus according to claim 2, wherein the recombinant adenovirus comprises one or more adenovirus genes.

8. The recombinant adenovirus according to claim 2, wherein the recombinant adenovirus is replication-defective.

9. The recombinant adenovirus according to claim 8, wherein the recombinant adenovirus is deleted in adenovirus E1.

10. A recombinant adenovirus having a capsid comprising a hexon containing a fragment of the AdPan7 hexon protein and a nucleic acid sequence heterologous to the AdPan7, wherein the fragment of the AdPan7 hexon protein is the AdPan7 hexon protein of SEQ ID NO:11 with an N-terminal or C-terminal truncation of about 50 amino acids or is selected from the group consisting of:

amino acid residues 125 to 443 of SEQ ID NO: 11;

amino acid residues 138 to 441 of SEQ ID NO: 11;

amino acid residues 138 to 163 of SEQ ID NO: 11;

amino acid residues 170 to 176 of SEQ ID NO: 11; and amino acid residues 404 to 430 of SEQ ID NO: 11.

11. An adenovirus having a capsid comprising an AdPan7 hexon protein having the amino acid sequence of SEQ ID NO:11, said capsid encapsidating a heterologous nucleic acid sequence operably linked to expression control sequences which direct transcription, translation, and/or expression thereof in a host cell.

12. The recombinant adenovirus according to claim 11, wherein the capsid further comprises an AdPan7 fiber protein.

13. The recombinant adenovirus according to claim 11, wherein the capsid further comprises an AdPan7 penton protein.

* * * * *

SEQUENCE LISTING

<160> NUMBER OF SEQ ID NOS: 39

<210> SEQ ID NO 1
<211> LENGTH: 36462
<212> TYPE: DNA
<213> ORGANISM: chimpanzee adenovirus serotype Pan5
<220> FEATURE:
<221> NAME/KEY: CDS
<222> LOCATION: (13898)..(15490)
<223> OTHER INFORMATION: L2 Penton
<220> FEATURE:
<221> NAME/KEY: CDS
<222> LOCATION: (18315)..(21116)
<223> OTHER INFORMATION: L3 Hexon
<220> FEATURE:
<221> NAME/KEY: CDS
<222> LOCATION: (32035)..(33372)
<223> OTHER INFORMATION: L5 Fiber

<400> SEQUENCE: 1

```
catcatcaat aatatacctc aaacttttgg tgcgcgttaa tatgcaaatg aggtatttga     60

atttggggat gcggggcggt gattggctgc gggagcggcg accgttaggg gcggggcggg    120

tgacgttttg atgacgtggc cgtgaggcgg agccggtttg caagttctcg tgggaaaagt    180

gacgtcaaac gaggtgtggt ttgaacacgg aaatactcaa ttttcccgcg ctctctgaca    240

ggaaatgagg tgtttctggg cggatgcaag tgaaaacggg ccattttcgc gcgaaaactg    300

aatgaggaag tgaaaatctg agtaattccg cgtttatggc agggaggagt atttgccgag    360
```

-continued

```
ggccgagtag actttgaccg attacgtggg ggtttcgatt accgtatttt tcacctaaat    420
ttccgcgtac ggtgtcaaag tccggtgttt ttacgtaggt gtcagctgat cgccagggta    480
tttaaacctg cgctctctag tcaagaggcc actcttgagt gccagcgagt agagttttct    540
cctccgcgcc gcgagtcaga tctacacttt gaaagatgag gcacctgaga gacctgcccg    600
gtaatgtttt cctggctact gggaacgaga ttctggaact ggtggtggac gccatgatgg    660
gtgacgaccc tccggagccc cctaccccat ttgaagcgcc ttcgctgtac gatttgtatg    720
atctggaggt ggatgtgccc gagaacgacc ccaacgagga ggcggtgaat gatttgttta    780
gcgatgccgc gctgctggct gccgagcagg ctaatacgga ctctggctca gacagcgatt    840
cctctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca gcgaaccagg gagtgaaaac agcgagcgag ggctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagctgggga ggcagagggt gactgggtgc tgactggttt   1200
atttatgtat atgtttttta tgtgtaggtc ccgtctctga cgtagatgag acccccacta   1260
cagagtgcat ttcatcaccc ccagaaattg gcgaggaacc gcccgaagat attattcata   1320
gaccagttgc agtgagagtc accgggcgta gagcagctgt ggagagtttg gatgacttgc   1380
tacagggtgg ggatgaacct ttggacttgt gtacccggaa acgccccagg cactaagtgc   1440
cacacatgtg tgtttactta aggtgatgtc agtatttata gggtgtggag tgcaataaaa   1500
tccgtgttga ctttaagtgc gtggtttatg actcaggggt ggggactgtg ggtatataag   1560
caggtgcaga cctgtgtggt cagttcagag caggactcat ggagatctgg acagtcttgg   1620
aagactttca ccagactaga cagctgctag agaactcatc ggagggagtc tcttacctgt   1680
ggagattctg cttcggtggg cctctagcta agctagtcta tagggccaag caggattata   1740
aggatcaatt tgaggatatt ttgagagagt gtcctggtat ttttgactct ctcaacttgg   1800
gccatcagtc tcactttaac cagagtattc tgagagccct tgacttttct actcctggca   1860
gaactaccgc cgcggtagcc ttttttgcct ttatccttga caaatggagt caagaaaccc   1920
atttcagcag ggattaccgt ctggactgct tagcagtagc tttgtggaga acatggaggt   1980
gccagcgcct gaatgcaatc tccggctact tgccagtaca gccggtagac acgctgagga   2040
tcctgagtct ccagtcaccc caggaacacc aacgccgcca gcagccgcag caggagcagc   2100
agcaagagga ggaccgagaa gagaacctga gagccggtct ggaccctccg gtggcggagg   2160
aggaggagta gctgacttgt ttcccgagct gcgccgggtg ctgactaggt cttccagtgg   2220
acgggagagg gggattaagc gggagaggca tgaggagact agccacagaa ctgaactgac   2280
tgtcagtctg atgagtcgca ggcgcccaga atcggtgtgg tggcatgagg tgcagtcgca   2340
ggggatagat gaggtctcag tgatgcatga gaaatattcc ctagaacaag tcaagacttg   2400
ttggttggag cccgaggatg attgggaggt agccatcagg aattatgcca agctggctct   2460
gaggccagac aagaagtaca agattaccaa actgattaat atcagaaatt cctgctacat   2520
ttcagggaat ggggccgagg tggagatcag tacccaggag agggtggcct tcagatgctg   2580
catgatgaat atgtacccgg gggtggtggg catggaggga gtcaccttta tgaacgcgag   2640
gttcaggggt gatgggtata atggggtggt ctttatggcc aacaccaagc tgacagtgca   2700
cggatgctcc ttctttggct tcaataacat gtgcattgag gcctggggca gtgtttcagt   2760
```

-continued

```
gaggggatgc agtttttcag ccaactggat gggggtcgtg ggcagaacca agagcatggt   2820
gtcagtgaag aaatgcctgt tcgagaggtg ccacctgggg gtgatgagcg agggcgaagc   2880
caaagtcaaa cactgcgcct ctaccgagac gggctgcttt gtactgatca agggcaatgc   2940
caaagtcaag cataatatga tctgtggggc ctcggatgag cgcggctacc agatgctgac   3000
ctgcgccggt gggaacagcc atatgctagc caccgtgcat gtggcctcgc acccccgcaa   3060
gacatggccc gagttcgagc acaacgtcat gacccgctgc aatgtgcacc tggggtcccg   3120
ccgaggcatg ttcatgccct accagtgcaa catgcaattt gtgaaggtgc tgctggagcc   3180
cgatgccatg tccagagtga gcctgacggg ggtgtttgac atgaatgtgg agctgtggaa   3240
aattctgaga tatgatgaat ccaagaccag gtgccgggcc tgcgaatgcg gaggcaagca   3300
cgccaggctt cagcccgtgt gtgtggaggt gacggaggac ctgcgacccg atcatttggt   3360
gttgtcctgc aacgggacgg agttcggctc cagcggggaa gaatctgact agagtgagta   3420
gtgtttggga ctgggtggga gcctgcatga tgggcagaat gactaaaatc tgtgtttttc   3480
tgcgcagcag catgagcgga agcgcctcct ttgagggagg ggtattcagc ccttatctga   3540
cggggcgtct cccctcctgg gcgggagtgc gtcagaatgt gatgggatcc acggtggacg   3600
gccggcccgt gcagcccgcg aactcttcaa ccctgaccta cgcgaccctg agctcctcgt   3660
ccgtggacgc agctgccgcc gcagctgctg cttccgccgc cagcgccgtg cgcggaatgg   3720
ccctgggcgc cggctactac agctctctgg tggccaactc gagttccacc aataatcccg   3780
ccagcctgaa cgaggagaag ctgctgctgc tgatggccca gctcgaggcc ctgacccagc   3840
gcctgggcga gctgacccag caggtggctc agctgcaggc ggagacgcgg gccgcggttg   3900
ccacggtgaa aaccaaataa aaaatgaatc aataaataaa cggagacggt tgttgatttt   3960
aacacagagt cttgaatctt tatttgattt ttcgcgcgcg gtaggccctg gaccaccggt   4020
ctcgatcatt gagcacccgg tggatctttt ccaggacccg gtagaggtgg gcttggatgt   4080
tgaggtacat gggcatgagc ccgtcccggg ggtggaggta gctccattgc agggcctcgt   4140
gctcgggggt ggtgttgtaa atcacccagt catagcaggg gcgcagggcg tggtgctgca   4200
cgatgtcctt gaggaggaga ctgatggcca cgggcagccc cttggtgtag gtgttgacga   4260
acctgttgag ctgggaggga tgcatgcggg gggagatgag atgcatcttg gcctggatct   4320
tgagattggc gatgttcccg cccagatccc gccgggggtt catgttgtgc aggaccacca   4380
gcacggtgta tccggtgcac ttggggaatt tgtcatgcaa cttggaaggg aaggcgtgaa   4440
agaatttgga gacgcccttg tgaccgccca ggttttccat gcactcatcc atgatgatgg   4500
cgatgggccc gtgggcggcg gcttgggcaa agacgtttcg gggggtcggac acatcgtagt   4560
tgtggtcctg ggtgagctcg tcataggcca ttttaatgaa tttggggcgg agggtgcccg   4620
actgggggac gaaggtgccc tcgatcccgg gggcgtagtt gccctcgcag atctgcatct   4680
cccaggcctt gagctcggag ggggggatca tgtccacctg cggggcgatg aaaaaaacgg   4740
tttccggggc gggggagatg agctgggccg aaagcaggtt ccggagcagc tgggacttgc   4800
cgcagccggt ggggccgtag atgaccccga tgaccggctg caggtggtag ttgagggaga   4860
gacagctgcc gtcctcgcgg aggagggggg ccacctcgtt catcatctcg cgcacatgca   4920
tgttctcgcg cacgagttcc gccaggaggc gctcgccccc aagcgagagg agctcttgca   4980
gcgaggcgaa gtttttcagc ggcttgagcc cgtcggccat gggcattttg gagagggtct   5040
gttgcaagag ttccagacgg tcccagagct cggtgatgtg ctctagggca tctcgatcca   5100
```

-continued

```
gcagacctcc tcgtttcgcg ggttggggcg actgcgggag tagggcacca ggcgatgggc   5160
gtccagcgag gccagggtcc ggtccttcca ggggcgcagg gtccgcgtca gcgtggtctc   5220
cgtcacggtg aaggggtgcg cgccgggctg ggcgcttgcg agggtgcgct tcaggctcat   5280
ccggctggtc gagaaccgct cccggtcggc gccctgcgcg tcggccaggt agcaattgag   5340
catgagttcg tagttgagcg cctcggccgc gtggcccttg gcgcggagct tacctttgga   5400
agtgtgtccg cagacgggac agaggaggga cttgagggcg tagagcttgg gggcgaggaa   5460
gacggactcg ggggcgtagg cgtccgcgcc gcagctggcg cagacggtct cgcactccac   5520
gagccaggtg aggtctggcc ggtcggggtc aaaaacgagg tttcctccgt gctttttgat   5580
gcgtttctta cctctggtct ccatgagctc gtgtccccgc tgggtgacaa agaggctgtc   5640
cgtgtccccg tagaccgact ttatgggccg gtcctcgagc ggggtgccgc ggtcctcgtc   5700
gtagaggaac ccgcccact ccgagacgaa ggcccgggtc caggccagca cgaaggaggc   5760
cacgtgggag gggtagcggt cgttgtccac cagcgggtcc accttctcca gggtatgcaa   5820
gcacatgtcc ccctcgtcca catccaggaa ggtgattggc ttgtaagtgt aggccacgtg   5880
accggggtc ccggccgggg gggtataaaa gggggcgggc ccctgctcgt cctcactgtc   5940
ttccggatcg ctgtccagga gcgccagctg ttggggtagg tattccctct cgaaggcggg   6000
catgacctcg gcactcaggt tgtcagtttc tagaaacgag gaggatttga tattgacggt   6060
gccgttggag acgcctttca tgagcccctc gtccatctgg tcagaaaaga cgatcttttt   6120
gttgtcgagc ttggtggcga aggagccgta gagggcgttg gagagcagct tggcgatgga   6180
gcgcatggtc tggttctttt ccttgtcggc gcgctccttg gcggcgatgt tgagctgcac   6240
gtactcgcgc gccacgcact tccattcggg gaagacggtg gtgagcttgt cgggcacgat   6300
tctgacccgc cagccgcggt tgtgcagggt gatgaggtcc acgctggtgg ccacctcgcc   6360
gcgcaggggc tcgttggtcc agcagaggcg cccgcccttg cgcgagcaga aggggggcag   6420
cgggtccagc atgagctcgt cggggggtc ggcgtccacg gtgaagatgc cgggcaggag   6480
ctcggggtcg aagtagctga tgcaggtgcc cagatcgtcc agcgccgctt gccagtcgcg   6540
cacggccagc gcgcgctcgt aggggctgag gggcgtgccc cagggcatgg ggtgcgtgag   6600
cgcggaggcg tacatgccgc agatgtcgta gacgtagagg ggctcctcga ggacgccgat   6660
gtaggtgggg tagcagcgcc ccccgcggat gctggcgcgc acgtagtcgt acagctcgtg   6720
cgagggcgcg aggagcccgg tgccgaggtt ggagcgctgc ggcttttcgg cgcggtagac   6780
gatctggcgg aagatggcgt gggagttgga ggagatggtg ggcctctgga agatgttgaa   6840
gtgggcgtgg ggcagtccga ccgagtccct gatgaagtgg gcgtaggagt cctgcagctt   6900
ggcgacgagc tcggcggtga cgaggacgtc cagggcgcag tagtcgaggg tctcttggat   6960
gatgtcgtac ttgagctggc ccttctgctt ccacagctcg cggttgagaa ggaactcttc   7020
gcggtccttc cagtactctt cgagggggaa cccgtcctga tcggcacggt aagagcccac   7080
catgtagaac tggttgacgg ccttgtaggc gcagcagccc ttctccacgg ggagggcgta   7140
agcttgcgcg gccttgcgca gggaggtgtg ggtgagggcg aaggtgtcgc gcaccatgac   7200
cttgaggaac tggtgcttga agtcgaggtc gtcgcagccg ccctgctccc agagctggaa   7260
gtccgtgcgc ttcttgtagg cggggttggg caaagcgaaa gtaacatcgt tgaagaggat   7320
cttgcccgcg cggggcatga agttgcgagt gatgcggaaa ggctggggca cctcggcccg   7380
gttgttgatg acctgggcgg cgaggacgat ctcgtcgaag ccgttgatgt tgtgcccgac   7440
gatgtagagt tccacgaatc gcgggcggcc cttgacgtgg ggcagcttct tgagctcgtc   7500
```

-continued

```
gtaggtgagc tcggcggggt cgctgaggcc gtgctgctcg agggcccagt cggcgaggtg   7560

ggggttggcg ccgaggaagg aagtccagag atccacggcc agggcggtct gcaagcggtc   7620

ccggtactga cggaactgct ggcccacggc catttttttcg ggggtgacgc agtagaaggt   7680

gcgggggtcg ccgtgccagc ggtcccactt gagctggagg gcgaggtcgt gggcgagctc   7740

gacgagcggc gggtccccgg agagtttcat gaccagcatg aaggggacga gctgcttgcc   7800

gaaggacccc atccaggtgt aggtttccac gtcgtaggtg aggaagagcc tttcggtgcg   7860

aggatgcgag ccgatgggga agaactggat ctcctgccac cagttggagg aatggctgtt   7920

gatgtgatgg aagtagaaat gccgacggcg cgccgagcac tcgtgcttgt gtttatacaa   7980

gcgtccgcag tgctcgcaac gctgcacggg atgcacgtgc tgcacgagct gtacctgggt   8040

tcctttgacg aggaatttca gtgggcagtg gagcgctggc ggctgcatct ggtgctgtac   8100

tacgtcctgg ccatcggcgt ggccatcgtc tgcctcgatg gtggtcatgc tgacgaggcc   8160

gcgcgggagg caggtccaga cctcggctcg gacgggtcgg agagcgagga cgagggcgcg   8220

caggccggag ctgtccaggg tcctgagacg ctgcggagtc aggtcagtgg gcagcggcgg   8280

cgcgcggttg acttgcagga gcttttccag ggcgcgcggg aggtccagat ggtacttgat   8340

ctccacggcg ccgttggtgg cgacgtccac ggcttgcagg gtcccgtgcc cctggggcgc   8400

caccaccgtg ccccgtttct tcttgggtgc tggcggcggc ggctccatgc ttagaagcgg   8460

cggcgaggac gcgcgccggg cggcaggggc ggctcggggc ccggaggcag gggcggcagg   8520

ggcacgtcgg cgccgcgcgc gggcaggttc tggtactgcg cccggagaag actggcgtga   8580

gcgacgacgc gacggttgac gtcctggatc tgacgcctct gggtgaaggc cacgggaccc   8640

gtgagtttga acctgaaaga gagttcgaca gaatcaatct cggtatcgtt gacggcggcc   8700

tgccgcagga tctcttgcac gtcgcccgag ttgtcctggt aggcgatctc ggtcatgaac   8760

tgctcgatct cctcctcctg aaggtctccg cgaccggcgc gctcgacggt ggccgcgagg   8820

tcgttggaga tgcggcccat gagctgcgag aaggcgttca tgccggcctc gttccagacg   8880

cggctgtaga ccacggctcc gtcggggtcg cgcgcgcgca tgaccacctg ggcgaggttg   8940

agctcgacgt ggcgcgtgaa gaccgcgtag ttgcagaggc gctggtagag gtagttgagc   9000

gtggtggcga tgtgctcggt gacgaagaag tacatgatcc agcggcggag cggcatctcg   9060

ctgacgtcgc ccagggcttc caagcgctcc atggcctcgt agaagtccac ggcgaagttg   9120

aaaaactggg agttgcgcgc cgagacggtc aactcctcct ccagaagacg gatgagctcg   9180

gcgatggtgg cgcgcacctc gcgctcgaag gccccggggg gctcctcttc ttccatctcc   9240

tcctcctctt ccatctcctc cactaacatc tcttctactt cctcctcagg aggcggcggc   9300

gggggagggg ccctgcgtcg ccggcggcgc acgggcagac ggtcgatgaa gcgctcgatg   9360

gtctccccgc gccggcgacg catggtctcg gtgacggcgc gcccgtcctc gcggggccgc   9420

agcgtgaaga cgccgccgcg catctccagg tggccgccgg gggggtctcc gttgggcagg   9480

gagagggcgc tgacgatgca tcttatcaat tggcccgtag ggactccgcg caaggacctg   9540

agcgtctcga gatccacggg atccgaaaac cgctgaacga aggcttcgag ccagtcgcag   9600

tcgcaaggta ggctgagccc ggtttcttgt tcttcgggta tttggtcggg aggcgggcgg   9660

gcgatgctgc tggtgatgaa gttgaagtag gcggtcctga gacggcggat ggtggcgagg   9720

agcaccaggt ccttgggccc ggcttgctgg atgcgcagac ggtcggccat gccccaggcg   9780

tggtcctgac acctggcgag gtccttgtag tagtcctgca tgagccgctc cacgggcacc   9840
```

-continued

```
tcctcctcgc ccgcgcggcc gtgcatgcgc gtgagcccga acccgcgctg cggctggacg   9900
agcgccaggt cggcgacgac gcgctcggcg aggatggcct gctggatctg ggtgagggtg   9960
gtctggaagt cgtcgaagtc gacgaagcgg tggtaggctc cggtgttgat ggtgtaggag  10020
cagttggcca tgacggacca gttgacggtc tggtggccgg ggcgcacgag ctcgtggtac  10080
ttgaggcgcg agtaggcgcg cgtgtcgaag atgtagtcgt tgcaggtgcg cacgaggtac  10140
tggtatccga cgaggaagtg cggcggcggc tggcggtaga gcggccatcg ctcggtggcg  10200
ggggcgccgg gcgcgaggtc ctcgagcatg aggcggtggt agccgtagat gtacctggac  10260
atccaggtga tgccggcggc ggtggtggag gcgcgcggga actcgcggac gcggttccag  10320
atgttgcgca gcggcaggaa gtagttcatg gtggccgcgg tctggcccgt gaggcgcgcg  10380
cagtcgtgga tgctctagac atacgggcaa aaacgaaagc ggtcagcggc tcgactccgt  10440
ggcctggagg ctaagcgaac gggttgggct gcgcgtgtac cccggttcga gtccctgctc  10500
gaatcaggct ggagccgcag ctaacgtggt actggcactc ccgtctcgac ccaagcctgc  10560
taacgaaacc tccaggatac ggaggcgggt cgttttggcc attttcgtca ggccggaaat  10620
gaaactagta agcgcggaaa gcggccgtcc gcgatggctc gctgccgtag tctggagaaa  10680
gaatcgccag ggttgcgttg cggtgtgccc cggttcgagc ctcagcgctc ggcgccggcc  10740
ggattccgcg gctaacgtgg gcgtggctgc cccgtcgttt ccaagacccc ttagccagcc  10800
gacttctcca gttacggagc gagcccctct ttttcttgtg tttttgccag atgcatcccg  10860
tactgcggca gatgcgcccc caccctccac cacaaccgcc cctaccgcag cagcagcaac  10920
agccggcgct tctgcccccg ccccagcagc agcagccagc cactaccgcg gcggccgccg  10980
tgagcggagc cggcgttcag tatgacctgg ccttggaaga gggcgagggg ctggcgcggc  11040
tgggggcgtc gtcgccggag cggcacccgc gcgtgcagat gaaaagggac gctcgcgagg  11100
cctacgtgcc caagcagaac ctgttcagag acaggagcgg cgaggagccc gaggagatgc  11160
gcgcctcccg cttccacgcg gggcgggagc tgcggcgcgg cctggaccga aagcgggtgc  11220
tgagggacga ggatttcgag gcggacgagc tgacggggat cagccccgcg cgcgcgcacg  11280
tggccgcggc caacctggtc acggcgtacg agcagaccgt gaaggaggag agcaacttcc  11340
aaaaatcctt caacaaccac gtgcgcacgc tgatcgcgcg cgaggaggtg accctgggcc  11400
tgatgcacct gtgggacctg ctggaggcca tcgtgcagaa ccccacgagc aagccgctga  11460
cggcgcagct gtttctggtg gtgcagcaca gtcgggacaa cgagacgttc agggaggcgc  11520
tgctgaatat caccgagccc gagggccgct ggctcctgga cctggtgaac attctgcaga  11580
gcatcgtggt gcaggagcgc gggctgccgc tgtccgagaa gctggcggcc atcaacttct  11640
cggtgctgag cctgggcaag tactacgcta ggaagatcta caagaccccg tacgtgccca  11700
tagacaagga ggtgaagatc gacgggtttt acatgcgcat gaccctgaaa gtgctgaccc  11760
tgagcgacga tctgggggtg taccgcaacg acaggatgca ccgcgcggtg agcgccagcc  11820
gccggcgcga gctgagcgac caggagctga tgcacagcct gcagcgggcc ctgaccgggg  11880
ccgggaccga gggggagagc tactttgaca tgggcgcgga cctgcgctgg cagcctagcc  11940
gccgggcctt ggaagctgcc ggcggttccc cctacgtgga ggaggtggac gatgaggagg  12000
aggagggcga gtacctggaa gactgatggc gcgaccgtat ttttgctaga tgcagcaaca  12060
gccaccgccg cctcctgatc ccgcgatgcg ggcggcgctg cagagccagc cgtccggcat  12120
taactcctcg gacgattgga cccaggccat gcaacgcatc atggcgctga cgacccgcaa  12180
tcccgaagcc tttagacagc agcctcaggc caaccgactc tcggccatcc tggaggccgt  12240
```

-continued

```
ggtgccctcg cgctcgaacc ccacgcacga gaaggtgctg gccatcgtga acgcgctggt  12300

ggagaacaag gccatccgcg gcgacgaggc cgggctggtg tacaacgcgc tgctggagcg  12360

cgtggcccgc tacaacagca ccaacgtgca gacgaacctg gaccgcatgg tgaccgacgt  12420

gcgcgaggcg gtgtcgcagc gcgagcggtt ccaccgcgag tcgaacctgg gctccatggt  12480

ggcgctgaac gccttcctga gcacgcagcc cgccaacgtg ccccggggcc aggaggacta  12540

caccaacttc atcagcgcgc tgcggctgat ggtggccgag gtgccccaga gcgaggtgta  12600

ccagtcgggg ccggactact tcttccagac cagtcgccag ggcttgcaga ccgtgaacct  12660

gagccaggct ttcaagaact tgcagggact gtggggcgtg caggccccgg tcggggaccg  12720

cgcgacggtg tcgagcctgc tgacgccgaa ctcgcgcctg ctgctgctgc tggtggcgcc  12780

cttcacggac agcggcagcg tgagccgcga ctcgtacctg ggctacctgc ttaacctgta  12840

ccgcgaggcc atcgggcagg cgcacgtgga cgagcagacc taccaggaga tcacccacgt  12900

gagccgcgcg ctgggccagg aggacccggg caacctggag gccaccctga acttcctgct  12960

gaccaaccgg tcgcagaaga tcccgcccca gtacgcgctg agcaccgagg aggagcgcat  13020

cctgcgctac gtgcagcaga gcgtggggct gttcctgatg caggaggggg ccacgcccag  13080

cgccgcgctc gacatgaccg cgcgcaacat ggagcccagc atgtacgccc gcaaccgccc  13140

gttcatcaat aagctgatgg actacttgca tcgggcggcc gccatgaact cggactactt  13200

taccaacgcc atcttgaacc cgcactggct cccgccgccc gggttctaca cgggcgagta  13260

cgacatgccc gaccccaacg acgggttcct gtgggacgac gtggacagca gcgtgttctc  13320

gccgcgcccc accaccacca ccgtgtggaa gaaagagggc ggggaccggc ggccgtcctc  13380

ggcgctgtcc ggtcgcgcgg gtgctgccgc ggcggtgccc gaggccgcca gccccttccc  13440

gagcctgccc ttttcgctga acagcgtgcg cagcagcgag ctgggtcggc tgacgcggcc  13500

gcgcctgctg ggcgaggagg agtacctgaa cgactccttg cttcggcccg agcgcgagaa  13560

gaacttcccc aataacggga tagagagcct ggtggacaag atgagccgct ggaagacgta  13620

cgcgcacgag cacagggacg agccccgagc tagcagcagc accggcgcca cccgtagacg  13680

ccagcggcac gacaggcagc ggggtctggt gtgggacgat gaggattccg ccgacgacag  13740

cagcgtgttg gacttgggtg ggagtggtgg tggtaacccg ttcgctcacc tgcgcccccg  13800

tatcgggcgc ctgatgtaag aatctgaaaa aataaaagac ggtactcacc aaggccatgg  13860

cgaccagcgt gcgttcttct ctgttgtttg tagtagt atg atg agg cgc gtg tac   13915
                                         Met Met Arg Arg Val Tyr
                                         1               5

ccg gag ggt cct cct ccc tcg tac gag agc gtg atg cag cag gcg gtg    13963
Pro Glu Gly Pro Pro Pro Ser Tyr Glu Ser Val Met Gln Gln Ala Val
            10                  15                  20

gcg gcg gcg atg cag ccc ccg ctg gag gcg cct tac gtg ccc ccg cgg    14011
Ala Ala Ala Met Gln Pro Pro Leu Glu Ala Pro Tyr Val Pro Pro Arg
        25                  30                  35

tac ctg gcg cct acg gag ggg cgg aac agc att cgt tac tcg gag ctg    14059
Tyr Leu Ala Pro Thr Glu Gly Arg Asn Ser Ile Arg Tyr Ser Glu Leu
    40                  45                  50

gca ccc ttg tac gat acc acc cgg ttg tac ctg gtg gac aac aag tcg    14107
Ala Pro Leu Tyr Asp Thr Thr Arg Leu Tyr Leu Val Asp Asn Lys Ser
55                  60                  65                  70

gcg gac atc gcc tcg ctg aac tac cag aac gac cac agc aac ttc ctg    14155
Ala Asp Ile Ala Ser Leu Asn Tyr Gln Asn Asp His Ser Asn Phe Leu
                75                  80                  85
```

-continued

```
acc acc gtg gtg cag aac aac gat ttc acc ccc acg gag gcc agc acc     14203
Thr Thr Val Val Gln Asn Asn Asp Phe Thr Pro Thr Glu Ala Ser Thr
            90                  95                  100

cag acc atc aac ttt gac gag cgc tcg cgg tgg ggc ggc cag ctg aaa     14251
Gln Thr Ile Asn Phe Asp Glu Arg Ser Arg Trp Gly Gly Gln Leu Lys
        105                 110                 115

acc atc atg cac acc aac atg ccc aac gtg aac gag ttc atg tac agc     14299
Thr Ile Met His Thr Asn Met Pro Asn Val Asn Glu Phe Met Tyr Ser
    120                 125                 130

aac aag ttc aag gcg cgg gtg atg gtc tcg cgc aag acc ccc aac ggg     14347
Asn Lys Phe Lys Ala Arg Val Met Val Ser Arg Lys Thr Pro Asn Gly
135                 140                 145                 150

gtc aca gta aca gat ggt agt cag gac gag ctg acc tac gag tgg gtg     14395
Val Thr Val Thr Asp Gly Ser Gln Asp Glu Leu Thr Tyr Glu Trp Val
                155                 160                 165

gag ttt gag ctg ccc gag ggc aac ttc tcg gtg acc atg acc atc gat     14443
Glu Phe Glu Leu Pro Glu Gly Asn Phe Ser Val Thr Met Thr Ile Asp
            170                 175                 180

ctg atg aac aac gcc atc atc gac aac tac ttg gcg gtg ggg cgg cag     14491
Leu Met Asn Asn Ala Ile Ile Asp Asn Tyr Leu Ala Val Gly Arg Gln
        185                 190                 195

aac ggg gtg ctg gag agc gac atc ggc gtg aag ttc gac acg cgc aac     14539
Asn Gly Val Leu Glu Ser Asp Ile Gly Val Lys Phe Asp Thr Arg Asn
    200                 205                 210

ttc cgg ctg ggc tgg gac ccc gtg acc gag ctg gtg atg ccg ggc gtg     14587
Phe Arg Leu Gly Trp Asp Pro Val Thr Glu Leu Val Met Pro Gly Val
215                 220                 225                 230

tac acc aac gag gcc ttc cac ccc gac atc gtc ctg ctg ccc ggc tgc     14635
Tyr Thr Asn Glu Ala Phe His Pro Asp Ile Val Leu Leu Pro Gly Cys
                235                 240                 245

ggc gtg gac ttc acc gag agc cgc ctc agc aac ctg ctg ggc atc cgc     14683
Gly Val Asp Phe Thr Glu Ser Arg Leu Ser Asn Leu Leu Gly Ile Arg
            250                 255                 260

aag cgg cag ccc ttc cag gag ggc ttc cag atc ctg tac gag gac ctg     14731
Lys Arg Gln Pro Phe Gln Glu Gly Phe Gln Ile Leu Tyr Glu Asp Leu
        265                 270                 275

gag ggg ggc aac atc ccc gcg ctg ctg gac gtg gac gcc tac gag aaa     14779
Glu Gly Gly Asn Ile Pro Ala Leu Leu Asp Val Asp Ala Tyr Glu Lys
    280                 285                 290

agc aag gag gat agc gcc gcc gcg gcg acc gca gcc gtg gcc acc gcc     14827
Ser Lys Glu Asp Ser Ala Ala Ala Ala Thr Ala Ala Val Ala Thr Ala
295                 300                 305                 310

tct acc gag gtg cgg ggc gat aat ttt gct agc gcc gcg aca ctg gca     14875
Ser Thr Glu Val Arg Gly Asp Asn Phe Ala Ser Ala Ala Thr Leu Ala
                315                 320                 325

gcg gcc gag gcg gct gaa acc gaa agt aag ata gtg atc cag ccg gtg     14923
Ala Ala Glu Ala Ala Glu Thr Glu Ser Lys Ile Val Ile Gln Pro Val
            330                 335                 340

gag aag gac agc aag gag agg agc tac aac gtg ctc gcg gac aag aaa     14971
Glu Lys Asp Ser Lys Glu Arg Ser Tyr Asn Val Leu Ala Asp Lys Lys
        345                 350                 355

aac acc gcc tac cgc agc tgg tac ctg gcc tac aac tac ggc gac ccc     15019
Asn Thr Ala Tyr Arg Ser Trp Tyr Leu Ala Tyr Asn Tyr Gly Asp Pro
    360                 365                 370

gag aag ggc gtg cgc tcc tgg acg ctg ctc acc acc tcg gac gtc acc     15067
Glu Lys Gly Val Arg Ser Trp Thr Leu Leu Thr Thr Ser Asp Val Thr
375                 380                 385                 390

tgc ggc gtg gag caa gtc tac tgg tcg ctg ccc gac atg atg caa gac     15115
Cys Gly Val Glu Gln Val Tyr Trp Ser Leu Pro Asp Met Met Gln Asp
                395                 400                 405
```

-continued

```
ccg gtc acc ttc cgc tcc acg cgt caa gtt agc aac tac ccg gtg gtg    15163
Pro Val Thr Phe Arg Ser Thr Arg Gln Val Ser Asn Tyr Pro Val Val
            410                 415                 420

ggc gcc gag ctc ctg ccc gtc tac tcc aag agc ttc ttc aac gag cag    15211
Gly Ala Glu Leu Leu Pro Val Tyr Ser Lys Ser Phe Phe Asn Glu Gln
        425                 430                 435

gcc gtc tac tcg cag cag ctg cgc gcc ttc acc tcg ctc acg cac gtc    15259
Ala Val Tyr Ser Gln Gln Leu Arg Ala Phe Thr Ser Leu Thr His Val
    440                 445                 450

ttc aac cgc ttc ccc gag aac cag atc ctc gtt cgc ccg ccc gcg ccc    15307
Phe Asn Arg Phe Pro Glu Asn Gln Ile Leu Val Arg Pro Pro Ala Pro
455                 460                 465                 470

acc att acc acc gtc agt gaa aac gtt cct gct ctc aca gat cac ggg    15355
Thr Ile Thr Thr Val Ser Glu Asn Val Pro Ala Leu Thr Asp His Gly
            475                 480                 485

acc ctg ccg ctg cgc agc agt atc cgg gga gtc cag cgc gtg acc gtc    15403
Thr Leu Pro Leu Arg Ser Ser Ile Arg Gly Val Gln Arg Val Thr Val
            490                 495                 500

act gac gcc aga cgc cgc acc tgc ccc tac gtc tac aag gcc ctg ggc    15451
Thr Asp Ala Arg Arg Arg Thr Cys Pro Tyr Val Tyr Lys Ala Leu Gly
        505                 510                 515

gta gtc gcg ccg cgc gtc ctc tcg agc cgc acc ttc taa aaaatgtcca     15500
Val Val Ala Pro Arg Val Leu Ser Ser Arg Thr Phe
    520                 525                 530

ttctcatctc gcccagtaat aacaccggtt ggggcctgcg cgcgcccagc aagatgtacg  15560

gaggcgctcg ccaacgctcc acgcaacacc ccgtgcgcgt gcgcgggcac ttccgcgctc  15620

cctggggcgc cctcaagggc cgcgtgcgct cgcgcaccac cgtcgacgac gtgatcgacc  15680

aggtggtggc cgacgcgcgc aactacacgc ccgccgccgc gcccgtctcc accgtggacg  15740

ccgtcatcga cagcgtggtg gccgacgcgc gccggtacgc ccgcgccaag agccggcggc  15800

ggcgcatcgc ccggcggcac cggagcaccc ccgccatgcg cgcggcgcga gccttgctgc  15860

gcagggccag gcgcacggga cgcagggcca tgctcagggc ggccagacgc gcggcctccg  15920

gcagcagcag cgccggcagg acccgcagac gcgcggccac ggcggcggcg gcggccatcg  15980

ccagcatgtc ccgcccgcgg cgcggcaacg tgtactgggt gcgcgacgcc gccaccggtg  16040

tgcgcgtgcc cgtgcgcacc cgcccccctc gcacttgaag atgctgactt cgcgatgttg  16100

atgtgtccca gcggcgagga ggatgtccaa gcgcaaattc aaggaagaga tgctccaggt  16160

catcgcgcct gagatctacg gcccggcggc ggtgaaggag gaaagaaagc cccgcaaact  16220

gaagcgggtc aaaaaggaca aaaaggagga ggaagatgtg gacggactgg tggagtttgt  16280

gcgcgagttc gccccccggc ggcgcgtgca gtggcgcggg cggaaagtga aaccggtgct  16340

gcgacccggc accacggtgg tcttcacgcc cggcgagcgt tccggctccg cctccaagcg  16400

ctcctacgac gaggtgtacg gggacgagga catcctcgag caggcggccg aacgtctggg  16460

cgagtttgct tacggcaagc gcagccgccc cgcgcccttg aaagaggagg cggtgtccat  16520

cccgctggac cacggcaacc ccacgccgag cctgaagccg gtgaccctgc agcaggtgct  16580

gcctggtgcg gcgccgcgcc ggggcttcaa gcgcgagggc ggcgaggatc tgtacccgac  16640

catgcagctg atggtgccca agcgccagaa gctggaggac gtgctggagc acatgaaggt  16700

ggaccccgag gtgcagcccg aggtcaaggt gcggcccatc aagcaggtgg ccccgggcct  16760

gggcgtgcag accgtggaca tcaagatccc cacggagccc atggaaacgc agaccgagcc  16820

cgtgaagccc agcaccagca ccatggaggt gcagacggat ccctggatgc cggcaccggc  16880
```

-continued

```
ttccaccacc cgccgaagac gcaagtacgg cgcggccagc ctgctgatgc ccaactacgc  16940

gctgcatcct tccatcatcc ccacgccggg ctaccgcggc acgcgcttct accgcggcta  17000

caccagcagc cgccgccgca agaccaccac ccgccgccgc cgtcgtcgca cccgccgcag  17060

cagcaccgcg acttccgccg ccgccctggt gcggagagtg taccgcagcg ggcgcgagcc  17120

tctgaccctg ccgcgcgcgc gctaccaccc gagcatcgcc atttaactac cgcctcctac  17180

ttgcagatat ggccctcaca tgccgcctcc gcgtccccat tacgggctac cgaggaagaa  17240

agccgcgccg tagaaggctg acggggaacg ggctgcgtcg ccatcaccac cggcggcggc  17300

gcgccatcag caagcggttg gggggaggct tcctgcccgc gctgatgccc atcatcgccg  17360

cggcgatcgg ggcgatcccc ggcatagctt ccgtggcggt gcaggcctct cagcgccact  17420

gagacacagc ttggaaaatt tgtaataaaa aatggactga cgctcctggt cctgtgatgt  17480

gtgtttttag atggaagaca tcaatttttc gtccctggca ccgcgacacg gcacgcggcc  17540

gtttatgggc acctggagcg acatcggcaa cagccaactg aacgggggcg ccttcaattg  17600

gagcagtctc tggagcgggc ttaagaattt cgggtccacg ctcaaaacct atggcaacaa  17660

ggcgtggaac agcagcacag ggcaggcgct gagggaaaag ctgaaagagc agaacttcca  17720

gcagaaggtg gtcgatggcc tggcctcggg catcaacggg gtggtggacc tggccaacca  17780

ggccgtgcag aaacagatca acagccgcct ggacgcggtc ccgcccgcgg ggtccgtgga  17840

gatgccccag gtggaggagg agctgcctcc cctggacaag cgcggcgaca agcgaccgcg  17900

tcccgacgcg gaggagacgc tgctgacgca cacggacgag ccgcccccgt acgaggaggc  17960

ggtgaaactg ggtctgccca ccacgcggcc cgtggcgcct ctggccaccg gggtgctgaa  18020

acccagcagc agcagcagcc agcccgcgac cctggacttg cctccgcctg cttcccgccc  18080

ctccacagtg gctaagcccc tgccgccggt ggccgtcgcg tcgcgcgccc cccgaggccg  18140

cccccaggcg aactggcaga gcactctgaa cagcatcgtg ggtctgggag tgcagagtgt  18200

gaagcgccgc cgctgctatt aaaagacact gtagcgctta acttgcttgt ctgtgtgtat  18260

atgtatgtcc gccgaccaga aggaggagga agaggcgcgt cgccgagttg caag atg    18317
                                                            Met

gcc acc cca tcg atg ctg ccc cag tgg gcg tac atg cac atc gcc gga    18365
Ala Thr Pro Ser Met Leu Pro Gln Trp Ala Tyr Met His Ile Ala Gly
            535                 540                 545

cag gac gct tcg gag tac ctg agt ccg ggt ctg gtg cag ttc gcc cgc    18413
Gln Asp Ala Ser Glu Tyr Leu Ser Pro Gly Leu Val Gln Phe Ala Arg
        550                 555                 560

gcc aca gac acc tac ttc agt ctg ggg aac aag ttt agg aac ccc acg    18461
Ala Thr Asp Thr Tyr Phe Ser Leu Gly Asn Lys Phe Arg Asn Pro Thr
    565                 570                 575

gtg gcg ccc acg cac gat gtg acc acc gac cgc agc cag cgg ctg acg    18509
Val Ala Pro Thr His Asp Val Thr Thr Asp Arg Ser Gln Arg Leu Thr
580                 585                 590                 595

ctg cgc ttc gtg ccc gtg gac cgc gag gac aac acc tac tcg tac aaa    18557
Leu Arg Phe Val Pro Val Asp Arg Glu Asp Asn Thr Tyr Ser Tyr Lys
                600                 605                 610

gtg cgc tac acg ctg gcc gtg ggc gac aac cgc gtg ctg gac atg gcc    18605
Val Arg Tyr Thr Leu Ala Val Gly Asp Asn Arg Val Leu Asp Met Ala
            615                 620                 625

agc acc tac ttt gac atc cgc ggc gtg ctg gat cgg ggc cct agc ttc    18653
Ser Thr Tyr Phe Asp Ile Arg Gly Val Leu Asp Arg Gly Pro Ser Phe
        630                 635                 640

aaa ccc tac tcc ggc acc gct tac aac agc ctg gct ccc aag gga gcg    18701
Lys Pro Tyr Ser Gly Thr Ala Tyr Asn Ser Leu Ala Pro Lys Gly Ala
```

-continued

```
    645                 650                 655

ccc aac act tgc cag tgg aca tat aaa gct gat ggt gat act ggt aca     18749
Pro Asn Thr Cys Gln Trp Thr Tyr Lys Ala Asp Gly Asp Thr Gly Thr
660                 665                 670                 675

gaa aaa acc tat aca tat gga aat gcg cct gtg caa ggc att agt att     18797
Glu Lys Thr Tyr Thr Tyr Gly Asn Ala Pro Val Gln Gly Ile Ser Ile
                680                 685                 690

aca aaa gat ggt att caa ctt gga act gac act gat gat cag ccc att     18845
Thr Lys Asp Gly Ile Gln Leu Gly Thr Asp Thr Asp Asp Gln Pro Ile
            695                 700                 705

tat gca gat aaa act tat caa cca gag cct caa gtg ggt gat gct gaa     18893
Tyr Ala Asp Lys Thr Tyr Gln Pro Glu Pro Gln Val Gly Asp Ala Glu
        710                 715                 720

tgg cat gac atc act ggt act gat gaa aaa tat gga ggc aga gct ctc     18941
Trp His Asp Ile Thr Gly Thr Asp Glu Lys Tyr Gly Gly Arg Ala Leu
    725                 730                 735

aag cct gac acc aaa atg aag ccc tgc tat ggt tct ttt gcc aag cct     18989
Lys Pro Asp Thr Lys Met Lys Pro Cys Tyr Gly Ser Phe Ala Lys Pro
740                 745                 750                 755

acc aat aaa gaa gga ggt cag gca aat gtg aaa acc gaa aca ggc ggt     19037
Thr Asn Lys Glu Gly Gly Gln Ala Asn Val Lys Thr Glu Thr Gly Gly
                760                 765                 770

acc aaa gaa tat gac att gac atg gca ttc ttc gat aat cga agt gca     19085
Thr Lys Glu Tyr Asp Ile Asp Met Ala Phe Phe Asp Asn Arg Ser Ala
                775                 780                 785

gct gcg gct ggc ctg gcc cca gaa att gtt ttg tat act gag aat gtg     19133
Ala Ala Ala Gly Leu Ala Pro Glu Ile Val Leu Tyr Thr Glu Asn Val
        790                 795                 800

gat ctg gaa act cca gat act cat att gta tac aag gcg ggc aca gat     19181
Asp Leu Glu Thr Pro Asp Thr His Ile Val Tyr Lys Ala Gly Thr Asp
    805                 810                 815

gac agc agc tct tct atc aat ttg ggt cag cag tcc atg ccc aac aga     19229
Asp Ser Ser Ser Ser Ile Asn Leu Gly Gln Gln Ser Met Pro Asn Arg
820                 825                 830                 835

ccc aac tac att ggc ttt aga gac aac ttt atc ggg ctc atg tac tac     19277
Pro Asn Tyr Ile Gly Phe Arg Asp Asn Phe Ile Gly Leu Met Tyr Tyr
                840                 845                 850

aac agc act ggc aac atg ggc gtg ctg gct ggt cag gcc tcc cag ctg     19325
Asn Ser Thr Gly Asn Met Gly Val Leu Ala Gly Gln Ala Ser Gln Leu
            855                 860                 865

aat gct gtg gtg gac ttg cag gac aga aac act gaa ctg tcc tac cag     19373
Asn Ala Val Val Asp Leu Gln Asp Arg Asn Thr Glu Leu Ser Tyr Gln
        870                 875                 880

ctc ttg ctt gac tct ctg ggc gac aga acc agg tat ttc agt atg tgg     19421
Leu Leu Leu Asp Ser Leu Gly Asp Arg Thr Arg Tyr Phe Ser Met Trp
    885                 890                 895

aat cag gcg gtg gac agc tat gac ccc gat gtg cgc att att gaa aat     19469
Asn Gln Ala Val Asp Ser Tyr Asp Pro Asp Val Arg Ile Ile Glu Asn
900                 905                 910                 915

cac ggt gtg gag gat gaa ctc cct aac tat tgc ttc ccc ctg gat gct     19517
His Gly Val Glu Asp Glu Leu Pro Asn Tyr Cys Phe Pro Leu Asp Ala
                920                 925                 930

gtg ggt aga act gat act tac cag gga att aag gcc aat ggt gct gat     19565
Val Gly Arg Thr Asp Thr Tyr Gln Gly Ile Lys Ala Asn Gly Ala Asp
            935                 940                 945

caa acc acc tgg acc aaa gat gat act gtt aat gat gct aat gaa ttg     19613
Gln Thr Thr Trp Thr Lys Asp Asp Thr Val Asn Asp Ala Asn Glu Leu
        950                 955                 960

ggc aag ggc aat cct ttc gcc atg gag atc aac atc cag gcc aac ctg     19661
```

-continued

```
Gly Lys Gly Asn Pro Phe Ala Met Glu Ile Asn Ile Gln Ala Asn Leu
    965                 970                 975

tgg cgg aac ttc ctc tac gcg aac gtg gcg ctg tac ctg ccc gac tcc      19709
Trp Arg Asn Phe Leu Tyr Ala Asn Val Ala Leu Tyr Leu Pro Asp Ser
980                 985                 990                 995

tac aag tac acg ccg  gcc aac atc acg ctg  ccg acc aac acc aac      19754
Tyr Lys Tyr Thr Pro  Ala Asn Ile Thr Leu  Pro Thr Asn Thr Asn
                1000                 1005                 1010

acc tac gat tac atg  aac ggc cgc gtg gtg  gcg ccc tcg ctg gtg      19799
Thr Tyr Asp Tyr Met  Asn Gly Arg Val Val  Ala Pro Ser Leu Val
                1015                 1020                 1025

gac gcc tac atc aac  atc ggg gcg cgc tgg  tcg ctg gac ccc atg      19844
Asp Ala Tyr Ile Asn  Ile Gly Ala Arg Trp  Ser Leu Asp Pro Met
                1030                 1035                 1040

gac aac gtc aac ccc  ttc aac cac cac cgc  aac gcg ggc ctg cgc      19889
Asp Asn Val Asn Pro  Phe Asn His His Arg  Asn Ala Gly Leu Arg
                1045                 1050                 1055

tac cgc tcc atg ctc  ctg ggc aac ggg cgc  tac gtg ccc ttc cac      19934
Tyr Arg Ser Met Leu  Leu Gly Asn Gly Arg  Tyr Val Pro Phe His
                1060                 1065                 1070

atc cag gtg ccc caa  aag ttc ttc gcc atc  aag agc ctc ctg ctc      19979
Ile Gln Val Pro Gln  Lys Phe Phe Ala Ile  Lys Ser Leu Leu Leu
                1075                 1080                 1085

ctg ccc ggg tcc tac  acc tac gag tgg aac  ttc cgc aag gac gtc      20024
Leu Pro Gly Ser Tyr  Thr Tyr Glu Trp Asn  Phe Arg Lys Asp Val
                1090                 1095                 1100

aac atg atc ctg cag  agc tcc ctc ggc aac  gac ctg cgc acg gac      20069
Asn Met Ile Leu Gln  Ser Ser Leu Gly Asn  Asp Leu Arg Thr Asp
                1105                 1110                 1115

ggg gcc tcc atc gcc  ttc acc agc atc aac  ctc tac gcc acc ttc      20114
Gly Ala Ser Ile Ala  Phe Thr Ser Ile Asn  Leu Tyr Ala Thr Phe
                1120                 1125                 1130

ttc ccc atg gcg cac  aac acc gcc tcc acg  ctc gag gcc atg ctg      20159
Phe Pro Met Ala His  Asn Thr Ala Ser Thr  Leu Glu Ala Met Leu
                1135                 1140                 1145

cgc aac gac acc aac  gac cag tcc ttc aac  gac tac ctc tcg gcg      20204
Arg Asn Asp Thr Asn  Asp Gln Ser Phe Asn  Asp Tyr Leu Ser Ala
                1150                 1155                 1160

gcc aac atg ctc tac  ccc atc ccg gcc aac  gcc acc aac gtg ccc      20249
Ala Asn Met Leu Tyr  Pro Ile Pro Ala Asn  Ala Thr Asn Val Pro
                1165                 1170                 1175

atc tcc atc ccc tcg  cgc aac tgg gcc gcc  ttc cgc gga tgg tcc      20294
Ile Ser Ile Pro Ser  Arg Asn Trp Ala Ala  Phe Arg Gly Trp Ser
                1180                 1185                 1190

ttc acg cgc ctc aag  acc cgc gag acg ccc  tcg ctc ggc tcc ggg      20339
Phe Thr Arg Leu Lys  Thr Arg Glu Thr Pro  Ser Leu Gly Ser Gly
                1195                 1200                 1205

ttc gac ccc tac ttc  gtc tac tcg ggc tcc  atc ccc tac ctc gac      20384
Phe Asp Pro Tyr Phe  Val Tyr Ser Gly Ser  Ile Pro Tyr Leu Asp
                1210                 1215                 1220

ggc acc ttc tac ctc  aac cac acc ttc aag  aag gtc tcc atc acc      20429
Gly Thr Phe Tyr Leu  Asn His Thr Phe Lys  Lys Val Ser Ile Thr
                1225                 1230                 1235

ttc gac tcc tcc gtc  agc tgg ccc ggc aac  gac cgc ctc ctg acg      20474
Phe Asp Ser Ser Val  Ser Trp Pro Gly Asn  Asp Arg Leu Leu Thr
                1240                 1245                 1250

ccc aac gag ttc gaa  atc aag cgc acc gtc  gac gga gag ggg tac      20519
Pro Asn Glu Phe Glu  Ile Lys Arg Thr Val  Asp Gly Glu Gly Tyr
                1255                 1260                 1265
```

-continued

```
aac gtg gcc cag tgc  aac atg acc aag gac  tgg ttc ctg gtc cag      20564
Asn Val Ala Gln Cys  Asn Met Thr Lys Asp  Trp Phe Leu Val Gln
                1270                 1275                 1280

atg ctg gcc cac tac  aac atc ggc tac cag  ggc ttc tac gtg ccc      20609
Met Leu Ala His Tyr  Asn Ile Gly Tyr Gln  Gly Phe Tyr Val Pro
                1285                 1290                 1295

gag ggc tac aag gac  cgc atg tac tcc ttc  ttc cgc aac ttc cag      20654
Glu Gly Tyr Lys Asp  Arg Met Tyr Ser Phe  Phe Arg Asn Phe Gln
                1300                 1305                 1310

ccc atg agc cgc cag  gtc gtg gac gag gtc  aac tac aag gac tac      20699
Pro Met Ser Arg Gln  Val Val Asp Glu Val  Asn Tyr Lys Asp Tyr
                1315                 1320                 1325

cag gcc gtc acc ctg  gcc tac cag cac aac  aac tcg ggc ttc gtc      20744
Gln Ala Val Thr Leu  Ala Tyr Gln His Asn  Asn Ser Gly Phe Val
                1330                 1335                 1340

ggc tac ctc gcg ccc  acc atg cgc cag gga  cag ccc tac ccc gcc      20789
Gly Tyr Leu Ala Pro  Thr Met Arg Gln Gly  Gln Pro Tyr Pro Ala
                1345                 1350                 1355

aac tac ccc tac ccg  ctc atc ggc aag agc  gcc gtc gcc agc gtc      20834
Asn Tyr Pro Tyr Pro  Leu Ile Gly Lys Ser  Ala Val Ala Ser Val
                1360                 1365                 1370

acc cag aaa aag ttc  ctc tgc gac cgg gtc  atg tgg cgc atc ccc      20879
Thr Gln Lys Lys Phe  Leu Cys Asp Arg Val  Met Trp Arg Ile Pro
                1375                 1380                 1385

ttc tcc agc aac ttc  atg tcc atg ggc gcg  ctc acc gac ctc ggc      20924
Phe Ser Ser Asn Phe  Met Ser Met Gly Ala  Leu Thr Asp Leu Gly
                1390                 1395                 1400

cag aac atg ctc tac  gcc aac tcc gcc cac  gcg cta gac atg aat      20969
Gln Asn Met Leu Tyr  Ala Asn Ser Ala His  Ala Leu Asp Met Asn
                1405                 1410                 1415

ttc gaa gtc gac ccc  atg gat gag tcc acc  ctt ctc tat gtt gtc      21014
Phe Glu Val Asp Pro  Met Asp Glu Ser Thr  Leu Leu Tyr Val Val
                1420                 1425                 1430

ttc gaa gtc ttc gac  gtc gtc cga gtg cac  cag ccc cac cgc ggc      21059
Phe Glu Val Phe Asp  Val Val Arg Val His  Gln Pro His Arg Gly
                1435                 1440                 1445

gtc atc gag gcc gtc  tac ctg cgc acg ccc  ttc tcg gcc ggc aac      21104
Val Ile Glu Ala Val  Tyr Leu Arg Thr Pro  Phe Ser Ala Gly Asn
                1450                 1455                 1460

gcc acc acc taa gccccgctct tgcttcttgc aagatgacgg cctgtgcggg       21156
Ala Thr Thr

ctccggcgag caggagctca gggccatcct ccgcgacctg ggctgcgggc cctgcttcct  21216

gggcaccttc gacaagcgct tcccgggatt catggccccg cacaagctgg cctgcgccat  21276

cgtcaacacg gccggccgcg agaccggggg cgagcactgg ctggccttcg cctggaaccc  21336

gcgctcccac acctgctacc tcttcgaccc cttcgggttc tcggacgagc gcctcaagca  21396

gatctaccag ttcgagtacg agggcctgct gcgccgcagc gccctggcca ccgaggaccg  21456

ctgcgtcacc ctggaaaagt ccacccagac cgtgcagggt ccgcgctcgg ccgcctgcgg  21516

gctcttctgc tgcatgttcc tgcacgcctt cgtgcactgg cccgaccgcc ccatggacaa  21576

gaaccccacc atgaacttgc tgacgggggt gcccaacggc atgctccagt cgccccaggt  21636

ggaacccacc ctgcgccgca accaggaggc gctctaccgc ttcctcaacg cccactccgc  21696

ctactttcgc tcccaccgcg cgcgcatcga gaaggccacc gccttcgacc gcatgaatca  21756

agacatgtaa accgtgtgtg tatgtgaatg ctttattcat aataaacagc acatgtttat  21816

gccacctttt ctgaggctct gactttattt agaaatcgaa ggggttctgc cggctctcgg  21876
```

-continued cgtgccccgc gggcagggat acgttgcgga actggtactt gggcagccac ttgaactcgg 21936
ggatcagcag cttcggcacg gggaggtcgg ggaacgagtc gctccacagc ttgcgcgtga 21996
gttgcagggc gcccagcagg tcgggcgcgg agatcttgaa atcgcagttg ggacccgcgt 22056
tctgcgcgcg ggagttgcgg tacacggggt tgcagcactg gaacaccatc agggccgggt 22116
gcttcacgct cgccagcacc gtcgcgtcgg tgatgccctc cacgtccaga tcctcggcgt 22176
tggccatccc gaaggggtc atcttgcagg tctgccgccc catgctgggc acgcagccgg 22236
gcttgtggtt gcaatcgcag tgcaggggga tcagcatcat ctgggcctgc tcggagctca 22296
tgcccgggta catggccttc atgaaagcct ccagctggcg gaaggcctgc tgcgccttgc 22356
cgccctcggt gaagaagacc ccgcaggact tgctagagaa ctggttggtg gcgcagccgg 22416
cgtcgtgcac gcagcagcgc gcgtcgttgt tggccagctg caccacgctg cgcccccagc 22476
ggttctgggt gatcttggcc cggtcggggt tctccttcag cgcgcgctgc ccgttctcgc 22536
tcgccacatc catctcgatc gtgtgctcct tctggatcat cacggtcccg tgcaggcatc 22596
gcagcttgcc ctcggcctcg gtgcacccgt gcagccacag cgcgcagccg gtgcactccc 22656
agttcttgtg ggcgatctgg gagtgcgagt gcacgaagcc ctgcaggaag cggcccatca 22716
tcgtggtcag ggtcttgttg ctggtgaagg tcagcgggat gccgcggtgc tcctcgttca 22776
catacaggtg gcagatgcgg cggtacacct cgccctgctc gggcatcagc tggaaggcgg 22836
acttcaggtc gctctccacg cggtaccggt ccatcagcag cgtcatgact tccatgccct 22896
tctcccaggc cgagacgatc ggcaggctca gggggttctt caccgccgtt gtcatcttag 22956
tcgccgccgc tgaggtcagg gggtcgttct cgtccagggt ctcaaacact cgcttgccgt 23016
ccttctcggt gatgcgcacg gggggaaagc tgaagcccac ggccgccagc tcctcctcgg 23076
cctgcctttc gtcctcgctg tcctggctga tgtcttgcaa aggcacatgc ttggtcttgc 23136
ggggtttctt tttgggcggc agaggcggcg gcggagacgt gctgggcgag cgcgagttct 23196
cgctcaccac gactatttct tcttcttggc cgtcgtccga gaccacgcgg cggtaggcat 23256
gcctcttctg gggcagaggc ggaggcgacg ggctctcgcg gttcggcggg cggctggcag 23316
agccccttcc gcgttcgggg gtgcgctcct ggcggcgctg ctctgactga cttcctccgc 23376
ggccggccat tgtgttctcc tagggagcaa caagcatgga gactcagcca tcgtcgccaa 23436
catcgccatc tgcccccgcc gccgccgacg agaaccagca gcagaatgaa agcttaaccg 23496
ccccgccgcc cagccccacc tccgacgccg ccgcggcccc agacatgcaa gagatggagg 23556
aatccatcga gattgacctg ggctacgtga cgcccgcgga gcacgaggag gagctggcag 23616
cgcgcttttc agccccggaa gagaaccacc aagagcagcc agagcaggaa gcagagagcg 23676
agcagcagca ggctgggctc gagcatggcg actacctgag cggggcagag gacgtgctca 23736
tcaagcatct ggcccgccaa tgcatcatcg tcaaggacgc gctgctcgac cgcgccgagg 23796
tgcccctcag cgtggcggag ctcagccgcg cctacgagcg caacctcttc tcgccgcgcg 23856
tgccccccaa gcgccagccc aacggcacct gcgagcccaa cccgcgcctc aacttctacc 23916
cggtcttcgc ggtgcccgag gccctggcca cctaccacct ctttttcaag aaccaaagga 23976
tccccgtctc ctgccgcgcc aaccgcaccc gcgccgacgc cctgctcaac ctgggtcccg 24036
gcgcccgcct acctgatatc gcctccttgg aagaggttcc caagatcttc gagggtctgg 24096
gcagcgacga gactcgggcc gcgaacgctc tgcaaggaag cggagaggag catgagcacc 24156
acagcgccct ggtggagttg gaaggcgaca acgcgcgcct ggcggtgctc aagcgcacgg 24216
tcgagctgac ccacttcgcc tacccggcgc tcaacctgcc ccccaaggtc atgagcgccg 24276

-continued

```
tcatggacca ggtgctcatc aagcgcgcct cgcccctctc ggatgaggac atgcaggacc  24336
ccgagagctc ggacgagggc aagcccgtgg tcagcgacga gcagctggcg cgctggctgg  24396
gagcgagtag caccccccag agcttggaag agcggcgcaa gctcatgatg gccgtggtcc  24456
tggtgaccgt ggagctggag tgtctgcgcc gcttcttcgc cgacgcagag accctgcgca  24516
aggtcgagga gaacctgcac tacctcttca ggcacgggtt tgtgcgccag gcctgcaaga  24576
tctccaacgt ggagctgacc aacctggtct cctacatggg catcctgcac gagaaccgcc  24636
tggggcagaa cgtgctgcac accaccctgc gcggggaggc ccgccgcgac tacatccgcg  24696
actgcgtcta cctgtacctc tgccacacct ggcagacggg catgggcgtg tggcagcagt  24756
gcctggagga gcagaacctg aaagagctct gcaagctcct gcagaagaac ctgaaggccc  24816
tgtggaccgg gttcgacgag cgcaccaccg cctcggacct ggccgacctc atcttccccg  24876
agcgcctgcg gctgacgctg cgcaacggac tgcccgactt tatgagtcaa agcatgttgc  24936
aaaactttcg ctctttcatc ctcgaacgct ccgggatcct gcccgccacc tgctccgcgc  24996
tgccctcgga cttcgtgccg ctgaccttcc gcgagtgccc cccgccgctc tggagccact  25056
gctacctgct gcgcctggcc aactacctgg cctaccactc ggacgtgatc gaggacgtca  25116
gcggcgaggg tctgctcgag tgccactgcc gctgcaacct ctgcacgccg caccgctccc  25176
tggcctgcaa cccccagctg ctgagcgaga cccagatcat cggcaccttc gagttgcaag  25236
gccccggcga gggcaagggg ggtctgaaac tcaccccggg gctgtggacc tcggcctact  25296
tgcgcaagtt cgtgcccgag gactaccatc ccttcgagat caggttctac gaggaccaat  25356
cccagccgcc caaggccgaa ctgtcggcct gcgtcatcac ccagggggcc atcctggccc  25416
aattgcaagc catccagaaa tcccgccaag aatttctgct gaaaaagggc cacggggtct  25476
acctggaccc ccagaccgga gaggagctca accccagctt cccccaggat gccccgagga  25536
agcagcaaga agctgaaagt ggagctgccg ccgccggagg atttggagga agactgggag  25596
agcagtcagg cagaggagga ggagatggaa gactgggaca gcactcaggc agaggaggac  25656
agcctgcaag acagtctgga agacgaggtg gaggaggagg cagaggaaga agcagccgcc  25716
gccagaccgt cgtcctcggc ggagaaagca agcagcacgg ataccatctc cgctccgggt  25776
cggggtcgcg gcgaccgggc ccacagtagg tgggacgaga ccgggcgctt cccgaacccc  25836
accacccaga ccggtaagaa ggagcggcag ggatacaagt cctggcgggg gcacaaaaac  25896
gccatcgtct cctgcttgca agcctgcggg ggcaacatct ccttcacccg ccgctacctg  25956
ctcttccacc gcggggtgaa cttccccccgc aacatcttgc attactaccg tcacctccac  26016
agcccctact actgtttcca agaagaggca gaaacccagc agcagcagaa aaccagcggc  26076
agcagcagct agaaaatcca cagcggcggc aggtggactg aggatcgcag cgaacgagcc  26136
ggcgcagacc cgggagctga ggaaccggat ctttcccacc ctctatgcca tcttccagca  26196
gagtcggggg caggagcagg aactgaaagt caagaaccgt tctctgcgct cgctcacccg  26256
cagttgtctg tatcacaaga gcgaagacca acttcagcgc actctcgagg acgccgaggc  26316
tctcttcaac aagtactgcg cgctcactct taaagagtag cccgcgcccg cccacacacg  26376
gaaaaaggcg ggaattacgt caccacctgc gcccttcgcc cgaccatcat catgagcaaa  26436
gagattccca cgccttacat gtggagctac cagccccaga tgggcctggc cgccggcgcc  26496
gcccaggact actccacccg catgaactgg ctcagcgccg ggcccgcgat gatctcacgg  26556
gtgaatgaca tccgcgcccg ccgaaaccag atactcctag aacagtcagc gatcaccgcc  26616
```

-continued

```
acgccccgcc atcaccttaa tccgcgtaat tggcccgccg ccctggtgta ccaggaaatt  26676
ccccagccca cgaccgtact acttccgcga gacgcccagg ccgaagtcca gctgactaac  26736
tcaggtgtcc agctggccgg cggcgccgcc ctgtgtcgtc accgccccgc tcagggtata  26796
aagcggctgg tgatccgagg cagaggcaca cagctcaacg acgaggtggt gagctcttcg  26856
ctgggtctgc gacctgacgg agtcttccaa ctcgccggat cggggagatc ttccttcacg  26916
cctcgtcagg ccgtcctgac tttggagagt tcgtcctcgc agccccgctc gggtggcatc  26976
ggcactctcc agttcgtgga ggagttcact ccctcggtct acttcaaccc cttctccggc  27036
tcccccggcc actacccgga cgagttcatc ccgaacttcg acgccatcag cgagtcggtg  27096
gacggctacg attgaatgtc ccatggtggc gcagctgacc tagctcggct tcgacacctg  27156
gaccactgcc gccgcttccg ctgcttcgct cgggatctcg ccgagtttgc ctactttgag  27216
ctgcccgagg agcaccctca gggcccggcc cacggagtgc ggatcatcgt cgaagggggc  27276
ctcgactccc acctgcttcg gatcttcagc cagcgaccga tcctggtcga gcgcgagcaa  27336
ggacagaccc ttctgaccct gtactgcatc tgcaaccacc ccggcctgca tgaaagtctt  27396
tgttgtctgc tgtgtactga gtataataaa agctgagatc agcgactact ccggactcga  27456
ttgtggtgtt cctgctatca accggtccct gttcttcacc gggaacgaga ccgagctcca  27516
gcttcagtgt aagccccaca agaagtacct cacctggctg ttccagggct ccccgatcgc  27576
cgttgtcaac cactgcgaca acgacggagt cctgctgagc ggccccgcca accttacttt  27636
ttccacccgc agaagcaagc tccagctctt ccaacccttc ctccccggga cctatcagtg  27696
cgtctcggga ccctgccatc acaccttcca cctgatcccg aataccacag cgccgctccc  27756
cgctactaac aaccaaacta cccaccatcg ccaccgtcgc gacctttctg aatctaacac  27816
taccacccac accggaggtg agctccgagg tcgaccaacc tctgggattt actacggccc  27876
ctgggaggtg gtggggttaa tagcgctagg cctagttgtg ggtgggcttt tggctctctg  27936
ctacctatac ctcccttgct gttcgtactt agtggtgctg tgttgctggt ttaagaaatg  27996
gggaagatca ccctagtgag ctgcggtgcg ctggtggcgg tggtggtgtt ttcgattgtg  28056
ggactgggcg gcgcggctgt agtgaaggag aaggccgatc cctgcttgca tttcaatccc  28116
gacaattgcc agctgagttt tcagcccgat ggcaatcggt gcgcggtgct gatcaagtgc  28176
ggatgggaat gcgagaacgt gagaatcgag tacaataaca agactcggaa caatactctc  28236
gcgtccgtgt ggcagcccgg ggaccccgag tggtacaccg tctctgtccc cggtgctgac  28296
ggctccccgc gcaccgtgaa caatactttc atttttgcgc acatgtgcga cacggtcatg  28356
tggatgagca agcagtacga tatgtggccc cccacgaagg agaacatcgt ggtcttctcc  28416
atcgcttaca gcgcgtgcac ggcgctaatc accgctatcg tgtgcctgag cattcacatg  28476
ctcatcgcta ttcgccccag aaataatgcc gaaaaagaga aacagccata acacgttttt  28536
tcacacacct ttttcagacc atggcctctg ttaaattttt gcttttattt gccagtctca  28596
ttactgttat aagtaatgag aaactcacta tttacattgg cactaaccac actttagacg  28656
gaattccaaa atcctcatgg tattgctatt ttgatcaaga tccagactta actatagaac  28716
tgtgtggtaa caagggaaaa aatacaagca ttcatttaat taactttaat tgcggagaca  28776
atttgaaatt aattaatatc actaaagagt atggaggtat gtattactat gttgcagaaa  28836
ataacaacat gcagttttat gaagttactg taactaatcc caccacacct agaacaacaa  28896
caaccaccac cacaaaaact acacctgtta ccactatgca gctcactacc aataacattt  28956
ttgccatgcg tcaaatggtc aacaatagca ctcaacccac cccacccagt gaggaaattc  29016
```

-continued

```
ccaaatccat gattggcatt attgttgctg tagtggtgtg catgttgatc atcgccttgt  29076
gcatggtgta ctatgccttc tgctacagaa agcacagact gaacgacaag ctggaacact  29136
tactaagtgt tgaattttaa ttttttagaa ccatgaagat cctaggcctt ttaatttttt  29196
ctatcattac ctctgctcta tgcaattctg acaatgagga cgttactgtc gttgtcggaa  29256
ccaattatac actgaaaggt ccagcgaagg gtatgctttc gtggtattgc tggtttggaa  29316
ctgacgagca acagacagag ctctgcaatg ctcaaaaagg caaaacctca aattctaaaa  29376
tctctaatta tcaatgcaat ggcactgact tagtactgct caatgtcacg aaagcatatg  29436
ctggcagcta cacctgccct ggagatgata ctgagaacat gatttttac aaagtggaag  29496
tggttgatcc cactactcca cctccaccca ccacaactac tcacaccaca cacacagaac  29556
aaaccacagc agaggaggca gcaaagttag ccttgcaggt ccaagacagt tcatttgttg  29616
gcattacccc tacacctgat cagcggtgtc cggggctgct cgtcagcggc attgtcggtg  29676
tgctttcggg attagcagtc ataatcatct gcatgttcat ttttgcttgc tgctatagaa  29736
ggctttaccg acaaaaatca gacccactgc tgaacctcta tgtttaattt tttccagagc  29796
catgaaggca gttagcactc tagtttttg ttctttgatt ggcactgttt ttagtgttag  29856
ctttttgaaa caaatcaatg ttactgaggg ggaaaatgtg acactggtag gcgtagaggg  29916
tgctcaaaat accacctgga caaaattcca tctagatggg tggaaagaaa tttgcacctg  29976
gaatgtcagt acttatacat gtgaaggagt taatcttacc attgtcaatg tcagccaaat  30036
tcaaaagggt tggattaaag ggcaatctgt tagtgttagc aatagtgggt actataccca  30096
gcatactctt atctatgaca ttatagttat accactgcct acacctagcc cacctagcac  30156
taccacacag acaacccaca ctacacaaac aaccacatac agtacatcaa atcagcctac  30216
caccactaca acagcagagg ttgccagctc gtctggggtc cgagtggcat tttgatgtt  30276
ggccccatct agcagtccca ctgctagtac caatgagcag actactgaat tttgtccac  30336
tgtcgagagc cacaccacag ctacctcgag tgccttctct agcaccgcca atctatcctc  30396
gctttcctct acaccaatca gtcccgctac tactcctacc cccgctattc tccccactcc  30456
cctgaagcaa acagacggcg acatgcaatg gcagatcacc ctgctcattg tgatcgggtt  30516
ggtcatcctg gccgtgttgc tctactacat cttctgccgc cgcattccca acgcgcaccg  30576
caagccggcc tacaagccca tcgttgtcgg gcagccggag ccgcttcagg tggaaggggg  30636
tctaaggaat cttctcttct cttttacagt atggtgattg aattatgatt cctagacaaa  30696
tcttgatcac tattcttatc tgcctcctcc aagtctgtgc caccctcgct ctggtggcca  30756
acgccagtcc agactgtatt gggcccttcg cctcctacgt gctctttgcc ttcatcacct  30816
gcatctgctg ctgtagcata gtctgcctgc ttatcacctt cttccagttc attgactgga  30876
tctttgtgcg catcgcctac ctgcgccacc acccccagta ccgcgaccag cgagtggcgc  30936
ggctgctcag gatcctctga taagcatgcg ggctctgcta cttctcgcgc ttctgctgtt  30996
agtgctcccc cgtcccgtcg acccccggac ccccacccag tcccccgagg aggtccgcaa  31056
atgcaaattc caagaaccct ggaaattcct caaatgctac cgccaaaaat cagacatgca  31116
tcccagctgg atcatgatca ttgggatcgt gaacattctg gcctgcaccc tcatctcctt  31176
tgtgatttac ccctgctttg actttggttg gaactcgcca gaggcgctct atctcccgcc  31236
tgaacctgac acaccaccac agcaacctca ggcacacgca ctaccaccac caccacagcc  31296
taggccacaa tacatgccca tattagacta tgaggccgag ccacagcgac ccatgctccc  31356
```

-continued

```
cgctattagt tacttcaatc taaccggcgg agatgactga cccactggcc aacaacaacg  31416

tcaacgacct tctcctggac atggacggcc gcgcctcgga gcagcgactc gcccaacttc  31476

gcattcgcca gcagcaggag agagccgtca aggagctgca ggacggcata gccatccacc  31536

agtgcaagaa aggcatcttc tgcctggtga aacaggccaa gatctcctac gaggtcaccc  31596

agaccgacca tcgcctctcc tacgagctcc tgcagcagcg ccagaagttc acctgcctgg  31656

tcggagtcaa ccccatcgtc atcacccagc agtcgggcga taccaagggg tgcatccact  31716

gctcctgcga ctcccccgac tgcgtccaca ctctgatcaa gaccctctgc ggcctccgcg  31776

acctcctccc catgaactaa tcacccccctt atccagtgaa ataaagatca tattgatgat  31836

ttgagtttaa taaaaataaa gaatcactta cttgaaatct gataccaggt ctctgtccat  31896

gttttctgcc aacaccactt cactcccctc ttcccagctc tggtactgca ggccccggcg  31956

ggctgcaaac ttcctccaca ccctgaaggg gatgtcaaat tcctcctgtc cctcaatctt  32016

cattttatct tctatcag atg tcc  aaa aag cgc gtc cgg  gtg gat gat gac  32067
                    Met Ser  Lys Lys Arg Val Arg  Val Asp Asp Asp
                        1465                 1470

ttc  gac ccc gtc tac ccc  tac gat gca gac aac  gca ccg acc gtg     32112
Phe  Asp Pro Val Tyr Pro  Tyr Asp Ala Asp Asn  Ala Pro Thr Val
1475                 1480                 1485

ccc  ttc atc aac ccc ccc  ttc gtc tct tca gat  gga ttc caa gag     32157
Pro  Phe Ile Asn Pro Pro  Phe Val Ser Ser Asp  Gly Phe Gln Glu
1490                 1495                 1500

aag  ccc ctg ggg gtg ctg  tcc ctg cgt ctg gcc  gat ccc gtc acc     32202
Lys  Pro Leu Gly Val Leu  Ser Leu Arg Leu Ala  Asp Pro Val Thr
1505                 1510                 1515

acc  aag aac ggg gaa atc  acc ctc aag ctg gga  gat ggg gtg gac     32247
Thr  Lys Asn Gly Glu Ile  Thr Leu Lys Leu Gly  Asp Gly Val Asp
1520                 1525                 1530

ctc  gac tcc tcg gga aaa  ctc atc tcc aac acg  gcc acc aag gcc     32292
Leu  Asp Ser Ser Gly Lys  Leu Ile Ser Asn Thr  Ala Thr Lys Ala
1535                 1540                 1545

gcc  gcc cct ctc agt ttt  tcc aac aac acc att  tcc ctt aac atg     32337
Ala  Ala Pro Leu Ser Phe  Ser Asn Asn Thr Ile  Ser Leu Asn Met
1550                 1555                 1560

gat  acc cct ttt tac aac  aac aat gga aag tta  ggc atg aaa gtc     32382
Asp  Thr Pro Phe Tyr Asn  Asn Asn Gly Lys Leu  Gly Met Lys Val
1565                 1570                 1575

act  gct cca ctg aag ata  cta gac aca gac ttg  cta aaa aca ctt     32427
Thr  Ala Pro Leu Lys Ile  Leu Asp Thr Asp Leu  Leu Lys Thr Leu
1580                 1585                 1590

gtt  gta gct tat gga caa  ggt tta gga aca aac  acc act ggt gcc     32472
Val  Val Ala Tyr Gly Gln  Gly Leu Gly Thr Asn  Thr Thr Gly Ala
1595                 1600                 1605

ctt  gtt gcc caa cta gca  tcc cca ctt gct ttt  gat agc aat agc     32517
Leu  Val Ala Gln Leu Ala  Ser Pro Leu Ala Phe  Asp Ser Asn Ser
1610                 1615                 1620

aaa  att gcc ctt aat tta  ggc aat gga cca ttg  aaa gtg gat gca     32562
Lys  Ile Ala Leu Asn Leu  Gly Asn Gly Pro Leu  Lys Val Asp Ala
1625                 1630                 1635

aat  aga ctg aac atc aat  tgc aat aga gga ctc  tat gtt act acc     32607
Asn  Arg Leu Asn Ile Asn  Cys Asn Arg Gly Leu  Tyr Val Thr Thr
1640                 1645                 1650

aca  aaa gat gca ctg gaa  gcc aat ata agt tgg  gct aat gct atg     32652
Thr  Lys Asp Ala Leu Glu  Ala Asn Ile Ser Trp  Ala Asn Ala Met
1655                 1660                 1665

aca  ttt ata gga aat gcc  atg ggt gtc aat att  gat aca caa aaa     32697
```

-continued

```
Thr  Phe Ile Gly Asn Ala  Met Gly Val Asn Ile  Asp Thr Gln Lys
1670                 1675                 1680

ggc  ttg caa ttt ggc acc  act agt acc gtc gca  gat gtt aaa aac     32742
Gly  Leu Gln Phe Gly Thr  Thr Ser Thr Val Ala  Asp Val Lys Asn
1685                 1690                 1695

gct  tac ccc ata caa atc  aaa ctt gga gct ggt  ctc aca ttt gac     32787
Ala  Tyr Pro Ile Gln Ile  Lys Leu Gly Ala Gly  Leu Thr Phe Asp
1700                 1705                 1710

agc  aca ggt gca att gtt  gca tgg aac aaa gat  gat gac aag ctt     32832
Ser  Thr Gly Ala Ile Val  Ala Trp Asn Lys Asp  Asp Asp Lys Leu
1715                 1720                 1725

aca  cta tgg acc aca gcc  gac ccc tct cca aat  tgt cac ata tat     32877
Thr  Leu Trp Thr Thr Ala  Asp Pro Ser Pro Asn  Cys His Ile Tyr
1730                 1735                 1740

tct  gaa aag gat gct aag  ctt aca ctt tgc ttg  aca aag tgt ggc     32922
Ser  Glu Lys Asp Ala Lys  Leu Thr Leu Cys Leu  Thr Lys Cys Gly
1745                 1750                 1755

agt  cag att ctg ggc act  gtt tcc ctc ata gct  gtt gat act ggc     32967
Ser  Gln Ile Leu Gly Thr  Val Ser Leu Ile Ala  Val Asp Thr Gly
1760                 1765                 1770

agt  tta aat ccc ata aca  gga aca gta acc act  gct ctt gtc tca     33012
Ser  Leu Asn Pro Ile Thr  Gly Thr Val Thr Thr  Ala Leu Val Ser
1775                 1780                 1785

ctt  aaa ttc gat gca aat  gga gtt ttg caa agc  agc tca aca cta     33057
Leu  Lys Phe Asp Ala Asn  Gly Val Leu Gln Ser  Ser Ser Thr Leu
1790                 1795                 1800

gac  tca gac tat tgg aat  ttc aga cag gga gat  gtt aca cct gct     33102
Asp  Ser Asp Tyr Trp Asn  Phe Arg Gln Gly Asp  Val Thr Pro Ala
1805                 1810                 1815

gaa  gcc tat act aat gct  ata ggt ttc atg ccc  aat cta aaa gca     33147
Glu  Ala Tyr Thr Asn Ala  Ile Gly Phe Met Pro  Asn Leu Lys Ala
1820                 1825                 1830

tac  cct aaa aac aca agt  gga gct gca aaa agt  cac att gtt ggg     33192
Tyr  Pro Lys Asn Thr Ser  Gly Ala Ala Lys Ser  His Ile Val Gly
1835                 1840                 1845

aaa  gtg tac cta cat ggg  gat aca ggc aaa cca  ctg gac ctc att     33237
Lys  Val Tyr Leu His Gly  Asp Thr Gly Lys Pro  Leu Asp Leu Ile
1850                 1855                 1860

att  act ttc aat gaa aca  agt gat gaa tct tgc  act tac tgt att     33282
Ile  Thr Phe Asn Glu Thr  Ser Asp Glu Ser Cys  Thr Tyr Cys Ile
1865                 1870                 1875

aac  ttt caa tgg cag tgg  ggg gct gat caa tat  aaa aat gaa aca     33327
Asn  Phe Gln Trp Gln Trp  Gly Ala Asp Gln Tyr  Lys Asn Glu Thr
1880                 1885                 1890

ctt  gcc gtc agt tca ttc  acc ttt tcc tat att  gct aaa gaa taa     33372
Leu  Ala Val Ser Ser Phe  Thr Phe Ser Tyr Ile  Ala Lys Glu
1895                 1900                 1905

accccactct gtaccccatc tctgtctatg gaaaaaactc tgaaacacaa aataaaataa  33432

agttcaagtg ttttattgat tcaacagttt tacaggattc gagcagttat ttttcctcca  33492

ccctcccagg acatggaata caccaccctc tccccccgca cagccttgaa catctgaatg  33552

ccattggtga tggacatgct tttggtctcc acgttccaca cagtttcaga gcgagccagt  33612

ctcgggtcgg tcagggagat gaaaccctcc gggcactccc gcatctgcac ctcacagctc  33672

aacagctgag gattgtcctc ggtggtcggg atcacggtta tctggaagaa gcagaagagc  33732

ggcggtggga atcatagtcc gcgaacggga tcggccggtg gtgtcgcatc aggccccgca  33792

gcagtcgctg tcgccgccgc tccgtcaagc tgctgctcag gggtccgggt tccagggact  33852
```

-continued

```
ccctcagcat gatgcccacg gccctcagca tcagtcgtct ggtgcggcgg gcgcagcagc  33912
gcatgcggat ctcgctcagg tcgctgcagt acgtgcaaca caggaccacc aggttgttca  33972
acagtccata gttcaacacg ctccagccga aactcatcgc gggaaggatg ctacccacgt  34032
ggccgtcgta ccagatcctc aggtaaatca agtggcgccc cctccagaac acgctgccca  34092
tgtacatgat ctccttgggc atgtggcggt tcaccacctc ccggtaccac atcaccctct  34152
ggttgaacat gcagccccgg atgatcctgc ggaaccacag ggccagcacc gccccgcccg  34212
ccatgcagcg aagagacccc gggtcccgac aatggcaatg gaggacccac cgctcgtacc  34272
cgtggatcat ctgggagctg aacaagtcta tgttggcaca gcacaggcat atgctcatgc  34332
atctcttcag cactctcagc tcctcggggg tcaaaaccat atcccagggc acggggaact  34392
cttgcaggac agcgaacccc gcagaacagg gcaatcctcg cacataactt acattgtgca  34452
tggacagggt atcgcaatca ggcagcaccg ggtgatcctc caccagagaa gcgcgggtct  34512
cggtctcctc acagcgtggt aagggggccg gccgatacgg gtgatggcgg gacgcggctg  34572
atcgtgttcg cgaccgtgtt atgatgcagt tgctttcgga cattttcgta cttgctgtag  34632
cagaacctgg tccgggcgct gcacaccgat cgccggcggc ggtcccggcg cttggaacgc  34692
tcggtgttga agttgtaaaa cagccactct ctcagaccgt gcagcagatc tagggcctca  34752
ggagtgatga agatcccatc atgcctgatg gctctaatca catcgaccac cgtggaatgg  34812
gccagaccca gccagatgat gcaattttgt tgggtttcgg tgacggcggg ggagggaaga  34872
acaggaagaa ccatgattaa cttttaatcc aaacggtctc ggagcacttc aaaatgaaga  34932
tcgcggagat ggcacctctc gcccccgctg tgttggtgga aaataacagc caggtcaaag  34992
gtgatacggt tctcgagatg ttccacggtg gcttccagca aagcctccac gcgcacatcc  35052
agaaacaaga caatagcgaa agcgggaggg ttctctaatt cctcaatcat catgttacac  35112
tcctgcacca tccccagata attttcattt ttccagcctt gaatgattcg aactagttcc  35172
tgaggtaaat ccaagccagc catgataaag agctcgcgca gagcgccctc caccggcatt  35232
cttaagcaca ccctcataat tccaagatat tctgctcctg gttcacctgc agcagattga  35292
caagcggaat atcaaaatct ctgccgcgat ccctaagctc ctccctcagc aataactgta  35352
agtactcttt catatcctct ccgaaatttt tagccatagg accaccagga ataagattag  35412
ggcaagccac agtacagata aaccgaagtc ctccccagtg agcattgcca aatgcaagac  35472
tgctataagc atgctggcta gacccggtga tatcttccag ataactggac agaaaatcgc  35532
ccaggcaatt tttaagaaaa tcaacaaaag aaaaatcctc caggtgcacg tttagagcct  35592
cgggaacaac gatggagtaa atgcaagcgg tgcgttccag catggttagt tagctgatct  35652
gtagaaaaaa acaaaaatga acattaaacc atgctagcct ggcgaacagg tgggtaaatc  35712
gttctctcca gcaccaggca ggccacgggg tctccggcac gaccctcgta aaaattgtcg  35772
ctatgattga aaccatcac agagagacgt tcccggtggc cggcgtgaat gattcgacaa  35832
gatgaataca cccccggaac attggcgtcc gcgagtgaaa aaaagcgccc aaggaagcaa  35892
taaggcacta caatgctcag tctcaagtcc agcaaagcga tgccatgcgg atgaagcaca  35952
aaattctcag gtgcgtacaa aatgtaatta ctcccctcct gcacaggcag caaagccccc  36012
gatccctcca ggtacacata caaagcctca gcgtccatag cttaccgagc agcagcacac  36072
aacaggcgca agagtcagag aaaggctgag ctctaacctg tccacccgct ctctgctcaa  36132
tatatagccc agatctacac tgacgtaaag gccaaagtct aaaaataccc gccaaataat  36192
cacacacgcc cagcacacgc ccagaaaccg gtgacacact caaaaaaata cgcgcacttc  36252
```

-continued

```
ctcaaacgcc caaactgccg tcatttccgg gttcccacgc tacgtcatca aaattcgact  36312

ttcaaattcc gtcgaccgtt aaaaacgtcg cccgccccgc ccctaacggt cgccgctccc  36372

gcagccaatc accgccccgc atccccaaat tcaaatacct catttgcata ttaacgcgca  36432

ccaaaagttt gaggtatatt attgatgatg                                   36462


<210> SEQ ID NO 2
<211> LENGTH: 530
<212> TYPE: PRT
<213> ORGANISM: chimpanzee adenovirus serotype Pan5

<400> SEQUENCE: 2

Met Met Arg Arg Val Tyr Pro Glu Gly Pro Pro Pro Ser Tyr Glu Ser
1               5                   10                  15

Val Met Gln Gln Ala Val Ala Ala Ala Met Gln Pro Pro Leu Glu Ala
            20                  25                  30

Pro Tyr Val Pro Pro Arg Tyr Leu Ala Pro Thr Glu Gly Arg Asn Ser
        35                  40                  45

Ile Arg Tyr Ser Glu Leu Ala Pro Leu Tyr Asp Thr Thr Arg Leu Tyr
    50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
    130                 135                 140

Arg Lys Thr Pro Asn Gly Val Thr Val Thr Asp Gly Ser Gln Asp Glu
145                 150                 155                 160

Leu Thr Tyr Glu Trp Val Glu Phe Glu Leu Pro Glu Gly Asn Phe Ser
                165                 170                 175

Val Thr Met Thr Ile Asp Leu Met Asn Asn Ala Ile Ile Asp Asn Tyr
            180                 185                 190

Leu Ala Val Gly Arg Gln Asn Gly Val Leu Glu Ser Asp Ile Gly Val
        195                 200                 205

Lys Phe Asp Thr Arg Asn Phe Arg Leu Gly Trp Asp Pro Val Thr Glu
    210                 215                 220

Leu Val Met Pro Gly Val Tyr Thr Asn Glu Ala Phe His Pro Asp Ile
225                 230                 235                 240

Val Leu Leu Pro Gly Cys Gly Val Asp Phe Thr Glu Ser Arg Leu Ser
                245                 250                 255

Asn Leu Leu Gly Ile Arg Lys Arg Gln Pro Phe Gln Glu Gly Phe Gln
            260                 265                 270

Ile Leu Tyr Glu Asp Leu Glu Gly Gly Asn Ile Pro Ala Leu Leu Asp
        275                 280                 285

Val Asp Ala Tyr Glu Lys Ser Lys Glu Asp Ser Ala Ala Ala Ala Thr
    290                 295                 300

Ala Ala Val Ala Thr Ala Ser Thr Glu Val Arg Gly Asp Asn Phe Ala
305                 310                 315                 320

Ser Ala Ala Thr Leu Ala Ala Ala Glu Ala Ala Glu Thr Glu Ser Lys
                325                 330                 335
```

-continued

```
Ile Val Ile Gln Pro Val Glu Lys Asp Ser Lys Glu Arg Ser Tyr Asn
            340                 345                 350

Val Leu Ala Asp Lys Lys Asn Thr Ala Tyr Arg Ser Trp Tyr Leu Ala
        355                 360                 365

Tyr Asn Tyr Gly Asp Pro Glu Lys Gly Val Arg Ser Trp Thr Leu Leu
    370                 375                 380

Thr Thr Ser Asp Val Thr Cys Gly Val Glu Gln Val Tyr Trp Ser Leu
385                 390                 395                 400

Pro Asp Met Met Gln Asp Pro Val Thr Phe Arg Ser Thr Arg Gln Val
                405                 410                 415

Ser Asn Tyr Pro Val Val Gly Ala Glu Leu Leu Pro Val Tyr Ser Lys
            420                 425                 430

Ser Phe Phe Asn Glu Gln Ala Val Tyr Ser Gln Gln Leu Arg Ala Phe
        435                 440                 445

Thr Ser Leu Thr His Val Phe Asn Arg Phe Pro Glu Asn Gln Ile Leu
    450                 455                 460

Val Arg Pro Pro Ala Pro Thr Ile Thr Thr Val Ser Glu Asn Val Pro
465                 470                 475                 480

Ala Leu Thr Asp His Gly Thr Leu Pro Leu Arg Ser Ser Ile Arg Gly
                485                 490                 495

Val Gln Arg Val Thr Val Thr Asp Ala Arg Arg Arg Thr Cys Pro Tyr
            500                 505                 510

Val Tyr Lys Ala Leu Gly Val Val Ala Pro Arg Val Leu Ser Ser Arg
        515                 520                 525

Thr Phe
    530
```

<210> SEQ ID NO 3
<211> LENGTH: 933
<212> TYPE: PRT
<213> ORGANISM: chimpanzee adenovirus serotype Pan5

<400> SEQUENCE: 3

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Cys Gln Trp Thr Tyr Lys Ala Asp Gly Asp Thr Gly
    130                 135                 140

Thr Glu Lys Thr Tyr Thr Tyr Gly Asn Ala Pro Val Gln Gly Ile Ser
145                 150                 155                 160

Ile Thr Lys Asp Gly Ile Gln Leu Gly Thr Asp Thr Asp Asp Gln Pro
```

-continued

```
                165                 170                 175

Ile Tyr Ala Asp Lys Thr Tyr Gln Pro Glu Pro Gln Val Gly Asp Ala
            180                 185                 190

Glu Trp His Asp Ile Thr Gly Thr Asp Glu Lys Tyr Gly Gly Arg Ala
        195                 200                 205

Leu Lys Pro Asp Thr Lys Met Lys Pro Cys Tyr Gly Ser Phe Ala Lys
    210                 215                 220

Pro Thr Asn Lys Glu Gly Gly Gln Ala Asn Val Lys Thr Glu Thr Gly
225                 230                 235                 240

Gly Thr Lys Glu Tyr Asp Ile Asp Met Ala Phe Phe Asp Asn Arg Ser
                245                 250                 255

Ala Ala Ala Ala Gly Leu Ala Pro Glu Ile Val Leu Tyr Thr Glu Asn
            260                 265                 270

Val Asp Leu Glu Thr Pro Asp Thr His Ile Val Tyr Lys Ala Gly Thr
        275                 280                 285

Asp Asp Ser Ser Ser Ser Ile Asn Leu Gly Gln Gln Ser Met Pro Asn
    290                 295                 300

Arg Pro Asn Tyr Ile Gly Phe Arg Asp Asn Phe Ile Gly Leu Met Tyr
305                 310                 315                 320

Tyr Asn Ser Thr Gly Asn Met Gly Val Leu Ala Gly Gln Ala Ser Gln
                325                 330                 335

Leu Asn Ala Val Val Asp Leu Gln Asp Arg Asn Thr Glu Leu Ser Tyr
            340                 345                 350

Gln Leu Leu Leu Asp Ser Leu Gly Asp Arg Thr Arg Tyr Phe Ser Met
        355                 360                 365

Trp Asn Gln Ala Val Asp Ser Tyr Asp Pro Asp Val Arg Ile Ile Glu
    370                 375                 380

Asn His Gly Val Glu Asp Glu Leu Pro Asn Tyr Cys Phe Pro Leu Asp
385                 390                 395                 400

Ala Val Gly Arg Thr Asp Thr Tyr Gln Gly Ile Lys Ala Asn Gly Ala
                405                 410                 415

Asp Gln Thr Thr Trp Thr Lys Asp Asp Thr Val Asn Asp Ala Asn Glu
            420                 425                 430

Leu Gly Lys Gly Asn Pro Phe Ala Met Glu Ile Asn Ile Gln Ala Asn
        435                 440                 445

Leu Trp Arg Asn Phe Leu Tyr Ala Asn Val Ala Leu Tyr Leu Pro Asp
    450                 455                 460

Ser Tyr Lys Tyr Thr Pro Ala Asn Ile Thr Leu Pro Thr Asn Thr Asn
465                 470                 475                 480

Thr Tyr Asp Tyr Met Asn Gly Arg Val Val Ala Pro Ser Leu Val Asp
                485                 490                 495

Ala Tyr Ile Asn Ile Gly Ala Arg Trp Ser Leu Asp Pro Met Asp Asn
            500                 505                 510

Val Asn Pro Phe Asn His His Arg Asn Ala Gly Leu Arg Tyr Arg Ser
        515                 520                 525

Met Leu Leu Gly Asn Gly Arg Tyr Val Pro Phe His Ile Gln Val Pro
    530                 535                 540

Gln Lys Phe Phe Ala Ile Lys Ser Leu Leu Leu Leu Pro Gly Ser Tyr
545                 550                 555                 560

Thr Tyr Glu Trp Asn Phe Arg Lys Asp Val Asn Met Ile Leu Gln Ser
                565                 570                 575

Ser Leu Gly Asn Asp Leu Arg Thr Asp Gly Ala Ser Ile Ala Phe Thr
            580                 585                 590
```

-continued

Ser Ile Asn Leu Tyr Ala Thr Phe Phe Pro Met Ala His Asn Thr Ala
595 600 605

Ser Thr Leu Glu Ala Met Leu Arg Asn Asp Thr Asn Asp Gln Ser Phe
610 615 620

Asn Asp Tyr Leu Ser Ala Ala Asn Met Leu Tyr Pro Ile Pro Ala Asn
625 630 635 640

Ala Thr Asn Val Pro Ile Ser Ile Pro Ser Arg Asn Trp Ala Ala Phe
645 650 655

Arg Gly Trp Ser Phe Thr Arg Leu Lys Thr Arg Glu Thr Pro Ser Leu
660 665 670

Gly Ser Gly Phe Asp Pro Tyr Phe Val Tyr Ser Gly Ser Ile Pro Tyr
675 680 685

Leu Asp Gly Thr Phe Tyr Leu Asn His Thr Phe Lys Lys Val Ser Ile
690 695 700

Thr Phe Asp Ser Ser Val Ser Trp Pro Gly Asn Asp Arg Leu Leu Thr
705 710 715 720

Pro Asn Glu Phe Glu Ile Lys Arg Thr Val Asp Gly Glu Gly Tyr Asn
725 730 735

Val Ala Gln Cys Asn Met Thr Lys Asp Trp Phe Leu Val Gln Met Leu
740 745 750

Ala His Tyr Asn Ile Gly Tyr Gln Gly Phe Tyr Val Pro Glu Gly Tyr
755 760 765

Lys Asp Arg Met Tyr Ser Phe Phe Arg Asn Phe Gln Pro Met Ser Arg
770 775 780

Gln Val Val Asp Glu Val Asn Tyr Lys Asp Tyr Gln Ala Val Thr Leu
785 790 795 800

Ala Tyr Gln His Asn Asn Ser Gly Phe Val Gly Tyr Leu Ala Pro Thr
805 810 815

Met Arg Gln Gly Gln Pro Tyr Pro Ala Asn Tyr Pro Tyr Pro Leu Ile
820 825 830

Gly Lys Ser Ala Val Ala Ser Val Thr Gln Lys Lys Phe Leu Cys Asp
835 840 845

Arg Val Met Trp Arg Ile Pro Phe Ser Ser Asn Phe Met Ser Met Gly
850 855 860

Ala Leu Thr Asp Leu Gly Gln Asn Met Leu Tyr Ala Asn Ser Ala His
865 870 875 880

Ala Leu Asp Met Asn Phe Glu Val Asp Pro Met Asp Glu Ser Thr Leu
885 890 895

Leu Tyr Val Val Phe Glu Val Phe Asp Val Val Arg Val His Gln Pro
900 905 910

His Arg Gly Val Ile Glu Ala Val Tyr Leu Arg Thr Pro Phe Ser Ala
915 920 925

Gly Asn Ala Thr Thr
930

<210> SEQ ID NO 4
<211> LENGTH: 445
<212> TYPE: PRT
<213> ORGANISM: chimpanzee adenovirus serotype Pan5

<400> SEQUENCE: 4

Met Ser Lys Lys Arg Val Arg Val Asp Asp Asp Phe Asp Pro Val Tyr
1 5 10 15

Pro Tyr Asp Ala Asp Asn Ala Pro Thr Val Pro Phe Ile Asn Pro Pro

-continued

```
            20                  25                  30

Phe Val Ser Ser Asp Gly Phe Gln Glu Lys Pro Leu Gly Val Leu Ser
        35                  40                  45

Leu Arg Leu Ala Asp Pro Val Thr Thr Lys Asn Gly Glu Ile Thr Leu
    50                  55                  60

Lys Leu Gly Asp Gly Val Asp Leu Asp Ser Ser Gly Lys Leu Ile Ser
65                  70                  75                  80

Asn Thr Ala Thr Lys Ala Ala Ala Pro Leu Ser Phe Ser Asn Asn Thr
                85                  90                  95

Ile Ser Leu Asn Met Asp Thr Pro Phe Tyr Asn Asn Asn Gly Lys Leu
            100                 105                 110

Gly Met Lys Val Thr Ala Pro Leu Lys Ile Leu Asp Thr Asp Leu Leu
        115                 120                 125

Lys Thr Leu Val Val Ala Tyr Gly Gln Gly Leu Gly Thr Asn Thr Thr
    130                 135                 140

Gly Ala Leu Val Ala Gln Leu Ala Ser Pro Leu Ala Phe Asp Ser Asn
145                 150                 155                 160

Ser Lys Ile Ala Leu Asn Leu Gly Asn Gly Pro Leu Lys Val Asp Ala
                165                 170                 175

Asn Arg Leu Asn Ile Asn Cys Asn Arg Gly Leu Tyr Val Thr Thr Thr
            180                 185                 190

Lys Asp Ala Leu Glu Ala Asn Ile Ser Trp Ala Asn Ala Met Thr Phe
        195                 200                 205

Ile Gly Asn Ala Met Gly Val Asn Ile Asp Thr Gln Lys Gly Leu Gln
    210                 215                 220

Phe Gly Thr Thr Ser Thr Val Ala Asp Val Lys Asn Ala Tyr Pro Ile
225                 230                 235                 240

Gln Ile Lys Leu Gly Ala Gly Leu Thr Phe Asp Ser Thr Gly Ala Ile
                245                 250                 255

Val Ala Trp Asn Lys Asp Asp Asp Lys Leu Thr Leu Trp Thr Thr Ala
            260                 265                 270

Asp Pro Ser Pro Asn Cys His Ile Tyr Ser Glu Lys Asp Ala Lys Leu
        275                 280                 285

Thr Leu Cys Leu Thr Lys Cys Gly Ser Gln Ile Leu Gly Thr Val Ser
    290                 295                 300

Leu Ile Ala Val Asp Thr Gly Ser Leu Asn Pro Ile Thr Gly Thr Val
305                 310                 315                 320

Thr Thr Ala Leu Val Ser Leu Lys Phe Asp Ala Asn Gly Val Leu Gln
                325                 330                 335

Ser Ser Ser Thr Leu Asp Ser Asp Tyr Trp Asn Phe Arg Gln Gly Asp
            340                 345                 350

Val Thr Pro Ala Glu Ala Tyr Thr Asn Ala Ile Gly Phe Met Pro Asn
        355                 360                 365

Leu Lys Ala Tyr Pro Lys Asn Thr Ser Gly Ala Ala Lys Ser His Ile
    370                 375                 380

Val Gly Lys Val Tyr Leu His Gly Asp Thr Gly Lys Pro Leu Asp Leu
385                 390                 395                 400

Ile Ile Thr Phe Asn Glu Thr Ser Asp Glu Ser Cys Thr Tyr Cys Ile
                405                 410                 415

Asn Phe Gln Trp Gln Trp Gly Ala Asp Gln Tyr Lys Asn Glu Thr Leu
            420                 425                 430

Ala Val Ser Ser Phe Thr Phe Ser Tyr Ile Ala Lys Glu
        435                 440                 445
```

-continued

<210> SEQ ID NO 5
<211> LENGTH: 36604
<212> TYPE: DNA
<213> ORGANISM: chimpanzee adenovirus serotype Pan6
<220> FEATURE:
<221> NAME/KEY: CDS
<222> LOCATION: (13878)..(15467)
<223> OTHER INFORMATION: L2 Penton
<220> FEATURE:
<221> NAME/KEY: CDS
<222> LOCATION: (18284)..(21112)
<223> OTHER INFORMATION: L3 Hexon
<220> FEATURE:
<221> NAME/KEY: CDS
<222> LOCATION: (32162)..(33493)
<223> OTHER INFORMATION: L5 Fiber

<400> SEQUENCE: 5
catcatcaat aatatacctc aaacttttgg tgcgcgttaa tatgcaaatg agctgtttga 60
atttggggag ggaggaaggt gattggctgc gggagcggcg accgttaggg gcggggcggg 120
tgacgttttg atgacgtggc tatgaggcgg agccggtttg caagttctcg tgggaaaagt 180
gacgtcaaac gaggtgtggt ttgaacacgg aaatactcaa ttttcccgcg ctctctgaca 240
ggaaatgagg tgtttctggg cggatgcaag tgaaaacggg ccattttcgc gcgaaaactg 300
aatgaggaag tgaaaatctg agtaatttcg cgtttatggc agggaggagt atttgccgag 360
ggccgagtag actttgaccg attacgtggg ggtttcgatt accgtatttt tcacctaaat 420
ttccgcgtac ggtgtcaaag tccggtgttt ttacgtaggc gtcagctgat cgccagggta 480
tttaaacctg cgctctctag tcaagaggcc actcttgagt gccagcgagt agagttttct 540
cctccgcgcc gcgagtcaga tctacacttt gaaagatgag gcacctgaga gacctgcccg 600
gtaatgtttt cctggctact gggaacgaga ttctggaatt ggtggtggac gccatgatgg 660
gtgacgaccc tccagagccc cctaccccat ttgaggcgcc ttcgctgtac gatttgtatg 720
atctggaggt ggatgtgccc gagagcgacc ctaacgagga ggcggtgaat gatttgttta 780
gcgatgccgc gctgctggct gccgagcagg ctaatacgga ctctggctca gacagcgatt 840
cctctctcca taccccgaga cccggcagag gtgagaaaaa gatccccgag cttaaagggg 900
aagagctcga cctgcgctgc tatgaggaat gcttgcctcc gagcgatgat gaggaggacg 960
aggaggcgat tcgagctgcg gtgaaccagg gagtgaaaac tgcgggcgag agctttagcc 1020
tggactgtcc tactctgccc ggacacggct gtaagtcttg tgaatttcat cgcatgaata 1080
ctggagataa gaatgtgatg tgtgccctgt gctatatgag agcttacaac cattgtgttt 1140
acagtaagtg tgattaactt tagttgggaa ggcagagggt gactgggtgc tgactggttt 1200
atttatgtat atgttttttt atgtgtaggt cccgtctctg acgtagatga gacccccact 1260
tcagagtgca tttcatcacc cccagaaatt ggcgaggaac cgcccgaaga tattattcat 1320
agaccagttg cagtgagagt caccgggcgg agagcagctg tggagagttt ggatgacttg 1380
ctacagggtg gggatgaacc tttggacttg tgtacccgga aacgccccag gcactaagtg 1440
ccacacatgt gtgtttactt aaggtgatgt cagtatttat agggtgtgga gtgcaataaa 1500
atccgtgttg actttaagtg cgtgttttat gactcagggg tggggactgt gggtatataa 1560
gcaggtgcag acctgtgtgg tcagttcaga gcaggactca tggagatctg gactgtcttg 1620
gaagactttc accagactag acagttgcta gagaactcat cggagggagt ctcttacctg 1680
tggagattct gcttcggtgg gcctctagct aagctagtct atagggccaa acaggattat 1740

-continued

```
aaggaacaat ttgaggatat tttgagagag tgtcctggta tttttgactc tctcaacttg   1800
ggccatcagt ctcactttaa ccagagtatt ctgagagccc ttgacttttc tactcctggc   1860
agaactaccg ccgcggtagc ctttttttgcc tttattcttg acaaatggag tcaagaaacc   1920
catttcagca gggattaccg tctggactgc ttagcagtag ctttgtggag aacatggagg   1980
tgccagcgcc tgaatgcaat ctccggctac ttgccagtac agccggtaga cacgctgagg   2040
atcctgagtc tccagtcacc ccaggaacac caacgccgcc agcagccgca gcaggagcag   2100
cagcaagagg aggaccgaga agagaacccg agagccggtc tggaccctcc ggtggcggag   2160
gaggaggagt agctgacttg tttcccgagc tgcgccgggt gctgactagg tcttccagtg   2220
gacgggagag ggggattaag cgggagaggc atgaggagac tagccacaga actgaactga   2280
ctgtcagtct gatgagccgc aggcgcccag aatcggtgtg gtggcatgag gtgcagtcgc   2340
aggggataga tgaggtctcg gtgatgcatg agaaatattc cctagaacaa gtcaagactt   2400
gttggttgga gcccgaggat gattgggagg tagccatcag gaattatgcc aagctggctc   2460
tgaagccaga caagaagtac aagattacca aactgattaa tatcagaaat tcctgctaca   2520
tttcagggaa tggggccgag gtggagatca gtacccagga gagggtggcc ttcagatgtt   2580
gtatgatgaa tatgtacccg gggtggtgg gcatggaggg agtcaccttt atgaacacga   2640
ggttcagggg tgatgggtat aatggggtgg tctttatggc caacaccaag ctgacagtgc   2700
acggatgctc cttctttggc ttcaataaca tgtgcatcga ggcctggggc agtgtttcag   2760
tgaggggatg cagcttttca gccaactgga tgggggtcgt gggcagaacc aagagcaagg   2820
tgtcagtgaa gaaatgcctg ttcgagaggt gccacctggg ggtgatgagc gagggcgaag   2880
ccaaagtcaa acactgcgcc tctaccgaga cgggctgctt tgtgctgatc aagggcaatg   2940
cccaagtcaa gcataacatg atctgtgggg cctcggatga gcgcggctac cagatgctga   3000
cctgcgccgg tgggaacagc catatgctgg ccaccgtgca tgtggcctcg cacccccgca   3060
agacatggcc cgagttcgag cacaacgtca tgacccgctg caatgtgcac ctgggctccc   3120
gccgaggcat gttcatgccc taccagtgca acatgcaatt tgtgaaggtg ctgctggagc   3180
ccgatgccat gtccagagtg agcctgacgg gggtgtttga catgaatgtg gagctgtgga   3240
aaattctgag atatgatgaa tccaagacca ggtgccgggc ctgcgaatgc ggaggcaagc   3300
acgccaggct tcagcccgtg tgtgtggagg tgacggagga cctgcgaccc gatcatttgg   3360
tgttgtcctg caacgggacg gagttcggct ccagcgggga agaatctgac tagagtgagt   3420
agtgtttggg gctgggtgtg agcctgcatg aggggcagaa tgactaaaat ctgtggtttt   3480
ctgtgtgttg cagcagcatg agcggaagcg cctcctttga gggaggggta ttcagccctt   3540
atctgacggg gcgtctcccc tcctgggcgg gagtgcgtca gaatgtgatg ggatccacgg   3600
tggacggccg gcccgtgcag cccgcgaact cttcaaccct gacctacgcg accctgagct   3660
cctcgtccgt ggacgcagct gccgccgcag ctgctgcttc cgccgccagc gccgtgcgcg   3720
gaatggccct gggcgccggc tactacagct ctctggtggc caactcgagt tccaccaata   3780
atcccgccag cctgaacgag gagaagctgc tgctgctgat ggcccagctc gaggccctga   3840
cccagcgcct gggcgagctg acccagcagg tggctcagct gcaggcggag acgcgggccg   3900
cggttgccac ggtgaaaacc aaataaaaaa tgaatcaata aataaacgga gacggttgtt   3960
gattttaaca cagagtcttg aatctttatt tgatttttcg cgcgcggtag gccctggacc   4020
accggtctcg atcattgagc acccggtgga tcttttccag gacccggtag aggtgggctt   4080
ggatgttgag gtacatgggc atgagcccgt cccgggggtg gaggtagctc cattgcaggg   4140
```

-continued

```
cctcgtgctc ggggatggtg ttgtaaatca cccagtcata gcaggggcgc agggcgtggt   4200
gctgcacgat gtccttgagg aggagactga tggccacggg cagccccttg gtgtaggtgt   4260
tgacgaacct gttgagctgg gagggatgca tgcgggggga gatgagatgc atcttggcct   4320
ggatcttgag attggcgatg ttcccgccca gatcccgccg gggggttcatg ttgtgcagga   4380
ccaccagcac ggtgtatccg gtgcacttgg ggaatttgtc atgcaacttg gaagggaagg   4440
cgtgaaagaa tttggagacg cccttgtgac cgcccaggtt ttccatgcac tcatccatga   4500
tgatggcgat gggcccgtgg gcggcggcct gggcaaagac gtttcggggg tcggacacat   4560
cgtagttgtg gtcctgggtg agctcgtcat aggccatttt aatgaatttg gggcggaggg   4620
tgcccgactg gggggacgaag gtgccctcga tcccgggggc gtagttgccc tcgcagatct   4680
gcatctccca ggccttgagc tcggaggggg ggatcatgtc cacctgcggg gcgatgaaaa   4740
aaacggtttc cggggcgggg gagatgagct gggccgaaag caggttccgg agcagctggg   4800
acttgccgca accggtgggg ccgtagatga ccccgatgac cggctgcagg tggtagttga   4860
gggagagaca gctgccgtcc tcgcggagga gggggggccac ctcgttcatc atctcgcgca   4920
catgcatgtt ctcgcgcacg agttccgcca ggaggcgctc gccccccagc gagaggagct   4980
cttgcagcga ggcgaagttt ttcagcggct tgagtccgtc ggccatgggc attttggaga   5040
gggtctgttg caagagttcc agacggtccc agagctcggt gatgtgctct agggcatctc   5100
gatccagcag acctcctcgt ttcgcgggtt ggggcgactg cgggagtagg gcaccaggcg   5160
atgggcgtcc agcgaggcca gggtccggtc cttccagggc cgcagggtcc gcgtcagcgt   5220
ggtctccgtc acggtgaagg ggtgcgcgcc gggctgggcg cttgcgaggg tgcgcttcag   5280
gctcatccgg ctggtcgaga accgctcccg gtcggcgccc tgcgcgtcgg ccaggtagca   5340
attgagcatg agttcgtagt tgagcgcctc ggccgcgtgg cccttggcgc ggagcttacc   5400
tttggaagtg tgtccgcaga cgggacagag gagggacttg agggcgtaga gcttgggggc   5460
gaggaagacg gactcggggg cgtaggcgtc cgcgccgcag ctggcgcaga cggtctcgca   5520
ctccacgagc caggtgaggt cggggcggtt ggggtcaaaa acgaggtttc ctccgtgctt   5580
tttgatgcgt ttcttacctc tggtctccat gagctcgtgt ccccgctggg tgacaaagag   5640
gctgtccgtg tccccgtaga ccgactttat gggccggtcc tcgagcgggg tgccgcggtc   5700
ctcgtcgtag aggaaccccg cccactccga gacgaaggcc cgggtccagg ccagcacgaa   5760
ggaggccacg tgggaggggt agcggtcgtt gtccaccagc gggtccacct tctccagggt   5820
atgcaagcac atgtccccct cgtccacatc caggaaggtg attggcttgt aagtgtaggc   5880
cacgtgaccg gggtcccgg ccgggggggt ataaaagggg gcgggcccct gctcgtcctc   5940
actgtcttcc ggatcgctgt ccaggagcgc cagctgttgg ggtaggtatt ccctctcgaa   6000
ggcgggcatg acctcggcac tcaggttgtc agtttctaga aacgaggagg atttgatatt   6060
gacggtgccg ttggagacgc ctttcatgag cccctcgtcc atttggtcag aaaagacgat   6120
ctttttgttg tcgagcttgg tggcgaagga gccgtagagg gcgttggaga gcagcttggc   6180
gatggagcgc atggtctggt tcttttcctt gtcggcgcgc tccttggcgg cgatgttgag   6240
ctgcacgtac tcgcgcgcca cgcacttcca ttcggggaag acggtggtga gctcgtcggg   6300
cacgattctg acccgccagc cgcggttgtg cagggtgatg aggtccacgc tggtggccac   6360
ctcgccgcgc aggggctcgt tggtccagca gaggcgcccg cccttgcgcg agcagaaggg   6420
gggcagcggg tccagcatga gctcgtcggg ggggtcggcg tccacggtga agatgccggg   6480
```

-continued

```
caggagctcg gggtcgaagt agctgatgca ggtgcccaga ttgtccagcg ccgcttgcca   6540
gtcgcgcacg gccagcgcgc gctcgtaggg gctgaggggc gtgccccagg gcatggggtg   6600
cgtgagcgcg gaggcgtaca tgccgcagat gtcgtagacg tagaggggct cctcgaggac   6660
gccgatgtag gtggggtagc agcgcccccc gcggatgctg gcgcgcacgt agtcgtacag   6720
ctcgtgcgag ggcgcgagga gccccgtgcc gaggttggag cgttgcggct tttcggcgcg   6780
gtagacgatc tggcggaaga tggcgtggga gttggaggag atggtgggcc tttggaagat   6840
gttgaagtgg gcgtgggggca ggccgaccga gtccctgatg aagtgggcgt aggagtcctg   6900
cagcttggcg acgagctcgg cggtgacgag gacgtccagg gcgcagtagt cgagggtctc   6960
ttggatgatg tcatacttga gctggccctt ctgcttccac agctcgcggt tgagaaggaa   7020
ctcttcgcgg tccttccagt actcttcgag ggggaacccg tcctgatcgg cacggtaaga   7080
gcccaccatg tagaactggt tgacggcctt gtaggcgcag cagcccttct ccacggggag   7140
ggcgtaagct tgcgcggcct tgcgcaggga ggtgtgggtg agggcgaagg tgtcgcgcac   7200
catgaccttg aggaactggt gcttgaagtc gaggtcgtcg cagccgccct gctcccagag   7260
ttggaagtcc gtgcgcttct tgtaggcggg gttaggcaaa gcgaaagtaa catcgttgaa   7320
gaggatcttg cccgcgcggg gcatgaagtt gcgagtgatg cggaaaggct ggggcacctc   7380
ggcccggttg ttgatgacct gggcggcgag gacgatctcg tcgaagccgt tgatgttgtg   7440
cccgacgatg tagagttcca cgaatcgcgg gcggcccttg acgtggggca gcttcttgag   7500
ctcgtcgtag gtgagctcgg cggggtcgct gagcccgtgc tgctcgaggg cccagtcggc   7560
gacgtggggg ttggcgctga ggaaggaagt ccagagatcc acggccaggg cggtctgcaa   7620
gcggtcccgg tactgacgga actgttggcc cacggccatt ttttcggggg tgacgcagta   7680
gaaggtgcgg gggtcgccgt gccagcggtc ccacttgagc tggagggcga ggtcgtgggc   7740
gagctcgacg agcggcgggt ccccggagag tttcatgacc agcatgaagg ggacgagctg   7800
cttgccgaag gaccccatcc aggtgtaggt ttccacatcg taggtgagga agagcctttc   7860
ggtgcgagga tgcgagccga tggggaagaa ctggatctcc tgccaccagt tggaggaatg   7920
gctgttgatg tgatggaagt agaaatgccg acggcgcgcc gagcactcgt gcttgtgttt   7980
atacaagcgt ccgcagtgct cgcaacgctg cacgggatgc acgtgctgca cgagctgtac   8040
ctgggttcct ttggcgagga atttcagtgg gcagtggagc gctggcggct gcatctcgtg   8100
ctgtactacg tcttggccat cggcgtggcc atcgtctgcc tcgatggtgg tcatgctgac   8160
gagcccgcgc gggaggcagg tccagacctc ggctcggacg ggtcggagag cgaggacgag   8220
ggcgcgcagg ccggagctgt ccagggtcct gagacgctgc ggagtcaggt cagtgggcag   8280
cggcggcgcg cggttgactt gcaggagctt ttccagggcg cgcgggaggt ccagatggta   8340
cttgatctcc acggcgccgt tggtggctac gtccacggct tgcagggtgc cgtgcccctg   8400
gggcgccacc accgtgcccc gtttcttctt gggcgctgct tccatgtcgg tcagaagcgg   8460
cggcgaggac gcgcgccggg cggcaggggc ggctcggggc ccggaggcag gggcggcagg   8520
ggcacgtcgg cgccgcgcgc gggcaggttc tggtactgcg cccggagaag actggcgtga   8580
gcgacgacgc gacggttgac gtcctggatc tgacgcctct gggtgaaggc cacgggaccc   8640
gtgagtttga acctgaaaga gagttcgaca gaatcaatct cggtatcgtt gacggcggcc   8700
tgccgcagga tctcttgcac gtcgcccgag ttgtcctggt aggcgatctc ggtcatgaac   8760
tgctcgatct cctcctcctg aaggtctccg cggccggcgc gctcgacggt ggccgcgagg   8820
tcgttggaga tgcggcccat gagctgcgag aaggcgttca tgccggcctc gttccagacg   8880
```

-continued cggctgtaga ccacggctcc gtcggggtcg cgcgcgcgca tgaccacctg ggcgaggttg 8940
agctcgacgt ggcgcgtgaa gaccgcgtag ttgcagaggc gctggtagag gtagttgagc 9000
gtggtggcga tgtgctcggt gacgaagaag tacatgatcc agcggcggag cggcatctcg 9060
ctgacgtcgc ccagggcttc caagcgttcc atggcctcgt agaagtccac ggcgaagttg 9120
aaaaactggg agttgcgcgc cgagacggtc aactcctcct ccagaagacg gatgagctcg 9180
gcgatggtgg cgcgcacctc gcgctcgaag gccccggggg gctcctcttc catctcctcc 9240
tcttcctcct ccactaacat ctcttctact tcctcctcag gaggcggtgg cgggggaggg 9300
gccctgcgtc gccggcggcg cacgggcaga cggtcgatga agcgctcgat ggtctccccg 9360
cgccggcgac gcatggtctc ggtgacggcg cgcccgtcct cgcggggccg cagcatgaag 9420
acgccgccgc gcatctccag gtggccgccg ggggggtctc cgttgggcag ggagagggcg 9480
ctgacgatgc atcttatcaa ttgacccgta gggactccgc gcaaggacct gagcgtctcg 9540
agatccacgg gatccgaaaa ccgctgaacg aaggcttcga gccagtcgca gtcgcaaggt 9600
aggctgagcc cggtttcttg ttcttcgggt atttggtcgg gaggcgggcg ggcgatgctg 9660
ctggtgatga agttgaagta ggcggtcctg agacggcgga tggtggcgag gagcaccagg 9720
tccttgggcc cggcttgctg gatgcgcaga cggtcggcca tgccccaggc gtggtcctga 9780
cacctggcga ggtccttgta gtagtcctgc atgagccgct ccacgggcac ctcctcctcg 9840
cccgcgcggc cgtgcatgcg cgtgagcccg aacccgcgct gcggctggac gagcgccagg 9900
tcggcgacga cgcgctcggt gaggatggcc tgctggatct gggtgagggt ggtctggaag 9960
tcgtcgaagt cgacgaagcg gtggtaggct ccggtgttga tggtgtagga gcagttggcc 10020
atgacggacc agttgacggt ctggtggccg ggtcgcacga gctcgtggta cttgaggcgc 10080
gagtaggcgc gcgtgtcgaa gatgtagtcg ttgcaggcgc gcacgaggta ctggtatccg 10140
acgaggaagt gcggcggcgg ctggcggtag agcggccatc gctcggtggc gggggcgccg 10200
ggcgcgaggt cctcgagcat gaggcggtgg tagccgtaga tgtacctgga catccaggtg 10260
atgccggcgg cggtggtgga ggcgcgcggg aactcgcgga cgcggttcca gatgttgcgc 10320
agcggcagga agtagttcat ggtggccgcg gtctggcccg tgaggcgcgc gcagtcgtgg 10380
atgctctaga catacgggca aaaacgaaag cggtcagcgg ctcgactccg tggcctggag 10440
gctaagcgaa cgggttgggc tgcgcgtgta ccccggttcg aatctcgaat caggctggag 10500
ccgcagctaa cgtggtactg gcactcccgt ctcgacccaa gcctgctaac gaaacctcca 10560
ggatacggag gcgggtcgtt ttttggcctt ggtcgctggt catgaaaaac tagtaagcgc 10620
ggaaagcggc cgcccgcgat ggctcgctgc cgtagtctgg agaaagaatc gccagggttg 10680
cgttgcggtg tgccccggtt cgagcctcag cgctcggcgc cggccggatt ccgcggctaa 10740
cgtgggcgtg gctgccccgt cgtttccaag accccttagc cagccgactt ctccagttac 10800
ggagcgagcc cctctttttt tttcttgtgt ttttgccaga tgcatcccgt actgcggcag 10860
atgcgccccc accctccacc acaaccgccc ctaccgcagc agcagcaaca gccggcgctt 10920
ctgcccccgc cccagcagca gccagccact accgcggcgg ccgccgtgag cggagccggc 10980
gttcagtatg acctggcctt ggaagagggc gaggggctgg cgcggctggg ggcgtcgtcg 11040
ccggagcggc acccgcgcgt gcagatgaaa agggacgctc gcgaggccta cgtgcccaag 11100
cagaacctgt tcagagacag gagcggcgag gagcccgagg agatgcgcgc ctcccgcttc 11160
cacgcggggc gggagctgcg gcgcggcctg gaccgaaagc gggtgctgag ggacgaggat 11220

-continued

```
ttcgaggcgg acgagctgac ggggatcagc cccgcgcgcg cgcacgtggc cgcggccaac  11280
ctggtcacgg cgtacgagca gaccgtgaag gaggagagca acttccaaaa atccttcaac  11340
aaccacgtgc gcacgctgat cgcgcgcgag gaggtgaccc tgggcctgat gcacctgtgg  11400
gacctgctgg aggccatcgt gcagaacccc acgagcaagc cgctgacggc gcagctgttt  11460
ctggtggtgc agcacagtcg ggacaacgag acgttcaggg aggcgctgct gaatatcacc  11520
gagcccgagg gccgctggct cctggacctg gtgaacattt tgcagagcat cgtggtgcag  11580
gagcgcgggc tgccgctgtc cgagaagctg gcggccatca acttctcggt gctgagtctg  11640
ggcaagtact acgctaggaa gatctacaag accccgtacg tgcccataga caaggaggtg  11700
aagatcgacg ggttttacat gcgcatgacc ctgaaagtgc tgaccctgag cgacgatctg  11760
ggggtgtacc gcaacgacag gatgcaccgc gcggtgagcg ccagccgccg gcgcgagctg  11820
agcgaccagg agctgatgca cagcctgcag cgggccctga ccggggccgg gaccgagggg  11880
gagagctact ttgacatggg cgcggacctg cgctggcagc ccagccgccg ggccttggaa  11940
gctgccggcg gttcccccta cgtggaggag gtggacgatg aggaggagga gggcgagtac  12000
ctggaagact gatggcgcga ccgtattttt gctagatgca gcaacagcca ccgccgccgc  12060
ctcctgatcc cgcgatgcgg gcggcgctgc agagccagcc gtccggcatt aactcctcgg  12120
acgattggac ccaggccatg caacgcatca tggcgctgac gacccgcaat cccgaagcct  12180
ttagacagca gcctcaggcc aaccggctct cggccatcct ggaggccgtg gtgccctcgc  12240
gctcgaaccc cacgcacgag aaggtgctgg ccatcgtgaa cgcgctggtg gagaacaagg  12300
ccatccgcgg tgacgaggcc gggctggtgt acaacgcgct gctggagcgc gtggcccgct  12360
acaacagcac caacgtgcag acgaacctgg accgcatggt gaccgacgtg cgcgaggcgg  12420
tgtcgcagcg cgagcggttc caccgcgagt cgaacctggg ctccatggtg gcgctgaacg  12480
ccttcctgag cacgcagccc gccaacgtgc cccggggcca ggaggactac accaacttca  12540
tcagcgcgct gcggctgatg gtggccgagg tgccccagag cgaggtgtac cagtcggggc  12600
cggactactt cttccagacc agtcgccagg gcttgcagac cgtgaacctg agccaggctt  12660
tcaagaactt gcagggactg tggggcgtgc aggccccggt cggggaccgc gcgacggtgt  12720
cgagcctgct gacgccgaac tcgcgcctgc tgctgctgct ggtggcgccc ttcacggaca  12780
gcggcagcgt gagccgcgac tcgtacctgg gctacctgct taacctgtac cgcgaggcca  12840
tcggacaggc gcacgtggac gagcagacct accaggagat cacccacgtg agccgcgcgc  12900
tgggccagga ggacccgggc aacctggagg ccaccctgaa cttcctgctg accaaccggt  12960
cgcagaagat cccgccccag tacgcgctga gcaccgagga ggagcgcatc ctgcgctacg  13020
tgcagcagag cgtggggctg ttcctgatgc aggagggggc cacgcccagc gcggcgctcg  13080
acatgaccgc gcgcaacatg gagcccagca tgtacgcccg caaccgcccg ttcatcaata  13140
agctgatgga ctacttgcat cgggcggccg ccatgaactc ggactacttt accaacgcca  13200
tcttgaaccc gcactggctc ccgccgcccg ggttctacac gggcgagtac gacatgcccg  13260
accccaacga cgggttcctg tgggacgacg tggacagcag cgtgttctcg ccgcgtccag  13320
gaaccaatgc cgtgtggaag aaagagggcg gggaccggcg gccgtcctcg gcgctgtccg  13380
gtcgcgcggg tgctgccgcg gcggtgcccg aggccgccag cccctcccg agcctgccct  13440
tttcgctgaa cagcgtgcgc agcagcgagc tgggtcggct gacgcgaccg cgcctgctgg  13500
gcgaggagga gtacctgaac gactccttgt tgaggcccga gcgcgagaag aacttcccca  13560
ataacgggat agagagcctg gtggacaaga tgagccgctg gaagacgtac gcgcacgagc  13620
```

-continued

```
acagggacga gccccgagct agcagcgcag gcacccgtag acgccagcgg cacgacaggc  13680

agcggggact ggtgtgggac gatgaggatt ccgccgacga cagcagcgtg ttggacttgg  13740

gtgggagtgg tggtaacccg ttcgctcacc tgcgcccccg tatcgggcgc ctgatgtaag  13800

aatctgaaaa aataaaagac ggtactcacc aaggccatgg cgaccagcgt gcgttcttct  13860

ctgttgtttg tagtagt atg atg agg cgc gtg tac ccg gag ggt cct cct     13910
                    Met Met Arg Arg Val Tyr Pro Glu Gly Pro Pro
                    1               5                   10

ccc tcg tac gag agc gtg atg cag cag gcg gtg gcg gcg gcg atg cag    13958
Pro Ser Tyr Glu Ser Val Met Gln Gln Ala Val Ala Ala Ala Met Gln
            15                  20                  25

ccc ccg ctg gag gcg cct tac gtg ccc ccg cgg tac ctg gcg cct acg    14006
Pro Pro Leu Glu Ala Pro Tyr Val Pro Pro Arg Tyr Leu Ala Pro Thr
        30                  35                  40

gag ggg cgg aac agc att cgt tac tcg gag ctg gca ccc ttg tac gat    14054
Glu Gly Arg Asn Ser Ile Arg Tyr Ser Glu Leu Ala Pro Leu Tyr Asp
    45                  50                  55

acc acc cgg ttg tac ctg gtg gac aac aag tcg gca gac atc gcc tcg    14102
Thr Thr Arg Leu Tyr Leu Val Asp Asn Lys Ser Ala Asp Ile Ala Ser
60                  65                  70                  75

ctg aac tac cag aac gac cac agc aac ttc ctg acc acc gtg gtg cag    14150
Leu Asn Tyr Gln Asn Asp His Ser Asn Phe Leu Thr Thr Val Val Gln
                80                  85                  90

aac aac gat ttc acc ccc acg gag gcc agc acc cag acc atc aac ttt    14198
Asn Asn Asp Phe Thr Pro Thr Glu Ala Ser Thr Gln Thr Ile Asn Phe
            95                  100                 105

gac gag cgc tcg cgg tgg ggc ggc cag ctg aaa acc atc atg cac acc    14246
Asp Glu Arg Ser Arg Trp Gly Gly Gln Leu Lys Thr Ile Met His Thr
        110                 115                 120

aac atg ccc aac gtg aac gag ttc atg tac agc aac aag ttc aag gcg    14294
Asn Met Pro Asn Val Asn Glu Phe Met Tyr Ser Asn Lys Phe Lys Ala
    125                 130                 135

cgg gtg atg gtc tcg cgc aag acc ccc aac ggg gtg gat gat gat tat    14342
Arg Val Met Val Ser Arg Lys Thr Pro Asn Gly Val Asp Asp Asp Tyr
140                 145                 150                 155

gat ggt agt cag gac gag ctg acc tac gag tgg gtg gag ttt gag ctg    14390
Asp Gly Ser Gln Asp Glu Leu Thr Tyr Glu Trp Val Glu Phe Glu Leu
                160                 165                 170

ccc gag ggc aac ttc tcg gtg acc atg acc atc gat ctg atg aac aac    14438
Pro Glu Gly Asn Phe Ser Val Thr Met Thr Ile Asp Leu Met Asn Asn
            175                 180                 185

gcc atc atc gac aac tac ttg gcg gtg ggg cgg cag aac ggg gtg ctg    14486
Ala Ile Ile Asp Asn Tyr Leu Ala Val Gly Arg Gln Asn Gly Val Leu
        190                 195                 200

gag agc gac atc ggc gtg aag ttc gac acg cgc aac ttc cgg ctg ggc    14534
Glu Ser Asp Ile Gly Val Lys Phe Asp Thr Arg Asn Phe Arg Leu Gly
    205                 210                 215

tgg gac ccc gtg acc gag ctg gtg atg ccg ggc gtg tac acc aac gag    14582
Trp Asp Pro Val Thr Glu Leu Val Met Pro Gly Val Tyr Thr Asn Glu
220                 225                 230                 235

gcc ttc cac ccc gac atc gtc ctg ctg ccc ggc tgc ggc gtg gac ttc    14630
Ala Phe His Pro Asp Ile Val Leu Leu Pro Gly Cys Gly Val Asp Phe
                240                 245                 250

acc gag agc cgc ctc agc aac ctg ctg ggc atc cgc aag cgg cag ccc    14678
Thr Glu Ser Arg Leu Ser Asn Leu Leu Gly Ile Arg Lys Arg Gln Pro
            255                 260                 265

ttc cag gag ggc ttc cag atc ctg tac gag gac ctg gag ggg ggc aac    14726
Phe Gln Glu Gly Phe Gln Ile Leu Tyr Glu Asp Leu Glu Gly Gly Asn
```

-continued

```
        270                 275                 280

atc ccc gcg ctc ttg gat gtc gaa gcc tac gag aaa agc aag gag gat    14774
Ile Pro Ala Leu Leu Asp Val Glu Ala Tyr Glu Lys Ser Lys Glu Asp
    285                 290                 295

agc acc gcc gcg gcg acc gca gcc gtg gcc acc gcc tct acc gag gtg    14822
Ser Thr Ala Ala Ala Thr Ala Ala Val Ala Thr Ala Ser Thr Glu Val
300                 305                 310                 315

cgg ggc gat aat ttt gct agc gct gcg gca gcg gcc gag gcg gct gaa    14870
Arg Gly Asp Asn Phe Ala Ser Ala Ala Ala Ala Ala Glu Ala Ala Glu
                320                 325                 330

acc gaa agt aag ata gtc atc cag ccg gtg gag aag gac agc aag gac    14918
Thr Glu Ser Lys Ile Val Ile Gln Pro Val Glu Lys Asp Ser Lys Asp
            335                 340                 345

agg agc tac aac gtg ctc gcg gac aag aaa aac acc gcc tac cgc agc    14966
Arg Ser Tyr Asn Val Leu Ala Asp Lys Lys Asn Thr Ala Tyr Arg Ser
        350                 355                 360

tgg tac ctg gcc tac aac tac ggc gac ccc gag aag ggc gtg cgc tcc    15014
Trp Tyr Leu Ala Tyr Asn Tyr Gly Asp Pro Glu Lys Gly Val Arg Ser
    365                 370                 375

tgg acg ctg ctc acc acc tcg gac gtc acc tgc ggc gtg gag caa gtc    15062
Trp Thr Leu Leu Thr Thr Ser Asp Val Thr Cys Gly Val Glu Gln Val
380                 385                 390                 395

tac tgg tcg ctg ccc gac atg atg caa gac ccg gtc acc ttc cgc tcc    15110
Tyr Trp Ser Leu Pro Asp Met Met Gln Asp Pro Val Thr Phe Arg Ser
                400                 405                 410

acg cgt caa gtt agc aac tac ccg gtg gtg ggc gcc gag ctc ctg ccc    15158
Thr Arg Gln Val Ser Asn Tyr Pro Val Val Gly Ala Glu Leu Leu Pro
            415                 420                 425

gtc tac tcc aag agc ttc ttc aac gag cag gcc gtc tac tcg cag cag    15206
Val Tyr Ser Lys Ser Phe Phe Asn Glu Gln Ala Val Tyr Ser Gln Gln
        430                 435                 440

ctg cgc gcc ttc acc tcg ctc acg cac gtc ttc aac cgc ttc ccc gag    15254
Leu Arg Ala Phe Thr Ser Leu Thr His Val Phe Asn Arg Phe Pro Glu
    445                 450                 455

aac cag atc ctc gtc cgc ccg ccc gcg ccc acc att acc acc gtc agt    15302
Asn Gln Ile Leu Val Arg Pro Pro Ala Pro Thr Ile Thr Thr Val Ser
460                 465                 470                 475

gaa aac gtt cct gct ctc aca gat cac ggg acc ctg ccg ctg cgc agc    15350
Glu Asn Val Pro Ala Leu Thr Asp His Gly Thr Leu Pro Leu Arg Ser
                480                 485                 490

agt atc cgg gga gtc cag cgc gtg acc gtc act gac gcc aga cgc cgc    15398
Ser Ile Arg Gly Val Gln Arg Val Thr Val Thr Asp Ala Arg Arg Arg
            495                 500                 505

acc tgc ccc tac gtc tac aag gcc ctg ggc gta gtc gcg ccg cgc gtc    15446
Thr Cys Pro Tyr Val Tyr Lys Ala Leu Gly Val Val Ala Pro Arg Val
        510                 515                 520

ctc tcg agc cgc acc ttc taa aaaatgtcca ttctcatctc gcccagtaat       15497
Leu Ser Ser Arg Thr Phe
    525

aacaccggtt ggggcctgcg cgcgcccagc aagatgtacg gaggcgctcg ccaacgctcc  15557

acgcaacacc ccgtgcgcgt gcgcgggcac ttccgcgctc cctggggcgc cctcaagggc  15617

cgcgtgcgct cgcgcaccac cgtcgacgac gtgatcgacc aggtggtggc cgacgcgcgc  15677

aactacacgc ccgccgccgc gcccgtctcc accgtggacg ccgtcatcga cagcgtggtg  15737

gccgacgcgc gccggtacgc ccgcaccaag agccggcggc ggcgcatcgc ccggcggcac  15797

cggagcaccc ccgccatgcg cgcggcgcga gccttgctgc gcagggccag gcgcacggga  15857

cgcagggcca tgctcagggc ggccagacgc gcggcctccg gcagcagcag cgccggcagg  15917
```

-continued

```
acccgcagac gcgcggccac ggcggcggcg gcggccatcg ccagcatgtc ccgcccgcgg  15977
cgcggcaacg tgtactgggt gcgcgacgcc gccaccggtg tgcgcgtgcc cgtgcgcacc  16037
cgcccccctc gcacttgaag atgctgactt cgcgatgttg atgtgtccca gcggcgagga  16097
ggatgtccaa gcgcaaatac aaggaagaga tgctccaggt catcgcgcct gagatctacg  16157
gccccgcggc ggcggtgaag gaggaaagaa agccccgcaa actgaagcgg gtcaaaaagg  16217
acaaaaagga ggaggaagat gacggactgg tggagtttgt gcgcgagttc gccccccggc  16277
ggcgcgtgca gtggcgcggg cggaaagtga aaccggtgct gcggcccggc accacggtgg  16337
tcttcacgcc cggcgagcgt tccggctccg cctccaagcg ctcctacgac gaggtgtacg  16397
gggacgagga catcctcgag caggcggtcg agcgtctggg cgagtttgcg tacggcaagc  16457
gcagccgccc cgcgcccttg aaagaggagg cggtgtccat cccgctggac cacggcaacc  16517
ccacgccgag cctgaagccg gtgaccctgc agcaggtgct accgagcgcg gcgccgcgcc  16577
ggggcttcaa gcgcgagggc ggcgaggatc tgtacccgac catgcagctg atggtgccca  16637
agcgccagaa gctggaggac gtgctggagc acatgaaggt ggaccccgag gtgcagcccg  16697
aggtcaaggt gcggcccatc aagcaggtgg ccccgggcct gggcgtgcag accgtggaca  16757
tcaagatccc cacggagccc atggaaacgc agaccgagcc cgtgaagccc agcaccagca  16817
ccatggaggt gcagacggat ccctggatgc cagcaccagc ttccaccagc actcgccgaa  16877
gacgcaagta cggcgcggcc agcctgctga tgcccaacta cgcgctgcat ccttccatca  16937
tccccacgcc gggctaccgc ggcacgcgct tctaccgcgg ctacaccagc agccgccgcc  16997
gcaagaccac cacccgccgc cgtcgtcgca gccgccgcag cagcaccgcg acttccgcct  17057
tggtgcggag agtgtatcgc agcgggcgcg agcctctgac cctgccgcgc gcgcgctacc  17117
acccgagcat cgccatttaa ctaccgcctc ctacttgcag atatggccct cacatgccgc  17177
ctccgcgtcc ccattacggg ctaccgagga agaaagccgc gccgtagaag gctgacgggg  17237
aacgggctgc gtcgccatca ccaccggcgg cggcgcgcca tcagcaagcg gttgggggga  17297
ggcttcctgc ccgcgctgat ccccatcatc gccgcggcga tcggggcgat ccccggcata  17357
gcttccgtgg cggtgcaggc ctctcagcgc cactgagaca caaaaaagca tggatttgta  17417
ataaaaaaaa aaatggactg acgctcctgg tcctgtgatg tgtgttttta gatggaagac  17477
atcaattttt cgtccctggc accgcgacac ggcacgcggc cgtttatggg cacctggagc  17537
gacatcggca acagccaact gaacgggggc gccttcaatt ggagcagtct ctggagcggg  17597
cttaagaatt tcgggtccac gctcaaaacc tatggcaaca aggcgtggaa cagcagcaca  17657
gggcaggcgc tgagggaaaa gctgaaagaa cagaacttcc agcagaaggt ggttgatggc  17717
ctggcctcag gcatcaacgg ggtggttgac ctggccaacc aggccgtgca gaaacagatc  17777
aacagccgcc tggacgcggt cccgcccgcg ggtccgtgg agatgcccca ggtggaggag  17837
gagctgcctc ccctggacaa gcgcggcgac aagcgaccgc gtcccgacgc ggaggagacg  17897
ctgctgacgc acacggacga gccgcccccg tacgaggagg cggtgaaact gggcctgccc  17957
accacgcggc ccgtggcgcc tctggccacc ggagtgctga aacccagcag cagccagccc  18017
gcgaccctgg acttgcctcc gcctcgcccc tccacagtgg ctaagcccct gccgccggtg  18077
gccgtcgcgt cgcgcgcccc ccgaggccgc ccccaggcga actggcagag cactctgaac  18137
agcatcgtgg gtctgggagt gcagagtgtg aagcgccgcc gctgctatta aaagacactg  18197
tagcgcttaa cttgcttgtc tgtgtgtata tgtatgtccg ccgaccagaa ggaggagtgt  18257
```

-continued

```
gaagaggcgc gtcgccgagt tgcaag atg gcc acc cca tcg atg ctg ccc cag   18310
                             Met Ala Thr Pro Ser Met Leu Pro Gln
                             530                 535

tgg gcg tac atg cac atc gcc gga cag gac gct tcg gag tac ctg agt    18358
Trp Ala Tyr Met His Ile Ala Gly Gln Asp Ala Ser Glu Tyr Leu Ser
    540                 545                 550

ccg ggt ctg gtg cag ttc gcc cgc gcc aca gac acc tac ttc agt ctg    18406
Pro Gly Leu Val Gln Phe Ala Arg Ala Thr Asp Thr Tyr Phe Ser Leu
555                 560                 565                 570

ggg aac aag ttt agg aac ccc acg gtg gcg ccc acg cac gat gtg acc    18454
Gly Asn Lys Phe Arg Asn Pro Thr Val Ala Pro Thr His Asp Val Thr
                575                 580                 585

acc gac cgc agc cag cgg ctg acg ctg cgc ttc gtg ccc gtg gac cgc    18502
Thr Asp Arg Ser Gln Arg Leu Thr Leu Arg Phe Val Pro Val Asp Arg
            590                 595                 600

gag gac aac acc tac tcg tac aaa gtg cgc tac acg ctg gcc gtg ggc    18550
Glu Asp Asn Thr Tyr Ser Tyr Lys Val Arg Tyr Thr Leu Ala Val Gly
        605                 610                 615

gac aac cgc gtg ctg gac atg gcc agc acc tac ttt gac atc cgc ggc    18598
Asp Asn Arg Val Leu Asp Met Ala Ser Thr Tyr Phe Asp Ile Arg Gly
    620                 625                 630

gtg ctg gac cgg ggc cct agc ttc aaa ccc tac tct ggc acc gcc tac    18646
Val Leu Asp Arg Gly Pro Ser Phe Lys Pro Tyr Ser Gly Thr Ala Tyr
635                 640                 645                 650

aac agc cta gct ccc aag gga gct ccc aat tcc agc cag tgg gag caa    18694
Asn Ser Leu Ala Pro Lys Gly Ala Pro Asn Ser Ser Gln Trp Glu Gln
                655                 660                 665

gca aaa aca ggc aat ggg gga act atg gaa aca cac aca tat ggt gtg    18742
Ala Lys Thr Gly Asn Gly Gly Thr Met Glu Thr His Thr Tyr Gly Val
            670                 675                 680

gcc cca atg ggc gga gag aat att aca aaa gat ggt ctt caa att gga    18790
Ala Pro Met Gly Gly Glu Asn Ile Thr Lys Asp Gly Leu Gln Ile Gly
        685                 690                 695

act gac gtt aca gcg aat cag aat aaa cca att tat gcc gac aaa aca    18838
Thr Asp Val Thr Ala Asn Gln Asn Lys Pro Ile Tyr Ala Asp Lys Thr
    700                 705                 710

ttt caa cca gaa ccg caa gta gga gaa gaa aat tgg caa gaa act gaa    18886
Phe Gln Pro Glu Pro Gln Val Gly Glu Glu Asn Trp Gln Glu Thr Glu
715                 720                 725                 730

aac ttt tat ggc ggt aga gct ctt aaa aaa gac aca aac atg aaa cct    18934
Asn Phe Tyr Gly Gly Arg Ala Leu Lys Lys Asp Thr Asn Met Lys Pro
                735                 740                 745

tgc tat ggc tcc tat gct aga ccc acc aat gaa aaa gga ggt caa gct    18982
Cys Tyr Gly Ser Tyr Ala Arg Pro Thr Asn Glu Lys Gly Gly Gln Ala
            750                 755                 760

aaa ctt aaa gtt gga gat gat gga gtt cca acc aaa gaa ttc gac ata    19030
Lys Leu Lys Val Gly Asp Asp Gly Val Pro Thr Lys Glu Phe Asp Ile
        765                 770                 775

gac ctg gct ttc ttt gat act ccc ggt ggc acc gtg aac ggt caa gac    19078
Asp Leu Ala Phe Phe Asp Thr Pro Gly Gly Thr Val Asn Gly Gln Asp
    780                 785                 790

gag tat aaa gca gac att gtc atg tat acc gaa aac acg tat ttg gaa    19126
Glu Tyr Lys Ala Asp Ile Val Met Tyr Thr Glu Asn Thr Tyr Leu Glu
795                 800                 805                 810

act cca gac acg cat gtg gta tac aaa cca ggc aag gat gat gca agt    19174
Thr Pro Asp Thr His Val Val Tyr Lys Pro Gly Lys Asp Asp Ala Ser
                815                 820                 825

tct gaa att aac ctg gtt cag cag tct atg ccc aac aga ccc aac tac    19222
Ser Glu Ile Asn Leu Val Gln Gln Ser Met Pro Asn Arg Pro Asn Tyr
            830                 835                 840
```

-continued

```
att ggg ttc agg gac aac ttt atc ggt ctt atg tac tac aac agc act    19270
Ile Gly Phe Arg Asp Asn Phe Ile Gly Leu Met Tyr Tyr Asn Ser Thr
        845                 850                 855

ggc aat atg ggt gtg ctt gct ggt cag gcc tcc cag ctg aat gct gtg    19318
Gly Asn Met Gly Val Leu Ala Gly Gln Ala Ser Gln Leu Asn Ala Val
    860                 865                 870

gtt gat ttg caa gac aga aac acc gag ctg tcc tac cag ctc ttg ctt    19366
Val Asp Leu Gln Asp Arg Asn Thr Glu Leu Ser Tyr Gln Leu Leu Leu
875                 880                 885                 890

gac tct ttg ggt gac aga acc cgg tat ttc agt atg tgg aac cag gcg    19414
Asp Ser Leu Gly Asp Arg Thr Arg Tyr Phe Ser Met Trp Asn Gln Ala
                895                 900                 905

gtg gac agt tat gac ccc gat gtg cgc atc atc gaa aac cat ggt gtg    19462
Val Asp Ser Tyr Asp Pro Asp Val Arg Ile Ile Glu Asn His Gly Val
            910                 915                 920

gag gat gaa ttg cca aac tat tgc ttc ccc ttg gac ggc tct ggc act    19510
Glu Asp Glu Leu Pro Asn Tyr Cys Phe Pro Leu Asp Gly Ser Gly Thr
        925                 930                 935

aac gcc gca tac caa ggt gtg aaa gta aaa gat ggt caa gat ggt gat    19558
Asn Ala Ala Tyr Gln Gly Val Lys Val Lys Asp Gly Gln Asp Gly Asp
    940                 945                 950

gtt gag agt gaa tgg gaa aat gac gat act gtt gca gct cga aat caa    19606
Val Glu Ser Glu Trp Glu Asn Asp Asp Thr Val Ala Ala Arg Asn Gln
955                 960                 965                 970

tta tgt aaa ggt aac att ttc gcc atg gag att aat ctc cag gct aac    19654
Leu Cys Lys Gly Asn Ile Phe Ala Met Glu Ile Asn Leu Gln Ala Asn
                975                 980                 985

ctg tgg aga agt ttc ctc tac tcg aac gtg gcc ctg tac ctg  ccc gac   19702
Leu Trp Arg Ser Phe Leu Tyr Ser Asn Val Ala Leu Tyr Leu  Pro Asp
            990                 995                 1000

tcc tac aag  tac acg ccg acc aac  gtc acg ctg ccg acc  aac acc     19747
Ser Tyr Lys  Tyr Thr Pro Thr Asn  Val Thr Leu Pro Thr  Asn Thr
        1005                 1010                 1015

aac acc tac  gat tac atg aat ggc  aga gtg aca cct ccc  tcg ctg     19792
Asn Thr Tyr  Asp Tyr Met Asn Gly  Arg Val Thr Pro Pro  Ser Leu
        1020                 1025                 1030

gta gac gcc  tac ctc aac atc ggg  gcg cgc tgg tcg ctg  gac ccc     19837
Val Asp Ala  Tyr Leu Asn Ile Gly  Ala Arg Trp Ser Leu  Asp Pro
        1035                 1040                 1045

atg gac aac  gtc aac ccc ttc aac  cac cac cgc aac gcg  ggc ctg     19882
Met Asp Asn  Val Asn Pro Phe Asn  His His Arg Asn Ala  Gly Leu
        1050                 1055                 1060

cgc tac cgc  tcc atg ctc ctg ggc  aac ggg cgc tac gtg  ccc ttc     19927
Arg Tyr Arg  Ser Met Leu Leu Gly  Asn Gly Arg Tyr Val  Pro Phe
        1065                 1070                 1075

cac atc cag  gtg ccc caa aag ttt  ttc gcc atc aag agc  ctc ctg     19972
His Ile Gln  Val Pro Gln Lys Phe  Phe Ala Ile Lys Ser  Leu Leu
        1080                 1085                 1090

ctc ctg ccc  ggg tcc tac acc tac  gag tgg aac ttc cgc  aag gac     20017
Leu Leu Pro  Gly Ser Tyr Thr Tyr  Glu Trp Asn Phe Arg  Lys Asp
        1095                 1100                 1105

gtc aac atg  atc ctg cag agc tcc  cta ggc aac gac ctg  cgc acg     20062
Val Asn Met  Ile Leu Gln Ser Ser  Leu Gly Asn Asp Leu  Arg Thr
        1110                 1115                 1120

gac ggg gcc  tcc atc gcc ttc acc  agc atc aac ctc tac  gcc acc     20107
Asp Gly Ala  Ser Ile Ala Phe Thr  Ser Ile Asn Leu Tyr  Ala Thr
        1125                 1130                 1135

ttc ttc ccc  atg gcg cac aac acc  gcc tcc acg ctc gag  gcc atg     20152
Phe Phe Pro  Met Ala His Asn Thr  Ala Ser Thr Leu Glu  Ala Met
```

-continued

```
        1140                1145                1150

ctg cgc aac  gac acc aac gac cag  tcc ttc aac gac tac  ctc tcg     20197
Leu Arg Asn  Asp Thr Asn Asp Gln  Ser Phe Asn Asp Tyr  Leu Ser
        1155                1160                1165

gcg gcc aac  atg ctc tac ccc atc  ccg gcc aac gcc acc  aac gtg     20242
Ala Ala Asn  Met Leu Tyr Pro Ile  Pro Ala Asn Ala Thr  Asn Val
        1170                1175                1180

ccc atc tcc  atc ccc tcg cgc aac  tgg gcc gcc ttc cgc  gga tgg     20287
Pro Ile Ser  Ile Pro Ser Arg Asn  Trp Ala Ala Phe Arg  Gly Trp
        1185                1190                1195

tcc ttc acg  cgc ctg aag acc cgc  gag acg ccc tcg ctc  ggc tcc     20332
Ser Phe Thr  Arg Leu Lys Thr Arg  Glu Thr Pro Ser Leu  Gly Ser
        1200                1205                1210

ggg ttc gac  ccc tac ttc gtc tac  tcg ggc tcc atc ccc  tac cta     20377
Gly Phe Asp  Pro Tyr Phe Val Tyr  Ser Gly Ser Ile Pro  Tyr Leu
        1215                1220                1225

gac ggc acc  ttc tac ctc aac cac  acc ttc aag aag gtc  tcc atc     20422
Asp Gly Thr  Phe Tyr Leu Asn His  Thr Phe Lys Lys Val  Ser Ile
        1230                1235                1240

acc ttc gac  tcc tcc gtc agc tgg  ccc ggc aac gac cgc  ctc ctg     20467
Thr Phe Asp  Ser Ser Val Ser Trp  Pro Gly Asn Asp Arg  Leu Leu
        1245                1250                1255

acg ccc aac  gag ttc gaa atc aag  cgc acc gtc gac gga  gag gga     20512
Thr Pro Asn  Glu Phe Glu Ile Lys  Arg Thr Val Asp Gly  Glu Gly
        1260                1265                1270

tac aac gtg  gcc cag tgc aac atg  acc aag gac tgg ttc  ctg gtc     20557
Tyr Asn Val  Ala Gln Cys Asn Met  Thr Lys Asp Trp Phe  Leu Val
        1275                1280                1285

cag atg ctg  gcc cac tac aac atc  ggc tac cag ggc ttc  tac gtg     20602
Gln Met Leu  Ala His Tyr Asn Ile  Gly Tyr Gln Gly Phe  Tyr Val
        1290                1295                1300

ccc gag ggc  tac aag gac cgc atg  tac tcc ttc ttc cgc  aac ttc     20647
Pro Glu Gly  Tyr Lys Asp Arg Met  Tyr Ser Phe Phe Arg  Asn Phe
        1305                1310                1315

cag ccc atg  agc cgc cag gtc gtg  gac gag gtc aac tac  aag gac     20692
Gln Pro Met  Ser Arg Gln Val Val  Asp Glu Val Asn Tyr  Lys Asp
        1320                1325                1330

tac cag gcc  gtc acc ctg gcc tac  cag cac aac aac tcg  ggc ttc     20737
Tyr Gln Ala  Val Thr Leu Ala Tyr  Gln His Asn Asn Ser  Gly Phe
        1335                1340                1345

gtc ggc tac  ctc gcg ccc acc atg  cgc cag ggc cag ccc  tac ccc     20782
Val Gly Tyr  Leu Ala Pro Thr Met  Arg Gln Gly Gln Pro  Tyr Pro
        1350                1355                1360

gcc aac tac  ccc tac ccg ctc atc  ggc aag agc gcc gtc  gcc agc     20827
Ala Asn Tyr  Pro Tyr Pro Leu Ile  Gly Lys Ser Ala Val  Ala Ser
        1365                1370                1375

gtc acc cag  aaa aag ttc ctc tgc  gac cgg gtc atg tgg  cgc atc     20872
Val Thr Gln  Lys Lys Phe Leu Cys  Asp Arg Val Met Trp  Arg Ile
        1380                1385                1390

ccc ttc tcc  agc aac ttc atg tcc  atg ggc gcg ctc acc  gac ctc     20917
Pro Phe Ser  Ser Asn Phe Met Ser  Met Gly Ala Leu Thr  Asp Leu
        1395                1400                1405

ggc cag aac  atg ctc tac gcc aac  tcc gcc cac gcg cta  gac atg     20962
Gly Gln Asn  Met Leu Tyr Ala Asn  Ser Ala His Ala Leu  Asp Met
        1410                1415                1420

aat ttc gaa  gtc gac ccc atg gat  gag tcc acc ctt ctc  tat gtt     21007
Asn Phe Glu  Val Asp Pro Met Asp  Glu Ser Thr Leu Leu  Tyr Val
        1425                1430                1435

gtc ttc gaa  gtc ttc gac gtc gtc  cga gtg cac cag ccc  cac cgc     21052
```

-continued

```
Val Phe Glu  Val Phe Asp Val Val  Arg Val His Gln Pro  His Arg
        1440                1445                1450

ggc gtc atc  gaa gcc gtc tac ctg  cgc acg ccc ttc tcg  gcc ggc    21097
Gly Val Ile  Glu Ala Val Tyr Leu  Arg Thr Pro Phe Ser  Ala Gly
        1455                1460                1465

aac gcc acc  acc taa gccgctcttg cttcttgcaa gatgacggcg ggctccggcg  21152
Asn Ala Thr  Thr
        1470

agcaggagct cagggccatc ctccgcgacc tgggctgcgg gccctgcttc ctgggcacct  21212

tcgacaagcg cttccctgga ttcatggccc cgcacaagct ggcctgcgcc atcgtgaaca  21272

cggccggccg cgagaccggg ggcgagcact ggctggcctt cgcctggaac ccgcgctccc  21332

acacatgcta cctcttcgac cccttcgggt tctcggacga gcgcctcaag cagatctacc  21392

agttcgagta cgagggcctg ctgcgtcgca gcgccctggc caccgaggac cgctgcgtca  21452

ccctggaaaa gtccacccag accgtgcagg gtccgcgctc ggccgcctgc gggctcttct  21512

gctgcatgtt cctgcacgcc ttcgtgcact ggcccgaccg ccccatggac aagaacccca  21572

ccatgaactt actgacgggg gtgcccaacg gcatgctcca gtcgccccag gtggaaccca  21632

ccctgcgccg caaccaggaa gcgctctacc gcttcctcaa tgcccactcc gcctactttc  21692

gctcccaccg cgcgcgcatc gagaaggcca ccgccttcga ccgcatgaat caagacatgt  21752

aaaaaaccgg tgtgtgtatg tgaatgcttt attcataata aacagcacat gtttatgcca  21812

ccttctctga ggctctgact ttatttagaa atcgaagggg ttctgccggc tctcggcatg  21872

gcccgcgggc agggatacgt tgcggaactg gtacttgggc agccacttga actcggggat  21932

cagcagcttg ggcacgggga ggtcggggaa cgagtcgctc cacagcttgc gcgtgagttg  21992

cagggcgccc agcaggtcgg gcgcggagat cttgaaatcg cagttgggac ccgcgttctg  22052

cgcgcgagag ttgcggtaca cggggttgca gcactggaac accatcaggg ccgggtgctt  22112

cacgcttgcc agcaccgtcg cgtcggtgat gccctccacg tccagatcct cggcgttggc  22172

catcccgaag gggtcatct tgcaggtctg ccgccccatg ctgggcacgc agccgggctt  22232

gtggttgcaa tcgcagtgca gggggatcag catcatctgg gcctgctcgg agctcatgcc  22292

cgggtacatg gccttcatga aagcctccag ctggcggaag gcctgctgcg ccttgccgcc  22352

ctcggtgaag aagaccccgc aggacttgct agagaactgg ttggtggcgc agccggcgtc  22412

gtgcacgcag cagcgcgcgt cgttgttggc cagctgcacc acgctgcgcc cccagcggtt  22472

ctgggtgatc ttggcccggt tggggttctc cttcagcgcg cgctgcccgt tctcgctcgc  22532

cacatccatc tcgatagtgt gctccttctg gatcatcacg gtcccgtgca ggcaccgcag  22592

cttgccctcg gcttcggtgc agccgtgcag ccacagcgcg cagccggtgc actcccagtt  22652

cttgtgggcg atctgggagt gcgagtgcac gaagccctgc aggaagcggc ccatcatcgc  22712

ggtcagggtc ttgttgctgg tgaaggtcag cgggatgccg cggtgctcct cgttcacata  22772

caggtggcag atgcggcggt acacctcgcc ctgctcgggc atcagctgga aggcggactt  22832

caggtcgctc tccacgcggt accggtccat cagcagcgtc atcacttcca tgcccttctc  22892

ccaggccgaa acgatcggca ggctcagggg gttcttcacc gccattgtca tcttagtcgc  22952

cgccgccgag gtcagggggt cgttctcgtc cagggtctca aacactcgct tgccgtcctt  23012

ctcgatgatg cgcacggggg gaaagctgaa gcccacggcc gccagctcct cctcggcctg  23072

cctttcgtcc tcgctgtcct ggctgatgtc ttgcaaaggc acatgcttgg tcttgcgggg  23132

tttctttttg ggcggcagag gcggcggcga tgtgctggga gagcgcgagt tctcgttcac  23192
```

-continued

```
cacgactatt tcttcttctt ggccgtcgtc cgagaccacg cggcggtagg catgcctctt  23252
ctggggcaga ggcggaggcg acgggctctc gcggttcggc gggcggctgg cagagcccct  23312
tccgcgttcg ggggtgcgct cctggcggcg ctgctctgac tgacttcctc cgcggccggc  23372
cattgtgttc tcctagggag caacaacaag catggagact cagccatcgt cgccaacatc  23432
gccatctgcc cccgccgcca ccgccgacga gaaccagcag cagaatgaaa gcttaaccgc  23492
cccgccgccc agccccacct ccgacgccgc ggccccagac atgcaagaga tggaggaatc  23552
catcgagatt gacctgggct acgtgacgcc cgcggagcac gaggaggagc tggcagcgcg  23612
cttttcagcc ccggaagaga accaccaaga gcagccagag caggaagcag agaacgagca  23672
gaaccaggct gggcacgagc atggcgacta cctgagcggg gcagaggacg tgctcatcaa  23732
gcatctggcc cgccaatgca tcatcgtcaa ggacgcgctg ctcgaccgcg ccgaggtgcc  23792
cctcagcgtg gcggagctca gccgcgccta cgagcgcaac ctcttctcgc cgcgcgtgcc  23852
ccccaagcgc cagcccaacg gcacctgtga gcccaacccg cgcctcaact tctacccggt  23912
cttcgcggtg cccgaggccc tggccaccta ccacctcttt ttcaagaacc aaaggatccc  23972
cgtctcctgc cgcgccaacc gcacccgcgc cgacgccctg ctcaacctgg gccccggcgc  24032
ccgcctacct gatatcacct ccttggaaga ggttcccaag atcttcgagg gtctgggcag  24092
cgacgagact cgggccgcga acgctctgca aggaagcgga gaggagcatg agcaccacag  24152
cgccctggtg gagttggaag gcgacaacgc gcgcctggcg gtcctcaagc gcacggtcga  24212
gctgacccac ttcgcctacc cggcgctcaa cctgcccccc aaggtcatga gcgccgtcat  24272
ggaccaggtg ctcatcaagc gcgcctcgcc cctctcggag gaggagatgc aggaccccga  24332
gagttcggac gagggcaagc ccgtggtcag cgacgagcag ctggcgcgct ggctgggagc  24392
gagtagcacc ccccagagcc tggaagagcg gcgcaagctc atgatggccg tggtcctggt  24452
gaccgtggag ctggagtgtc tgcgccgctt ctttgccgac gcggagaccc tgcgcaaggt  24512
cgaggagaac ctgcactacc tcttcaggca cgggttcgtg cgccaggcct gcaagatctc  24572
caacgtggag ctgaccaacc tggtctccta catgggcatc ctgcacgaga accgcctggg  24632
gcaaaacgtg ctgcacacca ccctgcgcgg ggaggcccgc cgcgactaca tccgcgactg  24692
cgtctacctg tacctctgcc acacctggca gacgggcatg ggcgtgtggc agcagtgcct  24752
ggaggagcag aacctgaaag agctctgcaa gctcctgcag aagaacctca aggccctgtg  24812
gaccgggttc gacgagcgta ccaccgcctc ggacctggcc gacctcatct tccccgagcg  24872
cctgcggctg acgctgcgca acgggctgcc cgactttatg agccaaagca tgttgcaaaa  24932
ctttcgctct ttcatcctcg aacgctccgg gatcctgccc gccacctgct ccgcgctgcc  24992
ctcggacttc gtgccgctga ccttccgcga gtgccccccg ccgctctgga gccactgcta  25052
cttgctgcgc ctggccaact acctggccta ccactcggac gtgatcgagg acgtcagcgg  25112
cgagggtctg ctggagtgcc actgccgctg caacctctgc acgccgcacc gctccctggc  25172
ctgcaacccc cagctgctga gcgagaccca gatcatcggc accttcgagt tgcaaggccc  25232
cggcgacggc gagggcaagg ggggtctgaa actcaccccg gggctgtgga cctcggccta  25292
cttgcgcaag ttcgtgcccg aggactacca tcccttcgag atcaggttct acgaggacca  25352
atcccagccg cccaaggccg agctgtcggc ctgcgtcatc acccaggggg ccatcctggc  25412
ccaattgcaa gccatccaga aatcccgcca agaatttctg ctgaaaaagg gccacggggt  25472
ctacttggac ccccagaccg gagaggagct caaccccagc ttcccccagg atgccccgag  25532
gaagcagcaa gaagctgaaa gtggagctgc cgccgccgga ggatttggag gaagactggg  25592
```

-continued agagcagtca ggcagaggag gaggagatgg aagactggga cagcactcag gcagaggagg 25652
acagcctgca agacagtctg gaggaggaag acgaggtgga ggaggcagag gaagaagcag 25712
ccgccgccag accgtcgtcc tcggcggaga aagcaagcag cacggatacc atctccgctc 25772
cgggtcgggg tcgcggcggc cgggcccaca gtaggtggga cgagaccggg cgcttcccga 25832
accccaccac ccagaccggt aagaaggagc ggcagggata caagtcctgg cgggggcaca 25892
aaaacgccat cgtctcctgc ttgcaagcct gcgggggcaa catctccttc acccggcgct 25952
acctgctctt ccaccgcggg gtgaacttcc cccgcaacat cttgcattac taccgtcacc 26012
tccacagccc ctactactgt ttccaagaag aggcagaaac ccagcagcag cagaaaacca 26072
gcggcagcag cagctagaaa atccacagcg gcggcaggtg gactgaggat cgcggcgaac 26132
gagccggcgc agacccggga gctgaggaac cggatctttc ccaccctcta tgccatcttc 26192
cagcagagtc gggggcagga gcaggaactg aaagtcaaga accgttctct gcgctcgctc 26252
acccgcagtt gtctgtatca caagagcgaa gaccaacttc agcgcactct cgaggacgcc 26312
gaggctctct tcaacaagta ctgcgcgctc actcttaaag agtagcccgc gcccgcccac 26372
acacggaaaa aggcgggaat tacgtcacca cctgcgccct tcgcccgacc atcatgagca 26432
aagagattcc cacgccttac atgtggagct accagcccca gatgggcctg gccgccggcg 26492
ccgcccagga ctactccacc cgcatgaact ggctcagtgc cgggcccgcg atgatctcac 26552
gggtgaatga catccgcgcc caccgaaacc agatactcct agaacagtca gcgatcaccg 26612
ccacgccccg ccatcacctt aatccgcgta attggcccgc cgccctggtg taccaggaaa 26672
ttccccagcc cacgaccgta ctacttccgc gagacgccca ggccgaagtc cagctgacta 26732
actcaggtgt ccagctggcc ggcggcgccg ccctgtgtcg tcaccgcccc gctcagggta 26792
taaagcggct ggtgatccga ggcagaggca cacagctcaa cgacgaggtg gtgagctctt 26852
cgctgggtct gcgacctgac ggagtcttcc aactcgccgg atcggggaga tcttccttca 26912
cgcctcgtca ggccgtcctg actttggaga gttcgtcctc gcagccccgc tcgggcggca 26972
tcggcactct ccagttcgtg gaggagttca ctccctcggt ctacttcaac cccttctccg 27032
gctcccccgg ccactacccg gacgagttca tcccgaactt cgacgccatc agcgagtcgg 27092
tggacggcta cgattgaatg tcccatggtg gcgcagctga cctagctcgg cttcgacacc 27152
tggaccactg ccgccgcttc cgctgcttcg ctcgggatct cgccgagttt gcctactttg 27212
agctgcccga ggagcaccct cagggcccag cccacggagt gcggatcatc gtcgaagggg 27272
gcctcgactc ccacctgctt cggatcttca gccagcgacc gatcctggtc gagcgcgaac 27332
aaggacagac ccttcttact ttgtactgca tctgcaacca ccccggcctg catgaaagtc 27392
tttgttgtct gctgtgtact gagtataata aaagctgaga tcagcgacta ctccggactc 27452
gattgtggtg ttcctgctat caaccggtcc ctgttcttca ccgggaacga gaccgagctc 27512
cagctccagt gtaagcccca caagaagtac ctcacctggc tgttccaggg ctccccgatc 27572
gccgttgtca accactgcga caacgacgga gtcctgctga gcggccctgc caaccttact 27632
ttttccaccc gcagaagcaa gctccagctc ttccaaccct tcctccccgg gacctatcag 27692
tgcgtctcag gaccctgcca tcacaccttc cacctgatcc cgaataccac agcgccgctc 27752
cccgctacta acaaccaaac tacccaccaa cgccaccgtc gcgacctttc ctctgaatct 27812
aataccacta ccggaggtga gctccgaggt cgaccaacct ctgggattta ctacggcccc 27872
tgggaggtgg tggggttaat agcgctaggc ctagttgcgg gtgggctttt ggttctctgc 27932

-continued

```
tacctatacc tcccttgctg ttcgtactta gtggtgctgt gttgctggtt taagaaatgg  27992
ggaagatcac cctagtgagc tgcggtgcgc tggtggcggt gttgctttcg attgtgggac  28052
tgggcggcgc ggctgtagtg aaggagaagg ccgatccctg cttgcatttc aatcccaaca  28112
aatgccagct gagttttcag cccgatggca atcggtgcgc ggtactgatc aagtgcggat  28172
gggaatgcga gaacgtgaga atcgagtaca ataacaagac tcggaacaat actctcgcgt  28232
ccgtgtggca gcccggggac cccgagtggt acaccgtctc tgtccccggt gctgacggct  28292
ccccgcgcac cgtgaataat actttcattt ttgcgcacat gtgcaacacg gtcatgtgga  28352
tgagcaagca gtacgatatg tggcccccca cgaaggagaa catcgtggtc ttctccatcg  28412
cttacagcct gtgcacggcg ctaatcaccg ctatcgtgtg cctgagcatt cacatgctca  28472
tcgctattcg ccccagaaat aatgccgaga aagagaaaca gccataacac gtttttttcac  28532
acaccttgtt tttacagaca atgcgtctgt taaatttttt aaacattgtg ctcagtattg  28592
cttatgcctc tggttatgca aacatacaga aaaccccttta tgtaggatct gatggtacac  28652
tagagggtac ccaatcacaa gccaaggttg catggtattt ttatagaacc aacactgatc  28712
cagttaaact ttgtaagggt gaattgccgc gtacacataa aactccactt acatttagtt  28772
gcagcaataa taatcttaca cttttttcaa ttacaaaaca atatactggt acttattaca  28832
gtacaaactt tcatacagga caagataaat attatactgt taaggtagaa aatcctacca  28892
ctcctagaac taccaccacc accactactg caaagcccac tgtgaaaact acaactagga  28952
ccaccacaac tacagaaacc accaccagca caacacttgc tgcaactaca cacacacaca  29012
ctaagctaac cttacagacc actaatgatt tgatcgccct gctgcaaaag gggggataaca  29072
gcaccacttc caatgaggag atacccaaat ccatgattgg cattattgtt gctgtagtgg  29132
tgtgcatgtt gatcatcgcc ttgtgcatgg tgtactatgc cttctgctac agaaagcaca  29192
gactgaacga caagctggaa cacttactaa gtgttgaatt ttaatttttt agaaccatga  29252
agatcctagg ccttttttagt ttttctatca ttacctctgc tctttgtgaa tcagtggata  29312
gagatgttac tattaccact ggttctaatt atacactgaa agggccaccc tcaggtatgc  29372
tttcgtggta ttgctatttt ggaactgaca ctgatcaaac tgaattatgc aattttcaaa  29432
aaggcaaaac ctcaaactct aaaatctcta attatcaatg caatggcact gatctgatac  29492
tactcaatgt cacgaaagca tatggtggca gttattattg ccctggacaa aacactgaag  29552
aaatgatttt ttacaaagtg gaagtggttg atcccactac accacccacc accacaacta  29612
ttcataccac acacacagaa caaacaccag aggcaacaga agcagagttg gccttccagg  29672
ttcacggaga ttcctttgct gtcaataccc ctacacccga tcagcggtgt ccggggccgc  29732
tagtcagcgg cattgtcggt gtgctttcgg gattagcagt cataatcatc tgcatgttca  29792
tttttgcttg ctgctataga aggctttacc gacaaaaatc agacccactg ctgaacctct  29852
atgtttaatt ttttccagag ccatgaaggc agttagcgct ctagtttttt gttctttgat  29912
tggcattgtt tttaatagta aaattaccag agttagcttt attaaacatg ttaatgtaac  29972
tgaaggagat aacatcacac tagcaggtgt agaaggtgct caaaacacca cctggacaaa  30032
ataccatcta ggatggagag atatttgcac ctggaatgta acttattatt gcataggagt  30092
taatcttacc attgttaacg ctaaccaatc tcagaatggg ttaattaaag gacagagtgt  30152
tagtgtgacc agtgatgggt actataccca gcatagtttt aactacaaca ttactgtcat  30212
accactgcct acgcctagcc cacctagcac taccacacag acaaccacat acagtacatc  30272
aaatcagcct accaccacta cagcagcaga ggttgccagc tcgtctgggg tccgagtggc  30332
```

-continued

```
atttttgatg ttggccccat ctagcagtcc cactgctagt accaatgagc agactactga  30392

atttttgtcc actgtcgaga gccacaccac agctacctcc agtgccttct ctagcaccgc  30452

caatctctcc tcgctttcct ctacaccaat cagccccgct actactccta gccccgctcc  30512

tcttcccact cccctgaagc aaacagacgg cggcatgcaa tggcagatca ccctgctcat  30572

tgtgatcggg ttggtcatcc tggccgtgtt gctctactac atcttctgcc gccgcattcc  30632

caacgcgcac cgcaagccgg cctacaagcc catcgttatc gggcagccgg agccgcttca  30692

ggtggaaggg ggtctaagga atcttctctt ctcttttaca gtatggtgat tgaactatga  30752

ttcctagaca attcttgatc actattctta tctgcctcct ccaagtctgt gccaccctcg  30812

ctctggtggc caacgccagt ccagactgta ttgggccctt cgcctcctac gtgctctttg  30872

ccttcgtcac ctgcatctgc tgctgtagca tagtctgcct gcttatcacc ttcttccagt  30932

tcattgactg gatctttgtg cgcatcgcct acctgcgcca ccacccccag taccgcgacc  30992

agcgagtggc gcagctgctc aggctcctct gataagcatg cgggctctgc tacttctcgc  31052

gcttctgctg ttagtgctcc cccgtcccgt cgacccccgg tcccccactc agtcccccga  31112

ggaggttcgc aaatgcaaat tccaagaacc ctggaaattc ctcaaatgct accgccaaaa  31172

atcagacatg catcccagct ggatcatgat cattgggatc gtgaacattc tggcctgcac  31232

cctcatctcc tttgtgattt acccctgctt tgactttggt tggaactcgc cagaggcgct  31292

ctatctcccg cctgaacctg acacaccacc acagcagcaa cctcaggcac acgcactacc  31352

accaccacag cctaggccac aatacatgcc catattagac tatgaggccg agccacagcg  31412

acccatgctc cccgctatta gttacttcaa tctaaccggc ggagatgact gacccactgg  31472

ccaataacaa cgtcaacgac cttctcctgg acatggacgg ccgcgcctcg gagcagcgac  31532

tcgcccaact tcgcattcgt cagcagcagg agagagccgt caaggagctg caggacggca  31592

tagccatcca ccagtgcaag agaggcatct tctgcctggt gaaacaggcc aagatctcct  31652

acgaggtcac ccagaccgac catcgcctct cctacgagct cctgcagcag cgccagaagt  31712

tcacctgcct ggtcggagtc aaccccatcg tcatcaccca gcagtcgggc gataccaagg  31772

ggtgcatcca ctgctcctgc gactcccccg actgcgtcca cactctgatc aagaccctct  31832

gcggcctccg cgacctcctc cccatgaact aatcaccccc ttatccagtg aaataaagat  31892

catattgatg atgatttaaa taaaaaaaat aatcatttga tttgaaataa agatacaatc  31952

atattgatga tttgagttta acaaaaaataa agaatcactt acttgaaatc tgataccagg  32012

tctctgtcca tgttttctgc caacaccacc tcactcccct cttcccagct ctggtactgc  32072

aggccccggc gggctgcaaa cttcctccac acgctgaagg ggatgtcaaa ttcctcctgt  32132

ccctcaatct tcattttatc ttctatcag atg tcc aaa aag  cgc gtc cgg gtg   32185
                                Met Ser Lys Lys  Arg Val Arg Val
                                            1475

gat  gat gac ttc gac ccc  gtc tac ccc tac gat  gca gac aac gca     32230
Asp  Asp Asp Phe Asp Pro  Val Tyr Pro Tyr Asp  Ala Asp Asn Ala
1480                 1485                 1490

ccg  acc gtg ccc ttc atc  aac ccc ccc ttc gtc  tct tca gat gga     32275
Pro  Thr Val Pro Phe Ile  Asn Pro Pro Phe Val  Ser Ser Asp Gly
1495                 1500                 1505

ttc  caa gag aag ccc ctg  ggg gtg ttg tcc ctg  cga ctg gct gac     32320
Phe  Gln Glu Lys Pro Leu  Gly Val Leu Ser Leu  Arg Leu Ala Asp
1510                 1515                 1520

ccc  gtc acc acc aag aac  ggg gaa atc acc ctc  aag ctg gga gag     32365
Pro  Val Thr Thr Lys Asn  Gly Glu Ile Thr Leu  Lys Leu Gly Glu
```

-continued

```
1525                1530                1535

ggg  gtg gac ctc gac tcg  tcg gga aaa ctc atc  tcc aac acg gcc     32410
Gly  Val Asp Leu Asp Ser  Ser Gly Lys Leu Ile  Ser Asn Thr Ala
1540                1545                1550

acc  aag gcc gcc gcc cct  ctc agt att tca aac  aac acc att tcc     32455
Thr  Lys Ala Ala Ala Pro  Leu Ser Ile Ser Asn  Asn Thr Ile Ser
1555                1560                1565

ctt  aaa act gct gcc cct  ttc tac aac aac aat  gga act tta agc     32500
Leu  Lys Thr Ala Ala Pro  Phe Tyr Asn Asn Asn  Gly Thr Leu Ser
1570                1575                1580

ctc  aat gtc tcc aca cca  tta gca gta ttt ccc  aca ttt aac act     32545
Leu  Asn Val Ser Thr Pro  Leu Ala Val Phe Pro  Thr Phe Asn Thr
1585                1590                1595

tta  ggc ata agt ctt gga  aac ggt ctt cag act  tca aat aag ttg     32590
Leu  Gly Ile Ser Leu Gly  Asn Gly Leu Gln Thr  Ser Asn Lys Leu
1600                1605                1610

ttg  act gta caa cta act  cat cct ctt aca ttc  agc tca aat agc     32635
Leu  Thr Val Gln Leu Thr  His Pro Leu Thr Phe  Ser Ser Asn Ser
1615                1620                1625

atc  aca gta aaa aca gac  aaa ggg cta tat att  aac tcc agt gga     32680
Ile  Thr Val Lys Thr Asp  Lys Gly Leu Tyr Ile  Asn Ser Ser Gly
1630                1635                1640

aac  aga gga ctt gag gct  aat ata agc cta aaa  aga gga cta gtt     32725
Asn  Arg Gly Leu Glu Ala  Asn Ile Ser Leu Lys  Arg Gly Leu Val
1645                1650                1655

ttt  gac ggt aat gct att  gca aca tat att gga  aat ggc tta gac     32770
Phe  Asp Gly Asn Ala Ile  Ala Thr Tyr Ile Gly  Asn Gly Leu Asp
1660                1665                1670

tat  gga tct tat gat agt  gat gga aaa aca aga  ccc gta att acc     32815
Tyr  Gly Ser Tyr Asp Ser  Asp Gly Lys Thr Arg  Pro Val Ile Thr
1675                1680                1685

aaa  att gga gca gga tta  aat ttt gat gct aac  aaa gca ata gct     32860
Lys  Ile Gly Ala Gly Leu  Asn Phe Asp Ala Asn  Lys Ala Ile Ala
1690                1695                1700

gtc  aaa cta ggc aca ggt  tta agt ttt gac tcc  gct ggt gcc ttg     32905
Val  Lys Leu Gly Thr Gly  Leu Ser Phe Asp Ser  Ala Gly Ala Leu
1705                1710                1715

aca  gct gga aac aaa cag  gat gac aag cta aca  ctt tgg act acc     32950
Thr  Ala Gly Asn Lys Gln  Asp Asp Lys Leu Thr  Leu Trp Thr Thr
1720                1725                1730

cct  gac cca agc cct aat  tgt caa tta ctt tca  gac aga gat gcc     32995
Pro  Asp Pro Ser Pro Asn  Cys Gln Leu Leu Ser  Asp Arg Asp Ala
1735                1740                1745

aaa  ttt act ctc tgt ctt  aca aaa tgc ggt agt  caa ata cta ggc     33040
Lys  Phe Thr Leu Cys Leu  Thr Lys Cys Gly Ser  Gln Ile Leu Gly
1750                1755                1760

act  gtg gca gtg gcg gct  gtt act gta gga tca  gca cta aat cca     33085
Thr  Val Ala Val Ala Ala  Val Thr Val Gly Ser  Ala Leu Asn Pro
1765                1770                1775

att  aat gac aca gtc aaa  agc gcc ata gtt ttc  ctt aga ttt gat     33130
Ile  Asn Asp Thr Val Lys  Ser Ala Ile Val Phe  Leu Arg Phe Asp
1780                1785                1790

tcc  gat ggt gta ctc atg  tca aac tca tca atg  gta ggt gat tac     33175
Ser  Asp Gly Val Leu Met  Ser Asn Ser Ser Met  Val Gly Asp Tyr
1795                1800                1805

tgg  aac ttt agg gag gga  cag acc act caa agt  gta gcc tat aca     33220
Trp  Asn Phe Arg Glu Gly  Gln Thr Thr Gln Ser  Val Ala Tyr Thr
1810                1815                1820

aat  gct gtg gga ttc atg  cca aat ata ggt gca  tat cca aaa acc     33265
```

-continued

```
Asn  Ala Val Gly Phe Met  Pro Asn Ile Gly Ala  Tyr Pro Lys Thr
1825                 1830                 1835

caa  agt aaa aca cct aaa  aat agc ata gtc agt  cag gta tat tta     33310
Gln  Ser Lys Thr Pro Lys  Asn Ser Ile Val Ser  Gln Val Tyr Leu
1840                 1845                 1850

act  gga gaa act act atg  cca atg aca cta acc  ata act ttc aat     33355
Thr  Gly Glu Thr Thr Met  Pro Met Thr Leu Thr  Ile Thr Phe Asn
1855                 1860                 1865

ggc  act gat gaa aaa gac  aca acc cca gtt agc  acc tac tct atg     33400
Gly  Thr Asp Glu Lys Asp  Thr Thr Pro Val Ser  Thr Tyr Ser Met
1870                 1875                 1880

act  ttt aca tgg cag tgg  act gga gac tat aag  gac aaa aat att     33445
Thr  Phe Thr Trp Gln Trp  Thr Gly Asp Tyr Lys  Asp Lys Asn Ile
1885                 1890                 1895

acc  ttt gct acc aac tca  ttc tct ttt tcc tac  atc gcc cag gaa     33490
Thr  Phe Ala Thr Asn Ser  Phe Ser Phe Ser Tyr  Ile Ala Gln Glu
1900                 1905                 1910

taa tcccacccag caagccaacc ccttttccca ccacctttgt ctatatggaa         33543

actctgaaac agaaaaataa agttcaagtg ttttattgaa tcaacagttt tacaggactc  33603

gagcagttat ttttcctcca ccctcccagg acatggaata caccaccctc tccccccgca  33663

cagccttgaa catctgaatg ccattggtga tggacatgct tttggtctcc acgttccaca  33723

cagtttcaga gcgagccagt ctcggatcgg tcagggagat gaaaccctcc gggcactccc  33783

gcatctgcac ctcacagctc aacagctgag gattgtcctc ggtggtcggg atcacggtta  33843

tctggaagaa gcagaagagc ggcggtggga atcatagtcc gcgaacggga tcggccggtg  33903

gtgtcgcatc aggccccgca gcagtcgctg ccgccgccgc tccgtcaagc tgctgctcag  33963

ggggttcggg tccagggact ccctcagcat gatgcccacg gccctcagca tcagtcgtct  34023

ggtgcggcgg gcgcagcagc gcatgcgaat ctcgctcagg tcactgcagt acgtgcaaca  34083

caggaccacc aggttgttca acagtccata gttcaacacg ctccagccga aactcatcgc  34143

gggaaggatg ctacccacgt ggccgtcgta ccagatcctc aggtaaatca agtggcgctc  34203

cctccagaag acgctgccca tgtacatgat ctccttgggc atgtggcggt tcaccacctc  34263

ccggtaccac atcaccctct ggttgaacat gcagccccgg atgatcctgc ggaaccacag  34323

ggccagcacc gccccgcccg ccatgcagcg aagagacccc ggatcccggc aatgacaatg  34383

gaggacccac cgctcgtacc cgtggatcat ctgggagctg aacaagtcta tgttggcaca  34443

gcacaggcat atgctcatgc atctcttcag cactctcagc tcctcggggg tcaaaaccat  34503

atcccagggc acggggaact cttgcaggac agcgaacccc gcagaacagg gcaatcctcg  34563

cacataactt acattgtgca tggacagggt atcgcaatca ggcagcaccg ggtgatcctc  34623

caccagagaa gcgcgggtct cggtctcctc acagcgtggt aagggggccg gccgatacgg  34683

gtgatggcgg gacgcggctg atcgtgttct cgaccgtgtc atgatgcagt tgctttcgga  34743

cattttcgta cttgctgtag cagaacctgg tccgggcgct gcacaccgat cgccggcggc  34803

ggtctcggcg cttggaacgc tcggtgttaa agttgtaaaa cagccactct ctcagaccgt  34863

gcagcagatc tagggcctca ggagtgatga agatcccatc atgcctgata gctctgatca  34923

catcgaccac cgtggaatgg gccaggccca gccagatgat gcaattttgt tgggtttcgg  34983

tgacggcggg ggagggaaga acaggaagaa ccatgattaa cttttaatcc aaacggtctc  35043

ggagcacttc aaaatgaagg tcacggagat ggcacctctc gcccccgctg tgttggtgga  35103

aaataacagc caggtcaaag gtgatacggt tctcgagatg ttccacggtg gcttccagca  35163
```

-continued

```
aagcctccac gcgcacatcc agaaacaaga caatagcgaa agcgggaggg ttctctaatt  35223

cctcaaccat catgttacac tcctgcacca tccccagata attttcattt ttccagcctt  35283

gaatgattcg aactagttcc tgaggtaaat ccaagccagc catgataaaa agctcgcgca  35343

gagcaccctc caccggcatt cttaagcaca ccctcataat tccaagatat tctgctcctg  35403

gttcacctgc agcagattga caagcggaat atcaaaatct ctgccgcgat ccctgagctc  35463

ctccctcagc aataactgta agtactcttt catatcgtct ccgaaatttt tagccatagg  35523

acccccagga ataagagaag ggcaagccac attacagata aaccgaagtc ccccccagtg  35583

agcattgcca aatgtaagat tgaaataagc atgctggcta gacccggtga tatcttccag  35643

ataactggac agaaaatcgg gtaagcaatt tttaagaaaa tcaacaaaag aaaaatcttc  35703

caggtgcacg tttagggcct cgggaacaac gatggagtaa gtgcaagggg tgcgttccag  35763

catggttagt tagctgatct gtaaaaaaac aaaaaataaa acattaaacc atgctagcct  35823

ggcgaacagg tgggtaaatc gttctctcca gcaccaggca ggccacgggg tctccggcgc  35883

gaccctcgta aaaattgtcg ctatgattga aaaccatcac agagagacgt tcccggtggc  35943

cggcgtgaat gattcgagaa gaagcataca cccccggaac attggagtcc gtgagtgaaa  36003

aaaagcggcc gaggaagcaa tgaggcacta caacgctcac tctcaagtcc agcaaagcga  36063

tgccatgcgg atgaagcaca aaattttcag gtgcgtaaaa aatgtaatta ctcccctcct  36123

gcacaggcag cgaagctccc gatccctcca gatacacata caaagcctca gcgtccatag  36183

cttaccgagc ggcagcagca gcggcacaca acaggcgcaa gagtcagaga aaagactgag  36243

ctctaacctg tccgcccgct ctctgctcaa tatatagccc cagatctaca ctgacgtaaa  36303

ggccaaagtc taaaaatacc cgccaaataa tcacacacgc ccagcacacg cccagaaacc  36363

ggtgacacac tcagaaaaat acgcgcactt cctcaaacgg ccaaactgcc gtcatttccg  36423

ggttcccacg ctacgtcatc aaaacacgac tttcaaattc cgtcgaccgt taaaaacatc  36483

acccgccccg cccctaacgg tcgccgctcc cgcagccaat caccttcctc cctccccaaa  36543

ttcaaacagc tcatttgcat attaacgcgc accaaaagtt tgaggtatat tattgatgat  36603

g                                                                 36604
```

```
<210> SEQ ID NO 6
<211> LENGTH: 529
<212> TYPE: PRT
<213> ORGANISM: chimpanzee adenovirus serotype Pan6

<400> SEQUENCE: 6

Met Met Arg Arg Val Tyr Pro Glu Gly Pro Pro Pro Ser Tyr Glu Ser
1               5                   10                  15

Val Met Gln Gln Ala Val Ala Ala Ala Met Gln Pro Pro Leu Glu Ala
            20                  25                  30

Pro Tyr Val Pro Pro Arg Tyr Leu Ala Pro Thr Glu Gly Arg Asn Ser
        35                  40                  45

Ile Arg Tyr Ser Glu Leu Ala Pro Leu Tyr Asp Thr Thr Arg Leu Tyr
    50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110
```

-continued

```
Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
    130                 135                 140

Arg Lys Thr Pro Asn Gly Val Asp Asp Asp Tyr Asp Gly Ser Gln Asp
145                 150                 155                 160

Glu Leu Thr Tyr Glu Trp Val Glu Phe Glu Leu Pro Glu Gly Asn Phe
                165                 170                 175

Ser Val Thr Met Thr Ile Asp Leu Met Asn Asn Ala Ile Ile Asp Asn
            180                 185                 190

Tyr Leu Ala Val Gly Arg Gln Asn Gly Val Leu Glu Ser Asp Ile Gly
        195                 200                 205

Val Lys Phe Asp Thr Arg Asn Phe Arg Leu Gly Trp Asp Pro Val Thr
    210                 215                 220

Glu Leu Val Met Pro Gly Val Tyr Thr Asn Glu Ala Phe His Pro Asp
225                 230                 235                 240

Ile Val Leu Leu Pro Gly Cys Gly Val Asp Phe Thr Glu Ser Arg Leu
                245                 250                 255

Ser Asn Leu Leu Gly Ile Arg Lys Arg Gln Pro Phe Gln Glu Gly Phe
            260                 265                 270

Gln Ile Leu Tyr Glu Asp Leu Glu Gly Gly Asn Ile Pro Ala Leu Leu
        275                 280                 285

Asp Val Glu Ala Tyr Glu Lys Ser Lys Glu Asp Ser Thr Ala Ala Ala
    290                 295                 300

Thr Ala Ala Val Ala Thr Ala Ser Thr Glu Val Arg Gly Asp Asn Phe
305                 310                 315                 320

Ala Ser Ala Ala Ala Ala Ala Glu Ala Ala Glu Thr Glu Ser Lys Ile
                325                 330                 335

Val Ile Gln Pro Val Glu Lys Asp Ser Lys Asp Arg Ser Tyr Asn Val
            340                 345                 350

Leu Ala Asp Lys Lys Asn Thr Ala Tyr Arg Ser Trp Tyr Leu Ala Tyr
        355                 360                 365

Asn Tyr Gly Asp Pro Glu Lys Gly Val Arg Ser Trp Thr Leu Leu Thr
    370                 375                 380

Thr Ser Asp Val Thr Cys Gly Val Glu Gln Val Tyr Trp Ser Leu Pro
385                 390                 395                 400

Asp Met Met Gln Asp Pro Val Thr Phe Arg Ser Thr Arg Gln Val Ser
                405                 410                 415

Asn Tyr Pro Val Val Gly Ala Glu Leu Leu Pro Val Tyr Ser Lys Ser
            420                 425                 430

Phe Phe Asn Glu Gln Ala Val Tyr Ser Gln Gln Leu Arg Ala Phe Thr
        435                 440                 445

Ser Leu Thr His Val Phe Asn Arg Phe Pro Glu Asn Gln Ile Leu Val
    450                 455                 460

Arg Pro Pro Ala Pro Thr Ile Thr Thr Val Ser Glu Asn Val Pro Ala
465                 470                 475                 480

Leu Thr Asp His Gly Thr Leu Pro Leu Arg Ser Ser Ile Arg Gly Val
                485                 490                 495

Gln Arg Val Thr Val Thr Asp Ala Arg Arg Arg Thr Cys Pro Tyr Val
            500                 505                 510

Tyr Lys Ala Leu Gly Val Val Ala Pro Arg Val Leu Ser Ser Arg Thr
        515                 520                 525

Phe
```

<210> SEQ ID NO 7
<211> LENGTH: 942
<212> TYPE: PRT
<213> ORGANISM: chimpanzee adenovirus serotype Pan6

<400> SEQUENCE: 7

```
Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Ser Ser Gln Trp Glu Gln Ala Lys Thr Gly Asn Gly Gly
    130                 135                 140

Thr Met Glu Thr His Thr Tyr Gly Val Ala Pro Met Gly Gly Glu Asn
145                 150                 155                 160

Ile Thr Lys Asp Gly Leu Gln Ile Gly Thr Asp Val Thr Ala Asn Gln
                165                 170                 175

Asn Lys Pro Ile Tyr Ala Asp Lys Thr Phe Gln Pro Glu Pro Gln Val
            180                 185                 190

Gly Glu Glu Asn Trp Gln Glu Thr Glu Asn Phe Tyr Gly Gly Arg Ala
        195                 200                 205

Leu Lys Lys Asp Thr Asn Met Lys Pro Cys Tyr Gly Ser Tyr Ala Arg
    210                 215                 220

Pro Thr Asn Glu Lys Gly Gly Gln Ala Lys Leu Lys Val Gly Asp Asp
225                 230                 235                 240

Gly Val Pro Thr Lys Glu Phe Asp Ile Asp Leu Ala Phe Phe Asp Thr
                245                 250                 255

Pro Gly Gly Thr Val Asn Gly Gln Asp Glu Tyr Lys Ala Asp Ile Val
            260                 265                 270

Met Tyr Thr Glu Asn Thr Tyr Leu Glu Thr Pro Asp Thr His Val Val
        275                 280                 285

Tyr Lys Pro Gly Lys Asp Asp Ala Ser Ser Glu Ile Asn Leu Val Gln
    290                 295                 300

Gln Ser Met Pro Asn Arg Pro Asn Tyr Ile Gly Phe Arg Asp Asn Phe
305                 310                 315                 320

Ile Gly Leu Met Tyr Tyr Asn Ser Thr Gly Asn Met Gly Val Leu Ala
                325                 330                 335

Gly Gln Ala Ser Gln Leu Asn Ala Val Val Asp Leu Gln Asp Arg Asn
            340                 345                 350

Thr Glu Leu Ser Tyr Gln Leu Leu Leu Asp Ser Leu Gly Asp Arg Thr
        355                 360                 365

Arg Tyr Phe Ser Met Trp Asn Gln Ala Val Asp Ser Tyr Asp Pro Asp
```

-continued

```
370                 375                 380

Val Arg Ile Ile Glu Asn His Gly Val Glu Asp Glu Leu Pro Asn Tyr
385                 390                 395                 400

Cys Phe Pro Leu Asp Gly Ser Gly Thr Asn Ala Ala Tyr Gln Gly Val
                405                 410                 415

Lys Val Lys Asp Gly Gln Asp Gly Asp Val Glu Ser Glu Trp Glu Asn
            420                 425                 430

Asp Asp Thr Val Ala Ala Arg Asn Gln Leu Cys Lys Gly Asn Ile Phe
        435                 440                 445

Ala Met Glu Ile Asn Leu Gln Ala Asn Leu Trp Arg Ser Phe Leu Tyr
    450                 455                 460

Ser Asn Val Ala Leu Tyr Leu Pro Asp Ser Tyr Lys Tyr Thr Pro Thr
465                 470                 475                 480

Asn Val Thr Leu Pro Thr Asn Thr Asn Thr Tyr Asp Tyr Met Asn Gly
                485                 490                 495

Arg Val Thr Pro Pro Ser Leu Val Asp Ala Tyr Leu Asn Ile Gly Ala
            500                 505                 510

Arg Trp Ser Leu Asp Pro Met Asp Asn Val Asn Pro Phe Asn His His
        515                 520                 525

Arg Asn Ala Gly Leu Arg Tyr Arg Ser Met Leu Leu Gly Asn Gly Arg
    530                 535                 540

Tyr Val Pro Phe His Ile Gln Val Pro Gln Lys Phe Phe Ala Ile Lys
545                 550                 555                 560

Ser Leu Leu Leu Leu Pro Gly Ser Tyr Thr Tyr Glu Trp Asn Phe Arg
                565                 570                 575

Lys Asp Val Asn Met Ile Leu Gln Ser Ser Leu Gly Asn Asp Leu Arg
            580                 585                 590

Thr Asp Gly Ala Ser Ile Ala Phe Thr Ser Ile Asn Leu Tyr Ala Thr
        595                 600                 605

Phe Phe Pro Met Ala His Asn Thr Ala Ser Thr Leu Glu Ala Met Leu
    610                 615                 620

Arg Asn Asp Thr Asn Asp Gln Ser Phe Asn Asp Tyr Leu Ser Ala Ala
625                 630                 635                 640

Asn Met Leu Tyr Pro Ile Pro Ala Asn Ala Thr Asn Val Pro Ile Ser
                645                 650                 655

Ile Pro Ser Arg Asn Trp Ala Ala Phe Arg Gly Trp Ser Phe Thr Arg
            660                 665                 670

Leu Lys Thr Arg Glu Thr Pro Ser Leu Gly Ser Gly Phe Asp Pro Tyr
        675                 680                 685

Phe Val Tyr Ser Gly Ser Ile Pro Tyr Leu Asp Gly Thr Phe Tyr Leu
    690                 695                 700

Asn His Thr Phe Lys Lys Val Ser Ile Thr Phe Asp Ser Ser Val Ser
705                 710                 715                 720

Trp Pro Gly Asn Asp Arg Leu Leu Thr Pro Asn Glu Phe Glu Ile Lys
                725                 730                 735

Arg Thr Val Asp Gly Glu Gly Tyr Asn Val Ala Gln Cys Asn Met Thr
            740                 745                 750

Lys Asp Trp Phe Leu Val Gln Met Leu Ala His Tyr Asn Ile Gly Tyr
        755                 760                 765

Gln Gly Phe Tyr Val Pro Glu Gly Tyr Lys Asp Arg Met Tyr Ser Phe
    770                 775                 780

Phe Arg Asn Phe Gln Pro Met Ser Arg Gln Val Val Asp Glu Val Asn
785                 790                 795                 800
```

-continued

```
Tyr Lys Asp Tyr Gln Ala Val Thr Leu Ala Tyr Gln His Asn Asn Ser
                805                 810                 815

Gly Phe Val Gly Tyr Leu Ala Pro Thr Met Arg Gln Gly Gln Pro Tyr
            820                 825                 830

Pro Ala Asn Tyr Pro Tyr Pro Leu Ile Gly Lys Ser Ala Val Ala Ser
        835                 840                 845

Val Thr Gln Lys Lys Phe Leu Cys Asp Arg Val Met Trp Arg Ile Pro
    850                 855                 860

Phe Ser Ser Asn Phe Met Ser Met Gly Ala Leu Thr Asp Leu Gly Gln
865                 870                 875                 880

Asn Met Leu Tyr Ala Asn Ser Ala His Ala Leu Asp Met Asn Phe Glu
                885                 890                 895

Val Asp Pro Met Asp Glu Ser Thr Leu Leu Tyr Val Val Phe Glu Val
            900                 905                 910

Phe Asp Val Val Arg Val His Gln Pro His Arg Gly Val Ile Glu Ala
        915                 920                 925

Val Tyr Leu Arg Thr Pro Phe Ser Ala Gly Asn Ala Thr Thr
    930                 935                 940


<210> SEQ ID NO 8
<211> LENGTH: 443
<212> TYPE: PRT
<213> ORGANISM: chimpanzee adenovirus serotype Pan6

<400> SEQUENCE: 8

Met Ser Lys Lys Arg Val Arg Val Asp Asp Asp Phe Asp Pro Val Tyr
1               5                   10                  15

Pro Tyr Asp Ala Asp Asn Ala Pro Thr Val Pro Phe Ile Asn Pro Pro
            20                  25                  30

Phe Val Ser Ser Asp Gly Phe Gln Glu Lys Pro Leu Gly Val Leu Ser
        35                  40                  45

Leu Arg Leu Ala Asp Pro Val Thr Thr Lys Asn Gly Glu Ile Thr Leu
    50                  55                  60

Lys Leu Gly Glu Gly Val Asp Leu Asp Ser Ser Gly Lys Leu Ile Ser
65                  70                  75                  80

Asn Thr Ala Thr Lys Ala Ala Ala Pro Leu Ser Ile Ser Asn Asn Thr
                85                  90                  95

Ile Ser Leu Lys Thr Ala Ala Pro Phe Tyr Asn Asn Asn Gly Thr Leu
            100                 105                 110

Ser Leu Asn Val Ser Thr Pro Leu Ala Val Phe Pro Thr Phe Asn Thr
        115                 120                 125

Leu Gly Ile Ser Leu Gly Asn Gly Leu Gln Thr Ser Asn Lys Leu Leu
    130                 135                 140

Thr Val Gln Leu Thr His Pro Leu Thr Phe Ser Ser Asn Ser Ile Thr
145                 150                 155                 160

Val Lys Thr Asp Lys Gly Leu Tyr Ile Asn Ser Ser Gly Asn Arg Gly
                165                 170                 175

Leu Glu Ala Asn Ile Ser Leu Lys Arg Gly Leu Val Phe Asp Gly Asn
            180                 185                 190

Ala Ile Ala Thr Tyr Ile Gly Asn Gly Leu Asp Tyr Gly Ser Tyr Asp
        195                 200                 205

Ser Asp Gly Lys Thr Arg Pro Val Ile Thr Lys Ile Gly Ala Gly Leu
    210                 215                 220

Asn Phe Asp Ala Asn Lys Ala Ile Ala Val Lys Leu Gly Thr Gly Leu
```

-continued

```
225                 230                 235                 240

Ser Phe Asp Ser Ala Gly Ala Leu Thr Ala Gly Asn Lys Gln Asp Asp
                245                 250                 255

Lys Leu Thr Leu Trp Thr Thr Pro Asp Pro Ser Pro Asn Cys Gln Leu
            260                 265                 270

Leu Ser Asp Arg Asp Ala Lys Phe Thr Leu Cys Leu Thr Lys Cys Gly
        275                 280                 285

Ser Gln Ile Leu Gly Thr Val Ala Val Ala Ala Val Thr Val Gly Ser
    290                 295                 300

Ala Leu Asn Pro Ile Asn Asp Thr Val Lys Ser Ala Ile Val Phe Leu
305                 310                 315                 320

Arg Phe Asp Ser Asp Gly Val Leu Met Ser Asn Ser Ser Met Val Gly
                325                 330                 335

Asp Tyr Trp Asn Phe Arg Glu Gly Gln Thr Thr Gln Ser Val Ala Tyr
            340                 345                 350

Thr Asn Ala Val Gly Phe Met Pro Asn Ile Gly Ala Tyr Pro Lys Thr
        355                 360                 365

Gln Ser Lys Thr Pro Lys Asn Ser Ile Val Ser Gln Val Tyr Leu Thr
    370                 375                 380

Gly Glu Thr Thr Met Pro Met Thr Leu Thr Ile Thr Phe Asn Gly Thr
385                 390                 395                 400

Asp Glu Lys Asp Thr Thr Pro Val Ser Thr Tyr Ser Met Thr Phe Thr
                405                 410                 415

Trp Gln Trp Thr Gly Asp Tyr Lys Asp Lys Asn Ile Thr Phe Ala Thr
            420                 425                 430

Asn Ser Phe Ser Phe Ser Tyr Ile Ala Gln Glu
        435                 440
```

<210> SEQ ID NO 9
<211> LENGTH: 36535
<212> TYPE: DNA
<213> ORGANISM: chimpanzee adenovirus serotype Pan7
<220> FEATURE:
<221> NAME/KEY: CDS
<222> LOCATION: (13874)..(15469)
<223> OTHER INFORMATION: L2 Penton
<220> FEATURE:
<221> NAME/KEY: CDS
<222> LOCATION: (18288)..(21086)
<223> OTHER INFORMATION: L3 Hexon
<220> FEATURE:
<221> NAME/KEY: CDS
<222> LOCATION: (32094)..(33425)
<223> OTHER INFORMATION: L5 Fiber

<400> SEQUENCE: 9

```
catcatcaat aatatacctc aaacttttgg tgcgcgttaa tatgcaaatg agctgtttga     60

atttggggag ggaggaaggt gattggccga gagacgggcg accgttaggg gcggggcggg    120

tgacgttttt aatacgtggc cgtgaggcgg agccggtttg caagttctcg tgggaaaagt    180

gacgtcaaac gaggtgtggt ttgaacacgg aaatactcaa ttttcccgcg ctctctgaca    240

ggaaatgagg tgtttctggg cggatgcaag tgaaaacggg ccattttcgc gcgaaaactg    300

aatgaggaag tgaaaatctg agtaatttcg cgtttatggc agggaggagt atttgccgag    360

ggccgagtag actttgaccg attacgtggg ggtttcgatt accgtatttt tcacctaaat    420

ttccgcgtac ggtgtcaaag tccggtgttt ttacgtaggc gtcagctgat cgccagggta    480

tttaaacctg cgctctctag tcaagaggcc actcttgagt gccagcgagt agagttttct    540
```

-continued

```
cctccgcgcc gcgagtcaga tctacacttt gaaagatgag gcacctgaga gacctgcccg    600
gtaatgtttt cctggctact gggaacgaga ttctggaatt ggtggtggac gccatgatgg    660
gtggcgaccc tcctgagccc cctaccccat ttgaggcgcc ttcgctgtac gatttgtatg    720
atctggaggt ggatgtgccc gagaacgacc ccaacgagga ggcggtgaat gatttgttta    780
gcgatgccgc gctgctggct gccgagcagg ctaatacgga ctctggctca gacagcgatt    840
cctctctcca taccccgaga cccggcagag gtgagaaaaa gatccccgag cttaaagggg    900
aagagctcga cctgcgctgc tatgaggaat gcttgcctcc gagcgatgat gaggaggacg    960
aggaggcgat tcgagctgca tcgaaccagg gagtgaaagc tgcgggcgaa agctttagcc   1020
tggactgtcc tactctgccc ggacacggct gtaagtcttg tgaatttcat cgcatgaata   1080
ctggagataa gaatgtgatg tgtgccctgt gctatatgag agcttacaac cattgtgttt   1140
acagtaagtg tgattaactt tagttgggaa ggcagagggt gactgggtgc tgactggttt   1200
atttatgtat atgttttttt atgtgtaggt cccgtctctg acgtagatga gacccccact   1260
tcagagtgca tttcatcacc cccagaaatt ggcgaggaac cgcccgaaga tattattcat   1320
agaccagttg cagtgagagt caccgggcgg agagcagctg tggagagttt ggatgacttg   1380
ctacagggtg gggatgaacc tttggacttg tgtacccgga aacgccccag gcactaagtg   1440
ccacacatgt gtgtttactt aaggtgatgt cagtatttat agggtgtgga gtgcaataaa   1500
atccgtgttg actttaagtg cgtggtttat gactcagggg tggggactgt gggtatataa   1560
gcaggtgcag acctgtgtgg tcagttcaga gcaggactca tggagatctg gacggtcttg   1620
gaagactttc accagactag acagctgcta gagaactcat cggagggggt ctcttacctg   1680
tggagattct gcttcggtgg gcctctagct aagctagtct atagggccaa acaggattat   1740
aaggatcaat ttgaggatat tttgagagag tgtcctggta tttttgactc tctcaacttg   1800
ggccatcagt ctcactttaa ccagagtatt ctgagagccc ttgacttttc tactcctggc   1860
agaactaccg ccgcggtagc ctttttttgcc tttatccttg acaaatggag tcaagaaacc   1920
catttcagca gggattaccg tctggactgc ttagcagtag ctttgtggag aacatggagg   1980
tgccagcgcc tgaatgcaat ctccggctac ttgccagtac agccggtaga cacgctgagg   2040
atcctgagtc tccagtcacc ccaggaacac caacgccgcc agcagccgca gcaggagcag   2100
cagcaagagg aggaggagga tcgagaagag aacccgagag ccggtctgga ccctccggtg   2160
gcggaggagg aggagtagct gacttgtttc ccgagctgcg ccgggtgctg actaggtctt   2220
ccagtggacg ggagaggggg attaagcggg agaggcatga ggagactagc cacagaactg   2280
aactgactgt cagtctgatg agccgcaggc gcccagaatc ggtgtggtgg catgaggttc   2340
agtcgcaggg gatagatgag gtctcggtga tgcatgagaa atattccctg gaacaagtca   2400
agacttgttg gttggagcct gaggatgatt gggaggtagc catcaggaat tatgccaagc   2460
tggctctgaa gccagacaag aagtacaaga ttaccaaact gattaatatc agaaattcct   2520
gctacatttc agggaatggg gccgaggtgg agatcagtac ccaggagagg gtggccttca   2580
gatgttgtat gatgaatatg tacccggggg tggtgggcat ggagggagtc acctttatga   2640
acgcgaggtt caggggtgat gggtataatg gggtggtctt tatggccaac accaagctga   2700
cagtgcacgg atgctccttc tttgggttca ataacatgtg catcgaggcc tggggcagtg   2760
tttcagtgag gggatgcagc ttttcagcca actggatggg ggtcgtgggc agaaccaaga   2820
gcaaggtgtc agtgaagaaa tgcctgttcg agaggtgcca cctgggggtg atgagcgagg   2880
gcgaagccaa agtcaaacac tgcgcctcta ctgagacggg ctgctttgtg ctgatcaagg   2940
```

-continued

```
gcaatgccca agtcaagcat aacatgatct gtggggcctc ggatgagcgc ggctaccaga   3000
tgctgacctg cgccggtggg aacagccata tgctggccac cgtgcatgtg acctcgcacc   3060
cccgcaagac atggcccgag ttcgagcaca acgtcatgac ccgatgcaat gtgcacctgg   3120
ggtcccgccg aggcatgttc atgccctacc agtgcaacat gcaatttgtg aaggtgctgc   3180
tggagcccga tgccatgtcc agagtgagcc tgacgggggt gtttgacatg aatgtggagc   3240
tgtggaaaat tctgagatat gatgaatcca agaccaggtg ccgggcctgc gaatgcggag   3300
gcaagcacgc caggcttcag cccgtgtgtg tggaggtgac ggaggacctg cgacccgatc   3360
atttggtgtt gtcctgcaac gggacggagt tcggctccag cggggaagaa tctgactaga   3420
gtgagtagtg tttgggggag gtggagggct tgtatgaggg gcagaatgac taaaatctgt   3480
gtttttctgt gtgttgcagc agcatgagcg gaagcgcctc ctttgaggga ggggtattca   3540
gcccttatct gacggggcgt ctcccctcct gggcgggagt gcgtcagaat gtgatgggat   3600
ccacggtgga cggccggccc gtgcagcccg cgaactcttc aaccctgacc tacgcgaccc   3660
tgagctcctc gtccgtggac gcagctgccg ccgcagctgc tgcttccgcc gccagcgccg   3720
tgcgcggaat ggccctgggc gccggctact acagctctct ggtggccaac tcgacttcca   3780
ccaataatcc cgccagcctg aacgaggaga agctgctgct gctgatggcc cagctcgagg   3840
ccctgaccca gcgcctgggc gagctgaccc agcaggtggc tcagctgcag gcggagacgc   3900
gggccgcggt tgccacggtg aaaaccaaat aaaaaatgaa tcaataaata aacggagacg   3960
gttgttgatt ttaacacaga gtcttgaatc tttatttgat tttcgcgcg cggtaggccc   4020
tggaccaccg gtctcgatca ttgagcaccc ggtggatttt ttccaggacc cggtagaggt   4080
gggcttggat gttgaggtac atgggcatga gcccgtcccg ggggtggagg tagctccatt   4140
gcagggcctc gtgctcgggg gtggtgttgt aaatcaccca gtcatagcag gggcgcaggg   4200
cgtggtgctg cacgatgtcc ttgaggagga gactgatggc cacgggcagc cccttggtgt   4260
aggtgttgac gaacctgttg agctgggagg gatgcatgcg gggggagatg agatgcatct   4320
tggcctggat cttgagattg gcgatgttcc cgcccagatc ccgccggggg ttcatgttgt   4380
gcaggaccac cagcacggtg tatccggtgc acttggggaa tttgtcatgc aacttggaag   4440
ggaaggcgtg aaagaatttg gagacgccct tgtgaccgcc caggttttcc atgcactcat   4500
ccatgatgat ggcgatgggc ccgtgggcgg cggcctgggc aaagacgttt cgggggtcgg   4560
acacatcgta gttgtggtcc tgggtgagct cgtcataggc cattttaatg aatttggggc   4620
ggagggtgcc cgactggggg acgaaggtgc cctcgatccc gggggcgtag ttgccctcgc   4680
agatctgcat ctcccaggcc ttgagctcgg aggggggat catgtccacc tgcggggcga   4740
tgaaaaaaac ggtttccggg gcgggggaga tgagctgggc cgaaagcagg ttccggagca   4800
gctgggactt gccgcagccg gtggggccgt agatgacccc gatgaccggc tgcaggtggt   4860
agttgaggga gagacagctg ccgtcctcgc ggaggagggg ggccacctcg ttcatcatct   4920
cgcgcacatg catgttctcg cgcacgagtt ccgccaggag gcgctcgccc cccagcgaga   4980
ggagctcttg cagcgaggcg aagtttttca gcggcttgag yccgtcggcc atgggcattt   5040
tggagagggt ctgttgcaag agttccagac ggtcccagag ctcggtgatg tgctctaggg   5100
catctcgatc cagcagacct cctcgtttcg cgggttgggg cgactgcggg agtagggcac   5160
caggcgatgg gcgtccagcg aggccagggt ccggtccttc cagggtcgca gggtccgcgt   5220
cagcgtggtc tccgtcacgg tgaaggggtg cgcgccgggc tgggcgcttg cgagggtgcg   5280
```

-continued

```
cttcaggctc atccggctgg tcgagaaccg ctcccggtcg gcgccctgcg cgtcggccag   5340
gtagcaattg agcatgagtt cgtagttgag cgcctcggcc gcgtggccct tggcgcggag   5400
cttacctttg gaagtgtgtc cgcagacggg acagaggagg gacttgaggg cgtagagctt   5460
gggggcgagg aagacggact cgggggcgta ggcgtccgcg ccgcagctgg cgcagacggt   5520
ctcgcactcc acgagccagg tgaggtcggg ccggttgggg tcaaaaacga ggtttcctcc   5580
gtgctttttg atgcgtttct tacctctggt ctccatgagc tcgtgtcccc gctgggtgac   5640
aaagaggctg tccgtgtccc cgtagaccga ctttatgggc cggtcctcga gcggggtgcc   5700
gcggtcctcg tcgtagagga accccgccca ctccgagacg aaggcccggg tccaggccag   5760
cacgaaggag gccacgtggg aggggtagcg gtcgttgtcc accagcgggt ccaccttctc   5820
cagggtatgc aagcacatgt ccccctcgtc cacatccagg aaggtgattg gcttgtaagt   5880
gtaggccacg tgaccggggg tcccggccgg gggggtataa aagggggcgg gcccctgctc   5940
gtcctcactg tcttccggat cgctgtccag gagcgccagc tgttggggta ggtattccct   6000
ctcgaaggct ggcataacct cggcactcag gttgtcagtt tctagaaacg aggaggattt   6060
gatattgacg gtgccgttgg agacgccttt catgagcccc tcgtccatct ggtcagaaaa   6120
gacgatcttt ttgttgtcga gcttggtggc gaaggagccg tagagggcgt tggagaggag   6180
cttggcgatg gagcgcatgg tctggttctt ttccttgtcg gcgcgctcct tggcggcgat   6240
gttgagctgc acgtactcgc gcgccacgca cttccattcg gggaagacgg tggtgagctc   6300
gtcgggcacg attctgaccc gccagccgcg gttgtgcagg gtgatgaggt ccacgctggt   6360
ggccacctcg ccgcgcaggg gctcgttggt ccagcagagg cgcccgccct tgcgcgagca   6420
gaagggggc agcgggtcca gcatgagctc gtcggggggg tcggcgtcca cggtgaagat   6480
gccgggcaga agctcggggt cgaagtagct gatgcaggtg tccagatcgt ccagcgccgc   6540
ttgccagtcg cgcacggcca gcgcgcgctc gtaggggctg aggggcgtgc cccagggcat   6600
ggggtgcgtg agcgcggagg cgtacatgcc gcagatgtcg tagacgtaga ggggctcctc   6660
gaggacgccg atgtaggtgg ggtagcagcg ccccccgcgg atgctggcgc gcacgtagtc   6720
gtacagctcg tgcgagggcg cgaggagccc cgtgccgagg ttggagcgtt gcggcttttc   6780
ggcgcggtag acgatctggc ggaagatggc gtgggagttg gaggagatgg tgggcctctg   6840
gaagatgttg aagtgggcgt ggggcaggcc gaccgagtcc ctgatgaagt gggcgtagga   6900
gtcctgcagc ttggcgacga gctcggcggt gacgaggacg tccagggcgc agtagtcgag   6960
ggtctcttgg atgatgtcgt acttgagctg gcccttctgc ttccacagct cgcggttgag   7020
aaggaactct tcgcggtcct tccagtactc ttcgaggggg aacccgtcct gatcggcacg   7080
gtaagagccc accatgtaga actggttgac ggccttgtag gcgcagcagc ccttctccac   7140
ggggagggcg taagcttgtg cggccttgcg cagggaggtg tgggtgaggg cgaaggtgtc   7200
gcgcaccatg accttgagga actggtgctt gaagtcgagg tcgtcgcagc cgccctgctc   7260
ccagagctgg aagtccgtgc gcttcttgta ggcggggttg ggcaaagcga aagtaacatc   7320
gttgaagagg atcttgcccg cgcggggcat gaagttgcga gtgatgcgga aaggctgggg   7380
cacctcggcc cggttgttga tgacctgggc ggcgaggacg atctcgtcga agccgttgat   7440
gttgtgcccg acgatgtaga gttccacgaa tcgcgggcgg cccttaacgt ggggcagctt   7500
cttgagctcg tcgtaggtga gctcggcggg gtcgctgagc ccgtgctgct cgagggccca   7560
gtcggcgacg tgggggttgg cgctgaggaa ggaagtccag agatccacgg ccagggcggt   7620
ctgcaagcgg tcccggtact gacggaactg ctggcccacg gccatttttt cgggggtgac   7680
```

-continued

```
gcagtagaag gtgcgggggt cgccgtgcca gcggtcccac ttgagctgga gggcgaggtc   7740
gtgggcgagc tcgacgagcg gcgggtcccc ggagagtttc atgaccagca tgaaggggac   7800
gagctgcttg ccgaaggacc ccatccaggt gtaggtttcc acatcgtagg tgaggaagag   7860
cctttcggtg cgaggatgcg agccgatggg gaagaactgg atctcctgcc accagttgga   7920
ggaatggctg ttgatgtgat ggaagtagaa atgccgacgg cgcgccgagc actcgtgctt   7980
gtgtttatac aagcgtccgc agtgctcgca acgctgcacg ggatgcacgt gctgcacgag   8040
ctgtacctgg gttcctttga cgaggaattt cagtgggcag tggagcgctg gcggctgcat   8100
ctggtgctgt actacgtcct ggccatcggc gtggccatcg tctgcctcga tggtggtcat   8160
gctgacgagc ccgcgcggga ggcaggtcca gacttcggct cggacgggtc ggagagcgag   8220
gacgagggcg cgcaggccgg agctgtccag ggtcctgaga cgctgcggag tcaggtcagt   8280
gggcagcggc ggcgcgcggt tgacttgcag gagcttttcc agggcgcgcg ggaggtccag   8340
atggtacttg atctccacgg cgccgttggt ggcgacgtcc acggcttgca gggtcccgtg   8400
cccctggggc gccaccaccg tgccccgttt cttcttgggc gctgcttcca tgccggtcag   8460
aagcggcggc gaggacgcgc gccgggcggc aggggcggct cgggacccgg aggcaggggc   8520
ggcaggggca cgtcggcgcc gcgcgcgggc aggttctggt actgcgcccg gagaagactg   8580
gcgtgagcga cgacgcgacg gttgacgtcc tggatctgac gcctctgggt gaaggccacg   8640
ggacccgtga gtttgaacct gaaagagagt tcgacagaat caatctcggt atcgttgacg   8700
gcggcctgcc gcaggatctc ttgcacgtcg cccgagttgt cctggtaggc gatctcggtc   8760
atgaactgct cgatctcctc ctcctgaagg tctccgcggc cggcgcgctc gacggtggcc   8820
gcgaggtcgt tggagatgcg gcccatgagc tgcgagaagg cgttcatgcc ggcctcgttc   8880
cagacgcggc tgtagaccac ggctccgtcg gggtcgcgcg cgcgcatgac cacctgggcg   8940
aggttgagct cgacgtggcg cgtgaagacc gcgtagttgc agaggcgctg gtagaggtag   9000
ttgagcgtgg tggcgatgtg ctcggtgacg aagaagtaca tgatccagcg gcggagcggc   9060
atctcgctga cgtcgcccag ggcttccaag cgctccatgg cctcgtagaa gtccacggcg   9120
aagttgaaaa actgggagtt gcgcgccgag acggtcaact cctcctccag aagacggatg   9180
agctcagcga tggtggcgcg cacctcgcgc tcgaaggccc cgggggggctc ctcttcttcc   9240
atctcttcct cctccactaa catctcttct acttcctcct caggaggcgg cggcggggga   9300
ggggccctgc gtcgccggcg gcgcacgggc agacggtcga tgaagcgctc gatggtctcc   9360
ccgcgccggc gacgcatggt ctcggtgacg gcgcgcccgt cctcgcgggg ccgcagcgtg   9420
aagacgccgc cgcgcatctc caggtggccg ccgggggggt ctccgttggg cagggagagg   9480
gcgctgacga tgcatcttat caattggccc gtagggactc cgcgcaagga cctgagcgtc   9540
tcgagatcca cgggatccga aaaccgctga acgaaggctt cgagccagtc gcagtcgcaa   9600
ggtaggctga gcccggtttc ttgttcttcg gggatttcgg gaggcgggcg ggcgatgctg   9660
ctggtgatga agttgaagta ggcggtcctg agacggcgga tggtggcgag gagcaccagg   9720
tccttgggcc cggcttgctg gatgcgcaga cggtcggcca tgccccaggc gtggtcctga   9780
cacctggcga ggtccttgta gtagtcctgc atgagccgct ccacgggcac ctcctcctcg   9840
cccgcgcggc cgtgcatgcg cgtgagcccg aacccgcgct ggggctggac gagcgccagg   9900
tcggcgacga cgcgctcggc gaggatggcc tgctgtatct gggtgagggt ggtctggaag   9960
tcgtcgaagt cgacgaagcg gtggtaggct ccggtgttga tggtatagga gcagttggcc  10020
```

-continued atgacggacc agttgacggt ctggtggccg ggtcgcacga gctcgtggta cttgaggcgc 10080
gagtaggcgc gcgtgtcgaa gatgtagtcg ttgcaggtgc gcacgaggta ctggtatccg 10140
acgaggaagt gcggcggcgg ctggcggtag agcggccatc gctcggtggc gggggcgccg 10200
ggcgcgaggt cctcgagcat gaggcggtgg tagccgtaga tgtacctgga catccaggtg 10260
atgccggcgg cggtggtgga ggcgcgcggg aactcgcgga cgcggttcca gatgttgcgc 10320
agcggcagga agtagttcat ggtggccgcg gtctggcccg tgaggcgcgc gcagtcgtgg 10380
atgctctaga catacgggca aaaacgaaag cggtcagcgg ctcgactccg tggcctggag 10440
gctaagcgaa cgggttgggc tgcgcgtgta ccccggttcg aatctcgaat caggctggag 10500
ccgcagctaa cgtggtactg gcactcccgt ctcgacccaa gcctgctaac gaaacctcca 10560
ggatacggag gcgggtcgtt ttttggcctt ggtcgctggt catgaaaaac tagtaagcgc 10620
ggaaagcgac cgcccgcgat ggctcgctgc cgtagtctgg agaaagaatc gccagggttg 10680
cgttgcggtg tgccccggtt cgagcctcag cgctcggcgc cggccggatt ccgcggctaa 10740
cgtgggcgtg gctgccccgt cgtttccaag accccttagc cagccgactt ctccagttac 10800
ggagcgagcc cctctttttc ttgtgttttt gccagatgca tcccgtactg cggcagatgc 10860
gcccccaccc tccacctcaa ccgcccctac cgccgcagca gcagcaacag ccggcgcttc 10920
tgcccccgcc ccagcagcag ccagccacta ccgcggcggc cgccgtgagc ggagccggcg 10980
ttcagtatga cctggccttg gaagagggcg aggggctggc gcggctgggg gcgtcgtcgc 11040
cggagcggca cccgcgcgtg cagatgaaaa gggacgctcg cgaggcctac gtgcccaagc 11100
agaacctgtt cagagacagg agcggcgagg agcccgagga gatgcgcgcc tcccgcttcc 11160
acgcggggcg ggagctgcgg cgcggcctgg accgaaagcg ggtgctgagg gacgaggatt 11220
tcgaggcgga cgagctgacg gggatcagcc ccgcgcgcgc gcacgtggcc gcggccaacc 11280
tggtcacggc gtacgagcag accgtgaagg aggagagcaa cttccaaaaa tccttcaaca 11340
accacgtgcg cacgctgatc gcgcgcgagg aggtgaccct gggcctgatg cacctgtggg 11400
acctgctgga ggccatcgtg cagaacccca cgagcaagcc gctgacggcg cagctgtttc 11460
tggtggtgca gcacagtcgg gacaacgaga cgttcaggga ggcgctgctg aatatcaccg 11520
agcccgaggg ccgctggctc ctggacctgg tgaacattct gcagagcatc gtggtgcagg 11580
agcgcgggct gccgctgtcc gagaagctgg cggctatcaa cttctcggtg ctgagcctgg 11640
gcaagtacta cgctaggaag atctacaaga ccccgtacgt gcccatagac aaggaggtga 11700
agatcgacgg gttttacatg cgcatgaccc tgaaagtgct gaccctgagc gacgatctgg 11760
gggtgtaccg caacgacagg atgcaccgcg cggtgagcgc cagccgccgg cgcgagctga 11820
gcgaccagga gctgatgcac agcctgcagc gggccctgac cggggccggg accgaggggg 11880
agagctactt tgacatgggc gcggacctgc gctggcagcc cagccgccgg gccttggaag 11940
ctgccggcgg ttcccccctac gtggaggagg tggacgatga ggaggaggag ggcgagtacc 12000
tggaagactg atggcgcgac cgtatttttg ctagatgcag caacagccac cgcctcctga 12060
tcccgcgatg cgggcggcgc tgcagagcca gccgtccggc attaactcct cggacgattg 12120
gacccaggcc atgcaacgca tcatggcgct gacgacccgc aatcccgaag cctttagaca 12180
gcagcctcag gccaaccggc tctcggccat cctggaggcc gtggtgccct cgcgctcgaa 12240
ccccacgcac gagaaggtgc tggccatcgt gaacgcgctg gtggagaaca aggccatccg 12300
cggcgacgag gccgggctgg tgtacaacgc gctgctggag cgcgtggccc gctacaacag 12360
caccaacgtg cagacgaacc tggaccgcat ggtgaccgac gtgcgcgagg cggtgtcgca 12420

-continued

```
gcgcgagcgg ttccaccgcg agtcgaacct gggctccatg gtggcgctga acgccttcct  12480

gagcacgcag cccgccaacg tgccccgggg ccaggaggac tacaccaact tcatcagcgc  12540

gctgcggctg atggtggccg aggtgcccca gagcgaggtg taccagtcgg ggccggacta  12600

cttcttccag accagtcgcc agggcttgca gaccgtgaac ctgagccagg ctttcaagaa  12660

cttgcaggga ctgtggggcg tgcaggcccc ggtcggggac cgcgcgacgg tgtcgagcct  12720

gctgacgccg aactcgcgcc tgctgctgct gctggtggcg cccttcacgg acagcggcag  12780

cgtgagccgc gactcgtacc tgggctacct gcttaacctg taccgcgagg ccatcgggca  12840

ggcgcacgtg gacgagcaga cctaccagga gatcacccac gtgagccgcg cgctgggcca  12900

ggaggacccg ggcaacctgg aggccaccct gaacttcctg ctgaccaacc ggtcgcagaa  12960

gatcccgccc cagtacgcgc tgagcaccga ggaggagcgc atcctgcgct acgtgcagca  13020

gagcgtgggg ctgttcctga tgcaggaggg ggccacgccc agcgccgcgc tcgacatgac  13080

cgcgcgcaac atggagccca gcatgtacgc tcgcaaccgc ccgttcatca ataagctgat  13140

ggactacttg catcgggcgg ccgccatgaa ctcggactac tttaccaacg ccatcttgaa  13200

cccgcactgg ctcccgccgc ccgggttcta cacgggcgag tacgacatgc ccgaccccaa  13260

cgacgggttc ctgtgggacg acgtggacag cagcgtgttc tcgccgcgcc ccgccaccac  13320

cgtgtggaag aaagagggcg gggaccggcg gccgtcctcg gcgctgtccg gtcgcgcggg  13380

tgctgccgcg gcggtgcctg aggccgccag ccccttcccg agcctgccct tttcgctgaa  13440

cagcgtgcgc agcagcgagc tgggtcggct gacgcggccg cgcctgctgg gcgaggagga  13500

gtacctgaac gactccttgt tgaggcccga gcgcgagaag aacttcccca ataacgggat  13560

agagagcctg gtggacaaga tgagccgctg gaagacgtac gcgcacgagc acagggacga  13620

gccccgagct agcagcagcg caggcacccg tagacgccag cgacacgaca ggcagcgggg  13680

tctggtgtgg gacgatgagg attccgccga cgacagcagc gtgttggact tgggtgggag  13740

tggtggtggt aacccgttcg ctcacttgcg cccccgtatc gggcgcctga tgtaagaatc  13800

tgaaaaaata aaaaacggta ctcaccaagg ccatggcgac cagcgtgcgt tcttctctgt  13860

tgtttgtagt agt atg atg agg cgc gtg tac ccg gag ggt cct cct ccc     13909
               Met Met Arg Arg Val Tyr Pro Glu Gly Pro Pro Pro
               1               5                   10

tcg tac gag agc gtg atg cag cag gcg gtg gcg gcg gcg atg cag ccc     13957
Ser Tyr Glu Ser Val Met Gln Gln Ala Val Ala Ala Ala Met Gln Pro
        15                  20                  25

ccg ctg gag gcg cct tac gtg ccc ccg cgg tac ctg gcg cct acg gag     14005
Pro Leu Glu Ala Pro Tyr Val Pro Pro Arg Tyr Leu Ala Pro Thr Glu
    30                  35                  40

ggg cgg aac agc att cgt tac tcg gag ctg gca ccc ttg tac gat acc     14053
Gly Arg Asn Ser Ile Arg Tyr Ser Glu Leu Ala Pro Leu Tyr Asp Thr
45                  50                  55                  60

acc cgg ttg tac ctg gtg gac aac aag tcg gcg gac atc gcc tcg ctg     14101
Thr Arg Leu Tyr Leu Val Asp Asn Lys Ser Ala Asp Ile Ala Ser Leu
                65                  70                  75

aac tac cag aac gac cac agc aac ttc ctg acc acc gtg gtg cag aac     14149
Asn Tyr Gln Asn Asp His Ser Asn Phe Leu Thr Thr Val Val Gln Asn
            80                  85                  90

aac gat ttc acc ccc acg gag gcc agc acc cag acc atc aac ttt gac     14197
Asn Asp Phe Thr Pro Thr Glu Ala Ser Thr Gln Thr Ile Asn Phe Asp
        95                  100                 105

gag cgc tcg cgg tgg ggc ggc cag ctg aaa acc atc atg cac acc aac     14245
Glu Arg Ser Arg Trp Gly Gly Gln Leu Lys Thr Ile Met His Thr Asn
```

-continued

```
    110                 115                 120

atg ccc aac gtg aac gag ttc atg tac agc aac aag ttc aag gcg cgg     14293
Met Pro Asn Val Asn Glu Phe Met Tyr Ser Asn Lys Phe Lys Ala Arg
125                 130                 135                 140

gtg atg gtc tcg cgc aag acc ccc aat ggg gtc gcg gtg gat gag aat     14341
Val Met Val Ser Arg Lys Thr Pro Asn Gly Val Ala Val Asp Glu Asn
                145                 150                 155

tat gat ggt agt cag gac gag ctg act tac gag tgg gtg gag ttt gag     14389
Tyr Asp Gly Ser Gln Asp Glu Leu Thr Tyr Glu Trp Val Glu Phe Glu
            160                 165                 170

ctg ccc gag ggc aac ttc tcg gtg acc atg acc atc gat ctg atg aac     14437
Leu Pro Glu Gly Asn Phe Ser Val Thr Met Thr Ile Asp Leu Met Asn
        175                 180                 185

aac gcc atc atc gac aac tac ttg gcg gtg ggg cgt cag aac ggg gtg     14485
Asn Ala Ile Ile Asp Asn Tyr Leu Ala Val Gly Arg Gln Asn Gly Val
    190                 195                 200

ctg gag agc gac atc ggc gtg aag ttc gac acg cgc aac ttc cgg ctg     14533
Leu Glu Ser Asp Ile Gly Val Lys Phe Asp Thr Arg Asn Phe Arg Leu
205                 210                 215                 220

ggc tgg gac ccc gtg acc gag ctg gtg atg ccg ggc gtg tac acc aac     14581
Gly Trp Asp Pro Val Thr Glu Leu Val Met Pro Gly Val Tyr Thr Asn
                225                 230                 235

gag gcc ttc cac ccc gac atc gtc ctg ctg ccc ggc tgc ggc gtg gac     14629
Glu Ala Phe His Pro Asp Ile Val Leu Leu Pro Gly Cys Gly Val Asp
            240                 245                 250

ttc acc gag agc cgc ctc agc aac ctg ctg ggc atc cgc aag cgg cag     14677
Phe Thr Glu Ser Arg Leu Ser Asn Leu Leu Gly Ile Arg Lys Arg Gln
        255                 260                 265

ccc ttc cag gag ggc ttc cag atc ctg tac gag gac ctg gag ggg ggc     14725
Pro Phe Gln Glu Gly Phe Gln Ile Leu Tyr Glu Asp Leu Glu Gly Gly
    270                 275                 280

aac atc ccc gcg ctc ttg gat gtc gaa gcc tat gag aaa agc aag gag     14773
Asn Ile Pro Ala Leu Leu Asp Val Glu Ala Tyr Glu Lys Ser Lys Glu
285                 290                 295                 300

gag gcc gcc gca gcg gcg acc gca gcc gtg gcc acc gcc tct acc gag     14821
Glu Ala Ala Ala Ala Ala Thr Ala Ala Val Ala Thr Ala Ser Thr Glu
                305                 310                 315

gtg cgg ggc gat aat ttt gct agc gcc gcg gca gtg gcc gag gcg gct     14869
Val Arg Gly Asp Asn Phe Ala Ser Ala Ala Ala Val Ala Glu Ala Ala
            320                 325                 330

gaa acc gaa agt aag ata gtc atc cag ccg gtg gag aag gac agc aag     14917
Glu Thr Glu Ser Lys Ile Val Ile Gln Pro Val Glu Lys Asp Ser Lys
        335                 340                 345

gac agg agc tac aac gtg ctc gcg gac aag aaa aac acc gcc tac cgc     14965
Asp Arg Ser Tyr Asn Val Leu Ala Asp Lys Lys Asn Thr Ala Tyr Arg
    350                 355                 360

agc tgg tac ctg gcc tac aac tac ggc gac ccc gag aag ggc gtg cgc     15013
Ser Trp Tyr Leu Ala Tyr Asn Tyr Gly Asp Pro Glu Lys Gly Val Arg
365                 370                 375                 380

tcc tgg acg ctg ctc acc acc tcg gac gtc acc tgc ggc gtg gag caa     15061
Ser Trp Thr Leu Leu Thr Thr Ser Asp Val Thr Cys Gly Val Glu Gln
                385                 390                 395

gtc tac tgg tcg ctg ccc gac atg atg caa gac ccg gtc acc ttc cgc     15109
Val Tyr Trp Ser Leu Pro Asp Met Met Gln Asp Pro Val Thr Phe Arg
            400                 405                 410

tcc acg cgt caa gtt agc aac tac ccg gtg gtg ggc gcc gag ctc ctg     15157
Ser Thr Arg Gln Val Ser Asn Tyr Pro Val Val Gly Ala Glu Leu Leu
        415                 420                 425

ccc gtc tac tcc aag agc ttc ttc aac gag cag gcc gtc tac tcg cag     15205
```

-continued

```
Pro Val Tyr Ser Lys Ser Phe Phe Asn Glu Gln Ala Val Tyr Ser Gln
    430                 435                 440

cag ctg cgc gcc ttc acc tcg ctc acg cac gtc ttc aac cgc ttc ccc    15253
Gln Leu Arg Ala Phe Thr Ser Leu Thr His Val Phe Asn Arg Phe Pro
445                 450                 455                 460

gag aac cag atc ctc gtc cgc ccg ccc gcg ccc acc att acc acc gtc    15301
Glu Asn Gln Ile Leu Val Arg Pro Pro Ala Pro Thr Ile Thr Thr Val
                465                 470                 475

agt gaa aac gtt cct gct ctc aca gat cac ggg acc ctg ccg ctg cgc    15349
Ser Glu Asn Val Pro Ala Leu Thr Asp His Gly Thr Leu Pro Leu Arg
            480                 485                 490

agc agt atc cgg gga gtc cag cgc gtg acc gtc act gac gcc aga cgc    15397
Ser Ser Ile Arg Gly Val Gln Arg Val Thr Val Thr Asp Ala Arg Arg
        495                 500                 505

cgc acc tgc ccc tac gtc tac aag gcc ctg ggc gta gtc gcg ccg cgc    15445
Arg Thr Cys Pro Tyr Val Tyr Lys Ala Leu Gly Val Val Ala Pro Arg
    510                 515                 520

gtc ctc tcg agc cgc acc ttc taa aaaatgtcca ttctcatctc gcccagtaat   15499
Val Leu Ser Ser Arg Thr Phe
525                 530

aacaccggtt ggggcctgcg cgcgcccagc aagatgtacg gaggcgctcg ccaacgctcc  15559

acgcaacacc ccgtgcgcgt gcgcgggcac ttccgcgctc cctggggcgc cctcaagggc  15619

cgcgtgcgct cgcgcaccac cgtcgacgac gtgatcgacc aggtggtggc cgacgcgcgc  15679

aactacacgc ccgccgccgc gcccgcctcc accgtggacg ccgtcatcga cagcgtggtg  15739

gccgatgcgc gccggtacgc ccgcgccaag agccggcggc ggcgcatcgc ccggcggcac  15799

cggagcaccc ccgccatgcg cgcggcgcga gccttgctgc gcagggccag gcgcacggga  15859

cgcagggcca tgctcagggc ggccagacgc gcggcctccg gcagcagcag cgccggcagg  15919

acccgcagac gcgcggccac ggcggcggcg gcggccatcg ccagcatgtc ccgcccgcgg  15979

cgcggcaacg tgtactgggt gcgcgacgcc gccaccggtg tgcgcgtgcc cgtgcgcacc  16039

cgcccccctc gcacttgaag atgctgactt cgcgatgttg atgtgtccca gcggcgagga  16099

ggatgtccaa gcgcaaatac aaggaagaga tgctccaggt catcgcgcct gagatctacg  16159

gccccgcggt gaaggaggaa agaaagcccc gcaaactgaa gcgggtcaaa aaggacaaaa  16219

aggaggagga agatgtggac ggactggtgg agtttgtgcg cgagttcgcc ccccggcggc  16279

gcgtgcagtg gcgcgggcgg aaagtgaaac cggtgctgcg gcccggcacc acggtggtct  16339

tcacgcccgg cgagcgttcc ggctccgcct ccaagcgctc ctacgacgag gtgtacgggg  16399

acgaggacat cctcgagcag gcggtcgagc gtctgggcga gtttgcttac ggcaagcgca  16459

gccgccccgc gcccttgaaa gaggaggcgg tgtccatccc gctggaccac ggcaacccca  16519

cgccgagcct gaagccggtg accctgcagc aggtgctgcc gagcgcggcg ccgcgccggg  16579

gcttcaagcg cgagggcggc gaggatctgt acccgaccat gcagctgatg gtgcccaagc  16639

gccagaagct ggaggacgtg ctggagcaca tgaaggtgga ccccgaggtg cagcccgagg  16699

tcaaggtgcg gcccatcaag caggtggccc cgggcctggg cgtgcagacc gtggacatca  16759

agatccccac ggagcccatg gaaacgcaga ccgagcccgt gaagcccagc accagcacca  16819

tggaggtgca gacggatccc tggatgccgg cgccggcttc caccactcgc cgaagacgca  16879

agtacggcgc ggccagcctg ctgatgccca actacgcgct gcatccttcc atcatcccca  16939

cgccgggcta ccgcggcacg cgcttctacc gcggctacac cagcagccgc cgcaagacca  16999

ccacccgccg ccgccgtcgt cgcacccgcc gcagcagcac cgcgacttcc gccgccgccc  17059
```

-continued

```
tggtgcggag agtgtaccgc agcgggcgcg agcctctgac cctgccgcgc gcgcgctacc  17119

acccgagcat cgccatttaa ctctgccgtc gcctcctact tgcagatatg gccctcacat  17179

gccgcctccg cgtccccatt acgggctacc gaggaagaaa gccgcgccgt agaaggctga  17239

cggggaacgg gctgcgtcgc catcaccacc ggcggcggcg cgccatcagc aagcggttgg  17299

ggggaggctt cctgcccgcg ctgatcccca tcatcgccgc ggcgatcggg gcgatccccg  17359

gcatagcttc cgtggcggtg caggcctctc agcgccactg agacacagct tggaaaattt  17419

gtaataaaaa aatggactga cgctcctggt cctgtgatgt gtgtttttag atggaagaca  17479

tcaatttttc gtccctggca ccgcgacacg gcacgcggcc gtttatgggc acctggagcg  17539

acatcggcaa cagccaactg aacgggggcg ccttcaattg gagcagtctc tggagcgggc  17599

ttaagaattt cgggtccacg ctcaaaacct atggcaacaa ggcgtggaac agcagcacag  17659

ggcaggcgct gagggaaaag ctgaaagagc agaacttcca gcagaaggtg gtcgatggcc  17719

tggcctcggg catcaacggg gtggtggacc tggccaacca ggccgtgcag aaacagatca  17779

acagccgcct ggacgcggtc ccgcccgcgg ggtccgtgga gatgccccag gtggaggagg  17839

agctgcctcc cctggacaag cgcggcgaca agcgaccgcg tcccgacgcg gaggagacgc  17899

tgctgacgca cacggacgag ccgcccccgt acgaggaggc ggtgaaactg ggtctgccca  17959

ccacgcggcc cgtggcgcct ctggccaccg gggtgctgaa acccagcagc agcagccagc  18019

ccgcgaccct ggacttgcct ccgcctgctt cccgcccctc cacagtggct aagcccctgc  18079

cgccggtggc cgtcgcgtcg cgcgcccccc gaggccgccc ccaggcgaac tggcagagca  18139

ctctgaacag catcgtgggt ctgggagtgc agagtgtgaa gcgccgccgc tgctattaaa  18199

agacactgta gcgcttaact tgcttgtctg tgtgtatatg tatgtccgcc gaccagaagg  18259

aggaagaggc gcgtcgccga gttgcaag atg gcc acc cca tcg atg ctg ccc     18311
                               Met Ala Thr Pro Ser Met Leu Pro
                                           535

cag tgg gcg tac atg cac atc gcc gga cag gac gct tcg gag tac ctg     18359
Gln Trp Ala Tyr Met His Ile Ala Gly Gln Asp Ala Ser Glu Tyr Leu
540                 545                 550                 555

agt ccg ggt ctg gtg cag ttc gcc cgc gcc aca gac acc tac ttc agt     18407
Ser Pro Gly Leu Val Gln Phe Ala Arg Ala Thr Asp Thr Tyr Phe Ser
                560                 565                 570

ctg ggg aac aag ttt agg aac ccc acg gtg gcg ccc acg cac gat gtg     18455
Leu Gly Asn Lys Phe Arg Asn Pro Thr Val Ala Pro Thr His Asp Val
            575                 580                 585

acc acc gac cgc agc cag cgg ctg acg ctg cgc ttc gtg ccc gtg gac     18503
Thr Thr Asp Arg Ser Gln Arg Leu Thr Leu Arg Phe Val Pro Val Asp
        590                 595                 600

cgc gag gac aac acc tac tcg tac aaa gtg cgc tac acg ctg gcc gtg     18551
Arg Glu Asp Asn Thr Tyr Ser Tyr Lys Val Arg Tyr Thr Leu Ala Val
    605                 610                 615

ggc gac aac cgc gtg ctg gac atg gcc agc acc tac ttt gac atc cgc     18599
Gly Asp Asn Arg Val Leu Asp Met Ala Ser Thr Tyr Phe Asp Ile Arg
620                 625                 630                 635

ggc gtg ctg gat cgg ggg ccc agc ttc aaa ccc tac tcc ggc acc gcc     18647
Gly Val Leu Asp Arg Gly Pro Ser Phe Lys Pro Tyr Ser Gly Thr Ala
                640                 645                 650

tac aac agc ctg gct ccc aag gga gcg ccc aac act tgc cag tgg aca     18695
Tyr Asn Ser Leu Ala Pro Lys Gly Ala Pro Asn Thr Cys Gln Trp Thr
            655                 660                 665

tat aaa gct ggt gat act gat aca gaa aaa acc tat aca tat gga aat     18743
Tyr Lys Ala Gly Asp Thr Asp Thr Glu Lys Thr Tyr Thr Tyr Gly Asn
        670                 675                 680
```

-continued

```
gca cct gtg caa ggc att agc att aca aag gat ggt att caa ctt gga     18791
Ala Pro Val Gln Gly Ile Ser Ile Thr Lys Asp Gly Ile Gln Leu Gly
    685                 690                 695

act gac agc gat ggt cag gca atc tat gca gac gaa act tat caa cca     18839
Thr Asp Ser Asp Gly Gln Ala Ile Tyr Ala Asp Glu Thr Tyr Gln Pro
700                 705                 710                 715

gag cct caa gtg ggt gat gct gaa tgg cat gac atc act ggt act gat     18887
Glu Pro Gln Val Gly Asp Ala Glu Trp His Asp Ile Thr Gly Thr Asp
                720                 725                 730

gaa aaa tat gga ggc aga gct ctt aag cct gac acc aaa atg aag cct     18935
Glu Lys Tyr Gly Gly Arg Ala Leu Lys Pro Asp Thr Lys Met Lys Pro
            735                 740                 745

tgc tat ggt tct ttt gcc aag cct acc aat aaa gaa gga ggc cag gca     18983
Cys Tyr Gly Ser Phe Ala Lys Pro Thr Asn Lys Glu Gly Gly Gln Ala
        750                 755                 760

aat gtg aaa acc gaa aca ggc ggt acc aaa gaa tat gac att gac atg     19031
Asn Val Lys Thr Glu Thr Gly Gly Thr Lys Glu Tyr Asp Ile Asp Met
    765                 770                 775

gca ttc ttc gat aat cga agt gca gct gcc gcc ggc cta gcc cca gaa     19079
Ala Phe Phe Asp Asn Arg Ser Ala Ala Ala Ala Gly Leu Ala Pro Glu
780                 785                 790                 795

att gtt ttg tat act gag aat gtg gat ctg gaa act cca gat acc cat     19127
Ile Val Leu Tyr Thr Glu Asn Val Asp Leu Glu Thr Pro Asp Thr His
                800                 805                 810

att gta tac aag gca ggt aca gat gac agt agc tct tct atc aat ttg     19175
Ile Val Tyr Lys Ala Gly Thr Asp Asp Ser Ser Ser Ser Ile Asn Leu
            815                 820                 825

ggt cag cag tcc atg ccc aac aga ccc aac tac att ggc ttc aga gac     19223
Gly Gln Gln Ser Met Pro Asn Arg Pro Asn Tyr Ile Gly Phe Arg Asp
        830                 835                 840

aac ttt atc ggt ctg atg tac tac aac agc act ggc aat atg ggt gta     19271
Asn Phe Ile Gly Leu Met Tyr Tyr Asn Ser Thr Gly Asn Met Gly Val
    845                 850                 855

ctg gct gga cag gcc tcc cag ctg aat gct gtg gtg gac ttg cag gac     19319
Leu Ala Gly Gln Ala Ser Gln Leu Asn Ala Val Val Asp Leu Gln Asp
860                 865                 870                 875

aga aac acc gaa ctg tcc tac cag ctc ttg ctt gac tct ctg ggt gac     19367
Arg Asn Thr Glu Leu Ser Tyr Gln Leu Leu Leu Asp Ser Leu Gly Asp
                880                 885                 890

aga acc agg tat ttc agt atg tgg aat cag gcg gtg gac agt tat gac     19415
Arg Thr Arg Tyr Phe Ser Met Trp Asn Gln Ala Val Asp Ser Tyr Asp
            895                 900                 905

ccc gat gtg cgc att att gaa aat cac ggt gtg gag gat gaa ctt cct     19463
Pro Asp Val Arg Ile Ile Glu Asn His Gly Val Glu Asp Glu Leu Pro
        910                 915                 920

aac tat tgc ttc ccc ctg gat gct gtg ggt aga act gat act tac cag     19511
Asn Tyr Cys Phe Pro Leu Asp Ala Val Gly Arg Thr Asp Thr Tyr Gln
    925                 930                 935

gga att aag gcc aat ggt gat aat caa acc acc tgg acc aaa gat gat     19559
Gly Ile Lys Ala Asn Gly Asp Asn Gln Thr Thr Trp Thr Lys Asp Asp
940                 945                 950                 955

act gtt aat gat gct aat gaa ttg ggc aag ggc aat cct ttc gcc atg     19607
Thr Val Asn Asp Ala Asn Glu Leu Gly Lys Gly Asn Pro Phe Ala Met
                960                 965                 970

gag atc aac atc cag gcc aac ctg tgg cgg aac ttc ctc tac gcg aac     19655
Glu Ile Asn Ile Gln Ala Asn Leu Trp Arg Asn Phe Leu Tyr Ala Asn
            975                 980                 985

gtg gcg ctg tac ctg ccc gac tcc tac aag tac acg ccg  gcc aac atc     19703
Val Ala Leu Tyr Leu Pro Asp Ser Tyr Lys Tyr Thr Pro  Ala Asn Ile
```

-continued

```
        990                 995                 1000

acg ctg  ccc acc aac acc aac  acc tac gat tac atg  aac ggc cgc      19748
Thr Leu  Pro Thr Asn Thr Asn  Thr Tyr Asp Tyr Met  Asn Gly Arg
    1005                 1010                 1015

gtg gtg  gcg ccc tcg ctg gtg  gac gcc tac atc aac  atc ggg gcg      19793
Val Val  Ala Pro Ser Leu Val  Asp Ala Tyr Ile Asn  Ile Gly Ala
    1020                 1025                 1030

cgc tgg  tcg ctg gac ccc atg  gac aac gtc aac ccc  ttc aac cac      19838
Arg Trp  Ser Leu Asp Pro Met  Asp Asn Val Asn Pro  Phe Asn His
    1035                 1040                 1045

cac cgc  aac gcg ggc ctg cga  tac cgc tcc atg ctc  ctg ggc aac      19883
His Arg  Asn Ala Gly Leu Arg  Tyr Arg Ser Met Leu  Leu Gly Asn
    1050                 1055                 1060

ggg cgc  tac gtg ccc ttc cac  atc cag gtg ccc caa  aag ttt ttc      19928
Gly Arg  Tyr Val Pro Phe His  Ile Gln Val Pro Gln  Lys Phe Phe
    1065                 1070                 1075

gcc atc  aag agc ctc ctg ctc  ctg ccc ggg tcc tac  acc tac gag      19973
Ala Ile  Lys Ser Leu Leu Leu  Leu Pro Gly Ser Tyr  Thr Tyr Glu
    1080                 1085                 1090

tgg aac  ttc cgc aag gac gtc  aac atg atc ctg cag  agc tcc ctc      20018
Trp Asn  Phe Arg Lys Asp Val  Asn Met Ile Leu Gln  Ser Ser Leu
    1095                 1100                 1105

ggc aac  gac ctg cgc acg gac  ggg gcc tcc atc gcc  ttc acc agc      20063
Gly Asn  Asp Leu Arg Thr Asp  Gly Ala Ser Ile Ala  Phe Thr Ser
    1110                 1115                 1120

atc aac  ctc tac gcc acc ttc  ttc ccc atg gcg cac  aac acc gcc      20108
Ile Asn  Leu Tyr Ala Thr Phe  Phe Pro Met Ala His  Asn Thr Ala
    1125                 1130                 1135

tcc acg  ctc gag gcc atg ctg  cgc aac gac acc aac  gac cag tcc      20153
Ser Thr  Leu Glu Ala Met Leu  Arg Asn Asp Thr Asn  Asp Gln Ser
    1140                 1145                 1150

ttc aac  gac tac ctc tcg gcg  gcc aac atg ctc tac  ccc atc ccg      20198
Phe Asn  Asp Tyr Leu Ser Ala  Ala Asn Met Leu Tyr  Pro Ile Pro
    1155                 1160                 1165

gcc aac  gcc acc aac gtg ccc  atc tcc atc ccc tcg  cgc aac tgg      20243
Ala Asn  Ala Thr Asn Val Pro  Ile Ser Ile Pro Ser  Arg Asn Trp
    1170                 1175                 1180

gcc gcc  ttc cgc ggc tgg tcc  ttc acg cgc ctc aag  acc cgc gag      20288
Ala Ala  Phe Arg Gly Trp Ser  Phe Thr Arg Leu Lys  Thr Arg Glu
    1185                 1190                 1195

acg ccc  tcg ctc ggc tcc ggg  ttc gac ccc tac ttc  gtc tac tcg      20333
Thr Pro  Ser Leu Gly Ser Gly  Phe Asp Pro Tyr Phe  Val Tyr Ser
    1200                 1205                 1210

ggc tcc  atc ccc tac ctc gac  ggc acc ttc tac ctc  aac cac acc      20378
Gly Ser  Ile Pro Tyr Leu Asp  Gly Thr Phe Tyr Leu  Asn His Thr
    1215                 1220                 1225

ttc aag  aag gtc tcc atc acc  ttc gac tcc tcc gtc  agc tgg ccc      20423
Phe Lys  Lys Val Ser Ile Thr  Phe Asp Ser Ser Val  Ser Trp Pro
    1230                 1235                 1240

ggc aac  gac cgc ctc ctg acg  ccc aac gag ttc gaa  atc aag cgc      20468
Gly Asn  Asp Arg Leu Leu Thr  Pro Asn Glu Phe Glu  Ile Lys Arg
    1245                 1250                 1255

acc gtc  gac gga gag ggg tac  aac gtg gcc cag tgc  aac atg acc      20513
Thr Val  Asp Gly Glu Gly Tyr  Asn Val Ala Gln Cys  Asn Met Thr
    1260                 1265                 1270

aag gac  tgg ttc ctg gtc cag  atg ctg gcc cac tac  aac atc ggc      20558
Lys Asp  Trp Phe Leu Val Gln  Met Leu Ala His Tyr  Asn Ile Gly
    1275                 1280                 1285

tac cag  ggc ttc tac gtg ccc  gag ggc tac aag gac  cgc atg tac      20603
```

-continued

```
Tyr Gln  Gly Phe Tyr Val Pro  Glu Gly Tyr Lys Asp  Arg Met Tyr
    1290                 1295                 1300

tcc ttc  ttc cgc aac ttc cag  ccc atg agc cgc cag  gtc gtg gac     20648
Ser Phe  Phe Arg Asn Phe Gln  Pro Met Ser Arg Gln  Val Val Asp
    1305                 1310                 1315

gag gtc  aac tac aag gac tac  cag gcc gtc acc ctg  gcc tac cag     20693
Glu Val  Asn Tyr Lys Asp Tyr  Gln Ala Val Thr Leu  Ala Tyr Gln
    1320                 1325                 1330

cac aac  aac tcg ggc ttc gtc  ggc tac ctc gcg ccc  acc atg cgc     20738
His Asn  Asn Ser Gly Phe Val  Gly Tyr Leu Ala Pro  Thr Met Arg
    1335                 1340                 1345

cag ggc  cag ccc tac ccc gcc  aac tac ccc tac ccg  ctc atc ggc     20783
Gln Gly  Gln Pro Tyr Pro Ala  Asn Tyr Pro Tyr Pro  Leu Ile Gly
    1350                 1355                 1360

aag agc  gcc gtc gcc agc gtc  acc cag aaa aag ttc  ctc tgc gac     20828
Lys Ser  Ala Val Ala Ser Val  Thr Gln Lys Lys Phe  Leu Cys Asp
    1365                 1370                 1375

cgg gtc  atg tgg cgc atc ccc  ttc tcc agc aac ttc  atg tcc atg     20873
Arg Val  Met Trp Arg Ile Pro  Phe Ser Ser Asn Phe  Met Ser Met
    1380                 1385                 1390

ggc gcg  ctc acc gac ctc ggc  cag aac atg ctc tac  gcc aac tcc     20918
Gly Ala  Leu Thr Asp Leu Gly  Gln Asn Met Leu Tyr  Ala Asn Ser
    1395                 1400                 1405

gcc cac  gcg cta gac atg aat  ttc gaa gtc gac ccc  atg gat gag     20963
Ala His  Ala Leu Asp Met Asn  Phe Glu Val Asp Pro  Met Asp Glu
    1410                 1415                 1420

tcc acc  ctt ctc tat gtt gtc  ttc gaa gtc ttc gac  gtc gtc cga     21008
Ser Thr  Leu Leu Tyr Val Val  Phe Glu Val Phe Asp  Val Val Arg
    1425                 1430                 1435

gtg cac  cag ccc cac cgc ggc  gtc atc gag gcc gtc  tac ctg cgc     21053
Val His  Gln Pro His Arg Gly  Val Ile Glu Ala Val  Tyr Leu Arg
    1440                 1445                 1450

acg ccc  ttc tcg gcc ggc aac  gcc acc acc taa gcctcttgct           21096
Thr Pro  Phe Ser Ala Gly Asn  Ala Thr Thr
    1455                 1460

tcttgcaaga tgacggcctg cgcgggctcc ggcgagcagg agctcagggc catcctccgc  21156

gacctgggct gcgggccctg cttcctgggc accttcgaca agcgcttccc gggattcatg  21216

gccccgcaca agctggcctg cgccatcgtc aacacggccg gccgcgagac cgggggcgag  21276

cactggctgg ccttcgcctg gaacccgcgc tcccacacct gctacctctt cgaccccttc  21336

gggttctcgg acgagcgcct caagcagatc taccagttcg agtacgaggg cctgctgcgt  21396

cgcagcgccc tggccaccga ggaccgctgc gtcaccctgg aaaagtccac ccagaccgtg  21456

cagggtccgc gctcggccgc ctgcgggctc ttctgctgca tgttcctgca cgccttcgtg  21516

cactggcccg accgccccat ggacaagaac ccccaccatga acttgctgac gggggtgccc  21576

aacggcatgc tccagtcgcc ccaggtggaa cccaccctgc gccgcaacca ggaggcgctc  21636

taccgcttcc tcaacgccca ctccgcctac tttcgctccc accgcgcgcg catcgagaag  21696

gccaccgcct tcgaccgcat gaatcaagac atgtaatccg gtgtgtgtat gtgaatgctt  21756

tattcatcat aataaacagc acatgtttat gccaccttct ctgaggctct gactttattt  21816

agaaatcgaa ggggttctgc cggctctcgg catggcccgc gggcagggat acgttgcgga  21876

actggtactt gggcagccac ttgaactcgg ggatcagcag cttcggcacg gggaggtcgg  21936

ggaacgagtc gctccacagc ttgcgcgtga gttgcagggc gcccagcagg tcgggcgcgg  21996

agatcttgaa atcgcagttg ggacccgcgt tctgcgcgcg agagttacgg tacacggggt  22056
```

-continued

```
tgcagcactg gaacaccatc agggccgggt gcttcacgct cgccagcacc gtcgcgtcgg  22116
tgatgccctc cacgtccaga tcctcggcgt tggccatccc gaagggggtc atcttgcagg  22176
tctgccgccc catgctgggc acgcagccgg gcttgtggtt gcaatcgcag tgcaggggga  22236
tcagcatcat ctgggcctgc tcggagctca tgcccgggta catggccttc atgaaagcct  22296
ccagctggcg gaaggcctgc tgcgccttgc cgccctcggt gaagaagacc ccgcaggact  22356
tgctagagaa ctggttggtg gcgcagccag cgtcgtgcac gcagcagcgc gcgtcgttgt  22416
tggccagctg caccacgctg cgccccccagc ggttctgggt gatcttggcc cggtcggggt  22476
tctccttcag cgcgcgctgc ccgttctcgc tcgccacatc catctcgatc gtgtgctcct  22536
tctggatcat cacggtcccg tgcaggcacc gcagcttgcc ctcggcctcg gtgcacccgt  22596
gcagccacag cgcgcagccg gtgctctccc agttcttgtg ggcgatctgg gagtgcgagt  22656
gcacgaagcc ctgcaggaag cggcccatca tcgtggtcag ggtcttgttg ctggtgaagg  22716
tcagcggaat gccgcggtgc tcctcgttca catacaggtg gcagatacgg cggtacacct  22776
cgccctgctc gggcatcagc tggaaggcgg acttcaggtc gctctccacg cggtaccggt  22836
ccatcagcag cgtcatcact tccatgccct tctcccaggc cgaaacgatc ggcaggctca  22896
gggggttctt caccgttgtc atcttagtcg ccgccgccga agtcaggggg tcgttctcgt  22956
ccagggtctc aaacactcgc ttgccgtcct tctcggtgat gcgcacgggg ggaaagctga  23016
agcccacggc cgccagctcc tcctcggcct gcctttcgtc ctcgctgtcc tggctgatgt  23076
cttgcaaagg cacatgcttg gtcttgcggg gtttcttttt gggcggcaga ggcggcggcg  23136
gagacgtgct gggcgagcgc gagttctcgc tcaccacgac tatttcttct ccttggccgt  23196
cgtccgagac cacgcggcgg taggcatgcc tcttctgggg cagaggcgga ggcgacgggc  23256
tctcgcggtt cggcgggcgg ctggcagagc cccttccgcg ttcgggggtg cgctcctggc  23316
ggcgctgctc tgactgactt cctccgcggc cggccattgt gttctcctag ggagcaagca  23376
tggagactca gccatcgtcg ccaacatcgc catctgcccc cgccgccgcc gacgagaacc  23436
agcagcagca gaatgaaagc ttaaccgccc cgccgcccag ccccacctcc gacgccgcag  23496
ccccagacat gcaagagatg gaggaatcca tcgagattga cctgggctac gtgacgcccg  23556
cggagcacga ggaggagctg gcagcgcgct tttcagcccc ggaagagaac caccaagagc  23616
agccagagca ggaagcagag agcgagcaga accaggctgg gctcgagcat ggcgactacc  23676
tgagcggggc agaggacgtg ctcatcaagc atctggcccg ccaatgcatc atcgtcaagg  23736
acgcgctgct cgaccgcgcc gaggtgcccc tcagcgtggc ggagctcagc cgcgcctacg  23796
agcgcaacct cttctcgccg cgcgtgcccc ccaagcgcca gcccaacggc acctgcgagc  23856
ccaacccgcg cctcaacttc tacccggtct tcgcggtgcc cgaggccctg gccacctacc  23916
acctcttttt caagaaccaa aggatccccg tctcctgccg cgccaaccgc acccgcgccg  23976
acgccctgct caacctgggc cccggcgccc gcctacctga tatcgcctcc ttggaagagg  24036
ttcccaagat cttcgagggt ctgggcagcg acgagactcg ggccgcgaac gctctgcaag  24096
gaagcggaga ggagcatgag caccacagcg ccctggtgga gttggaaggc gacaacgcgc  24156
gcctggcggt cctcaagcgc acggtcgagc tgacccactt cgcctacccg gcgctcaacc  24216
tgccccccaa ggtcatgagc gccgtcatgg accaggtgct catcaagcgc gcctcgcccc  24276
tctcggagga ggagatgcag gaccccgaga gctcggacga gggcaagccc gtggtcagcg  24336
acgagcagct ggcgcgctgg ctgggagcga gtagcacccc ccagagcctg gaagagcggc  24396
gcaagctcat gatggccgtg gtcctggtga ccgtggagct ggagtgtctg cgccgcttct  24456
```

-continued

```
tcgccgacgc ggagaccctg cgcaaggtcg aggagaacct gcactacctc ttcagacacg  24516
ggttcgtgcg ccaggcctgc aagatctcca acgtggagct gaccaacctg gtctcctaca  24576
tgggcatcct gcacgagaac cgcctggggc agaacgtgct gcacaccacc ctgcgcgggg  24636
aggcccgccg cgactacatc cgcgactgcg tctacctgta cctctgccac acctggcaga  24696
cgggcatggg cgtgtggcag cagtgcctgg aggagcagaa cctgaaagag ctctgcaagc  24756
tcctgcagaa gaacctcaag gccctgtgga ccgggttcga cgagcgcacc accgccgcgg  24816
acctggccga cctcatcttc cccgagcgcc tgcggctgac gctgcgcaac gggctgcccg  24876
actttatgag ccaaagcatg ttgcaaaact ttcgctcttt catcctcgaa cgctccggga  24936
tcctgcccgc cacctgctcc gcgctgccct cggacttcgt gccgctgacc ttccgcgagt  24996
gcccccgccc gctctggagc cactgctacc tgctgcgcct ggccaactac ctggcctacc  25056
actcggacgt gatcgaggac gtcagcggcg agggcctgct cgagtgccac tgccgctgca  25116
acctctgcac gccgcaccgc tccctggcct gcaacccccca gctgctgagc gagacccaga  25176
tcatcggcac cttcgagttg caaggccccg gcgagggcaa gggggtctg aaactcaccc  25236
cggggctgtg gacctcggcc tacttgcgca agttcgtgcc cgaggactac catcccttcg  25296
agatcaggtt ctacgaggac caatcccagc cgcccaaggc cgagctgtcg gcctgcgtca  25356
tcacccaggg ggccatcctg gcccaattgc aagccatcca gaaatcccgc caagaatttc  25416
tgctgaaaaa gggccacggg gtctacttgg acccccagac cggagaggag ctcaacccca  25476
gcttccccca ggatgccccg aggaagcagc aagaagctga aagtggagct gccgccgccg  25536
ccggaggatt tggaggaaga ctgggagagc agtcaggcag aggaggagga gatggaagac  25596
tgggacagca ctcaggcaga ggaggacagc ctgcaagaca gtctggagga ggaagacgag  25656
gtggaggagg cagaggaaga agcagccgcc gccagaccgt cgtcctcggc ggaggaggag  25716
aaagcaagca gcacggatac catctccgct ccgggtcggg gtcgcggcgg ccgggcccac  25776
agtagatggg acgagaccgg gcgcttcccg aaccccacca cccagaccgg taagaaggag  25836
cggcagggat acaagtcctg gcgggggcac aaaaacgcca tcgtctcctg cttgcaagcc  25896
tgcgggggca acatctcctt cacccggcgc tacctgctct tccaccgcgg ggtgaacttc  25956
ccccgcaaca tcttgcatta ctaccgtcac ctccacagcc cctactactg tttccaagaa  26016
gaggcagaaa cccagcagca gcagcagcag cagaaaacca gcggcagcag ctagaaaatc  26076
cacagcggcg gcaggtggac tgaggatcgc ggcgaacgag ccggcgcaga cccgggagct  26136
gaggaaccgg atctttccca ccctctatgc catcttccag cagagtcggg ggcaagagca  26196
ggaactgaaa gtcaagaacc gttctctgcg ctcgctcacc cgcagttgtc tgtatcacaa  26256
gagcgaagac caacttcagc gcactctcga ggacgccgag gctctcttca acaagtactg  26316
cgcgctcact cttaaagagt agcccgcgcc cgcccacaca cggaaaaagg cgggaattac  26376
gtcaccacct gcgcccttcg cccgaccatc atcatgagca aagagattcc cacgccttac  26436
atgtggagct accagcccca gatgggcctg gccgccggcg ccgcccagga ctactccacc  26496
cgcatgaact ggctcagtgc cgggcccgcg atgatctcac gggtgaatga catccgcgcc  26556
caccgaaacc agatactcct agaacagtca gcgatcaccg ccacgccccg ccatcacctt  26616
aatccgcgta attggcccgc cgccctggtg taccaggaaa ttccccagcc cacgaccgta  26676
ctacttccgc gagacgccca ggccgaagtc cagctgacta actcaggtgt ccagctggcc  26736
ggcggcgccg ccctgtgtcg tcaccgcccc gctcagggta taaagcggct ggtgatccga  26796
```

-continued

```
ggcagaggca cacagctcaa cgacgaggtg gtgagctctt cgctgggtct gcgacctgac  26856
ggagtcttcc aactcgccgg atcggggaga tcttccttca cgcctcgtca ggccgtcctg  26916
actttggaga gttcgtcctc gcagccccgc tcgggtggca tcggcactct ccagttcgtg  26976
gaggagttca ctccctcggt ctacttcaac cccttctccg gctcccccgg ccactacccg  27036
gacgagttca tcccgaactt cgacgccatc agcgagtcgg tggacggcta cgattgaatg  27096
tcccatggtg gcgcggctga cctagctcgg cttcgacacc tggaccactg ccgccgcttc  27156
cgctgcttcg ctcgggatct cgccgagttt gcctactttg agctgcccga ggagcaccct  27216
cagggcccgg cccacggagt gcggatcgtc gtcgaagggg gtctcgactc ccacctgctt  27276
cggatcttca gccagcgtcc gatcctggcc gagcgcgagc aaggacagac ccttctgacc  27336
ctgtactgca tctgcaacca ccccggcctg catgaaagtc tttgttgtct gctgtgtact  27396
gagtataata aaagctgaga tcagcgacta ctccggactt ccgtgtgttc ctgctatcaa  27456
ccagtccctg ttcttcaccg ggaacgagac cgagctccag ctccagtgta agccccacaa  27516
gaagtacctc acctggctgt tccagggctc tccgatcgcc gttgtcaacc actgcgacaa  27576
cgacggagtc ctgctgagcg gccctgccaa ccttactttt tccacccgca gaagcaagct  27636
ccagctcttc caacccttcc tccccgggac ctatcagtgc gtctcgggac cctgccatca  27696
caccttccac ctgatcccga ataccacagc gtcgctcccc gctactaaca accaaactac  27756
ccaccaacgc caccgtcgcg acctttcctc tgggtctaat accactaccg gaggtgagct  27816
ccgaggtcga ccaacctctg ggatttacta cggcccctgg gaggtggtag ggttaatagc  27876
gctaggccta gttgcgggtg ggcttttggc tctctgctac ctatacctcc cttgctgttc  27936
gtacttagtg gtgctgtgtt gctggtttaa gaaatgggga agatcaccct agtgagctgc  27996
ggtgtgctgg tggcggtggt gctttcgatt gtgggactgg gcggcgcggc tgtagtgaag  28056
gagaaggccg atccctgctt gcatttcaat cccgacaaat gccagctgag ttttcagccc  28116
gatggcaatc ggtgcgcggt gctgatcaag tgcggatggg aatgcgagaa cgtgagaatc  28176
gagtacaata acaagactcg gaacaatact ctcgcgtccg tgtggcagcc cggggacccc  28236
gagtggtaca ccgtctctgt ccccggtgct gacggctccc cgcgcaccgt gaataatact  28296
ttcatttttg cgcacatgtg cgacacggtc atgtggatga gcaagcagta cgatatgtgg  28356
ccccccacga aggagaacat cgtggtcttc tccatcgctt acagcgtgtg cacggcgcta  28416
atcaccgcta tcgtgtgcct gagcattcac atgctcatcg ctattcgccc cagaaataat  28476
gccgaaaaag aaaaacagcc ataacacgtt ttttcacaca cctttttcag accatggcct  28536
ctgttaaatt tttgctttta tttgccagtc tcattgccgt cattcatgga atgagtaatg  28596
agaaaattac tatttacact ggcactaatc acacattgaa aggtccagaa aaagccacag  28656
aagtttcatg gtattgttat tttaatgaat cagatgtatc tactgaactc tgtggaaaca  28716
ataacaaaaa aaatgagagc attactctca tcaagtttca atgtggatct gacttaaccc  28776
taattaacat cactagagac tatgtaggta tgtattatgg aactacagca ggcatttcgg  28836
acatggaatt ttatcaagtt tctgtgtctg aacccaccac gcctagaatg accacaacca  28896
caaaaactac acctgttacc actatacagc tcactaccaa tggctttctt gccatgcttc  28956
aagtggctga aaatagcacc agcattcaac ccaccccacc cagtgaggaa attcccagat  29016
ccatgattgg cattattgtt gctgtagtgg tgtgcatgtt gatcatcgcc ttgtgcatgg  29076
tgtactatgc cttctgctac agaaagcaca gactgaacga caagctggaa cacttactaa  29136
gtgttgaatt ttaatttttt agaaccatga agatcctagg ccttttagtt ttttctatca  29196
```

-continued

```
ttacctctgc tctatgcaat tctgacaatg aggacgttac tgtcgttgtc ggatcaaatt  29256
atacactaaa aggtccagca aaaggtatgc tttcgtggta ttgttggttc ggaactgacg  29316
agcaacagac agaactttgc aatgctcaaa aaggcaaaac ctcaaattct aaaatctcta  29376
attatcaatg caatggcact gacttagtat tgctcaatgt cacgaaagca tatgctggca  29436
gttacacctg ccctggagat gatgccgaca atatgatttt ttacaaagtg gaagtggttg  29496
atcccactac tccaccgccc accaccacaa ctactcatac cacacacaca gaacaaacac  29556
cagaggcagc agaagcagag ttggccttcc aggttcacgg agattccttt gctgtcaata  29616
cccctacacc cgatcagcgg tgtccggggc tgctcgtcag cggcattgtc ggtgtgcttt  29676
cgggattagc agtcataatc atctgcatgt tcatttttgc ttgctgctat agaaggcttt  29736
accgacaaaa atcagaccca ctgctgaacc tctatgttta attttttcca gagccatgaa  29796
ggcagttagc gctctagttt tttgttcttt gattggcatt gtttttagtg ctgggttttt  29856
gaaaaatctt accatttatg aaggtgagaa tgccactcta gtgggcatca gtggtcaaaa  29916
tgtcagctgg ctaaaatacc atctagatgg gtggaaagac atttgcgatt ggaatgtcac  29976
tgtgtataca tgtaatggag ttaacctcac cattactaat gccacccaag atcagaatgg  30036
taggtttaag ggccagagtt tcactagaaa taatgggtat gaatcccata acatgtttat  30096
ctatgacgtc actgtcatca gaaatgagac tgccaccacc acacagatgc ccactacaca  30156
cagttctacc actactacca tgcaaaccac acagacaacc actacatcaa ctcagcatat  30216
gaccaccact acagcagcaa agccaagtag tgcagcgcct cagccccagg ctttggcttt  30276
gaaagctgca caacctagta caactactag gaccaatgag cagactactg aatttttgtc  30336
cactgtcgag agccacacca cagctacctc cagtgccttc tctagcaccg ccaatctctc  30396
ctcgctttcc tctacaccaa tcagtcccgc tactactccc accccagctc ttctccccac  30456
tcccctgaag caaactgagg acagcggcat gcaatggcag atcaccctgc tcattgtgat  30516
cgggttggtc atcctggccg tgttgctcta ctacatcttc tgccgccgca ttcccaacgc  30576
gcaccgcaaa ccggcctaca agcccatcgt tatcgggcag ccggagccgc ttcaggtgga  30636
agggggtcta aggaatcttc tcttctcttt tacagtatgg tgattgaact atgattccta  30696
gacaattctt gatcactatt cttatctgcc tcctccaagt ctgtgccacc ctcgctctgg  30756
tggccaacgc cagtccagac tgtattgggc ccttcgcctc ctacgtgctc tttgccttca  30816
tcacctgcat ctgctgctgt agcatagtct gcctgcttat caccttcttc cagttcattg  30876
actggatctt tgtgcgcatc gcctacctgc gccaccaccc ccagtaccgc gaccagcgag  30936
tggcgcggct gctcaggctc ctctgataag catgcgggct ctgctacttc tcgcgcttct  30996
gctgttagtg ctcccccgcc ccgtcgaccc ccggtccccc actcagtccc ccgaagaggt  31056
ccgcaaatgc aaattccaag aaccctggaa attcctcaaa tgctaccgcc aaaaatcaga  31116
catgcttccc agctggatca tgatcattgg gatcgtgaac attctggcct gcaccctcat  31176
ctcctttgtg atttacccct gctttgactt tggttggaac tcgccagagg cgctctatct  31236
cccgcctgaa cctgacacac caccacagca acctcaggca cacgcactac caccaccaca  31296
gcctaggcca caatacatgc ccatattaga ctatgaggcc gagccacagc gacccatgct  31356
ccccgctatt agttacttca atctaaccgg cggagatgac tgacccactg gccaacaaca  31416
acgtcaacga ccttctcctg gacatggacg gccgcgcctc ggagcagcga ctcgcccaac  31476
ttcgcattcg ccagcagcag gagagagccg tcaaggagct gcaggacggc atagccatcc  31536
```

-continued

| | |
|---|---|
| accagtgcaa gaaaggcatc ttctgcctgg tgaaacaggc caagatctcc tacgaggtca | 31596 |
| ccccgaccga ccatcgcctc tcctacgagc tcctgcagca gcgccagaag ttcacctgcc | 31656 |
| tggtcggagt caaccccatc gtcatcaccc agcagtcggg cgataccaag gggtgcatcc | 31716 |
| actgctcctg cgactccccc gactgcgtcc acactctgat caagaccctc tgcggcctcc | 31776 |
| gcgacctcct ccccatgaac taatcacccc cttatccagt gaaataaata tcatattgat | 31836 |
| gatgatttaa ataaaaaata atcatttgat ttgaaataaa gatacaatca tattgatgat | 31896 |
| ttgagtttta aaaaataaag aatcacttac ttgaaatctg ataccaggtc tctgtccatg | 31956 |
| ttttctgcca acaccacctc actcccctct tcccagctct ggtactgcag accccggcgg | 32016 |
| gctgcaaact tcctccacac gctgaagggg atgtcaaatt cctcctgtcc ctcaatcttc | 32076 |

```
attttatctt ctatcag atg tcc aaa aag cgc gtc cgg gtg gat gat gac      32126
                Met Ser Lys Lys Arg Val Arg Val Asp Asp Asp
                    1465            1470

ttc gac ccc gtc tac ccc tac gat gca gac aac gca ccg acc gtg        32171
Phe Asp Pro Val Tyr Pro Tyr Asp Ala Asp Asn Ala Pro Thr Val
1475            1480            1485

ccc ttc atc aac ccc ccc ttc gtc tct tca gat gga ttc caa gag        32216
Pro Phe Ile Asn Pro Pro Phe Val Ser Ser Asp Gly Phe Gln Glu
1490            1495            1500

aag ccc ctg ggg gtg ctg tcc ctg cga ctg gct gac ccc gtc acc        32261
Lys Pro Leu Gly Val Leu Ser Leu Arg Leu Ala Asp Pro Val Thr
1505            1510            1515

acc aag aac ggg gaa atc acc ctc aag ctg gga gag ggg gtg gac        32306
Thr Lys Asn Gly Glu Ile Thr Leu Lys Leu Gly Glu Gly Val Asp
1520            1525            1530

ctc gac tcc tcg gga aaa ctc atc tcc aac acg gcc acc aag gcc        32351
Leu Asp Ser Ser Gly Lys Leu Ile Ser Asn Thr Ala Thr Lys Ala
1535            1540            1545

gcc gcc cct ctc agt ttt tcc aac aac acc att tcc ctt aac atg        32396
Ala Ala Pro Leu Ser Phe Ser Asn Asn Thr Ile Ser Leu Asn Met
1550            1555            1560

gat acc cct ctt tat acc aaa gat gga aaa tta tcc tta caa gtt        32441
Asp Thr Pro Leu Tyr Thr Lys Asp Gly Lys Leu Ser Leu Gln Val
1565            1570            1575

tct cca ccg tta aac ata tta aaa tca acc att ctg aac aca tta        32486
Ser Pro Pro Leu Asn Ile Leu Lys Ser Thr Ile Leu Asn Thr Leu
1580            1585            1590

gct gta gct tat gga tca ggt tta gga ctg agt ggt ggc act gct        32531
Ala Val Ala Tyr Gly Ser Gly Leu Gly Leu Ser Gly Gly Thr Ala
1595            1600            1605

ctt gca gta cag ttg gcc tct cca ctc act ttt gat gaa aaa gga        32576
Leu Ala Val Gln Leu Ala Ser Pro Leu Thr Phe Asp Glu Lys Gly
1610            1615            1620

aat att aaa att aac cta gcc agt ggt cca tta aca gtt gat gca        32621
Asn Ile Lys Ile Asn Leu Ala Ser Gly Pro Leu Thr Val Asp Ala
1625            1630            1635

agt cga ctt agt atc aac tgc aaa aga ggg gtc act gtc act acc        32666
Ser Arg Leu Ser Ile Asn Cys Lys Arg Gly Val Thr Val Thr Thr
1640            1645            1650

tca gga gat gca att gaa agc aac ata agc tgg cct aaa ggt ata        32711
Ser Gly Asp Ala Ile Glu Ser Asn Ile Ser Trp Pro Lys Gly Ile
1655            1660            1665

aga ttt gaa ggt aat ggc ata gct gca aac att ggc aga gga ttg        32756
Arg Phe Glu Gly Asn Gly Ile Ala Ala Asn Ile Gly Arg Gly Leu
1670            1675            1680

gaa ttt gga acc act agt aca gag act gat gtc aca gat gca tac        32801
```

-continued

```
Glu  Phe Gly Thr Thr Ser  Thr Glu Thr Asp Val  Thr Asp Ala Tyr
1685                 1690                 1695

cca  att caa gtt aaa ttg  ggt act ggc ctt acc  ttt gac agt aca     32846
Pro  Ile Gln Val Lys Leu  Gly Thr Gly Leu Thr  Phe Asp Ser Thr
1700                 1705                 1710

ggc  gcc att gtt gct tgg  aac aaa gag gat gat  aaa ctt aca tta     32891
Gly  Ala Ile Val Ala Trp  Asn Lys Glu Asp Asp  Lys Leu Thr Leu
1715                 1720                 1725

tgg  acc aca gcc gac ccc  tcg cca aat tgc aaa  ata tac tct gaa     32936
Trp  Thr Thr Ala Asp Pro  Ser Pro Asn Cys Lys  Ile Tyr Ser Glu
1730                 1735                 1740

aaa  gat gcc aaa ctc aca  ctt tgc ttg aca aag  tgt gga agt caa     32981
Lys  Asp Ala Lys Leu Thr  Leu Cys Leu Thr Lys  Cys Gly Ser Gln
1745                 1750                 1755

att  ctg ggt act gtg act  gta ttg gca gtg aat  aat gga agt ctc     33026
Ile  Leu Gly Thr Val Thr  Val Leu Ala Val Asn  Asn Gly Ser Leu
1760                 1765                 1770

aac  cca atc aca aac aca  gta agc act gca ctc  gtc tcc ctc aag     33071
Asn  Pro Ile Thr Asn Thr  Val Ser Thr Ala Leu  Val Ser Leu Lys
1775                 1780                 1785

ttt  gat gca agt gga gtt  ttg cta agc agc tcc  aca tta gac aaa     33116
Phe  Asp Ala Ser Gly Val  Leu Leu Ser Ser Ser  Thr Leu Asp Lys
1790                 1795                 1800

gaa  tat tgg aac ttc aga  aag gga gat gtt aca  cct gct gag ccc     33161
Glu  Tyr Trp Asn Phe Arg  Lys Gly Asp Val Thr  Pro Ala Glu Pro
1805                 1810                 1815

tat  act aat gct ata ggt  ttt atg cct aac ata  aag gcc tat cct     33206
Tyr  Thr Asn Ala Ile Gly  Phe Met Pro Asn Ile  Lys Ala Tyr Pro
1820                 1825                 1830

aaa  aac aca tct gca gct  tca aaa agc cat att  gtc agt caa gtt     33251
Lys  Asn Thr Ser Ala Ala  Ser Lys Ser His Ile  Val Ser Gln Val
1835                 1840                 1845

tat  ctc aat ggg gat gag  gcc aaa cca ctg atg  ctg att att act     33296
Tyr  Leu Asn Gly Asp Glu  Ala Lys Pro Leu Met  Leu Ile Ile Thr
1850                 1855                 1860

ttt  aat gaa act gag gat  gca act tgc acc tac  agt atc act ttt     33341
Phe  Asn Glu Thr Glu Asp  Ala Thr Cys Thr Tyr  Ser Ile Thr Phe
1865                 1870                 1875

caa  tgg aaa tgg gat agt  act aag tac aca ggt  gaa aca ctt gct     33386
Gln  Trp Lys Trp Asp Ser  Thr Lys Tyr Thr Gly  Glu Thr Leu Ala
1880                 1885                 1890

acc  agc tcc ttc acc ttc  tcc tac atc gcc caa  gaa tga acactgtatc  33435
Thr  Ser Ser Phe Thr Phe  Ser Tyr Ile Ala Gln  Glu
1895                 1900                 1905

ccaccctgca tgccaaccct tcccacccca ctctgtctat ggaaaaaact ctgaagcaca  33495

aaataaaata aagttcaagt gttttattga ttcaacagtt ttacaggatt cgagcagtta  33555

tttttcctcc accctcccag gacatggaat acaccaccct ctccccccgc acagccttga  33615

acatctgaat gccattggtg atggacatgc ttttggtctc cacgttccac acagtttcag  33675

agcgagccag tctcgggtcg gtcagggaga tgaaaccctc cgggcactcc cgcatctgca  33735

cctcacagct caacagctga ggattgtcct cggtggtcgg gatcacggtt atctggaaga  33795

agcagaagag cggcggtggg aatcatagtc cgcgaacggg atcggccggt ggtgtcgcat  33855

caggccccgc agcagtcgct gccgccgccg ctccgtcaag ctgctgctca gggggtccgg  33915

gtccagggac tccctcagca tgatgcccac ggccctcagc atcagtcgtc tggtgcggcg  33975

ggcgcagcag cgcatgcgga tctcgctcag gtcgctgcag tacgtgcaac acaggaccac  34035
```

-continued

```
caggttgttc aacagtccat agttcaacac gctccagccg aaactcatcg cgggaaggat  34095
gctacccacg tggccgtcgt accagatcct caggtaaatc aagtggcgct ccctccagaa  34155
cacgctgccc acgtacatga tctccttggg catgtggcgg ttcaccacct cccggtacca  34215
catcaccctc tggttgaaca tgcagccccg gatgatcctg cggaaccaca gggccagcac  34275
cgccccgccc gccatgcagc gaagagaccc cgggtcccgg caatggcaat ggaggaccca  34335
ccgctcgtac ccgtggatca tctgggagct gaacaagtct atgttggcac agcacaggca  34395
tatgctcatg catctcttca gcactctcag ctcctcgggg gtcaaaacca tatcccaggg  34455
cacggggaac tcttgcagga cagcgaaccc cgcagaacag ggcaatcctc gcacataact  34515
tacattgtgc atggacaggg tatcgcaatc aggcagcacc gggtgatcct ccaccagaga  34575
agcgcgggtc tcggtctcct cacagcgtgg taagggggcc ggccgatacg ggtgatggcg  34635
ggacgcggct gatcgtgttc gcgaccgtgt catgatgcag ttgctttcgg acattttcgt  34695
acttgctgta gcagaacctg gtccgggcgc tgcacaccga tcgccggcgg cggtcccggc  34755
gcttggaacg ctcggtgttg aaattgtaaa acagccactc tctcagaccg tgcagcagat  34815
ctagggcctc aggagtgatg aagatcccat catgcctgat agctctgatc acatcgacca  34875
ccgtggaatg ggccagaccc agccagatga tgcaattttg ttgggtttcg gtgacggcgg  34935
gggagggaag aacaggaaga accatgatta acttttaatc caaacggtct cggagcactt  34995
caaaatgaag gtcgcggaga tggcacctct cgccccccgct gtgttggtgg aaaataacag  35055
ccaggtcaaa ggtgatacgg ttctcgagat gttccacggt ggcttccagc aaagcctcca  35115
cgcgcacatc cagaaacaag acaatagcga aagcgggagg gttctctaat tcctcaatca  35175
tcatgttaca ctcctgcacc atccccagat aattttcatt tttccagcct tgaatgattc  35235
gaactagttc ctgaggtaaa tccaagccag ccatgataaa gagctcgcgc agagcgccct  35295
ccaccggcat tcttaagcac accctcataa ttccaagata ttctgctcct ggttcacctg  35355
cagcagattg acaagcggaa tatcaaaatc tctgccgcga tccctaagct cctccctcag  35415
caataactgt aagtactctt tcatatcctc tccgaaattt ttagccatag gaccaccagg  35475
aataagatta gggcaagcca cagtacagat aaaccgaagt cctccccagt gagcattgcc  35535
aaatgcaaga ctgctataag catgctggct agacccggtg atatcttcca gataactgga  35595
cagaaaatca cccaggcaat ttttaagaaa atcaacaaaa gaaaaatcct ccaggtgcac  35655
gtttagagcc tcgggaacaa cgatgaagta aatgcaagcg gtgcgttcca gcatggttag  35715
ttagctgatc tgtaaaaaac aaaaaataaa acattaaacc atgctagcct ggcgaacagg  35775
tgggtaaatc gttctctcca gcaccaggca ggccacgggg tctccggcgc gaccctcgta  35835
aaaattgtcg ctatgattga aaccatcac agagagacgt tcccggtggc cggcgtgaat  35895
gattcgacaa gatgaataca cccccggaac attggcgtcc gcgagtgaaa aaaagcgccc  35955
gaggaagcaa taaggcacta caatgctcag tctcaagtcc agcaaagcga tgccatgcgg  36015
atgaagcaca aaatcctcag gtgcgtacaa aatgtaatta ctcccctcct gcacaggcag  36075
cgaagccccc gatccctcca gatacacata caaagcctca gcgtccatag cttaccgagc  36135
agcagcacac aacaggcgca agagtcagag aaaggctgag ctctaacctg tccacccgct  36195
ctctgctcaa tatatagccc agatctacac tgacgtaaag gccaaagtct aaaaataccc  36255
gccaaataat cacacacgcc cagcacacgc ccagaaaccg gtgacacact caaaaaaata  36315
cgcgcacttc ctcaaacgcc caaactgccg tcatttccgg gttcccacgc tacgtcatcg  36375
gaattcgact ttcaaattcc gtcgaccgtt aaaaacgtca cccgccccgc ccctaacggt  36435
```

-continued

```
cgcccgtctc tcggccaatc accttcctcc ctccccaaat tcaaacagct catttgcata  36495

ttaacgcgca ccaaaagttt gaggtatatt attgatgatg                        36535


<210> SEQ ID NO 10
<211> LENGTH: 531
<212> TYPE: PRT
<213> ORGANISM: chimpanzee adenovirus serotype Pan7

<400> SEQUENCE: 10

Met Met Arg Arg Val Tyr Pro Glu Gly Pro Pro Pro Ser Tyr Glu Ser
1               5                   10                  15

Val Met Gln Gln Ala Val Ala Ala Ala Met Gln Pro Pro Leu Glu Ala
            20                  25                  30

Pro Tyr Val Pro Pro Arg Tyr Leu Ala Pro Thr Glu Gly Arg Asn Ser
        35                  40                  45

Ile Arg Tyr Ser Glu Leu Ala Pro Leu Tyr Asp Thr Thr Arg Leu Tyr
    50                  55                  60

Leu Val Asp Asn Lys Ser Ala Asp Ile Ala Ser Leu Asn Tyr Gln Asn
65                  70                  75                  80

Asp His Ser Asn Phe Leu Thr Thr Val Val Gln Asn Asn Asp Phe Thr
                85                  90                  95

Pro Thr Glu Ala Ser Thr Gln Thr Ile Asn Phe Asp Glu Arg Ser Arg
            100                 105                 110

Trp Gly Gly Gln Leu Lys Thr Ile Met His Thr Asn Met Pro Asn Val
        115                 120                 125

Asn Glu Phe Met Tyr Ser Asn Lys Phe Lys Ala Arg Val Met Val Ser
    130                 135                 140

Arg Lys Thr Pro Asn Gly Val Ala Val Asp Glu Asn Tyr Asp Gly Ser
145                 150                 155                 160

Gln Asp Glu Leu Thr Tyr Glu Trp Val Glu Phe Glu Leu Pro Glu Gly
                165                 170                 175

Asn Phe Ser Val Thr Met Thr Ile Asp Leu Met Asn Asn Ala Ile Ile
            180                 185                 190

Asp Asn Tyr Leu Ala Val Gly Arg Gln Asn Gly Val Leu Glu Ser Asp
        195                 200                 205

Ile Gly Val Lys Phe Asp Thr Arg Asn Phe Arg Leu Gly Trp Asp Pro
    210                 215                 220

Val Thr Glu Leu Val Met Pro Gly Val Tyr Thr Asn Glu Ala Phe His
225                 230                 235                 240

Pro Asp Ile Val Leu Leu Pro Gly Cys Gly Val Asp Phe Thr Glu Ser
                245                 250                 255

Arg Leu Ser Asn Leu Leu Gly Ile Arg Lys Arg Gln Pro Phe Gln Glu
            260                 265                 270

Gly Phe Gln Ile Leu Tyr Glu Asp Leu Glu Gly Gly Asn Ile Pro Ala
        275                 280                 285

Leu Leu Asp Val Glu Ala Tyr Glu Lys Ser Lys Glu Glu Ala Ala Ala
    290                 295                 300

Ala Ala Thr Ala Ala Val Ala Thr Ala Ser Thr Glu Val Arg Gly Asp
305                 310                 315                 320

Asn Phe Ala Ser Ala Ala Ala Val Ala Glu Ala Ala Glu Thr Glu Ser
                325                 330                 335

Lys Ile Val Ile Gln Pro Val Glu Lys Asp Ser Lys Asp Arg Ser Tyr
            340                 345                 350
```

-continued

```
Asn Val Leu Ala Asp Lys Lys Asn Thr Ala Tyr Arg Ser Trp Tyr Leu
        355                 360                 365

Ala Tyr Asn Tyr Gly Asp Pro Glu Lys Gly Val Arg Ser Trp Thr Leu
    370                 375                 380

Leu Thr Thr Ser Asp Val Thr Cys Gly Val Glu Gln Val Tyr Trp Ser
385                 390                 395                 400

Leu Pro Asp Met Met Gln Asp Pro Val Thr Phe Arg Ser Thr Arg Gln
            405                 410                 415

Val Ser Asn Tyr Pro Val Val Gly Ala Glu Leu Leu Pro Val Tyr Ser
            420                 425                 430

Lys Ser Phe Phe Asn Glu Gln Ala Val Tyr Ser Gln Gln Leu Arg Ala
        435                 440                 445

Phe Thr Ser Leu Thr His Val Phe Asn Arg Phe Pro Glu Asn Gln Ile
    450                 455                 460

Leu Val Arg Pro Pro Ala Pro Thr Ile Thr Thr Val Ser Glu Asn Val
465                 470                 475                 480

Pro Ala Leu Thr Asp His Gly Thr Leu Pro Leu Arg Ser Ser Ile Arg
            485                 490                 495

Gly Val Gln Arg Val Thr Val Thr Asp Ala Arg Arg Arg Thr Cys Pro
            500                 505                 510

Tyr Val Tyr Lys Ala Leu Gly Val Val Ala Pro Arg Val Leu Ser Ser
        515                 520                 525

Arg Thr Phe
    530


SEQ ID NO 11
LENGTH: 932
TYPE: PRT
ORGANISM: chimpanzee adenovirus serotype Pan7

SEQUENCE: 11

Met Ala Thr Pro Ser Met Leu Pro Gln Trp Ala Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Asn Thr Tyr Ser Tyr
65                  70                  75                  80

Lys Val Arg Tyr Thr Leu Ala Val Gly Asp Asn Arg Val Leu Asp Met
            85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Thr Cys Gln Trp Thr Tyr Lys Ala Gly Asp Thr Asp Thr
    130                 135                 140

Glu Lys Thr Tyr Thr Tyr Gly Asn Ala Pro Val Gln Gly Ile Ser Ile
145                 150                 155                 160

Thr Lys Asp Gly Ile Gln Leu Gly Thr Asp Ser Asp Gly Gln Ala Ile
            165                 170                 175

Tyr Ala Asp Glu Thr Tyr Gln Pro Glu Pro Gln Val Gly Asp Ala Glu
            180                 185                 190
```

-continued

```
Trp His Asp Ile Thr Gly Thr Asp Glu Lys Tyr Gly Gly Arg Ala Leu
        195                 200                 205

Lys Pro Asp Thr Lys Met Lys Pro Cys Tyr Gly Ser Phe Ala Lys Pro
    210                 215                 220

Thr Asn Lys Glu Gly Gly Gln Ala Asn Val Lys Thr Glu Thr Gly Gly
225                 230                 235                 240

Thr Lys Glu Tyr Asp Ile Asp Met Ala Phe Phe Asp Asn Arg Ser Ala
                245                 250                 255

Ala Ala Ala Gly Leu Ala Pro Glu Ile Val Leu Tyr Thr Glu Asn Val
            260                 265                 270

Asp Leu Glu Thr Pro Asp Thr His Ile Val Tyr Lys Ala Gly Thr Asp
        275                 280                 285

Asp Ser Ser Ser Ser Ile Asn Leu Gly Gln Gln Ser Met Pro Asn Arg
    290                 295                 300

Pro Asn Tyr Ile Gly Phe Arg Asp Asn Phe Ile Gly Leu Met Tyr Tyr
305                 310                 315                 320

Asn Ser Thr Gly Asn Met Gly Val Leu Ala Gly Gln Ala Ser Gln Leu
                325                 330                 335

Asn Ala Val Val Asp Leu Gln Asp Arg Asn Thr Glu Leu Ser Tyr Gln
            340                 345                 350

Leu Leu Leu Asp Ser Leu Gly Asp Arg Thr Arg Tyr Phe Ser Met Trp
        355                 360                 365

Asn Gln Ala Val Asp Ser Tyr Asp Pro Asp Val Arg Ile Ile Glu Asn
    370                 375                 380

His Gly Val Glu Asp Glu Leu Pro Asn Tyr Cys Phe Pro Leu Asp Ala
385                 390                 395                 400

Val Gly Arg Thr Asp Thr Tyr Gln Gly Ile Lys Ala Asn Gly Asp Asn
                405                 410                 415

Gln Thr Thr Trp Thr Lys Asp Asp Thr Val Asn Asp Ala Asn Glu Leu
            420                 425                 430

Gly Lys Gly Asn Pro Phe Ala Met Glu Ile Asn Ile Gln Ala Asn Leu
        435                 440                 445

Trp Arg Asn Phe Leu Tyr Ala Asn Val Ala Leu Tyr Leu Pro Asp Ser
    450                 455                 460

Tyr Lys Tyr Thr Pro Ala Asn Ile Thr Leu Pro Thr Asn Thr Asn Thr
465                 470                 475                 480

Tyr Asp Tyr Met Asn Gly Arg Val Val Ala Pro Ser Leu Val Asp Ala
                485                 490                 495

Tyr Ile Asn Ile Gly Ala Arg Trp Ser Leu Asp Pro Met Asp Asn Val
            500                 505                 510

Asn Pro Phe Asn His His Arg Asn Ala Gly Leu Arg Tyr Arg Ser Met
        515                 520                 525

Leu Leu Gly Asn Gly Arg Tyr Val Pro Phe His Ile Gln Val Pro Gln
    530                 535                 540

Lys Phe Phe Ala Ile Lys Ser Leu Leu Leu Leu Pro Gly Ser Tyr Thr
545                 550                 555                 560

Tyr Glu Trp Asn Phe Arg Lys Asp Val Asn Met Ile Leu Gln Ser Ser
                565                 570                 575

Leu Gly Asn Asp Leu Arg Thr Asp Gly Ala Ser Ile Ala Phe Thr Ser
            580                 585                 590

Ile Asn Leu Tyr Ala Thr Phe Phe Pro Met Ala His Asn Thr Ala Ser
        595                 600                 605
```

-continued

Thr Leu Glu Ala Met Leu Arg Asn Asp Thr Asn Asp Gln Ser Phe Asn
610 615 620

Asp Tyr Leu Ser Ala Ala Asn Met Leu Tyr Pro Ile Pro Ala Asn Ala
625 630 635 640

Thr Asn Val Pro Ile Ser Ile Pro Ser Arg Asn Trp Ala Ala Phe Arg
645 650 655

Gly Trp Ser Phe Thr Arg Leu Lys Thr Arg Glu Thr Pro Ser Leu Gly
660 665 670

Ser Gly Phe Asp Pro Tyr Phe Val Tyr Ser Gly Ser Ile Pro Tyr Leu
675 680 685

Asp Gly Thr Phe Tyr Leu Asn His Thr Phe Lys Lys Val Ser Ile Thr
690 695 700

Phe Asp Ser Ser Val Ser Trp Pro Gly Asn Asp Arg Leu Leu Thr Pro
705 710 715 720

Asn Glu Phe Glu Ile Lys Arg Thr Val Asp Gly Glu Gly Tyr Asn Val
725 730 735

Ala Gln Cys Asn Met Thr Lys Asp Trp Phe Leu Val Gln Met Leu Ala
740 745 750

His Tyr Asn Ile Gly Tyr Gln Gly Phe Tyr Val Pro Glu Gly Tyr Lys
755 760 765

Asp Arg Met Tyr Ser Phe Phe Arg Asn Phe Gln Pro Met Ser Arg Gln
770 775 780

Val Val Asp Glu Val Asn Tyr Lys Asp Tyr Gln Ala Val Thr Leu Ala
785 790 795 800

Tyr Gln His Asn Asn Ser Gly Phe Val Gly Tyr Leu Ala Pro Thr Met
805 810 815

Arg Gln Gly Gln Pro Tyr Pro Ala Asn Tyr Pro Tyr Pro Leu Ile Gly
820 825 830

Lys Ser Ala Val Ala Ser Val Thr Gln Lys Lys Phe Leu Cys Asp Arg
835 840 845

Val Met Trp Arg Ile Pro Phe Ser Ser Asn Phe Met Ser Met Gly Ala
850 855 860

Leu Thr Asp Leu Gly Gln Asn Met Leu Tyr Ala Asn Ser Ala His Ala
865 870 875 880

Leu Asp Met Asn Phe Glu Val Asp Pro Met Asp Glu Ser Thr Leu Leu
885 890 895

Tyr Val Val Phe Glu Val Phe Asp Val Val Arg Val His Gln Pro His
900 905 910

Arg Gly Val Ile Glu Ala Val Tyr Leu Arg Thr Pro Phe Ser Ala Gly
915 920 925

Asn Ala Thr Thr
930

<210> SEQ ID NO 12
<211> LENGTH: 443
<212> TYPE: PRT
<213> ORGANISM: chimpanzee adenovirus serotype Pan7

<400> SEQUENCE: 12

Met Ser Lys Lys Arg Val Arg Val Asp Asp Asp Phe Asp Pro Val Tyr
1 5 10 15

Pro Tyr Asp Ala Asp Asn Ala Pro Thr Val Pro Phe Ile Asn Pro Pro
20 25 30

Phe Val Ser Ser Asp Gly Phe Gln Glu Lys Pro Leu Gly Val Leu Ser
35 40 45

-continued

```
Leu Arg Leu Ala Asp Pro Val Thr Thr Lys Asn Gly Glu Ile Thr Leu
    50                  55                  60

Lys Leu Gly Glu Gly Val Asp Leu Asp Ser Ser Gly Lys Leu Ile Ser
65                  70                  75                  80

Asn Thr Ala Thr Lys Ala Ala Ala Pro Leu Ser Phe Ser Asn Asn Thr
                85                  90                  95

Ile Ser Leu Asn Met Asp Thr Pro Leu Tyr Thr Lys Asp Gly Lys Leu
            100                 105                 110

Ser Leu Gln Val Ser Pro Pro Leu Asn Ile Leu Lys Ser Thr Ile Leu
        115                 120                 125

Asn Thr Leu Ala Val Ala Tyr Gly Ser Gly Leu Gly Leu Ser Gly Gly
    130                 135                 140

Thr Ala Leu Ala Val Gln Leu Ala Ser Pro Leu Thr Phe Asp Glu Lys
145                 150                 155                 160

Gly Asn Ile Lys Ile Asn Leu Ala Ser Gly Pro Leu Thr Val Asp Ala
                165                 170                 175

Ser Arg Leu Ser Ile Asn Cys Lys Arg Gly Val Thr Val Thr Thr Ser
            180                 185                 190

Gly Asp Ala Ile Glu Ser Asn Ile Ser Trp Pro Lys Gly Ile Arg Phe
        195                 200                 205

Glu Gly Asn Gly Ile Ala Ala Asn Ile Gly Arg Gly Leu Glu Phe Gly
    210                 215                 220

Thr Thr Ser Thr Glu Thr Asp Val Thr Asp Ala Tyr Pro Ile Gln Val
225                 230                 235                 240

Lys Leu Gly Thr Gly Leu Thr Phe Asp Ser Thr Gly Ala Ile Val Ala
                245                 250                 255

Trp Asn Lys Glu Asp Asp Lys Leu Thr Leu Trp Thr Thr Ala Asp Pro
            260                 265                 270

Ser Pro Asn Cys Lys Ile Tyr Ser Glu Lys Asp Ala Lys Leu Thr Leu
        275                 280                 285

Cys Leu Thr Lys Cys Gly Ser Gln Ile Leu Gly Thr Val Thr Val Leu
    290                 295                 300

Ala Val Asn Asn Gly Ser Leu Asn Pro Ile Thr Asn Thr Val Ser Thr
305                 310                 315                 320

Ala Leu Val Ser Leu Lys Phe Asp Ala Ser Gly Val Leu Leu Ser Ser
                325                 330                 335

Ser Thr Leu Asp Lys Glu Tyr Trp Asn Phe Arg Lys Gly Asp Val Thr
            340                 345                 350

Pro Ala Glu Pro Tyr Thr Asn Ala Ile Gly Phe Met Pro Asn Ile Lys
        355                 360                 365

Ala Tyr Pro Lys Asn Thr Ser Ala Ala Ser Lys Ser His Ile Val Ser
    370                 375                 380

Gln Val Tyr Leu Asn Gly Asp Glu Ala Lys Pro Leu Met Leu Ile Ile
385                 390                 395                 400

Thr Phe Asn Glu Thr Glu Asp Ala Thr Cys Thr Tyr Ser Ile Thr Phe
                405                 410                 415

Gln Trp Lys Trp Asp Ser Thr Lys Tyr Thr Gly Glu Thr Leu Ala Thr
            420                 425                 430

Ser Ser Phe Thr Phe Ser Tyr Ile Ala Gln Glu
        435                 440
```

<210> SEQ ID NO 13
<211> LENGTH: 338

-continued

<212> TYPE: PRT
<213> ORGANISM: simian serotype C1

<400> SEQUENCE: 13

```
Ala Pro Lys Gly Ala Pro Asn Thr Ser Gln Trp Leu Asp Lys Gly Val
1               5                   10                  15

Thr Thr Thr Asp Asn Asn Thr Glu Asn Gly Asp Glu Glu Asp Glu Val
            20                  25                  30

Ala Glu Glu Gly Glu Glu Glu Lys Gln Ala Thr Tyr Thr Phe Gly Asn
        35                  40                  45

Ala Pro Val Lys Ala Glu Ala Glu Ile Thr Lys Glu Gly Leu Pro Ile
    50                  55                  60

Gly Leu Glu Val Pro Ser Glu Gly Asp Pro Lys Pro Ile Tyr Ala Asp
65                  70                  75                  80

Lys Leu Tyr Gln Pro Glu Pro Gln Val Gly Glu Glu Ser Trp Thr Asp
                85                  90                  95

Thr Asp Gly Thr Asp Glu Lys Tyr Gly Gly Arg Ala Leu Lys Pro Glu
            100                 105                 110

Thr Lys Met Lys Pro Cys Tyr Gly Ser Phe Ala Lys Pro Thr Asn Val
        115                 120                 125

Lys Gly Gly Gln Ala Lys Val Lys Lys Val Glu Glu Gly Lys Val Glu
    130                 135                 140

Tyr Asp Ile Asp Met Asn Phe Phe Asp Leu Arg Ser Gln Lys Thr Gly
145                 150                 155                 160

Leu Lys Pro Lys Ile Val Met Tyr Ala Glu Asn Val Asp Leu Glu Thr
                165                 170                 175

Pro Asp Thr His Val Val Tyr Lys Pro Gly Ala Ser Asp Ala Ser Ser
            180                 185                 190

His Ala Asn Leu Gly Gln Gln Ser Met Pro Asn Arg Pro Asn Tyr Ile
        195                 200                 205

Gly Phe Arg Asp Asn Phe Ile Gly Leu Met Tyr Tyr Asn Ser Thr Gly
    210                 215                 220

Asn Met Gly Val Leu Ala Gly Gln Ala Ser Gln Leu Asn Ala Val Val
225                 230                 235                 240

Asp Leu Gln Asp Arg Asn Thr Glu Leu Ser Tyr Gln Leu Leu Leu Asp
                245                 250                 255

Ser Leu Gly Asp Arg Thr Arg Tyr Phe Ser Met Trp Asn Gln Ala Val
            260                 265                 270

Asp Ser Tyr Asp Pro Asp Val Arg Val Ile Glu Asn His Gly Val Glu
        275                 280                 285

Asp Glu Leu Pro Asn Tyr Cys Phe Pro Leu Asp Gly Val Gly Pro Arg
    290                 295                 300

Thr Asp Ser Tyr Lys Gly Ile Glu Thr Asn Gly Asp Glu Asn Thr Thr
305                 310                 315                 320

Trp Lys Asp Leu Asp Pro Asn Gly Ile Ser Glu Leu Ala Lys Gly Asn
                325                 330                 335

Pro Phe
```

<210> SEQ ID NO 14
<211> LENGTH: 315
<212> TYPE: PRT
<213> ORGANISM: chimpanzee adenovirus Pan-9

<400> SEQUENCE: 14

```
Ala Pro Lys Gly Ala Pro Asn Thr Cys Gln Trp Thr Tyr Lys Ala Asp
```

-continued

```
1               5                   10                  15

Gly Glu Thr Ala Thr Glu Lys Thr Tyr Thr Tyr Gly Asn Ala Pro Val
            20                  25                  30

Gln Gly Ile Asn Ile Thr Lys Asp Gly Ile Gln Leu Gly Thr Asp Thr
        35                  40                  45

Asp Asp Gln Pro Ile Tyr Ala Asp Lys Thr Tyr Gln Pro Glu Pro Gln
    50                  55                  60

Val Gly Asp Ala Glu Trp His Asp Ile Thr Gly Thr Asp Glu Lys Tyr
65                  70                  75                  80

Gly Gly Arg Ala Leu Lys Pro Asp Thr Lys Met Lys Pro Cys Tyr Gly
                85                  90                  95

Ser Phe Ala Lys Pro Thr Asn Lys Glu Gly Gly Gln Ala Asn Val Lys
            100                 105                 110

Thr Gly Thr Gly Thr Thr Lys Glu Tyr Asp Ile Asp Met Ala Phe Phe
        115                 120                 125

Asp Asn Arg Ser Ala Ala Ala Ala Gly Leu Ala Pro Glu Ile Val Leu
    130                 135                 140

Tyr Thr Glu Asn Val Asp Leu Glu Thr Pro Asp Thr His Ile Val Tyr
145                 150                 155                 160

Lys Ala Gly Thr Asp Asp Ser Ser Ser Ser Ile Asn Leu Gly Gln Gln
                165                 170                 175

Ala Met Pro Asn Arg Pro Asn Tyr Ile Gly Phe Arg Asp Asn Phe Ile
            180                 185                 190

Gly Leu Met Tyr Tyr Asn Ser Thr Gly Asn Met Gly Val Leu Ala Gly
        195                 200                 205

Gln Ala Ser Gln Leu Asn Ala Val Val Asp Leu Gln Asp Arg Asn Thr
    210                 215                 220

Glu Leu Ser Tyr Gln Leu Leu Leu Asp Ser Leu Gly Asp Arg Thr Arg
225                 230                 235                 240

Tyr Phe Ser Met Trp Asn Gln Ala Val Asp Ser Tyr Asp Pro Asp Val
                245                 250                 255

Arg Ile Ile Glu Asn His Gly Val Glu Asp Glu Leu Pro Asn Tyr Cys
            260                 265                 270

Phe Pro Leu Asp Ala Val Gly Arg Thr Asp Thr Tyr Gln Gly Ile Lys
        275                 280                 285

Ala Asn Gly Thr Asp Gln Thr Thr Trp Thr Lys Asp Asp Ser Val Asn
    290                 295                 300

Asp Ala Asn Glu Ile Gly Lys Gly Asn Pro Phe
305                 310                 315


<210> SEQ ID NO 15
<211> LENGTH: 315
<212> TYPE: PRT
<213> ORGANISM: chimpanzee adenovirus Pan-5

<400> SEQUENCE: 15

Ala Pro Lys Gly Ala Pro Asn Thr Cys Gln Trp Thr Tyr Lys Ala Asp
1               5                   10                  15

Gly Asp Thr Gly Thr Glu Lys Thr Tyr Thr Tyr Gly Asn Ala Pro Val
            20                  25                  30

Gln Gly Ile Ser Ile Thr Lys Asp Gly Ile Gln Leu Gly Thr Asp Thr
        35                  40                  45

Asp Asp Gln Pro Ile Tyr Ala Asp Lys Thr Tyr Gln Pro Glu Pro Gln
    50                  55                  60
```

-continued

Val Gly Asp Ala Glu Trp His Asp Ile Thr Gly Thr Asp Glu Lys Tyr
65 70 75 80

Gly Gly Arg Ala Leu Lys Pro Asp Thr Lys Met Lys Pro Cys Tyr Gly
85 90 95

Ser Phe Ala Lys Pro Thr Asn Lys Glu Gly Gly Gln Ala Asn Val Lys
100 105 110

Thr Glu Thr Gly Gly Thr Lys Glu Tyr Asp Ile Asp Met Ala Phe Phe
115 120 125

Asp Asn Arg Ser Ala Ala Ala Ala Gly Leu Ala Pro Glu Ile Val Leu
130 135 140

Tyr Thr Glu Asn Val Asp Leu Glu Thr Pro Asp Thr His Ile Val Tyr
145 150 155 160

Lys Ala Gly Thr Asp Asp Ser Ser Ser Ser Ile Asn Leu Gly Gln Gln
165 170 175

Ser Met Pro Asn Arg Pro Asn Tyr Ile Gly Phe Arg Asp Asn Phe Ile
180 185 190

Gly Leu Met Tyr Tyr Asn Ser Thr Gly Asn Met Gly Val Leu Ala Gly
195 200 205

Gln Ala Ser Gln Leu Asn Ala Val Val Asp Leu Gln Asp Arg Asn Thr
210 215 220

Glu Leu Ser Tyr Gln Leu Leu Leu Asp Ser Leu Gly Asp Arg Thr Arg
225 230 235 240

Tyr Phe Ser Met Trp Asn Gln Ala Val Asp Ser Tyr Asp Pro Asp Val
245 250 255

Arg Ile Ile Glu Asn His Gly Val Glu Asp Glu Leu Pro Asn Tyr Cys
260 265 270

Phe Pro Leu Asp Ala Val Gly Arg Thr Asp Thr Tyr Gln Gly Ile Lys
275 280 285

Ala Asn Gly Ala Asp Gln Thr Thr Trp Thr Lys Asp Asp Thr Val Asn
290 295 300

Asp Ala Asn Glu Leu Gly Lys Gly Asn Pro Phe
305 310 315

<210> SEQ ID NO 16
<211> LENGTH: 324
<212> TYPE: PRT
<213> ORGANISM: chimpanzee adenovirus Pan-6

<400> SEQUENCE: 16

Ala Pro Lys Gly Ala Pro Asn Ser Ser Gln Trp Glu Gln Ala Lys Thr
1 5 10 15

Gly Asn Gly Gly Thr Met Glu Thr His Thr Tyr Gly Val Ala Pro Met
20 25 30

Gly Gly Glu Asn Ile Thr Lys Asp Gly Leu Gln Ile Gly Thr Asp Val
35 40 45

Thr Ala Asn Gln Asn Lys Pro Ile Tyr Ala Asp Lys Thr Phe Gln Pro
50 55 60

Glu Pro Gln Val Gly Glu Glu Asn Trp Gln Glu Thr Glu Asn Phe Tyr
65 70 75 80

Gly Gly Arg Ala Leu Lys Lys Asp Thr Lys Met Lys Pro Cys Tyr Gly
85 90 95

Ser Tyr Ala Arg Pro Thr Asn Glu Lys Gly Gly Gln Ala Lys Leu Lys
100 105 110

Val Gly Asp Asp Gly Val Pro Thr Lys Glu Phe Asp Ile Asp Leu Ala
115 120 125

-continued

```
Phe Phe Asp Thr Pro Gly Gly Thr Val Asn Gly Gln Asp Glu Tyr Lys
    130                 135                 140

Ala Asp Ile Val Met Tyr Thr Glu Asn Thr Tyr Leu Glu Thr Pro Asp
145                 150                 155                 160

Thr His Val Val Tyr Lys Pro Gly Lys Asp Asp Ala Ser Ser Glu Ile
                165                 170                 175

Asn Leu Val Gln Gln Ser Met Pro Asn Arg Pro Asn Tyr Ile Gly Phe
            180                 185                 190

Arg Asp Asn Phe Ile Gly Leu Met Tyr Tyr Asn Ser Thr Gly Asn Met
        195                 200                 205

Gly Val Leu Ala Gly Gln Ala Ser Gln Leu Asn Ala Val Val Asp Leu
    210                 215                 220

Gln Asp Arg Asn Thr Glu Leu Ser Tyr Gln Leu Leu Leu Asp Ser Leu
225                 230                 235                 240

Gly Asp Arg Thr Arg Tyr Phe Ser Met Trp Asn Gln Ala Val Asp Ser
                245                 250                 255

Tyr Asp Pro Asp Val Arg Ile Ile Glu Asn His Gly Val Glu Asp Glu
            260                 265                 270

Leu Pro Asn Tyr Cys Phe Pro Leu Asp Gly Ser Gly Thr Asn Ala Ala
        275                 280                 285

Tyr Gln Gly Val Lys Val Lys Asp Gly Gln Asp Gly Asp Val Glu Ser
    290                 295                 300

Glu Trp Glu Asn Asp Asp Thr Val Ala Ala Arg Asn Gln Leu Cys Lys
305                 310                 315                 320

Gly Asn Ile Phe


<210> SEQ ID NO 17
<211> LENGTH: 314
<212> TYPE: PRT
<213> ORGANISM: chimpanzee adenovirus Pan-7

<400> SEQUENCE: 17

Ala Pro Lys Gly Ala Pro Asn Thr Cys Gln Trp Thr Tyr Lys Ala Gly
1               5                   10                  15

Asp Thr Asp Thr Glu Lys Thr Tyr Thr Tyr Gly Asn Ala Pro Val Gln
            20                  25                  30

Gly Ile Ser Ile Thr Lys Asp Gly Ile Gln Leu Gly Thr Asp Ser Asp
        35                  40                  45

Gly Gln Ala Ile Tyr Ala Asp Glu Thr Tyr Gln Pro Glu Pro Gln Val
    50                  55                  60

Gly Asp Ala Glu Trp His Asp Ile Thr Gly Thr Asp Glu Lys Tyr Gly
65                  70                  75                  80

Gly Arg Ala Leu Lys Pro Asp Thr Lys Met Lys Pro Cys Tyr Gly Ser
                85                  90                  95

Phe Ala Lys Pro Thr Asn Lys Glu Gly Gly Gln Ala Asn Val Lys Thr
            100                 105                 110

Glu Thr Gly Gly Thr Lys Glu Tyr Asp Ile Asp Met Ala Phe Phe Asp
        115                 120                 125

Asn Arg Ser Ala Ala Ala Ala Gly Leu Ala Pro Glu Ile Val Leu Tyr
    130                 135                 140

Thr Glu Asn Val Asp Leu Glu Thr Pro Asp Thr His Ile Val Tyr Lys
145                 150                 155                 160

Ala Gly Thr Asp Asp Ser Ser Ser Ser Ile Asn Leu Gly Gln Gln Ser
                165                 170                 175
```

-continued

```
Met Pro Asn Arg Pro Asn Tyr Ile Gly Phe Arg Asp Asn Phe Ile Gly
            180                 185                 190

Leu Met Tyr Tyr Asn Ser Thr Gly Asn Met Gly Val Leu Ala Gly Gln
        195                 200                 205

Ala Ser Gln Leu Asn Ala Val Val Asp Leu Gln Asp Arg Asn Thr Glu
    210                 215                 220

Leu Ser Tyr Gln Leu Leu Leu Asp Ser Leu Gly Asp Arg Thr Arg Tyr
225                 230                 235                 240

Phe Ser Met Trp Asn Gln Ala Val Asp Ser Tyr Asp Pro Asp Val Arg
                245                 250                 255

Ile Ile Glu Asn His Gly Val Glu Asp Glu Leu Pro Asn Tyr Cys Phe
            260                 265                 270

Pro Leu Asp Ala Val Gly Arg Thr Asp Thr Tyr Gln Gly Ile Lys Ala
        275                 280                 285

Asn Gly Asp Asn Gln Thr Thr Trp Thr Lys Asp Asp Thr Val Asn Asp
    290                 295                 300

Ala Asn Glu Leu Gly Lys Gly Asn Pro Phe
305                 310


<210> SEQ ID NO 18
<211> LENGTH: 179
<212> TYPE: PRT
<213> ORGANISM: chimpanzee adenovirus Pan9

<400> SEQUENCE: 18

Thr Leu Trp Thr Thr Pro Asp Pro Ser Pro Asn Cys Gln Ile Leu Ala
1               5                   10                  15

Glu Asn Asp Ala Lys Leu Thr Leu Cys Leu Thr Lys Cys Gly Ser Gln
            20                  25                  30

Ile Leu Ala Thr Val Ser Val Leu Val Val Gly Ser Gly Asn Leu Asn
        35                  40                  45

Pro Ile Thr Gly Thr Val Ser Ser Ala Gln Val Phe Leu Arg Phe Asp
    50                  55                  60

Ala Asn Gly Val Leu Leu Thr Glu His Ser Thr Leu Lys Lys Tyr Trp
65                  70                  75                  80

Gly Tyr Arg Gln Gly Asp Ser Ile Asp Gly Thr Pro Tyr Thr Asn Ala
                85                  90                  95

Val Gly Phe Met Pro Asn Leu Lys Ala Tyr Pro Lys Ser Gln Ser Ser
            100                 105                 110

Thr Thr Lys Asn Asn Ile Val Gly Gln Val Tyr Met Asn Gly Asp Val
        115                 120                 125

Ser Lys Pro Met Leu Leu Thr Ile Thr Leu Asn Gly Thr Asp Asp Ser
    130                 135                 140

Asn Ser Thr Tyr Ser Met Ser Phe Ser Tyr Thr Trp Thr Asn Gly Ser
145                 150                 155                 160

Tyr Val Gly Ala Thr Phe Gly Ala Asn Ser Tyr Thr Phe Ser Tyr Ile
                165                 170                 175

Ala Gln Glu


<210> SEQ ID NO 19
<211> LENGTH: 185
<212> TYPE: PRT
<213> ORGANISM: chimpanzee adenovirus Pan6

<400> SEQUENCE: 19
```

-continued

Thr Leu Trp Thr Thr Pro Asp Pro Ser Pro Asn Cys Gln Leu Leu Ser
1 5 10 15

Asp Arg Asp Ala Lys Phe Thr Leu Cys Leu Thr Lys Cys Gly Ser Gln
20 25 30

Ile Leu Gly Thr Val Ala Val Ala Ala Val Thr Val Gly Ser Ala Leu
35 40 45

Asn Pro Ile Asn Asp Thr Val Lys Ser Ala Ile Val Phe Leu Arg Phe
50 55 60

Asp Ser Asp Gly Val Leu Met Ser Asn Ser Ser Met Val Gly Asp Tyr
65 70 75 80

Trp Asn Phe Arg Glu Gly Gln Thr Thr Gln Ser Val Ala Tyr Thr Asn
85 90 95

Ala Val Gly Phe Met Pro Asn Ile Gly Ala Tyr Pro Lys Thr Gln Ser
100 105 110

Lys Thr Pro Lys Asn Ser Ile Val Ser Gln Val Tyr Leu Thr Gly Glu
115 120 125

Thr Thr Met Pro Met Thr Leu Thr Ile Thr Phe Asn Gly Thr Asp Glu
130 135 140

Lys Asp Thr Thr Pro Val Ser Thr Tyr Ser Met Thr Phe Thr Trp Gln
145 150 155 160

Trp Thr Gly Asp Tyr Lys Asp Lys Asn Ile Thr Phe Ala Thr Asn Ser
165 170 175

Phe Ser Phe Ser Tyr Ile Ala Gln Glu
180 185

<210> SEQ ID NO 20
<211> LENGTH: 179
<212> TYPE: PRT
<213> ORGANISM: chimpanzee adenovirus Pan7

<400> SEQUENCE: 20

Thr Leu Trp Thr Thr Ala Asp Pro Ser Pro Asn Cys Lys Ile Tyr Ser
1 5 10 15

Glu Lys Asp Ala Lys Leu Thr Leu Cys Leu Thr Lys Cys Gly Ser Gln
20 25 30

Ile Leu Gly Thr Val Thr Val Leu Ala Val Asn Asn Gly Ser Leu Asn
35 40 45

Pro Ile Thr Asn Thr Val Ser Thr Ala Leu Val Ser Leu Lys Phe Asp
50 55 60

Ala Ser Gly Val Leu Leu Ser Ser Ser Thr Leu Asp Lys Glu Tyr Trp
65 70 75 80

Asn Phe Arg Lys Gly Asp Val Thr Pro Ala Glu Pro Tyr Thr Asn Ala
85 90 95

Ile Gly Phe Met Pro Asn Ile Lys Ala Tyr Pro Lys Asn Thr Ser Ala
100 105 110

Ala Ser Lys Ser His Ile Val Ser Gln Val Tyr Leu Asn Gly Asp Glu
115 120 125

Ala Lys Pro Leu Met Leu Ile Ile Thr Phe Asn Glu Thr Glu Asp Ala
130 135 140

Thr Cys Thr Tyr Ser Ile Thr Phe Gln Trp Lys Trp Asp Ser Thr Lys
145 150 155 160

Tyr Thr Gly Glu Thr Leu Ala Thr Ser Ser Phe Thr Phe Ser Tyr Ile
165 170 175

Ala Gln Glu

-continued

<210> SEQ ID NO 21
<211> LENGTH: 179
<212> TYPE: PRT
<213> ORGANISM: chimpanzee adenovirus Pan5

<400> SEQUENCE: 21

```
Thr Leu Trp Thr Thr Ala Asp Pro Ser Pro Asn Cys His Ile Tyr Ser
1               5                   10                  15

Glu Lys Asp Ala Lys Leu Thr Leu Cys Leu Thr Lys Cys Gly Ser Gln
            20                  25                  30

Ile Leu Gly Thr Val Ser Leu Ile Ala Val Asp Thr Gly Ser Leu Asn
        35                  40                  45

Pro Ile Thr Gly Thr Val Thr Thr Ala Leu Val Ser Leu Lys Phe Asp
    50                  55                  60

Ala Asn Gly Val Leu Gln Ser Ser Ser Thr Leu Asp Ser Asp Tyr Trp
65                  70                  75                  80

Asn Phe Arg Gln Gly Asp Val Thr Pro Ala Glu Ala Tyr Thr Asn Ala
                85                  90                  95

Ile Gly Phe Met Pro Asn Leu Lys Ala Tyr Pro Lys Asn Thr Ser Gly
            100                 105                 110

Ala Ala Lys Ser His Ile Val Gly Lys Val Tyr Leu His Gly Asp Thr
        115                 120                 125

Gly Lys Pro Leu Asp Leu Ile Ile Thr Phe Asn Glu Thr Ser Asp Glu
    130                 135                 140

Ser Cys Thr Tyr Cys Ile Asn Phe Gln Trp Gln Trp Gly Ala Asp Gln
145                 150                 155                 160

Tyr Lys Asn Glu Thr Leu Ala Val Ser Ser Phe Thr Phe Ser Tyr Ile
                165                 170                 175

Ala Lys Glu
```

<210> SEQ ID NO 22
<211> LENGTH: 183
<212> TYPE: PRT
<213> ORGANISM: human adenovirus Ad 2

<400> SEQUENCE: 22

```
Thr Leu Trp Thr Thr Pro Asp Pro Ser Pro Asn Cys Arg Ile His Ser
1               5                   10                  15

Asp Asn Asp Cys Lys Phe Thr Leu Val Leu Thr Lys Cys Gly Ser Gln
            20                  25                  30

Val Leu Ala Thr Val Ala Ala Leu Ala Val Ser Gly Asp Leu Ser Ser
        35                  40                  45

Met Thr Gly Thr Val Ala Ser Val Ser Ile Phe Leu Arg Phe Asp Gln
    50                  55                  60

Asn Gly Val Leu Met Glu Asn Ser Ser Leu Lys Lys His Tyr Trp Asn
65                  70                  75                  80

Phe Arg Asn Gly Asn Ser Thr Asn Ala Asn Pro Tyr Thr Asn Ala Val
                85                  90                  95

Gly Phe Met Pro Asn Leu Leu Ala Tyr Pro Lys Thr Gln Ser Gln Thr
            100                 105                 110

Ala Lys Asn Asn Ile Val Ser Gln Val Tyr Leu His Gly Asp Lys Thr
        115                 120                 125

Lys Pro Met Ile Leu Thr Ile Thr Leu Asn Gly Thr Ser Glu Ser Thr
    130                 135                 140

Glu Thr Ser Glu Val Ser Thr Tyr Ser Met Ser Phe Thr Trp Ser Trp
```

-continued

```
145                 150                 155                 160

Glu Ser Gly Lys Tyr Thr Thr Glu Thr Phe Ala Thr Asn Ser Tyr Thr
                165                 170                 175

Phe Ser Tyr Ile Ala Gln Glu
            180


<210> SEQ ID NO 23
<211> LENGTH: 182
<212> TYPE: PRT
<213> ORGANISM: human adenovirus Ad 5

<400> SEQUENCE: 23

Thr Leu Trp Thr Thr Pro Ala Pro Ser Pro Asn Cys Arg Leu Asn Ala
1               5                   10                  15

Glu Lys Asp Ala Lys Leu Thr Leu Val Leu Thr Lys Cys Gly Ser Gln
            20                  25                  30

Ile Leu Ala Thr Val Ser Val Leu Ala Val Lys Gly Ser Leu Ala Pro
        35                  40                  45

Ile Ser Gly Thr Val Gln Ser Ala His Leu Ile Ile Arg Phe Asp Glu
    50                  55                  60

Asn Gly Val Leu Ile Asn Asn Ser Phe Leu Asp Pro Glu Tyr Trp Asn
65                  70                  75                  80

Phe Arg Asn Gly Asp Leu Thr Glu Gly Thr Ala Tyr Thr Asn Ala Val
                85                  90                  95

Gly Phe Met Pro Asn Leu Ser Ala Tyr Pro Lys Ser His Gly Lys Thr
            100                 105                 110

Ala Lys Ser Asn Ile Val Ser Gln Val Tyr Leu Asn Gly Asp Lys Thr
        115                 120                 125

Lys Pro Val Thr Leu Thr Ile Thr Leu Asn Gly Thr Gln Glu Thr Gly
    130                 135                 140

Asp Thr Thr Pro Ser Ala Tyr Ser Met Ser Phe Ser Trp Asp Trp Ser
145                 150                 155                 160

Gly His Asn Tyr Ile Asn Glu Ile Phe Ala Thr Ser Ser Tyr Thr Glu
                165                 170                 175

Ser Tyr Ile Ala Gln Glu
            180


<210> SEQ ID NO 24
<211> LENGTH: 34264
<212> TYPE: DNA
<213> ORGANISM: simian adenovirus SV-1
<220> FEATURE:
<221> NAME/KEY: CDS
<222> LOCATION: (12454)..(13965)
<223> OTHER INFORMATION: L2 Penton
<220> FEATURE:
<221> NAME/KEY: CDS
<222> LOCATION: (16841)..(19636)
<223> OTHER INFORMATION: L3 Hexon
<220> FEATURE:
<221> NAME/KEY: CDS
<222> LOCATION: (28059)..(29150)
<223> OTHER INFORMATION: L5 Fiber #2
<220> FEATURE:
<221> NAME/KEY: CDS
<222> LOCATION: (29183)..(30865)
<223> OTHER INFORMATION: L5 Fiber #1

<400> SEQUENCE: 24

tccttattct ggaaacgtgc caatatgata atgagcgggg aggagcgagg cggggccggg      60

gtgacgtgcg gtgacgtggg gtgacgcggg gtggcgcgag ggcggggcgg gagtggggag     120
```

-continued

```
gcgcttagtt tttacgtatg cggaaggagg ttttataccg gaagttgggt aatttgggcg    180
tatacttgta agttttgtgt aatttggcgc gaaaaccggg taatgaggaa gttgaggtta    240
atatgtactt tttatgactg ggcggaattt ctgctgatca gcagtgaact ttgggcgctg    300
acggggaggt ttcgctacgt ggcagtacca cgagaaggct caaaggtccc atttattgta    360
ctcctcagcg ttttcgctgg gtatttaaac gctgtcagat catcaagagg ccactcttga    420
gtgccggcga gtagagtttt ctcctccgcg ctgccgcgat gaggctggtt cccgagatgt    480
acggtgtttt ctgcagcgag acggcccgga actcagatga gctgcttaat acagatctgc    540
tggatgttcc caactcgcct gtggcttcgc ctccgtcgct tcatgatctt ttcgatgtgg    600
aagtggatcc accgcaagat cccaacgagg acgcggtaaa cagtatgttc cctgaatgtc    660
tgtttgaggc ggctgaggag ggttctcaca gcagtgaaga gagcagacgg ggagaggaac    720
tggacttgaa atgctacgag gaatgtctgc cttctagcga ttctgaaacg gaacagacag    780
ggggagacgg ctgtgagtcg gcaatgaaaa atgaacttgt attagactgt ccagaacatc    840
ctggtcatgg ctgccgtgcc tgtgcttttc atagaaatgc cagcggaaat cctgagactc    900
tatgtgctct gtgttatctg cgccttacca gcgattttgt atacagtaag taaagtgttt    960
tcattggcgt acggtagggg attcgttgaa gtgctttgtg acttattatg tgtcattatt   1020
tctaggtgac gtgtccgacg tggaagggga aggagataga tcaggggctg ctaattctcc   1080
ttgcactttg gggctgtgg ttccagttgg catttttaaa ccgagtggtg gaggagaacg   1140
agccggagga gaccgagaat ctgagagccg gcctggaccc tccagtggaa gactaggtgc   1200
tgaggatgat cctgaagagg ggactagtgg gggtgctagg aaaaagcaaa aaactgagcc   1260
tgaacctaga aactttttga atgagttgac tgtaagccta atgaatcggc agcgtcctga   1320
gacggtgttt tggactgagt tggaggatga gttcaagaag gggggaattaa acctcttgta  1380
caagtatggg tttgagcagt tgaaaactca ctggttggag ccgtgggagg atatggaaat   1440
ggctctagac acctttgcta aagtggctct gcggccggat aaagtttaca ctattcgccg   1500
cactgttaat ataaaaaaga gtgtttatgt tatcggccat ggagctctgg tgcaggtgca   1560
gaccccagac cgggtggctt tcaattgcgg catgcagagt ttgggccccg gggtgatagg   1620
tttgaatgga gttacatttc aaaatgtcag gtttactggt gatgatttta atggctctgt   1680
gtttgtgact agcacccagc taaccctcca cggtgtttac ttttttaact ttaacaatac   1740
atgtgtggag tcatggggta gggtgtctct gaggggctgc agttttcatg gttgctggaa   1800
ggcggtggtg ggaagaatta aaagtgtcat gtctgtgaag aaatgcatat ttgaacgctg   1860
tgtgatagct ctagcagtag aggggtacgg acggatcagg aataacgccg catctgagaa   1920
tggatgtttt cttttgctga aaggtacggc cagcgttaag cataatatga tttgcggcag   1980
cggcctgtgc ccctcgcagc tcttaacttg cgcagatgga aactgtcaca ccttgcgcac   2040
cgtgcacata gtgtcccact cgcgccgcac ctggccaaca tttgagcaca atatgctcat   2100
gcgttgcgcc gttcacctag gtgctagacg cggcgtgttt atgccttatc aatgtaactt   2160
tagtcatact aagattttgc tggaaactga ttccttccct cgagtatgtt tcaatggggt   2220
gtttgacatg tcaatggaac tttttaaagt gataagatat gatgaaacca agtctcgttg   2280
tcgctcatgt gaatgcggag ctaatcattt gaggttgtat cctgtaaccc tgaacgttac   2340
cgaggagctg aggacggacc accacatgct gtcttgcctg cgtaccgact atgaatccag   2400
cgatgaggag tgaggtgagg ggcggagcca caaagggtat aaaggggcat gaggggtggg   2460
```

-continued

```
cgcggtgttt caaaatgagc gggacgacgg acggcaatgc gtttgagggg ggagtgttca   2520

gcccatatct gacatctcgt cttccttcct gggcaggagt tcgtcagaat gtagtgggct   2580

ccaccgtgga cggacggccg gtcgcccctg caaattccgc caccctcacc tatgccaccg   2640

tgggatcatc gttggacact gccgcggcag ctgccgcttc tgctgccgct tctactgctc   2700

gcggcatggc ggctgatttt ggactatata accaactggc cactgcagct gtggcgtctc   2760

ggtctctggt tcaagaagat gccctgaatg tgatcttgac tcgcctggag atcatgtcac   2820

gtcgcctgga cgaactggct gcgcagatat cccaagctaa ccccgatacc gcttcagaat   2880

cttaaaataa agacaaacaa atttgttgaa aagtaaaatg gctttatttg tttttttttgg   2940

ctcggtaggc tcgggtccac ctgtctcggt cgttaaggac tttgtgtatg ttttccaaaa   3000

cacggtacag atgggcttgg atgttcaagt acatgggcat gaggccatct tggggtgga   3060

gataggacca ctgaagagcg tcatgttccg gggtggtatt gtaaatcacc cagtcgtagc   3120

agggtttttg agcgtggaac tggaatatgt ccttcaggag caggctaatg gccaagggta   3180

gacccttagt gtaggtgttt acaaagcggt tgagctggga gggatgcatg cgggggggaga   3240

tgatatgcat cttggcttgg attttgaggt tagctatgtt accacccagg tctctgcggg   3300

ggttcatgtt atgaaggacc accagcacgg tatagccagt gcatttgggg aacttgtcat   3360

gcagtttgga ggggaaggcg tggaagaatt tagatacccc cttgtgcccc cctaggtttt   3420

ccatgcactc atccataata atggcaatgg gacccctggc ggccgcttta gcaaacacgt   3480

tttgggggtt ggaaacatca tagttttgct ctagagtgag ctcatcatag gccatcttta   3540

caaagcgggg taggagggtg cccgactggg ggatgatagt tccatctggg cctggagcgt   3600

agttgccctc acagatctgc atctcccagg ccttaatttc cgaggggggg atcatgtcca   3660

cctgggggc gataaaaaac acggtttctg gcgggggtt aatgagctgg gtggaaagca   3720

agttacgcaa cagctgggat ttgccgcaac cggtgggacc gtagatgacc ccgatgacgg   3780

gttgcagctg gtagttcaga gaggaacagc tgccgtcggg gcgcaggagg ggagctacct   3840

cattcatcat gcttctgaca tgtttatttt cactcactaa gttttgcaag agcctctccc   3900

cacccaggga taagagttct tccaggctgt tgaagtgttt cagcggtttc aggccgtcgg   3960

ccatgggcat cttttcaagc gactgacgaa gcaagtacag tcggtcccag agctcggtga   4020

cgtgctctat ggaatctcga tccagcagac ttcttggttt cggggggttgg gccgactttc   4080

gctgtagggc accagccggt gggcgtccag ggccgcgagg gttctgtcct tccagggtct   4140

cagcgttcgg gtgagggtgg tctcggtgac ggtgaaggga tgagccccgg gctgggcgct   4200

tgcgagggtg cgcttcaggc tcatcctgct ggtgctgaag cgggcgtcgt ctccctgtga   4260

gtcggccaga tagcaacgaa gcatgaggtc gtagctgagg gactcggccg cgtgtccctt   4320

ggcgcgcagc tttcccttgg aaacgtgctg acatttggtg cagtgcagac acttgagggc   4380

gtagagtttt ggggccagga agaccgactc gggcgagtag gcgtcggctc cgcactgagc   4440

gcagacggtc tcgcactcca ccagccacgt gagctcgggt ttagcgggat caaaaaccaa   4500

gttgcctcca tttttttga tgcgtttctt accttgcgtc tccatgagtc tgtgtcccgc   4560

ttccgtgaca aaaaggctgt cggtatcccc gtagaccgac ttgagggggc gatcttccaa   4620

aggtgttccg aggtcttccg cgtacaggaa ctgggaccac tccgagacaa aggctcgggt   4680

ccaggctaac acgaaggagg cgatctgcga ggggtatctg tcgttttcaa tgagggggtc   4740

caccttttcc agggtgtgca gacacaggtc gtcctcctcc gcgtccacga aggtgattgg   4800

cttgtaagtg taggtcacgt gacccgcacc cccccaaggg gtataaaagg gggcgtgccc   4860
```

-continued

```
actctccccg tcactttctt ccgcatcgct gtggaccaga gccagctgtt cgggtgagta   4920
ggccctctca aaagccggca tgatttcggc gctcaagttg tcagtttcta caaacgaggt   4980
ggatttgata ttcacgtgcc ccgcggcgat gcttttgatg gtggaggggt ccatctgatc   5040
agaaaacacg atctttttat tgtcaagttt ggtggcgaaa gacccgtaga gggcgttgga   5100
aagcaacttg gcgatggagc gcagggtctg atttttctcc cgatcggccc tctccttggc   5160
ggcgatgttg agttgcacgt actcgcgggc cacgcaccgc cactcgggga acacggcggt   5220
gcgctcgtcg ggcaggatgc gcacgcgcca gccgcggttg tgcagggtga tgaggtccac   5280
gctggtggcc acctccccgc ggaggggctc gttggtccaa cacaatcgcc cccctttct   5340
ggagcagaac ggaggcaggg gatctagcaa gttggcgggc ggggggtcgg cgtcgatggt   5400
aaatatgccg ggtagcagaa ttttattaaa ataatcgatt tcggtgtccg tgtcttgcaa   5460
cgcgtcttcc cacttcttca ccgccagggc cctttcgtag ggattcaggg gcggtcccca   5520
gggcatgggg tgggtcaggg ccgaggcgta catgccgcag atgtcgtaca cgtacagggg   5580
ctccctcaac accccgatgt aagtggggta acagcgcccc ccgcggatgc tggctcgcac   5640
gtagtcgtac atctcgtgag agggagccat gagcccgtct cccaagtggg tcttgtgggg   5700
tttttcggcc cggtagagga tctgcctgaa gatggcgtgg gagttggaag agatagtggg   5760
gcgttggaag acgttaaagt tggctccggg cagtcccacg gagtcttgga tgaactgggc   5820
gtaggattcc cggagcttgt ccaccagggc tgcggttacc agcacgtcga gagcgcagta   5880
gtccaacgtc tcgcggacca ggttgtaggc cgtctcttgt tttttctccc acagttcgcg   5940
attgaggagg tattcctcgc ggtctttcca gtactcttcg gcgggaaatc ctttttcgtc   6000
cgctcggtaa gaacctaaca tgtaaaattc gttcacggct ttgtatggac aacagccttt   6060
ttctaccggc agggcgtacg cttgagcggc ctttctgaga gaggtgtggg tgagggcgaa   6120
ggtgtcccgc accatcactt tcaggtactg atgtttgaag tccgtgtcgt cgcaggcgcc   6180
ctgttcccac agcgtgaagt cggtgcgctt tttctgcctg ggattgggga gggcgaatgt   6240
gacgtcgtta aagaggattt tcccggcgcg gggcatgaag ttgcgagaga tcctgaaggg   6300
tccgggcacg tccgagcggt tgttgatgac ttgcgccgcc aggacgatct cgtcgaagcc   6360
gttgatgttg tggcccacga tgtaaagttc gataaagcgc ggctgtccct tgagggccgg   6420
cgcttttttc aactcctcgt aggtgagaca gtccggcgag gagagaccca gctccgcccg   6480
ggcccagtcg gagagctgag ggttagccgc gaggaaagag ctccacaggt caagggctag   6540
cagagtttgc aagcggtcgc ggaactcgcg aaactttttc cccacggcca ttttctccgg   6600
cgtcaccacg tagaaagtgc aggggcggtc gttccagacg tcccatcgga gctctagggc   6660
cagctcgcag gcttgacgaa cgagggtctc ctcgcccgag acgtgcatga ccagcatgaa   6720
gggtaccaac tgtttcccga acgagcccat ccatgtgtag gtttctacgt cgtaggtgac   6780
aaagagccgc tgggtgcgcg cgtgggagcc gatcgggaag aagctgatct cctgccacca   6840
gttggaggaa tgggtgttga tgtggtgaaa gtagaagtcc cgccggcgca cagagcattc   6900
gtgctgatgt ttgtaaaagc gaccgcagta gtcgcagcgc tgcacgctct gtatctcctg   6960
aatgagatgc gcttttcgcc cgcgcaccag aaaccggagg gggaagttga gacgggggct   7020
tggtggggcg gcatcccctt cgccttggcg gtgggagtct gcgtctgcgc cctccttctc   7080
tgggtggacg acggtgggga cgacgacgcc ccgggtgccg caagtccaga tctccgccac   7140
ggaggggcgc aggcgttgca ggaggggacg cagctgcccg ctgtccaggg agtcgagggc   7200
```

-continued ggccgcgctg aggtcggcgg gaagcgtttg caagttcact ttcagaagac cggtaagagc 7260
gtgagccagg tgcacatggt acttgatttc cagggggggtg ttggaagagg cgtccacggc 7320
gtagaggagg ccgtgtccgc gcggggccac caccgtgccc cgaggaggtt ttatctcact 7380
cgtcgagggc gagcgccggg gggtagaggc ggctctgcgc cggggggcag cggaggcagt 7440
ggcacgtttt cgtgaggatt cggcagcggt tgatgacgag cccggagact gctggcgtgg 7500
gcgacgacgc ggcggttgag gtcctggatg tgccgtctct gcgtgaagac caccggcccc 7560
cgggtcctga acctgaaaga gagttccaca gaatcaatgt ctgcatcgtt aacggcggcc 7620
tgcctgagga tctcctgtac gtcgcccgag ttgtcttgat aggcgatctc ggccatgaac 7680
tgctccactt cttcctcgcg gaggtcgccg tggcccgctc gctccacggt ggcggccagg 7740
tcgttggaga tgcgacgcat gagttgagag aaggcgttga ggccgttctc gttccacacg 7800
cggctgtaca ccacgtttcc gaaggagtcg cgcgctcgca tgaccacctg ggccacgttg 7860
agttccacgt ggcgggcgaa gacggcgtag tttctgaggc gctggaagag gtagttgagc 7920
gtggtggcga tgtgctcgca gacgaagaag tacatgatcc agcgccgcag ggtcatctcg 7980
ttgatgtctc cgatggcttc gagacgctcc atggcctcgt agaagtcgac ggcgaagttg 8040
aaaaattggg agttgcgggc ggccaccgtg agttcttctt gcaggaggcg gatgagatcg 8100
gcgaccgtgt cgcgcacctc ctgctcgaaa gcgccccgag gcgcctctgc ttcttcctcc 8160
ggctcctcct cttccagggg cacgggttcc tccggcagct ctgcgacggg gacggggcgg 8220
cgacgtcgtc gtctgaccgg caggcggtcc acgaagcgct cgatcatttc gccgcgccgg 8280
cgacgcatgg tctcggtgac ggcgcgtccg ttttcgcgag gtcgcagttc gaagacgccg 8340
ccgcgcagag cgcccccgtg cagggagggt aagtggttag ggccgtcggg cagggacacg 8400
gcgctgacga tgcattttat caattgctgc gtaggcactc cgtgcaggga tctgagaacg 8460
tcgaggtcga cgggatccga gaacttctct aggaaagcgt ctatccaatc gcagtcgcaa 8520
ggtaagctga ggacggtggg ccgctggggg gcgtccgcgg gcagttggga ggtgatgctg 8580
ctgatgatgt aattaaagta ggcggtcttc aggcggcgga tggtggcgag gaggaccacg 8640
tctttgggcc cggcctgttg aatgcgcagg cgctcggcca tgccccaggc ctcgctctga 8700
cagcgacgca ggtctttgta gtagtcttgc atcagtctct ccaccggaac ctctgcttct 8760
cccctgtctg ccatgcgagt cgagccgaac cccgcagggg gctgcagcaa cgctaggtcg 8820
gccacgaccc tctcggccag cacggcctgt tggatctgcg tgagggtggt ctggaagtcg 8880
tccaggtcca cgaagcggtg ataggccccc gtgttgatgg tgtaggtgca gttggccatg 8940
acggaccagt tgacgacttg catgccgggt tgggtgatct ccgtgtactt gaggcgcgag 9000
taggcgcggg actcgaacac gtagtcgttg catgtgcgta ccagatactg gtagccaacc 9060
aggaagtggg gaggcggttc tcggtacagg ggccagccga ctgtggcggg ggcgccgggg 9120
gacaggtcgt ccagcatgag gcgatggtag tggtagatgt agcgggagag ccaggtgatg 9180
ccggccgagg tggtcgcggc cctggtgaat tcgcggacgc ggttccagat gttgcgcagg 9240
gggcgaaagc gctccatggt gggcacgctc tgccccgtga ggcgggcgca atcttgtacg 9300
ctctagatgg aaaaaagaca gggcggtcat cgactccctt ccgtagctcg gggggtaaag 9360
tcgcaagggt gcggcggcgg ggaaccccgg ttcgagaccg gccggatccg ccgctcccga 9420
tgcgcctggc cccgcatcca cgacgtccgc gtcgagaccc agccgcgacg ctccgcccca 9480
atacggaggg gagtcttttg gtgttttttc gtagatgcat ccggtgctgc ggcagatgcg 9540
acctcagacg cccaccacca ccgccgcggc ggcagtaaac ctgagcggag gcggtgacag 9600

-continued

```
ggaggaggag gagctggctt tagacctgga agagggagag gggctggccc ggctgggagc   9660
gccgtcccca gagagacacc ctagggttca gctcgtgagg gacgccaggc aggcttttgt   9720
gccgaagcag aacctgttta gggaccgcag cggtcaggag gcggaggaga tgcgcgattg   9780
caggtttcgg gcgggtagag agctgagggc gggcttcgat cgggagcggc tcctgagggc   9840
ggaggatttc gagcccgacg agcgttctgg ggtgagcccg gcccgcgctc acgtctcggc   9900
ggccaacctg gtgagcgcgt acgagcagac ggtgaacgag gagcgcaact tccaaaagag   9960
ctttaacaat cacgtgagga ccctgatcgc gagggaggag gtgaccatcg ggctgatgca  10020
tctgtgggac ttcgtggagg cctacgtgca gaacccggcc agcaaacctc tgacggccca  10080
gctgttcctg atcgtgcagc acagccgcga caacgagacg ttccgcgacg ccatgttgaa  10140
catcgcggag cccgagggtc gctggctctt ggatctgatt aacatcctgc agagcatcgt  10200
ggtgcaggag aggggcctca gcttagcgga caaggtggcg gccattaact attcgatgca  10260
gagcctgggg aagttctacg ctcgcaagat ctacaagagc ccttacgtgc ccatagacaa  10320
ggaggtgaag atagacagct tttacatgcg catggcgctg aaggtgctga cgctgagcga  10380
cgacctcggc gtgtaccgta acgacaagat ccacaaggcg gtgagcgcca gccgccggcg  10440
ggagctgagc gacagggagc tgatgcacag cctgcagagg gcgctggcgg gcgccgggga  10500
cgaggagcgc gaggcttact tcgacatggg agccgatctg cagtggcgtc ccagcgcgcg  10560
cgccttggag gcggcgggct accccgacga ggaggatcgg gacgatttgg aggaggcagg  10620
cgagtacgag gacgaagcct gaccgggcag gtgttgtttt agatgcagcg gccggcggac  10680
ggggccaccg cggatcccgc acttttggca tccatgcaga gtcaaccttc gggcgtgacc  10740
gcctccgatg actgggcggc ggccatggac cgcattatgg cgctgactac ccgcaacccc  10800
gaggctttta gacagcaacc ccaggccaac cgtttttcgg ccatcttgga agcggtggtg  10860
ccctcccgca ccaaccccac acacgagaaa gtcctgacta tcgtgaacgc cctggtagac  10920
agcaaggcca tccgccgcga cgaggcgggc ttgatttaca acgctctgct ggaacgggtg  10980
gcgcgctaca acagcactaa cgttcagacc aatctggatc gcctcaccac cgacgtgaag  11040
gaggcgctgg ctcagaagga gcggtttctg agggacagca atctgggctc tctggtggca  11100
ctcaacgcct tcctgagcac gcagccggcc aacgtgcccc gcgggcagga ggactacgtg  11160
agcttcatca gcgctctgag gctgctggtg tccgaggtgc cccagagcga ggtgtatcag  11220
tctgggccgg attacttctt ccagacgtcc cgacagggct tgcaaacggt gaacctgact  11280
caggccttta aaaacttgca aggcatgtgg ggcgttaagg ccccggtggg cgatcgagcc  11340
accatctcca gtctgctgac ccccaacact cgcctgctgc tgctcttgat cgcgccgttc  11400
accaacagta gcactatcag ccgtgactcg tacctgggtc atctcatcac tttgtaccgc  11460
gaggccatcg gtcaggctca gatcgacgag cacacatatc aggagatcac taacgtgagc  11520
cgggccctgg gtcaggaaga taccggcagc ctggaagcca cgttgaactt tttgctaacc  11580
aaccggaggc aaaaaatacc ctcccagttt acgttaagcg ccgaggagga gaggattctg  11640
cgatacgtgc agcagtccgt gagtctgtac ttgatgcggg agggcgccac cgcttccacg  11700
gctttagaca tgacggctcg gaacatggaa ccgtcctttt actccgccca ccggccgttc  11760
attaaccgtc tgatggacta cttccatcgc gcggccgcca tgaacgggga gtacttcacc  11820
aatgccatcc tgaatccgca ttggatgccc ccgtccggct tctacaccgg cgagtttgac  11880
ctgcccgaag ccgacgacgg ctttctttgg gacgacgtgt ccgacagcat tttcacgccg  11940
```

-continued

```
ggcaatcgcc gattccagaa gaaggagggc ggagacgagc tccccctctc cagcgtggag  12000

gcggcctcta ggggagagag tccctttccc agtctgtctt ccgccagcag tggtcgggta  12060

acgcgcccgc ggttgccggg ggagagcgac tacctgaacg accccttgct gcggccggct  12120

aggaagaaaa atttccccaa caacggggtg gaaagcttgg tggataaaat gaatcgttgg  12180

aagacctacg cccaggagca gcgggagtgg gaggacagtc agccgcgacc gctggttccg  12240

ccgcactggc gtcgtcagag agaagacccg gacgactccg cagacgatag tagcgtgttg  12300

gacctgggag ggagcggagc caaccccttt gctcacttgc aacccaaggg gcgttccagt  12360

cgcctctact aataaaaaag acgcggaaac ttaccagagc catggccaca gcgtgtgtcc  12420

tttcttcctc tctttcttcc tcggcgcggc aga atg aga aga gcg gtg aga gtc   12474
                                     Met Arg Arg Ala Val Arg Val
                                     1               5

acg ccg gcg gcg tat gag ggt ccg ccc cct tct tac gaa agc gtg atg    12522
Thr Pro Ala Ala Tyr Glu Gly Pro Pro Pro Ser Tyr Glu Ser Val Met
        10                  15                  20

gga tca gcg aac gtg ccg gcc acg ctg gag gcg cct tac gtt cct ccc    12570
Gly Ser Ala Asn Val Pro Ala Thr Leu Glu Ala Pro Tyr Val Pro Pro
    25                  30                  35

aga tac ctg gga cct acg gag ggc aga aac agc atc cgt tac tcc gag    12618
Arg Tyr Leu Gly Pro Thr Glu Gly Arg Asn Ser Ile Arg Tyr Ser Glu
40                  45                  50                  55

ctg gca ccc ctg tac gat acc acc aag gtg tac ctg gtg gac aac aag    12666
Leu Ala Pro Leu Tyr Asp Thr Thr Lys Val Tyr Leu Val Asp Asn Lys
                60                  65                  70

tcg gcg gac atc gcc tcc ctg aat tat caa aac gat cac agc aat ttt    12714
Ser Ala Asp Ile Ala Ser Leu Asn Tyr Gln Asn Asp His Ser Asn Phe
            75                  80                  85

ctg act acc gtg gtg cag aac aat gac ttc acc ccg acg gag gcg ggc    12762
Leu Thr Thr Val Val Gln Asn Asn Asp Phe Thr Pro Thr Glu Ala Gly
        90                  95                  100

acg cag acc att aac ttt gac gag cgt tcc cgc tgg ggc ggt cag ctg    12810
Thr Gln Thr Ile Asn Phe Asp Glu Arg Ser Arg Trp Gly Gly Gln Leu
    105                 110                 115

aaa acc atc ctg cac acc aac atg ccc aac atc aac gag ttc atg tcc    12858
Lys Thr Ile Leu His Thr Asn Met Pro Asn Ile Asn Glu Phe Met Ser
120                 125                 130                 135

acc aac aag ttc agg gcc agg ctg atg gtt aaa aag gct gaa aac cag    12906
Thr Asn Lys Phe Arg Ala Arg Leu Met Val Lys Lys Ala Glu Asn Gln
                140                 145                 150

cct ccc gag tac gaa tgg ttt gag ttc acc att ccc gag ggc aac tat    12954
Pro Pro Glu Tyr Glu Trp Phe Glu Phe Thr Ile Pro Glu Gly Asn Tyr
            155                 160                 165

tcc gag acc atg act atc gat ctg atg aac aat gcg atc gtg gac aat    13002
Ser Glu Thr Met Thr Ile Asp Leu Met Asn Asn Ala Ile Val Asp Asn
        170                 175                 180

tac ctg caa gtg ggg agg cag aac ggg gta ttg gaa agc gat atc ggc    13050
Tyr Leu Gln Val Gly Arg Gln Asn Gly Val Leu Glu Ser Asp Ile Gly
    185                 190                 195

gta aaa ttt gat acc aga aac ttc cga ctg ggg tgg gat ccc gtg acc    13098
Val Lys Phe Asp Thr Arg Asn Phe Arg Leu Gly Trp Asp Pro Val Thr
200                 205                 210                 215

aag ctg gtg atg cca ggc gtg tac acc aac gag gct ttt cac ccc gac    13146
Lys Leu Val Met Pro Gly Val Tyr Thr Asn Glu Ala Phe His Pro Asp
                220                 225                 230

atc gtg ctg ctg ccg ggg tgc ggt gtg gac ttc act cag agc cgt ttg    13194
Ile Val Leu Leu Pro Gly Cys Gly Val Asp Phe Thr Gln Ser Arg Leu
            235                 240                 245
```

-continued

```
agt aac ctg tta ggg atc aga aag cgc cgc ccc ttc caa gag ggc ttt    13242
Ser Asn Leu Leu Gly Ile Arg Lys Arg Arg Pro Phe Gln Glu Gly Phe
        250                 255                 260

cag atc atg tat gag gac ctg gaa gga ggt aac att cca ggt ttg cta    13290
Gln Ile Met Tyr Glu Asp Leu Glu Gly Gly Asn Ile Pro Gly Leu Leu
    265                 270                 275

gac gtg ccg gcg tat gaa gag agt gtt aaa cag gcg gag gcg cag gga    13338
Asp Val Pro Ala Tyr Glu Glu Ser Val Lys Gln Ala Glu Ala Gln Gly
280                 285                 290                 295

cga gag att cga ggc gac acc ttt gcc acg gaa cct cac gaa ctg gta    13386
Arg Glu Ile Arg Gly Asp Thr Phe Ala Thr Glu Pro His Glu Leu Val
                300                 305                 310

ata aaa cct ctg gaa caa gac agt aaa aaa cgg agt tac aac att ata    13434
Ile Lys Pro Leu Glu Gln Asp Ser Lys Lys Arg Ser Tyr Asn Ile Ile
            315                 320                 325

tcc ggc act atg aat acc ttg tac cgg agc tgg ttt ctg gct tac aac    13482
Ser Gly Thr Met Asn Thr Leu Tyr Arg Ser Trp Phe Leu Ala Tyr Asn
        330                 335                 340

tac ggg gat ccc gaa aag gga gtg aga tca tgg acc ata ctc acc acc    13530
Tyr Gly Asp Pro Glu Lys Gly Val Arg Ser Trp Thr Ile Leu Thr Thr
    345                 350                 355

acg gac gtg acc tgc ggc tcg cag caa gtg tac tgg tcc ctg ccg gat    13578
Thr Asp Val Thr Cys Gly Ser Gln Gln Val Tyr Trp Ser Leu Pro Asp
360                 365                 370                 375

atg atg caa gac ccg gtc acc ttc cgc ccc tcc acc caa gtc agc aac    13626
Met Met Gln Asp Pro Val Thr Phe Arg Pro Ser Thr Gln Val Ser Asn
                380                 385                 390

ttc ccg gtg gtg ggc acc gag ctg ctg ccc gtc cat gcc aag agc ttc    13674
Phe Pro Val Val Gly Thr Glu Leu Leu Pro Val His Ala Lys Ser Phe
            395                 400                 405

tac aac gaa cag gcc gtc tac tcg caa ctc att cgc cag tcc acc gcg    13722
Tyr Asn Glu Gln Ala Val Tyr Ser Gln Leu Ile Arg Gln Ser Thr Ala
        410                 415                 420

ctt acc cac gtg ttc aat cgc ttt ccc gag aac cag att ctg gtg cgc    13770
Leu Thr His Val Phe Asn Arg Phe Pro Glu Asn Gln Ile Leu Val Arg
    425                 430                 435

cct ccc gct cct acc att acc acc gtc agt gaa aac gtt ccc gcc ctc    13818
Pro Pro Ala Pro Thr Ile Thr Thr Val Ser Glu Asn Val Pro Ala Leu
440                 445                 450                 455

aca gat cac gga acc ctg ccg ctg cgc agc agt atc agt gga gtt cag    13866
Thr Asp His Gly Thr Leu Pro Leu Arg Ser Ser Ile Ser Gly Val Gln
                460                 465                 470

cgc gtg acc atc acc gac gcc aga cgt cga acc tgt ccc tac gtt tac    13914
Arg Val Thr Ile Thr Asp Ala Arg Arg Arg Thr Cys Pro Tyr Val Tyr
            475                 480                 485

aaa gct ctt ggc gta gtg gct cct aaa gtg ctc tct agt cgc acc ttc    13962
Lys Ala Leu Gly Val Val Ala Pro Lys Val Leu Ser Ser Arg Thr Phe
        490                 495                 500

taa acatgtccat cctcatctct cccgataaca acaccggctg ggactgggc        14015

tccggcaaga tgtacggcgg agccaaaagg cgctccagtc agcacccagt tcgagttcgg  14075

ggccacttcc gtgctccctg gggagcttac aagcgaggac tctcgggccg aacggcggta  14135

gacgatacca tagatgccgt gattgccgac gcccgccggt acaaccccgg accggtcgct  14195

agcgccgcct ccaccgtgga ttccgtgatc gacagcgtgg tagctggcgc tcgggcctat  14255

gctcgccgca agaggcggct gcatcggaga cgtcgcccca ccgccgccat gctggcagcc  14315

agggccgtgc tgaggcgggc ccggagggta ggcagaaggg ctatgcgccg cgctgccgcc  14375
```

-continued

```
aacgccgccg ccgggagggc ccgccgacag gctgcccgcc aggctgctgc cgccatcgct  14435
agcatggcca gacccaggag agggaacgtg tactgggtgc gcgattctgt gacgggagtc  14495
cgagtgccgg tgcgcagccg acctccccga agttagaaga tccaagctgc gaagacggcg  14555
gtactgagtc tccctgttgt tatcagccca acatgagcaa gcgcaagttt aaagaagaac  14615
tgctgcagac gctggtgcct gagatctatg gccctccgga cgtgaagcct gacattaagc  14675
cccgcgatat caagcgtgtt aaaaagcggg aaaagaaaga ggaactcgcg gtggtagacg  14735
atggcggagt ggaatttatt aggagtttcg ccccgcgacg cagggttcaa tggaaagggc  14795
ggcgggtaca acgcgttttg aggccgggca ccgcggtagt ttttaccccg ggagagcggt  14855
cggccgttag ggtttcaaa aggcagtacg acgaggtgta cggcgacgag gacatattgg  14915
aacaggcggc tcaacagatc ggagaatttg cctacggaaa gcgttcgcgt cgcgaagacc  14975
tggccatcgc tttagacagc ggcaacccca cgcccagcct caaacctgtg acgctgcagc  15035
aggtgctccc cgtgagcgcc agcacggaca gcaagagggg aataaaaaga gaaatggaag  15095
atctgcagcc caccatccag ctcatggtcc ctaaacggca gaggctggaa gaggtcctgg  15155
agaaaatgaa agtggaccca agcatagagc cggacgtcaa agtcaggccg atcaaagaag  15215
tggcccctgg tctcggggtg cagacggtgg atatccagat ccccgtcacg tcagcttcga  15275
ccgccgtgga agccatggaa acgcaaacgg aaacccctgc cgcgatcggt accagggaag  15335
tggcgttgca aaccgacccc tggtacgaat acgccgcccc tcggcgtcag aggcgacccg  15395
ctcgttacgg ccccgccaac gccatcatgc cagaatatgc gctgcatccg tctatcctgc  15455
ccaccccccgg ctaccgggga gtgacgtatc gcccgtcagg aacccgccgc cgaacccgtc  15515
gccgccgccg ctcccgtcgt gctctggccc ccgtgtcggt gcgccgcgta acacgccggg  15575
gaaagacagt taccattccc aacccgcgct accaccctag catcctttaa tgactctgcc  15635
gttttgcaga tggctctgac ttgccgcgtg cgccttcccg ttccgcacta tcgaggaaga  15695
tctcgtcgta ggagaggcat ggcgggtagt ggtcgccggc gggctttgcg caggcgcatg  15755
aaaggcggaa ttttacccgc tctgataccc ataatcgccg ccgccatcgg tgccataccc  15815
ggcgtcgctt cagtggcctt gcaagcagct cgtaataaat aaacgaaggc ttttgcactt  15875
atgtcctggt cctgactatt ttatgcagaa agagcatgga agacatcaat tttacgtcgc  15935
tggctccgcg gcacggctcg cggccgctca tgggcacctg gaacgacatc ggcaccagtc  15995
agctcaacgg gggcgctttc aattggggga gcctttggag cggcattaaa aactttggct  16055
ccacgattaa atcctacggc agcaaagcct ggaacagtag tgctggtcag atgctccgag  16115
ataaactgaa ggacaccaac ttccaagaaa aagtggtcaa tggggtggtg accggcatcc  16175
acggcgcggt agatctcgcc aaccaagcgg tgcagaaaga gattgacagg cgtttggaaa  16235
gctcgcgggt gccgccgcag agaggggatg aggtggaggt cgaggaagta gaagtagagg  16295
aaaagctgcc cccgctggag aaagttcccg gtgcgcctcc gagaccgcag aagcgaccca  16355
ggccagaact agaagaaact ctggtgacgg agagcaagga gcctccctcg tacgagcaag  16415
ccttgaaaga gggcgcctct ccaccctacc caatgacaaa accgatcgcg cctatggctc  16475
ggccggtgta cgggaaggac tacaagcctg tcacgctaga gctcccccccg ccgccaccgc  16535
cgccccccac gcgcccgacc gttcccccccc ccctgccggc tccgtcggcg ggacccgtgt  16595
ccgcacccgt cgccgtgcct ctgccagccg cccgcccagt ggccgtggcc actgccagaa  16655
accccagagg ccagagagga gccaactggc aaagcacgct gaacagcatc gtgggcctgg  16715
gagtgaaaag cctgaaacgc cgccgttgct attattaaaa gtgtagctaa aaaatttccc  16775
```

-continued

```
gttgtatacg cctcctatgt taccgccaga gacgcgtgac tgtcgccgcg agcgccgctt  16835

tcaag atg gcc acc cca tcg atg atg ccg cag tgg tct tac atg cac atc  16885
      Met Ala Thr Pro Ser Met Met Pro Gln Trp Ser Tyr Met His Ile
          505                 510                 515

gcc ggg cag gac gcc tcg gag tac ctg agc ccc ggt ctc gtg cag ttc    16933
Ala Gly Gln Asp Ala Ser Glu Tyr Leu Ser Pro Gly Leu Val Gln Phe
    520                 525                 530

gcc cgc gcc acc gac acc tac ttc agc ttg gga aac aag ttt aga aac    16981
Ala Arg Ala Thr Asp Thr Tyr Phe Ser Leu Gly Asn Lys Phe Arg Asn
535                 540                 545                 550

ccc acc gtg gcc ccc acc cac gat gta acc acg gac cgc tcg caa agg    17029
Pro Thr Val Ala Pro Thr His Asp Val Thr Thr Asp Arg Ser Gln Arg
                555                 560                 565

ctg acc ctg cgt ttt gtg ccc gta gac cgg gag gac acc gcg tac tct    17077
Leu Thr Leu Arg Phe Val Pro Val Asp Arg Glu Asp Thr Ala Tyr Ser
            570                 575                 580

tac aaa gtg cgc tac acg ctg gcc gta ggg gac aac cga gtg ctg gac    17125
Tyr Lys Val Arg Tyr Thr Leu Ala Val Gly Asp Asn Arg Val Leu Asp
        585                 590                 595

atg gcc agc acc tac ttt gac atc cgg gga gtg ctg gat cgc ggt ccc    17173
Met Ala Ser Thr Tyr Phe Asp Ile Arg Gly Val Leu Asp Arg Gly Pro
    600                 605                 610

agt ttt aag ccc tac tcg ggt acc gcg tac aat tcc ctg gct ccc aag    17221
Ser Phe Lys Pro Tyr Ser Gly Thr Ala Tyr Asn Ser Leu Ala Pro Lys
615                 620                 625                 630

ggc gct ccc aac cct gca gaa tgg acg aat tca gac agc aaa gtt aaa    17269
Gly Ala Pro Asn Pro Ala Glu Trp Thr Asn Ser Asp Ser Lys Val Lys
                635                 640                 645

gtg agg gca cag gcg cct ttt gtt agc tcg tat ggt gct aca gcg att    17317
Val Arg Ala Gln Ala Pro Phe Val Ser Ser Tyr Gly Ala Thr Ala Ile
            650                 655                 660

aca aaa gag ggt att cag gtg gga gta acc tta aca gac tcc gga tca    17365
Thr Lys Glu Gly Ile Gln Val Gly Val Thr Leu Thr Asp Ser Gly Ser
        665                 670                 675

aca cca cag tat gca gat aaa acg tat cag cct gag ccg caa att gga    17413
Thr Pro Gln Tyr Ala Asp Lys Thr Tyr Gln Pro Glu Pro Gln Ile Gly
    680                 685                 690

gaa cta cag tgg aac agc gat gtt gga acc gat gac aaa ata gca gga    17461
Glu Leu Gln Trp Asn Ser Asp Val Gly Thr Asp Asp Lys Ile Ala Gly
695                 700                 705                 710

aga gtg cta aag aaa aca acg ccc atg ttc cct tgt tac ggc tca tat    17509
Arg Val Leu Lys Lys Thr Thr Pro Met Phe Pro Cys Tyr Gly Ser Tyr
                715                 720                 725

gcc agg ccc act aat gaa aaa gga gga cag gca aca ccg tcc gct agt    17557
Ala Arg Pro Thr Asn Glu Lys Gly Gly Gln Ala Thr Pro Ser Ala Ser
            730                 735                 740

caa gac gtg caa aat ccc gaa tta caa ttt ttt gcc tct act aat gtc    17605
Gln Asp Val Gln Asn Pro Glu Leu Gln Phe Phe Ala Ser Thr Asn Val
        745                 750                 755

gcc aat aca cca aaa gca gtt cta tat gcg gag gac gtg tca att gaa    17653
Ala Asn Thr Pro Lys Ala Val Leu Tyr Ala Glu Asp Val Ser Ile Glu
    760                 765                 770

gcg cca gac act cac ttg gtg ttc aaa cca aca gtc act gaa ggc att    17701
Ala Pro Asp Thr His Leu Val Phe Lys Pro Thr Val Thr Glu Gly Ile
775                 780                 785                 790

aca agt tca gag gct cta ctg acc caa caa gct gct ccc aac cgt cca    17749
Thr Ser Ser Glu Ala Leu Leu Thr Gln Gln Ala Ala Pro Asn Arg Pro
                795                 800                 805
```

-continued

```
aac tac ata gcc ttt aga gat aat ttt att ggt ctc atg tac tac aat     17797
Asn Tyr Ile Ala Phe Arg Asp Asn Phe Ile Gly Leu Met Tyr Tyr Asn
            810                 815                 820

agc aca ggt aac atg gga gta ctg gca ggc cag gct tct cag cta aat     17845
Ser Thr Gly Asn Met Gly Val Leu Ala Gly Gln Ala Ser Gln Leu Asn
        825                 830                 835

gca gtt gtt gac ctg caa gac aga aat act gag ctg tcc tac caa ctc     17893
Ala Val Val Asp Leu Gln Asp Arg Asn Thr Glu Leu Ser Tyr Gln Leu
    840                 845                 850

atg ttg gac gcc ctc gga gac cgc agt cgg tac ttt tct atg tgg aac     17941
Met Leu Asp Ala Leu Gly Asp Arg Ser Arg Tyr Phe Ser Met Trp Asn
855                 860                 865                 870

caa gct gtg gat agt tac gat cct gat gta aga atc ata gaa aac cat     17989
Gln Ala Val Asp Ser Tyr Asp Pro Asp Val Arg Ile Ile Glu Asn His
                875                 880                 885

ggc gta gaa gat gaa ttg cct aat tat tgc ttt cct ttg gga ggc atg     18037
Gly Val Glu Asp Glu Leu Pro Asn Tyr Cys Phe Pro Leu Gly Gly Met
            890                 895                 900

gca gta acc gac acc tac tcg cct ata aag gtt aat gga gga ggc aat     18085
Ala Val Thr Asp Thr Tyr Ser Pro Ile Lys Val Asn Gly Gly Gly Asn
        905                 910                 915

gga tgg gaa gcc aat aac ggc gtt ttc acc gaa aga gga gtg gaa ata     18133
Gly Trp Glu Ala Asn Asn Gly Val Phe Thr Glu Arg Gly Val Glu Ile
    920                 925                 930

ggt tca ggg aac atg ttt gcc atg gag att aac ctg caa gcc aac cta     18181
Gly Ser Gly Asn Met Phe Ala Met Glu Ile Asn Leu Gln Ala Asn Leu
935                 940                 945                 950

tgg cgt agc ttt ctg tac tcc aat att ggg ctg tac ctg cca gac tct     18229
Trp Arg Ser Phe Leu Tyr Ser Asn Ile Gly Leu Tyr Leu Pro Asp Ser
                955                 960                 965

ctc aaa atc act cct gac aac atc aca ctc cca gag aac aaa aac acc     18277
Leu Lys Ile Thr Pro Asp Asn Ile Thr Leu Pro Glu Asn Lys Asn Thr
            970                 975                 980

tat cag tat atg aac ggt cgc gtg acg cca ccc ggg ctg gtt gac acc     18325
Tyr Gln Tyr Met Asn Gly Arg Val Thr Pro Pro Gly Leu Val Asp Thr
        985                 990                 995

tac gtt  aac gtg ggc gcg cgc  tgg tcc ccc gat gtc  atg gac agt     18370
Tyr Val  Asn Val Gly Ala Arg  Trp Ser Pro Asp Val  Met Asp Ser
    1000                 1005                 1010

att aac  cct ttt aat cac cac  cgc aac gcc gga ctc  cgc tac cgt     18415
Ile Asn  Pro Phe Asn His His  Arg Asn Ala Gly Leu  Arg Tyr Arg
    1015                 1020                 1025

tcc atg  ctc ctg gga aac gga  cgc tac gtg ccc ttc  cac atc cag     18460
Ser Met  Leu Leu Gly Asn Gly  Arg Tyr Val Pro Phe  His Ile Gln
    1030                 1035                 1040

gtg ccc  cag aaa ttc ttt gca  att aaa aac ctg ctg  ctg ctc ccc     18505
Val Pro  Gln Lys Phe Phe Ala  Ile Lys Asn Leu Leu  Leu Leu Pro
    1045                 1050                 1055

ggt tcc  tac acc tac gag tgg  aac ttc cgc aag gac  gtg aac atg     18550
Gly Ser  Tyr Thr Tyr Glu Trp  Asn Phe Arg Lys Asp  Val Asn Met
    1060                 1065                 1070

atc ttg  cag agc tcg ctg ggc  aat gac ctg cga gtg  gac ggg gcc     18595
Ile Leu  Gln Ser Ser Leu Gly  Asn Asp Leu Arg Val  Asp Gly Ala
    1075                 1080                 1085

agc atc  cgc ttc gac agc atc  aac ctg tac gcc aac  ttt ttc ccc     18640
Ser Ile  Arg Phe Asp Ser Ile  Asn Leu Tyr Ala Asn  Phe Phe Pro
    1090                 1095                 1100

atg gcc  cac aac acg gcc tcc  acc ctg gaa gcc atg  ctg cgc aac     18685
Met Ala  His Asn Thr Ala Ser  Thr Leu Glu Ala Met  Leu Arg Asn
    1105                 1110                 1115
```

-continued

```
gac acc  aac gac caa tct ttc  aac gac tac ctg tgc  gcg gcc aac     18730
Asp Thr  Asn Asp Gln Ser Phe  Asn Asp Tyr Leu Cys  Ala Ala Asn
    1120                 1125                 1130

atg ctg  tac ccc atc ccc gcc  aac gcc acc agc gtg  ccc atc tcc     18775
Met Leu  Tyr Pro Ile Pro Ala  Asn Ala Thr Ser Val  Pro Ile Ser
    1135                 1140                 1145

att ccc  tct cgc aac tgg gca  gcc ttc agg ggc tgg  agt ttc acc     18820
Ile Pro  Ser Arg Asn Trp Ala  Ala Phe Arg Gly Trp  Ser Phe Thr
    1150                 1155                 1160

cgc ctc  aaa acc aag gag acc  ccc tcg ctg ggc tcc  ggg ttc gac     18865
Arg Leu  Lys Thr Lys Glu Thr  Pro Ser Leu Gly Ser  Gly Phe Asp
    1165                 1170                 1175

ccc tac  ttc gtc tac tcc ggc  tcc atc ccc tac ctg  gac ggc acc     18910
Pro Tyr  Phe Val Tyr Ser Gly  Ser Ile Pro Tyr Leu  Asp Gly Thr
    1180                 1185                 1190

ttc tac  ctc aac cat act ttc  aaa aag gtg tca atc  atg ttc gac     18955
Phe Tyr  Leu Asn His Thr Phe  Lys Lys Val Ser Ile  Met Phe Asp
    1195                 1200                 1205

tcc tcc  gtc agc tgg ccc ggc  aac gac cgt ctg ctg  acg ccc aac     19000
Ser Ser  Val Ser Trp Pro Gly  Asn Asp Arg Leu Leu  Thr Pro Asn
    1210                 1215                 1220

gag ttc  gaa atc aag cgt tcg  gtg gac ggt gaa ggg  tac aac gtg     19045
Glu Phe  Glu Ile Lys Arg Ser  Val Asp Gly Glu Gly  Tyr Asn Val
    1225                 1230                 1235

gct cag  agc aac atg acc aag  gac tgg ttc ctg att  cag atg ctc     19090
Ala Gln  Ser Asn Met Thr Lys  Asp Trp Phe Leu Ile  Gln Met Leu
    1240                 1245                 1250

agc cac  tac aac atc ggc tac  cag ggc ttc tac gtg  ccc gaa aat     19135
Ser His  Tyr Asn Ile Gly Tyr  Gln Gly Phe Tyr Val  Pro Glu Asn
    1255                 1260                 1265

tac aag  gac cgc atg tac tct  ttc ttc aga aac ttc  caa ccc atg     19180
Tyr Lys  Asp Arg Met Tyr Ser  Phe Phe Arg Asn Phe  Gln Pro Met
    1270                 1275                 1280

agc cgc  caa att gta gat tca  acg gct tac act aat  tat cag gat     19225
Ser Arg  Gln Ile Val Asp Ser  Thr Ala Tyr Thr Asn  Tyr Gln Asp
    1285                 1290                 1295

gtg aaa  ctg cca tac cag cat  aac aac tca ggg ttc  gtg ggc tac     19270
Val Lys  Leu Pro Tyr Gln His  Asn Asn Ser Gly Phe  Val Gly Tyr
    1300                 1305                 1310

atg gga  ccc acc atg cga gag  ggg cag gcc tac ccg  gcc aac tat     19315
Met Gly  Pro Thr Met Arg Glu  Gly Gln Ala Tyr Pro  Ala Asn Tyr
    1315                 1320                 1325

ccc tat  ccc ctg att ggg gcc  acc gcc gtg ccc agc  ctc acg cag     19360
Pro Tyr  Pro Leu Ile Gly Ala  Thr Ala Val Pro Ser  Leu Thr Gln
    1330                 1335                 1340

aaa aag  ttc ctc tgc gac cgg  gtg atg tgg agg atc  ccc ttc tct     19405
Lys Lys  Phe Leu Cys Asp Arg  Val Met Trp Arg Ile  Pro Phe Ser
    1345                 1350                 1355

agc aac  ttc atg tct atg ggc  tcc ctc acc gac ctg  ggg cag aac     19450
Ser Asn  Phe Met Ser Met Gly  Ser Leu Thr Asp Leu  Gly Gln Asn
    1360                 1365                 1370

atg ctg  tac gcc aac tcc gct  cac gcc ttg gat atg  acc ttt gag     19495
Met Leu  Tyr Ala Asn Ser Ala  His Ala Leu Asp Met  Thr Phe Glu
    1375                 1380                 1385

gtg gat  ccc atg gat gag ccc  acg ctt ctc tat gtt  ctg ttt gaa     19540
Val Asp  Pro Met Asp Glu Pro  Thr Leu Leu Tyr Val  Leu Phe Glu
    1390                 1395                 1400

gtc ttc  gac gtg gtg cgc atc  cac cag ccg cac cgc  ggc gtc atc     19585
Val Phe  Asp Val Val Arg Ile  His Gln Pro His Arg  Gly Val Ile
```

-continued

```
    1405                1410                1415

gag gcc  gtc tac ctg cgc aca  cct ttc tct gcc ggt  aac gcc acc     19630
Glu Ala  Val Tyr Leu Arg Thr  Pro Phe Ser Ala Gly  Asn Ala Thr
    1420                1425                1430

acc taa agaagccgat gggctccagc gaacaggagc tgcaggccat tgttcgcgac     19686
Thr

ctgggctgcg ggccctactt tttgggcacc ttcgacaagc gttttcccgg cttcatgtcc  19746

ccccacaagc cggcctgtgc catcgttaac acggccggac gggagaccgg gggggtccac  19806

tggctcgcct tcgcctggaa cccgcgtaac cgcacctgct acctgttcga cccttttggt  19866

ttctccgacg aaaggctgaa gcagatctac cagttcgagt acgaggggct cctcaagcgc  19926

agcgctctgg cctccacgcc cgaccactgc gtcaccctgg aaaagtccac ccaaacggtc  19986

caggggcccc tctcggccgc ctgcgggctc ttctgttgca tgtttttgca cgccttcgtg  20046

cactggcctc acaccccat ggatcacaac cccaccatgg atctgctcac cggagtgccc   20106

aacagcatgc ttcacagccc ccaggtcgcc cccaccctgc gccgtaacca ggaacacctg  20166

tatcgctttc tggggaaaca ctctgcctat tttcgccgcc accggcagcg catcgaacgg  20226

gccacggcct tcgaaagcat gagccaaaga gtgtaatcaa taaaaaacat ttttatttga  20286

catgatacgc gcttctggcg ttttattaaa aatcgaaggg ttcgagggag gggtcctcgt  20346

gcccgctggg gagggacacg ttgcgatact ggaaacgggc gctccaacga aactcgggga  20406

tcaccagccg cggcaggggc acgtcttcta ggttctgctt ccaaaactgc cgcaccagct  20466

gcagggctcc catgacgtcg ggcgccgata tcttgaagtc gcagttaggg ccggagctcc  20526

cgcggctgtt gcggaacacg ggttggcac actggaacac cagcacgccg gggttgtgga   20586

tactggccag ggccgtcggg tcggtcacct ccgacgcatc cagatcctcg gcgttgctca  20646

gggcaaacgg ggtcagcttg cacatctgcc gcccaatctg ggtactaggg tcgcgcttgt  20706

tgaggcagtc gcagcgcaga gggatcagga tgcgtcgctg cccgcgttgc atgatagggt  20766

aactcgccgc caggaactcc tccatttgac ggaaggccat ctgggctttg ccgccctcgg  20826

tgtagaatag cccgcaggac ttgctagaga atacgttatg accgcagttg acgtcctccg  20886

cgcagcagcg ggcgtcttcg ttcttcagct gaaccacgtt gcggccccaa cggttctgga  20946

ccaccttggc tctagtgggg tgctccttca gcgcccgctg tccgttctcg ctggttacat  21006

ccatttccaa cacgtgctcc ttgcagacca tctccactcc gtggaagcaa aacaggacgc  21066

cctcctgctg ggtactgcga tgctcccata cggcgcatcc ggtgggctcc cagctcttgt  21126

gttttacccc cgcgtaggct tccatgtaag ccataaggaa tctgcccatc agctcggtga  21186

aggtcttctg gttggtgaag gttagcggca ggccgcggtg ctcctcgttc aaccaagttt  21246

gacagatctt gcggtacacc gctccctggt cgggcagaaa cttaaaagcc gctctgctgt  21306

cgttgtctac gtggaacttc tccattaaca tcatcatggt ttccataccc ttctcccacg  21366

ctgtcaccag tggtttgctg tcggggttct tcaccaacac ggcggtagag ggccctcgc   21426

cggccccgac gtccttcatg gtcattcttt gaaactccac ggagccgtcc gcgcgacgta  21486

ctctgcgcac cggagggtag ctgaagccca cctccaccac ggtgccttcg ccctcgctgt  21546

cggagacaat ctccggggat ggcggcggcg cgggtgtcgc cttgcgagcc ttcttcttgg  21606

gagggagctg aggcgcctcc tgctcgcgct cggggctcat ctcccgcaag taggggggtaa  21666

tggagctgcc tgcttggttc tgacggttgg ccattgtatc ctaggcagaa agacatggag  21726

cttatgcgcg aggaaacttt aaccgccccg tcccccgtca gcgacgaaga tgtcatcgtc  21786
```

-continued

```
gaacaggacc cgggctacgt tacgccgccc gaggatctgg aggggcctga ccggcgcgac  21846
gctagtgagc ggcaggaaaa tgagaaagag gaggcctgct acctcctgga aggcgacgtt  21906
ttgctaaagc atttcgccag gcagagcacc atagttaagg aggccttgca agaccgctcc  21966
gaggtgccct tggacgtcgc cgcgctctcc caggcctacg aggcgaacct tttctcgcct  22026
cgagtgcctc cgaagagaca gcccaacggc acctgcgagc ccaacccgcg actcaacttc  22086
taccccgtgt tcgccgtacc agaggcgctg gccacctatc acattttttt caaaaaccaa  22146
cgcatccccc tatcgtgccg ggccaaccgc accgcggccg ataggaatct caggcttaaa  22206
aacggagcca acatacctga tatcacgtcg ctggaggaag tgcccaagat tttcgagggt  22266
ctgggtcgag atgagaagcg ggcggcgaac gctctgcaga aagaacagaa agagagtcag  22326
aacgtgctgg tggagctgga gggggacaac gcgcgtctgg ccgtcctcaa acgctgcata  22386
gaagtctccc acttcgccta ccccgccctc aacttgccac ccaaagttat gaaatcggtc  22446
atggatcagc tgctcatcaa gagagctgag cccctggatc ccgaccaccc cgaggcggaa  22506
aactcagagg acggaaagcc cgtcgtcagc gacgaggagc tcgagcggtg gctggaaacc  22566
agggaccccc aacagttgca agagaggcgc aagatgatga tggcggccgt gctggtcacc  22626
gtggagctgg aatgcctgca acggtttttc agcgacgtgg agacgctacg caaaatcggg  22686
gaatccctgc actacacctt ccgccagggc tacgtccgcc aggcctgcaa gatctccaac  22746
gtggagctca gcaacctggt ctcctacatg ggcatcctcc acgagaaccg gctggggcag  22806
agcgtgctgc actgcacctt gcaaggcgag gcgcggcggg actacgtgcg agactgcatc  22866
tacctcttcc tcaccctcac ctggcagacc gccatgggcg tctggcagca gtgcttggaa  22926
gagagaaacc tcaaagagct agacaaactc ctctgccgcc agcggcgcgc cctgtggtcc  22986
ggtttcagcg agcgcacggt cgccagcgct ctggcggaca tcatcttccc ggagcgcctg  23046
atgaaaacct tgcaaaacgg cctgccggat ttcatcagtc aaagcatttt gcaaaacttc  23106
cgctcttttg tcctggaacg ctccgggatc ttgcccgcca tgagctgcgc gctaccttct  23166
gactttgtcc ccctctccta ccgcgagtgc cctcccccac tgtggagcca ctgctacctc  23226
ttccaactgg ccaactttct ggcctaccac tccgacctca tggaagacgt aagcggagag  23286
ggtttactgg agtgccactg ccgctgcaac ctgtgcaccc cccacagatc gctggcctgc  23346
aacaccgagc tactcagcga aacccaggtc ataggtacct tcgagatcca ggggccccag  23406
cagcaagagg gtgcttccgg cttgaagctc actccggcgc tgtggacctc ggcttactta  23466
cgcaaatttg tagccgagga ctaccacgcc cacaaaattc agttttacga agaccaatct  23526
cgaccaccga aagcccccct cacggcctgc gtcatcaccc agagcaagat cctggcccaa  23586
ttgcaatcca tcaaccaagc gcgccgcgat ttcctttttga aaaagggtcg gggggtgtac  23646
ctggaccccc agaccggcga ggaactcaac ccgtccacac tctccgtcga agcagccccc  23706
ccgagacatg ccgcccaagg gaaccgccaa gcagctgatc gctcggcaga gagcgaagaa  23766
gcaagagctg ctccagcagc aggtggagga cgaggaagag atgtgggaca gccaggcaga  23826
ggaggtgtca gaggacgagg aggagatgga aagctgggac agcctagacg aggaggagga  23886
cgagctttca gaggaagagg cgaccgaaga aaaaccacct gcatccagcg cgccttctct  23946
gagccgacag ccgaagcccc ggcccccgac gcccccggcc ggctcactca aagccagccg  24006
taggtgggac gccaccgaat ctccagcggc agcggcaacg gcagcgggta aggccaaacg  24066
cgagcggcgg gggtattgct cctggcgggc ccacaaaagc agtattgtga actgcttgca  24126
acactgcggg ggaaacatct cctttgcccg acgctacctc ctcttccatc acggtgtggc  24186
```

-continued

```
cttccctcgc aacgttctct attattaccg tcatctctac agcccctacg aaacgctcgg  24246
agaaaaaagc taaggcctcc tccgccgcga ggaaaaactc cgccgccgct gccgccgcca  24306
aggatccacc ggccaccgaa gagctgagaa agcgcatctt tcccactctg tatgctatct  24366
ttcagcaaag ccgcgggcag caccctcagc gcgaactgaa aataaaaaac cgctccttcc  24426
gctcgctcac ccgcagctgt ctgtaccaca agagagaaga ccagctgcag cgcaccctgg  24486
acgacgccga agcactgttc agcaaatact gctcagcgtc tcttaaagac taaaagaccc  24546
gcgctttttc cccctcggcc gccaaaaccc acgtcatcgc cagcatgagc aaggagattc  24606
ccacccccta catgtggagc tatcagcccc agatgggcct ggccgcgggg gccgcccagg  24666
actactccag caagatgaac tggctcagcg ccggccccca catgatctca cgagttaacg  24726
gcatccgagc ccaccgaaac cagattctct tagaacaggc ggcaatcacc gccacacccc  24786
ggcgccaact caacccgcct agttggcccg ccgcccaggt gtatcaggaa aatccccgcc  24846
cgaccacagt cctcctgcca cgcgacgcgg aggccgaagt cctcatgact aactctgggg  24906
tacaattagc gggcgggtcc aggtacgcca ggtacagagg tcgggccgct ccttactctc  24966
ccgggagtat aaagagggtg atcattcgag gccgaggtat ccagctcaac gacgagacgg  25026
tgagctcctc aaccggtctc agacctgacg gagtcttcca gctcggagga gcgggccgct  25086
cttccttcac cactcgccag gcctacctga ccctgcagag ctcttcctcg cagccgcgct  25146
ccgggggaat cggcactctc cagttcgtgg aagagttcgt tccctccgtc tacttcaacc  25206
ccttctccgg ctcgcctgga cgctacccgg acgccttcat tcccaacttt gacgcagtga  25266
gtgaatccgt ggacggctac gactgatgac agatggtgcg gccgtgagag ctcggctgcg  25326
acatctgcat cactgccgtc agcctcgctg ctacgctcgg gaggcgatcg tcttcagcta  25386
ctttgagctg ccggacgagc accctcaggg tccggctcac gggttgaaac tcgagatcga  25446
gaacgcgctc gagtctcgcc tcatcgacac cttcaccgcc cgacctctcc tggtagaaat  25506
ccaacggggg atcactacca tcaccctgtt ctgcatctgc ccccacgccg gattacatga  25566
agatctgtgt tgtcatcttt gcgctcagtt taataaaaac tgaacttttt gccgcacctt  25626
caacgccatc tgtgatttct acaacaaaaa gttcttctgg caaaggtaca caaactgtat  25686
tttattctaa ttctacctca tctatcgtgc tgaactgcgc ctgcactaac gaacttatcc  25746
agtggattgc aaacggtagt gtgtgcaagt acttttgggg gaacgatata gttagtagaa  25806
ataacagcct ttgcgagcac tgcaactcct ccacactaat cctttatccc ccatttgtta  25866
ctggatggta tatgtgcgtt ggctccggtt taaatcctag ttgctttcat aagtggtttc  25926
tacaaaaaga gacccttccc aacaattctg tttctttttt cgccctatcc tactgctgtt  25986
ctccctctgg ttactctttc aaacctctaa ttggtatttt agctttgata ctcataatct  26046
ttattaactt tataataatt aacaacttac agtaaacatg cttgttctac tgctcgccac  26106
atctttcgct ctctctcacg ccagaacaag tattgttggc gcaggttaca atgcaactct  26166
tcaatctgct tacatgccag attccgacca gataccccat attacgtggt acttacaaac  26226
ctccaaacct aattcttcat tttatgaagg aaacaaactc tgcgatgact ccgacaacag  26286
aacgcacaca tttccccacc cttcactaca attcgaatgc gtaaacaaaa gcttgaagct  26346
ttacaactta aagccttcag attctggctt gtaccatgct gtagttgaaa aaagtaattt  26406
agaagtccac agtgattaca ttgaattgac ggttgtggac ctgccacctc caaaatgtga  26466
ggtttcctcc tcttaccttg aagttcaagg cgtggatgcc tactgcctca tacacattaa  26526
```

-continued

```
ctgcagcaac tctaaatatc cagctagaat ttactataat ggacaggaaa gtaatctttt  26586

ttattattta acaacaagcg ctggtaacgg taaacagtta cctgactatt ttactgctgt  26646

tgttgaattt tccacctaca gagaaacgta tgccaagcgg ccttacaatt tctcataccc  26706

gtttaacgac ctttgcaatg aaatacaagc gctcgaaact ggaactgatt ttactccaat  26766

tttcattgct gccattgttg taagcttaat taccattatt gtcagcctag cattttactg  26826

cttttacaag cccaaaaacc ctaagtttga aaaacttaaa ctaaaacctg tcattcaaca  26886

agtgtgattt tgttttccag catggtagct gcatttctac ttctcctctg tctacccatc  26946

attttcgtct cttcaacttt cgccgcagtt tcccacctgg aaccagagtg cctaccgcct  27006

tttgacgtgt atctgattct cacctttgtt tgttgtatat ccatttgcag tatagcctgc  27066

ttttttataa caatctttca agccgccgac tatttttacg tgcgaattgc ttactttaga  27126

caccatcctg aatacagaaa tcaaaacgtt gcctccttac tttgtttggc atgattaagt  27186

tattgctgat acttaattat ttacccctaa tcaactgtaa ttgtccattc accaaaccct  27246

ggtcattcta cacctgttat gataaaatcc ccgacactcc tgttgcttgg ctttacgcag  27306

ccaccgccgc tttggtattt atatctactt gccttggagt aaaattgtat tttattttac  27366

acactgggtg gctacatccc agagaagatt tacctagata tcctcttgta aacgcttttc  27426

aattacagcc tctgcctcct cctgatcttc ttcctcgagc tccctctatt gtgagctact  27486

ttcaactcac cggtggagat gactgactct caggacatta atattagtgt ggaaagaata  27546

gctgctcagc gtcagcgaga aacgcgagtg ttggaatacc tggaactaca gcaacttaaa  27606

gagtcccact ggtgtgagaa aggagtgctg tgccatgtta agcaggcagc cctttcctac  27666

gatgtcagcg ttcagggaca tgaactgtct tacactttgc ctttgcagaa acaaaccttc  27726

tgcaccatga tgggctctac ctccatcaca atcacccaac aagccgggcc tgtagagggg  27786

gctatcctct gtcactgtca cgcacctgat tgcatgtcca aactaatcaa aactctctgt  27846

gctttaggtg atatttttaa ggtgtaaatc aataataaac ttaccttaaa tttgacaaca  27906

aatttctggt gacatcattc agcagcacca ctttaccctc ttcccagctc tcgtatggga  27966

tgcgatagtg ggtggcaaac ttcctccaaa ccctaaaaga aatattggta tccacttcct  28026

tgtcctcacc cacaatttcc atcttttcat ag atg  aaa aga acc aga gtt  gat  28079
                                    Met  Lys Arg Thr Arg Val  Asp
                                    1435                 1440

gaa gac ttc aac  ccc gtc tac ccc tat  gac acc aca acc act  cct     28124
Glu Asp Phe Asn  Pro Val Tyr Pro Tyr  Asp Thr Thr Thr Thr  Pro
            1445                 1450                 1455

gca gtt ccc ttt  ata tca ccc ccc ttt  gta aac agc gat ggt  ctt     28169
Ala Val Pro Phe  Ile Ser Pro Pro Phe  Val Asn Ser Asp Gly  Leu
            1460                 1465                 1470

cag gaa aac ccc  cca ggt gtt tta agt  ctg cga ata gct aaa  ccc     28214
Gln Glu Asn Pro  Pro Gly Val Leu Ser  Leu Arg Ile Ala Lys  Pro
            1475                 1480                 1485

cta tat ttc gac  atg gag aga aaa cta  gcc ctt tca ctt gga  aga     28259
Leu Tyr Phe Asp  Met Glu Arg Lys Leu  Ala Leu Ser Leu Gly  Arg
            1490                 1495                 1500

ggg ttg aca att  acc gcc gcc gga caa  tta gaa agt acg cag  agc     28304
Gly Leu Thr Ile  Thr Ala Ala Gly Gln  Leu Glu Ser Thr Gln  Ser
            1505                 1510                 1515

gta caa acc aac  cca ccg ttg ata att  acc aac aac aac aca  ctg     28349
Val Gln Thr Asn  Pro Pro Leu Ile Ile  Thr Asn Asn Asn Thr  Leu
            1520                 1525                 1530

acc cta cgt cat  tct ccc ccc tta aac  cta act gac aat agc  tta     28394
```

-continued

```
Thr Leu Arg His  Ser Pro Pro Leu Asn  Leu Thr Asp Asn Ser  Leu
            1535                 1540                 1545

gtg cta ggc tac  tcg agt cct ctc cgc  gtc aca gac aac aaa  ctt      28439
Val Leu Gly Tyr  Ser Ser Pro Leu Arg  Val Thr Asp Asn Lys  Leu
            1550                 1555                 1560

aca ttt aac ttc  aca tca cca ctc cgt  tat gaa aat gaa aac  ctt      28484
Thr Phe Asn Phe  Thr Ser Pro Leu Arg  Tyr Glu Asn Glu Asn  Leu
            1565                 1570                 1575

act ttt aac tat  aca gag cct ctt aaa  ctt ata aat aac agc  ctt      28529
Thr Phe Asn Tyr  Thr Glu Pro Leu Lys  Leu Ile Asn Asn Ser  Leu
            1580                 1585                 1590

gcc att gac atc  aat tcc tca aaa ggc  ctt agt agc gtc gga  ggc      28574
Ala Ile Asp Ile  Asn Ser Ser Lys Gly  Leu Ser Ser Val Gly  Gly
            1595                 1600                 1605

tca cta gct gta  aac ctg agt tca gac  tta aag ttt gac agc  aac      28619
Ser Leu Ala Val  Asn Leu Ser Ser Asp  Leu Lys Phe Asp Ser  Asn
            1610                 1615                 1620

gga tcc ata gct  ttt ggc ata caa acc  ctg tgg acc gct ccg  acc      28664
Gly Ser Ile Ala  Phe Gly Ile Gln Thr  Leu Trp Thr Ala Pro  Thr
            1625                 1630                 1635

tcg act ggc aac  tgc acc gtc tac agc  gag ggc gat tcc cta  ctt      28709
Ser Thr Gly Asn  Cys Thr Val Tyr Ser  Glu Gly Asp Ser Leu  Leu
            1640                 1645                 1650

agt ctc tgt tta  acc aaa tgc gga gct  cac gtc tta gga agt  gta      28754
Ser Leu Cys Leu  Thr Lys Cys Gly Ala  His Val Leu Gly Ser  Val
            1655                 1660                 1665

agt tta acc ggt  tta aca gga acc ata  acc caa atg act gat  att      28799
Ser Leu Thr Gly  Leu Thr Gly Thr Ile  Thr Gln Met Thr Asp  Ile
            1670                 1675                 1680

tct gtc acc att  caa ttt aca ttt gac  aac aat ggt aag cta  cta      28844
Ser Val Thr Ile  Gln Phe Thr Phe Asp  Asn Asn Gly Lys Leu  Leu
            1685                 1690                 1695

agc tct cca ctt  ata aac aac gcc ttt  agt att cga cag aat  gac      28889
Ser Ser Pro Leu  Ile Asn Asn Ala Phe  Ser Ile Arg Gln Asn  Asp
            1700                 1705                 1710

agt acg gcc tca  aac cct acc tac aac  gcc ctg gcg ttt atg  cct      28934
Ser Thr Ala Ser  Asn Pro Thr Tyr Asn  Ala Leu Ala Phe Met  Pro
            1715                 1720                 1725

aac agt acc ata  tat gca aga ggg gga  ggt ggt gaa cca cga  aac      28979
Asn Ser Thr Ile  Tyr Ala Arg Gly Gly  Gly Gly Glu Pro Arg  Asn
            1730                 1735                 1740

aac tac tac gtc  caa acg tat ctt agg  gga aat gtt caa aaa  cca      29024
Asn Tyr Tyr Val  Gln Thr Tyr Leu Arg  Gly Asn Val Gln Lys  Pro
            1745                 1750                 1755

atc att ctt act  gta acc tac aac tca  gtc gcc aca gga tat  tcc      29069
Ile Ile Leu Thr  Val Thr Tyr Asn Ser  Val Ala Thr Gly Tyr  Ser
            1760                 1765                 1770

tta tct ttt aag  tgg act gct ctt gca  cgt gaa aag ttt gca  acc      29114
Leu Ser Phe Lys  Trp Thr Ala Leu Ala  Arg Glu Lys Phe Ala  Thr
            1775                 1780                 1785

cca aca acc tcg  ttt tgc tac att aca  gaa caa taa aaccgtgtac       29160
Pro Thr Thr Ser  Phe Cys Tyr Ile Thr  Glu Gln
            1790                 1795

cccaccgttt cgttttttc ag atg aaa cgg  gcg aga gtt gat gaa  gac      29209
                        Met Lys Arg  Ala Arg Val Asp Glu  Asp
                                1800                 1805

ttc aac cca gtg  tac cct tat gac ccc  cca cat gct cct gtt  atg      29254
Phe Asn Pro Val  Tyr Pro Tyr Asp Pro  Pro His Ala Pro Val  Met
            1810                 1815                 1820
```

-continued

```
ccc ttc att act  cca cct ttt acc tcc  tcg gat ggg ttg cag  gaa     29299
Pro Phe Ile Thr  Pro Pro Phe Thr Ser  Ser Asp Gly Leu Gln  Glu
            1825                 1830                 1835

aaa cca ctt gga  gtg tta agt tta aac  tac aga gat ccc att  act     29344
Lys Pro Leu Gly  Val Leu Ser Leu Asn  Tyr Arg Asp Pro Ile  Thr
            1840                 1845                 1850

acg caa aat gag  tct ctt aca att aaa  cta gga aac ggc ctc  act     29389
Thr Gln Asn Glu  Ser Leu Thr Ile Lys  Leu Gly Asn Gly Leu  Thr
            1855                 1860                 1865

cta gac aac cag  gga caa cta aca tca  acc gct ggc gaa gta  gaa     29434
Leu Asp Asn Gln  Gly Gln Leu Thr Ser  Thr Ala Gly Glu Val  Glu
            1870                 1875                 1880

cct cca ctc act  aac gct aac aac aaa  ctt gca ctg gtc tat  agc     29479
Pro Pro Leu Thr  Asn Ala Asn Asn Lys  Leu Ala Leu Val Tyr  Ser
            1885                 1890                 1895

gat cct tta gca  gta aag cgc aac agc  cta acc tta tcg cac  acc     29524
Asp Pro Leu Ala  Val Lys Arg Asn Ser  Leu Thr Leu Ser His  Thr
            1900                 1905                 1910

gct ccc ctt gtt  att gct gat aac tct  tta gca ttg caa gtt  tca     29569
Ala Pro Leu Val  Ile Ala Asp Asn Ser  Leu Ala Leu Gln Val  Ser
            1915                 1920                 1925

gag cct att ttt  ata aat gac aag gac  aaa cta gcc ctg caa  aca     29614
Glu Pro Ile Phe  Ile Asn Asp Lys Asp  Lys Leu Ala Leu Gln  Thr
            1930                 1935                 1940

gcc gcg ccc ctt  gta act aac gct ggc  acc ctt cgc tta caa  agc     29659
Ala Ala Pro Leu  Val Thr Asn Ala Gly  Thr Leu Arg Leu Gln  Ser
            1945                 1950                 1955

gcc gcc cct tta  ggc att gca gac caa  acc cta aaa ctc ctg  ttt     29704
Ala Ala Pro Leu  Gly Ile Ala Asp Gln  Thr Leu Lys Leu Leu  Phe
            1960                 1965                 1970

acc aac cct ttg  tac ttg cag aat aac  ttt ctc acg tta gcc  att     29749
Thr Asn Pro Leu  Tyr Leu Gln Asn Asn  Phe Leu Thr Leu Ala  Ile
            1975                 1980                 1985

gaa cga ccc ctt  gcc att acc aat act  gga aag ctg gct cta  cag     29794
Glu Arg Pro Leu  Ala Ile Thr Asn Thr  Gly Lys Leu Ala Leu  Gln
            1990                 1995                 2000

ctc tcc cca ccg  cta caa aca gca gac  aca ggc ttg act ttg  caa     29839
Leu Ser Pro Pro  Leu Gln Thr Ala Asp  Thr Gly Leu Thr Leu  Gln
            2005                 2010                 2015

acc aac gtg cca  tta act gta agc aac  ggg acc cta ggc tta  gcc     29884
Thr Asn Val Pro  Leu Thr Val Ser Asn  Gly Thr Leu Gly Leu  Ala
            2020                 2025                 2030

ata aag cgc cca  ctt att att cag gac  aac aac ttg ttt ttg  gac     29929
Ile Lys Arg Pro  Leu Ile Ile Gln Asp  Asn Asn Leu Phe Leu  Asp
            2035                 2040                 2045

ttc aga gct ccc  ctg cgt ctt ttc aac  agc gac cca gta cta  ggg     29974
Phe Arg Ala Pro  Leu Arg Leu Phe Asn  Ser Asp Pro Val Leu  Gly
            2050                 2055                 2060

ctt aac ttt tac  acc cct ctt gcg gta  cgc gat gag gcg ctc  act     30019
Leu Asn Phe Tyr  Thr Pro Leu Ala Val  Arg Asp Glu Ala Leu  Thr
            2065                 2070                 2075

gtt aac aca ggc  cgc ggc ctc aca gtg  agt tac gat ggt tta  att     30064
Val Asn Thr Gly  Arg Gly Leu Thr Val  Ser Tyr Asp Gly Leu  Ile
            2080                 2085                 2090

tta aat ctt ggt  aag gat ctt cgc ttt  gac aac aac acc gtt  tct     30109
Leu Asn Leu Gly  Lys Asp Leu Arg Phe  Asp Asn Asn Thr Val  Ser
            2095                 2100                 2105

gtc gct ctt agt  gct gct ttg cct tta  caa tac act gat cag  ctt     30154
Val Ala Leu Ser  Ala Ala Leu Pro Leu  Gln Tyr Thr Asp Gln  Leu
            2110                 2115                 2120
```

-continued

```
cgc ctt aac gtg  ggc gct ggg ctg cgt  tac aat cca gtg agt  aag     30199
Arg Leu Asn Val  Gly Ala Gly Leu Arg  Tyr Asn Pro Val Ser  Lys
            2125                 2130                 2135

aaa ttg gac gtg  aac ccc aat caa aac  aag ggt tta acc tgg  gaa     30244
Lys Leu Asp Val  Asn Pro Asn Gln Asn  Lys Gly Leu Thr Trp  Glu
            2140                 2145                 2150

aat gac tac ctc  att gta aag cta gga  aat gga tta ggt ttt  gat     30289
Asn Asp Tyr Leu  Ile Val Lys Leu Gly  Asn Gly Leu Gly Phe  Asp
            2155                 2160                 2165

ggc gat gga aac  ata gct gtt tct cct  caa gtt aca tcg cct  gac     30334
Gly Asp Gly Asn  Ile Ala Val Ser Pro  Gln Val Thr Ser Pro  Asp
            2170                 2175                 2180

acc tta tgg acc  act gcc gac cca tcc  ccc aat tgt tcc atc  tac     30379
Thr Leu Trp Thr  Thr Ala Asp Pro Ser  Pro Asn Cys Ser Ile  Tyr
            2185                 2190                 2195

act gat tta gat  gcc aaa atg tgg ctc  tcg ttg gta aaa caa  ggg     30424
Thr Asp Leu Asp  Ala Lys Met Trp Leu  Ser Leu Val Lys Gln  Gly
            2200                 2205                 2210

ggt gtg gtt cac  ggt tct gtt gct tta  aaa gca ttg aaa gga  acc     30469
Gly Val Val His  Gly Ser Val Ala Leu  Lys Ala Leu Lys Gly  Thr
            2215                 2220                 2225

cta ttg agt cct  acg gaa agc gcc att  gtt att ata cta cat  ttt     30514
Leu Leu Ser Pro  Thr Glu Ser Ala Ile  Val Ile Ile Leu His  Phe
            2230                 2235                 2240

gac aat tat gga  gtg cga att ctc aat  tat ccc act ttg ggc  act     30559
Asp Asn Tyr Gly  Val Arg Ile Leu Asn  Tyr Pro Thr Leu Gly  Thr
            2245                 2250                 2255

caa ggc acg ttg  gga aat aat gca act  tgg ggt tat agg cag  gga     30604
Gln Gly Thr Leu  Gly Asn Asn Ala Thr  Trp Gly Tyr Arg Gln  Gly
            2260                 2265                 2270

gaa tct gca gac  act aat gta ctc aat  gca cta gca ttt atg  ccc     30649
Glu Ser Ala Asp  Thr Asn Val Leu Asn  Ala Leu Ala Phe Met  Pro
            2275                 2280                 2285

agt tca aaa agg  tac cca aga ggg cgt  gga agc gaa gtt cag  aat     30694
Ser Ser Lys Arg  Tyr Pro Arg Gly Arg  Gly Ser Glu Val Gln  Asn
            2290                 2295                 2300

caa act gtg ggc  tac act tgt ata cag  ggt gac ttt tct atg  ccc     30739
Gln Thr Val Gly  Tyr Thr Cys Ile Gln  Gly Asp Phe Ser Met  Pro
            2305                 2310                 2315

gta ccg tac caa  ata cag tac aac tat  gga cca act ggc tac  tcc     30784
Val Pro Tyr Gln  Ile Gln Tyr Asn Tyr  Gly Pro Thr Gly Tyr  Ser
            2320                 2325                 2330

ttt aaa ttt att  tgg aga act gtt tca  aga caa cca ttt gac  atc     30829
Phe Lys Phe Ile  Trp Arg Thr Val Ser  Arg Gln Pro Phe Asp  Ile
            2335                 2340                 2345

cca tgc tgt ttt  ttc tct tac att acg  gaa gaa taa aacaactttt       30875
Pro Cys Cys Phe  Phe Ser Tyr Ile Thr  Glu Glu
            2350                 2355

tctttttatt ttctttttat tttacacgca cagtaaggct tcctccaccc ttccatctca  30935

cagcatacac cagcctctcc cccttcatgg cagtaaactg ttgtgagtca gtccggtatt  30995

tgggagttaa gatccaaaca gtctctttgg tgatgaaaca tggatccgtg atggacacaa  31055

atccctggga caggttctcc aacgtttcgg taaaaaactg catgccgccc tacaaaacaa  31115

acaggttcag gctctccacg ggttatctcc ccgatcaaac tcagacagag taaaggtgcg  31175

atgatgttcc actaaaccac gcaggtggcg ctgtctgaac ctctcggtgc gactcctgtg  31235

aggctggtaa gaagttagat tgtccagcag cctcacagca tggatcatca gtctacgagt  31295
```

-continued

```
gcgtctggcg cagcagcgca tctgaatctc actgagattc cggcaagaat cgcacaccat  31355
cacaatcagg ttgttcatga tcccatagct gaacacgctc cagccaaagc tcattcgctc  31415
caacagcgcc accgcgtgtc cgtccaacct tactttaaca taaatcaggt gtctgccgcg  31475
tacaaacatg ctacccgcat acagaacctc ccggggcaaa cccctgttca ccacctgcct  31535
gtaccaggga aacctcacat ttatcaggga gccatagata gccattttaa accaattagc  31595
taacaccgcc ccaccagctc tacactgaag agaaccggga gagttacaat gacagtgaat  31655
aatccatctc tcataacccc taatggtctg atggaaatcc agatctaacg tggcacagca  31715
gatacacact ttcatataca ttttcatcac atgtttttcc caggccgtta aaatacaatc  31775
ccaatacacg ggccactcct gcagtacaat aaagctaata caagatggta tactcctcac  31835
ctcactaaca ttgtgcatgt tcatattttc acattctaag taccgagagt tctcctctac  31895
aacagcactg ccgcggtcct cacaaggtgg tagctggtga cgattgtaag gagccagtct  31955
gcagcgatac cgtctgtcgc gttgcatcgt agaccaggga ccgacgcact tcctcgtact  32015
tgtagtagca gaaccacgtc cgctgccagc acgtctccaa gtaacgccgg tccctgcgtc  32075
gctcacgctc cctcctcaac gcaaagtgca accactcttg taatccacac agatccctct  32135
cggcctccgg ggcgatgcac acctcaaacc tacagatgtc tcggtacagt tccaaacacg  32195
tagtgagggc gagttccaac caagacagac agcctgatct atcccgacac actggaggtg  32255
gaggaagaca cggaagaggc atgttattcc aagcgattca ccaacgggtc gaaatgaaga  32315
tcccgaagat gacaacggtc gcctccggag ccctgatgga atttaacagc cagatcaaac  32375
attatgcgat tttccaggct atcaatcgcg gcctccaaaa gagcctggac ccgcacttcc  32435
acaaacacca gcaaagcaaa agcgttatta tcaaactctt cgatcatcaa gctgcaggac  32495
tgtacaatgc ccaagtaatt ttcatttctc cactcgcgaa tgatgtcgcg gcaaatagtc  32555
tgaaggttca tgccgtgcat attaaaaagc tccgaaaggg cgccctctat agccatgcgt  32615
agacacacca tcatgactgc aagatatcgg gctcctgaga cacctgcagc agatttaaca  32675
gacccaggtc aggttgctct ccgcgatcgc gaatctccat ccgcaaagtc atttgcaaat  32735
aattaaatag atctgcgccg actaaatctg ttaactccgc gctaggaact aaatcaggtg  32795
tggctacgca gcacaaaagt tccagggatg gcgccaaact cactagaacc gctcccgagt  32855
agcaaaactg atgaatggga gtaacacagt gtaaaatgtt cagccaaaaa tcactaagct  32915
gctcctttaa aaagtccagt acttctatat tcagttcgtg caagtactga agcaactgtg  32975
cgggaatatg cacagcaaaa aaaatagggc ggctcagata catgttgacc taaaataaaa  33035
agaatcatta aactaaagaa gcctggcgaa cggtgggata tatgacacgc tccagcagca  33095
ggcaagcaac cggctgtccc cgggaaccgc ggtaaaattc atccgaatga ttaaaaagaa  33155
caacagagac ttcccaccat gtactcggtt ggatctcctg agcacagagc aataccccc  33215
tcacattcat atccgctaca gaaaaaaaac gtcccagata cccagcggga atatccaacg  33275
acagctgcaa agacagcaaa acaatccctc tgggagcaat cacaaaatcc tccggtgaaa  33335
aaagcacata catattagaa taaccctgtt gctggggcaa aaaggcccgt cgtcccagca  33395
aatgcacata aatatgttca tcagccattg ccccgtctta ccgcgtaaac agccacgaaa  33455
aaatcgagct aaaatccacc caacagccta tagctatata tacactccac ccaatgacgc  33515
taataccgca ccacccacga ccaaagttca cccacaccca caaaacccgc gaaaatccag  33575
cgccgtcagc acttccgcaa tttcagtctc acaacgtcac ttccgcgcgc cttttcactt  33635
tcccacacac gcccttcgcc cgcccgccct cgcgccaccc cgcgtcaccc cacgtcaccg  33695
```

-continued

```
cacgtcaccc cggccccgcc tcgctcctcc ccgctcatta tcatattggc acgtttccag  33755

aataaggtat attattgatg cagcaaaaca atccctctgg gagcaatcac aaaatcctcc  33815

ggtgaaaaaa gcacatacat attagaataa ccctgttgct ggggcaaaaa ggcccgtcgt  33875

cccagcaaat gcacataaat atgttcatca gccattgccc cgtcttaccg cgtaaacagc  33935

cacgaaaaaa tcgagctaaa atccacccaa cagcctatag ctatatatac actccaccca  33995

atgacgctaa taccgcacca cccacgacca aagttcaccc acacccacaa aacccgcgaa  34055

aatccagcgc cgtcagcact tccgcaattt cagtctcaca acgtcacttc cgcgcgcctt  34115

ttcactttcc cacacacgcc cttcgcccgc ccgccctcgc gccaccccgc gtcaccccac  34175

gtcaccgcac gtcaccccgg ccccgcctcg ctcctccccg ctcattatca tattggcacg  34235

tttccagaat aaggtatatt attgatgca                                    34264
```

<210> SEQ ID NO 25
<211> LENGTH: 503
<212> TYPE: PRT
<213> ORGANISM: simian adenovirus SV-1

<400> SEQUENCE: 25

```
Met Arg Arg Ala Val Arg Val Thr Pro Ala Ala Tyr Glu Gly Pro Pro
1               5                   10                  15

Pro Ser Tyr Glu Ser Val Met Gly Ser Ala Asn Val Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Thr Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
        115                 120                 125

Asn Ile Asn Glu Phe Met Ser Thr Asn Lys Phe Arg Ala Arg Leu Met
    130                 135                 140

Val Lys Lys Ala Glu Asn Gln Pro Pro Glu Tyr Glu Trp Phe Glu Phe
145                 150                 155                 160

Thr Ile Pro Glu Gly Asn Tyr Ser Glu Thr Met Thr Ile Asp Leu Met
                165                 170                 175

Asn Asn Ala Ile Val Asp Asn Tyr Leu Gln Val Gly Arg Gln Asn Gly
            180                 185                 190

Val Leu Glu Ser Asp Ile Gly Val Lys Phe Asp Thr Arg Asn Phe Arg
        195                 200                 205

Leu Gly Trp Asp Pro Val Thr Lys Leu Val Met Pro Gly Val Tyr Thr
    210                 215                 220

Asn Glu Ala Phe His Pro Asp Ile Val Leu Leu Pro Gly Cys Gly Val
225                 230                 235                 240

Asp Phe Thr Gln Ser Arg Leu Ser Asn Leu Leu Gly Ile Arg Lys Arg
                245                 250                 255

Arg Pro Phe Gln Glu Gly Phe Gln Ile Met Tyr Glu Asp Leu Glu Gly
            260                 265                 270
```

-continued

Gly Asn Ile Pro Gly Leu Leu Asp Val Pro Ala Tyr Glu Glu Ser Val
        275                 280                 285

Lys Gln Ala Glu Ala Gln Gly Arg Glu Ile Arg Gly Asp Thr Phe Ala
    290                 295                 300

Thr Glu Pro His Glu Leu Val Ile Lys Pro Leu Glu Gln Asp Ser Lys
305                 310                 315                 320

Lys Arg Ser Tyr Asn Ile Ile Ser Gly Thr Met Asn Thr Leu Tyr Arg
                325                 330                 335

Ser Trp Phe Leu Ala Tyr Asn Tyr Gly Asp Pro Glu Lys Gly Val Arg
            340                 345                 350

Ser Trp Thr Ile Leu Thr Thr Thr Asp Val Thr Cys Gly Ser Gln Gln
        355                 360                 365

Val Tyr Trp Ser Leu Pro Asp Met Met Gln Asp Pro Val Thr Phe Arg
    370                 375                 380

Pro Ser Thr Gln Val Ser Asn Phe Pro Val Val Gly Thr Glu Leu Leu
385                 390                 395                 400

Pro Val His Ala Lys Ser Phe Tyr Asn Glu Gln Ala Val Tyr Ser Gln
                405                 410                 415

Leu Ile Arg Gln Ser Thr Ala Leu Thr His Val Phe Asn Arg Phe Pro
            420                 425                 430

Glu Asn Gln Ile Leu Val Arg Pro Pro Ala Pro Thr Ile Thr Thr Val
        435                 440                 445

Ser Glu Asn Val Pro Ala Leu Thr Asp His Gly Thr Leu Pro Leu Arg
    450                 455                 460

Ser Ser Ile Ser Gly Val Gln Arg Val Thr Ile Thr Asp Ala Arg Arg
465                 470                 475                 480

Arg Thr Cys Pro Tyr Val Tyr Lys Ala Leu Gly Val Val Ala Pro Lys
                485                 490                 495

Val Leu Ser Ser Arg Thr Phe
            500

<210> SEQ ID NO 26
<211> LENGTH: 931
<212> TYPE: PRT
<213> ORGANISM: simian adenovirus SV-1

<400> SEQUENCE: 26

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ala Glu Trp Thr Asn Ser Asp Ser Lys Val Lys Val

-continued

```
    130                 135                 140

Arg Ala Gln Ala Pro Phe Val Ser Ser Tyr Gly Ala Thr Ala Ile Thr
145                 150                 155                 160

Lys Glu Gly Ile Gln Val Gly Val Thr Leu Thr Asp Ser Gly Ser Thr
                165                 170                 175

Pro Gln Tyr Ala Asp Lys Thr Tyr Gln Pro Glu Pro Gln Ile Gly Glu
            180                 185                 190

Leu Gln Trp Asn Ser Asp Val Gly Thr Asp Asp Lys Ile Ala Gly Arg
        195                 200                 205

Val Leu Lys Lys Thr Thr Pro Met Phe Pro Cys Tyr Gly Ser Tyr Ala
    210                 215                 220

Arg Pro Thr Asn Glu Lys Gly Gly Gln Ala Thr Pro Ser Ala Ser Gln
225                 230                 235                 240

Asp Val Gln Asn Pro Glu Leu Gln Phe Phe Ala Ser Thr Asn Val Ala
                245                 250                 255

Asn Thr Pro Lys Ala Val Leu Tyr Ala Glu Asp Val Ser Ile Glu Ala
            260                 265                 270

Pro Asp Thr His Leu Val Phe Lys Pro Thr Val Thr Glu Gly Ile Thr
        275                 280                 285

Ser Ser Glu Ala Leu Leu Thr Gln Gln Ala Ala Pro Asn Arg Pro Asn
    290                 295                 300

Tyr Ile Ala Phe Arg Asp Asn Phe Ile Gly Leu Met Tyr Tyr Asn Ser
305                 310                 315                 320

Thr Gly Asn Met Gly Val Leu Ala Gly Gln Ala Ser Gln Leu Asn Ala
                325                 330                 335

Val Val Asp Leu Gln Asp Arg Asn Thr Glu Leu Ser Tyr Gln Leu Met
            340                 345                 350

Leu Asp Ala Leu Gly Asp Arg Ser Arg Tyr Phe Ser Met Trp Asn Gln
        355                 360                 365

Ala Val Asp Ser Tyr Asp Pro Asp Val Arg Ile Ile Glu Asn His Gly
    370                 375                 380

Val Glu Asp Glu Leu Pro Asn Tyr Cys Phe Pro Leu Gly Gly Met Ala
385                 390                 395                 400

Val Thr Asp Thr Tyr Ser Pro Ile Lys Val Asn Gly Gly Gly Asn Gly
                405                 410                 415

Trp Glu Ala Asn Asn Gly Val Phe Thr Glu Arg Gly Val Glu Ile Gly
            420                 425                 430

Ser Gly Asn Met Phe Ala Met Glu Ile Asn Leu Gln Ala Asn Leu Trp
        435                 440                 445

Arg Ser Phe Leu Tyr Ser Asn Ile Gly Leu Tyr Leu Pro Asp Ser Leu
    450                 455                 460

Lys Ile Thr Pro Asp Asn Ile Thr Leu Pro Glu Asn Lys Asn Thr Tyr
465                 470                 475                 480

Gln Tyr Met Asn Gly Arg Val Thr Pro Pro Gly Leu Val Asp Thr Tyr
                485                 490                 495

Val Asn Val Gly Ala Arg Trp Ser Pro Asp Val Met Asp Ser Ile Asn
            500                 505                 510

Pro Phe Asn His His Arg Asn Ala Gly Leu Arg Tyr Arg Ser Met Leu
        515                 520                 525

Leu Gly Asn Gly Arg Tyr Val Pro Phe His Ile Gln Val Pro Gln Lys
    530                 535                 540

Phe Phe Ala Ile Lys Asn Leu Leu Leu Leu Pro Gly Ser Tyr Thr Tyr
545                 550                 555                 560
```

-continued

```
Glu Trp Asn Phe Arg Lys Asp Val Asn Met Ile Leu Gln Ser Ser Leu
                565                 570                 575

Gly Asn Asp Leu Arg Val Asp Gly Ala Ser Ile Arg Phe Asp Ser Ile
            580                 585                 590

Asn Leu Tyr Ala Asn Phe Phe Pro Met Ala His Asn Thr Ala Ser Thr
        595                 600                 605

Leu Glu Ala Met Leu Arg Asn Asp Thr Asn Asp Gln Ser Phe Asn Asp
    610                 615                 620

Tyr Leu Cys Ala Ala Asn Met Leu Tyr Pro Ile Pro Ala Asn Ala Thr
625                 630                 635                 640

Ser Val Pro Ile Ser Ile Pro Ser Arg Asn Trp Ala Ala Phe Arg Gly
                645                 650                 655

Trp Ser Phe Thr Arg Leu Lys Thr Lys Glu Thr Pro Ser Leu Gly Ser
            660                 665                 670

Gly Phe Asp Pro Tyr Phe Val Tyr Ser Gly Ser Ile Pro Tyr Leu Asp
        675                 680                 685

Gly Thr Phe Tyr Leu Asn His Thr Phe Lys Lys Val Ser Ile Met Phe
    690                 695                 700

Asp Ser Ser Val Ser Trp Pro Gly Asn Asp Arg Leu Leu Thr Pro Asn
705                 710                 715                 720

Glu Phe Glu Ile Lys Arg Ser Val Asp Gly Glu Gly Tyr Asn Val Ala
                725                 730                 735

Gln Ser Asn Met Thr Lys Asp Trp Phe Leu Ile Gln Met Leu Ser His
            740                 745                 750

Tyr Asn Ile Gly Tyr Gln Gly Phe Tyr Val Pro Glu Asn Tyr Lys Asp
        755                 760                 765

Arg Met Tyr Ser Phe Phe Arg Asn Phe Gln Pro Met Ser Arg Gln Ile
    770                 775                 780

Val Asp Ser Thr Ala Tyr Thr Asn Tyr Gln Asp Val Lys Leu Pro Tyr
785                 790                 795                 800

Gln His Asn Asn Ser Gly Phe Val Gly Tyr Met Gly Pro Thr Met Arg
                805                 810                 815

Glu Gly Gln Ala Tyr Pro Ala Asn Tyr Pro Tyr Pro Leu Ile Gly Ala
            820                 825                 830

Thr Ala Val Pro Ser Leu Thr Gln Lys Lys Phe Leu Cys Asp Arg Val
        835                 840                 845

Met Trp Arg Ile Pro Phe Ser Ser Asn Phe Met Ser Met Gly Ser Leu
    850                 855                 860

Thr Asp Leu Gly Gln Asn Met Leu Tyr Ala Asn Ser Ala His Ala Leu
865                 870                 875                 880

Asp Met Thr Phe Glu Val Asp Pro Met Asp Glu Pro Thr Leu Leu Tyr
                885                 890                 895

Val Leu Phe Glu Val Phe Asp Val Val Arg Ile His Gln Pro His Arg
            900                 905                 910

Gly Val Ile Glu Ala Val Tyr Leu Arg Thr Pro Phe Ser Ala Gly Asn
        915                 920                 925

Ala Thr Thr
    930
```

<210> SEQ ID NO 27
<211> LENGTH: 363
<212> TYPE: PRT
<213> ORGANISM: simian adenovirus SV-1

-continued

<400> SEQUENCE: 27

```
Met Lys Arg Thr Arg Val Asp Glu Asp Phe Asn Pro Val Tyr Pro Tyr
1               5                   10                  15

Asp Thr Thr Thr Thr Pro Ala Val Pro Phe Ile Ser Pro Pro Phe Val
            20                  25                  30

Asn Ser Asp Gly Leu Gln Glu Asn Pro Pro Gly Val Leu Ser Leu Arg
        35                  40                  45

Ile Ala Lys Pro Leu Tyr Phe Asp Met Glu Arg Lys Leu Ala Leu Ser
    50                  55                  60

Leu Gly Arg Gly Leu Thr Ile Thr Ala Ala Gly Gln Leu Glu Ser Thr
65                  70                  75                  80

Gln Ser Val Gln Thr Asn Pro Pro Leu Ile Ile Thr Asn Asn Asn Thr
                85                  90                  95

Leu Thr Leu Arg His Ser Pro Pro Leu Asn Leu Thr Asp Asn Ser Leu
            100                 105                 110

Val Leu Gly Tyr Ser Ser Pro Leu Arg Val Thr Asp Asn Lys Leu Thr
        115                 120                 125

Phe Asn Phe Thr Ser Pro Leu Arg Tyr Glu Asn Glu Asn Leu Thr Phe
    130                 135                 140

Asn Tyr Thr Glu Pro Leu Lys Leu Ile Asn Asn Ser Leu Ala Ile Asp
145                 150                 155                 160

Ile Asn Ser Ser Lys Gly Leu Ser Ser Val Gly Gly Ser Leu Ala Val
                165                 170                 175

Asn Leu Ser Ser Asp Leu Lys Phe Asp Ser Asn Gly Ser Ile Ala Phe
            180                 185                 190

Gly Ile Gln Thr Leu Trp Thr Ala Pro Thr Ser Thr Gly Asn Cys Thr
        195                 200                 205

Val Tyr Ser Glu Gly Asp Ser Leu Leu Ser Leu Cys Leu Thr Lys Cys
    210                 215                 220

Gly Ala His Val Leu Gly Ser Val Ser Leu Thr Gly Leu Thr Gly Thr
225                 230                 235                 240

Ile Thr Gln Met Thr Asp Ile Ser Val Thr Ile Gln Phe Thr Phe Asp
                245                 250                 255

Asn Asn Gly Lys Leu Leu Ser Ser Pro Leu Ile Asn Asn Ala Phe Ser
            260                 265                 270

Ile Arg Gln Asn Asp Ser Thr Ala Ser Asn Pro Thr Tyr Asn Ala Leu
        275                 280                 285

Ala Phe Met Pro Asn Ser Thr Ile Tyr Ala Arg Gly Gly Gly Gly Glu
    290                 295                 300

Pro Arg Asn Asn Tyr Tyr Val Gln Thr Tyr Leu Arg Gly Asn Val Gln
305                 310                 315                 320

Lys Pro Ile Ile Leu Thr Val Thr Tyr Asn Ser Val Ala Thr Gly Tyr
                325                 330                 335

Ser Leu Ser Phe Lys Trp Thr Ala Leu Ala Arg Glu Lys Phe Ala Thr
            340                 345                 350

Pro Thr Thr Ser Phe Cys Tyr Ile Thr Glu Gln
        355                 360
```

<210> SEQ ID NO 28
<211> LENGTH: 560
<212> TYPE: PRT
<213> ORGANISM: simian adenovirus SV-1

<400> SEQUENCE: 28

-continued

```
Met Lys Arg Ala Arg Val Asp Glu Asp Phe Asn Pro Val Tyr Pro Tyr
1               5                   10                  15

Asp Pro Pro His Ala Pro Val Met Pro Phe Ile Thr Pro Pro Phe Thr
            20                  25                  30

Ser Ser Asp Gly Leu Gln Glu Lys Pro Leu Gly Val Leu Ser Leu Asn
        35                  40                  45

Tyr Arg Asp Pro Ile Thr Thr Gln Asn Glu Ser Leu Thr Ile Lys Leu
    50                  55                  60

Gly Asn Gly Leu Thr Leu Asp Asn Gln Gly Gln Leu Thr Ser Thr Ala
65                  70                  75                  80

Gly Glu Val Glu Pro Pro Leu Thr Asn Ala Asn Asn Lys Leu Ala Leu
                85                  90                  95

Val Tyr Ser Asp Pro Leu Ala Val Lys Arg Asn Ser Leu Thr Leu Ser
            100                 105                 110

His Thr Ala Pro Leu Val Ile Ala Asp Asn Ser Leu Ala Leu Gln Val
        115                 120                 125

Ser Glu Pro Ile Phe Ile Asn Asp Lys Asp Lys Leu Ala Leu Gln Thr
    130                 135                 140

Ala Ala Pro Leu Val Thr Asn Ala Gly Thr Leu Arg Leu Gln Ser Ala
145                 150                 155                 160

Ala Pro Leu Gly Ile Ala Asp Gln Thr Leu Lys Leu Leu Phe Thr Asn
                165                 170                 175

Pro Leu Tyr Leu Gln Asn Asn Phe Leu Thr Leu Ala Ile Glu Arg Pro
            180                 185                 190

Leu Ala Ile Thr Asn Thr Gly Lys Leu Ala Leu Gln Leu Ser Pro Pro
        195                 200                 205

Leu Gln Thr Ala Asp Thr Gly Leu Thr Leu Gln Thr Asn Val Pro Leu
    210                 215                 220

Thr Val Ser Asn Gly Thr Leu Gly Leu Ala Ile Lys Arg Pro Leu Ile
225                 230                 235                 240

Ile Gln Asp Asn Asn Leu Phe Leu Asp Phe Arg Ala Pro Leu Arg Leu
                245                 250                 255

Phe Asn Ser Asp Pro Val Leu Gly Leu Asn Phe Tyr Thr Pro Leu Ala
            260                 265                 270

Val Arg Asp Glu Ala Leu Thr Val Asn Thr Gly Arg Gly Leu Thr Val
        275                 280                 285

Ser Tyr Asp Gly Leu Ile Leu Asn Leu Gly Lys Asp Leu Arg Phe Asp
    290                 295                 300

Asn Asn Thr Val Ser Val Ala Leu Ser Ala Ala Leu Pro Leu Gln Tyr
305                 310                 315                 320

Thr Asp Gln Leu Arg Leu Asn Val Gly Ala Gly Leu Arg Tyr Asn Pro
                325                 330                 335

Val Ser Lys Lys Leu Asp Val Asn Pro Asn Gln Asn Lys Gly Leu Thr
            340                 345                 350

Trp Glu Asn Asp Tyr Leu Ile Val Lys Leu Gly Asn Gly Leu Gly Phe
        355                 360                 365

Asp Gly Asp Gly Asn Ile Ala Val Ser Pro Gln Val Thr Ser Pro Asp
    370                 375                 380

Thr Leu Trp Thr Thr Ala Asp Pro Ser Pro Asn Cys Ser Ile Tyr Thr
385                 390                 395                 400

Asp Leu Asp Ala Lys Met Trp Leu Ser Leu Val Lys Gln Gly Gly Val
                405                 410                 415

Val His Gly Ser Val Ala Leu Lys Ala Leu Lys Gly Thr Leu Leu Ser
```

-continued

```
            420                 425                 430

Pro Thr Glu Ser Ala Ile Val Ile Ile Leu His Phe Asp Asn Tyr Gly
        435                 440                 445

Val Arg Ile Leu Asn Tyr Pro Thr Leu Gly Thr Gln Gly Thr Leu Gly
    450                 455                 460

Asn Asn Ala Thr Trp Gly Tyr Arg Gln Gly Glu Ser Ala Asp Thr Asn
465                 470                 475                 480

Val Leu Asn Ala Leu Ala Phe Met Pro Ser Ser Lys Arg Tyr Pro Arg
                485                 490                 495

Gly Arg Gly Ser Glu Val Gln Asn Gln Thr Val Gly Tyr Thr Cys Ile
            500                 505                 510

Gln Gly Asp Phe Ser Met Pro Val Pro Tyr Gln Ile Gln Tyr Asn Tyr
        515                 520                 525

Gly Pro Thr Gly Tyr Ser Phe Lys Phe Ile Trp Arg Thr Val Ser Arg
    530                 535                 540

Gln Pro Phe Asp Ile Pro Cys Cys Phe Phe Ser Tyr Ile Thr Glu Glu
545                 550                 555                 560
```

<210> SEQ ID NO 29
<211> LENGTH: 31044
<212> TYPE: DNA
<213> ORGANISM: simian adenovirus SV-25
<220> FEATURE:
<221> NAME/KEY: CDS
<222> LOCATION: (12284)..(13801)
<223> OTHER INFORMATION: Penton
<220> FEATURE:
<221> NAME/KEY: CDS
<222> LOCATION: (16681)..(19446)
<223> OTHER INFORMATION: Hexon
<220> FEATURE:
<221> NAME/KEY: CDS
<222> LOCATION: (25380)..(26423)
<223> OTHER INFORMATION: Fiber #2
<220> FEATURE:
<221> NAME/KEY: CDS
<222> LOCATION: (26457)..(28136)
<223> OTHER INFORMATION: Fiber #1

<400> SEQUENCE: 29

```
catcatcaat aatatacctt attctggaaa cgtgccaata tgataatgag cggggaggag     60

cgaggcgggg ccggggtgac gtgcggtgac gcggggtggc gcgagggcgg ggcgaagggc    120

gcgggtgtgt gtgtgggagg cgcttagttt ttacgtatgc ggaaggaggt tttataccgg    180

aagatgggta atttgggcgt atacttgtaa gttttgtgta atttggcgcg aaaactgggt    240

aatgaggaag ttgaggttaa tatgtacttt ttatgactgg gcggaatttc tgctgatcag    300

cagtgaactt tgggcgctga cggggaggtt tcgctacgtg acagtaccac gagaaggctc    360

aaaggtccca tttattgtac tcttcagcgt tttcgctggg tatttaaacg ctgtcagatc    420

atcaagaggc cactcttgag tgctggcgag aagagttttc tcctccgtgc tgccacgatg    480

aggctggtcc ccgagatgta cggtgttttt agcgacgaga cggtgcgtaa ctcagatgac    540

ctgctgaatt cagacgcgct ggaaatttcc aattcgcctg tgctttcgcc gccgtcactt    600

cacgacctgt ttgtgttttg gctcaacgct tagcaacgtg ttatataggg tcaagaagga    660

gcaggagacg cagtttgcta ggctgttggc cgatactcct ggagtttttg tggctctgga    720

tctaggccat cactctcttt tccaagagaa aattatcaaa aacttaactt ttacgtctcc    780

tggtcgcacg gttgcttccg ctgcctttat tacctatatt ttggatcaat ggagcaacag    840

cgacagccac ctgtcgtggg agtacatgct ggattacatg tcgatggcgc tgtggagggc    900
```

-continued

```
catgctgcgg aggagggttt gcatttactt gcgggcgcag cctccgcggc tggaccgagt    960
ggaggaggag gacgagccgg gggagaccga gaacctgagg gccgggctgg accctccaac   1020
ggaggactag gtgctgagga tgatcccgaa gaggggacta gtggggctag gaagaagcaa   1080
aagactgagt ctgaacctcg aaactttttg aatgagttga ctgtgagttt gatgaatcgt   1140
cagcgtccgg agacaatttt ctggtctgaa ttggaggagg aattcaggag gggggaactg   1200
aacctgctat acaagtatgg gtttgaacag ttaaaaactc actggttgga gccgtgggag   1260
gattttgaaa ccgccttgga cacttttgct aaagtggctc tgcggccgga taaggtttac   1320
actatccgcc gcactgttaa cataaagaag agtgtttatg ttataggcca tggagctctg   1380
gtgcaggtgc aaaccgtcga ccgggtggcc tttagttgcg gtatgcaaaa tctgggcccc   1440
ggggtgatag gcttaaatgg tgtaacattt cacaatgtaa ggtttactgg tgaaagtttt   1500
aacggctctg tgtttgcaaa taacacacag ctgacgctcc acggcgttta ctttttttaac  1560
tttaataaca catgtgtgga gtcgtggggc agggtgtctt tgaggggctg ctgttttcac   1620
ggctgctgga aggcggtggt gggaagactt aaaagtgtaa catctgtaaa aaaatgcgtg   1680
tttgagcggt gtgtgttggc tttaactgtg gagggctgtg gacgcattag gaataatgcg   1740
gcgtctgaga atggatgttt tcttttgcta aaaggcacgg ctagtattaa gcataacatg   1800
atatgcggca gcggtctgta cccttcacag ctgttaactt gcgcggatgg aaactgtcag   1860
accttgcgca ccgtgcacat agcgtcccac cagcgccgcg cctggccaac attcgagcac   1920
aatatgctta tgcgttgtgc cgtccacttg ggccctaggc gaggcgtgtt tgtgccttac   1980
cagtgtaact ttagccatac caagatttta ctagaacctg ataccttctc tcgagtgtgt   2040
ttcaatgggg tgtttgacat gtcaatggaa ctgtttaaag tgataagata tgatgaatcc   2100
aagtctcgtt gtcgcccatg tgaatgcgga gctaatcatc tgaggttgta tcctgtaacc   2160
ctaaacgtta ccgaggagct gaggacggat caccacatgt tgtcctgcct gcgcaccgac   2220
tatgaatcca gcgacgagga gtgaggtgag ggcggagcc acaaagggta taaaggggcg    2280
tgaggggtgg gtgtgatgat tcaaaatgag cgggacgacg gacggcaacg cgtttgaggg   2340
tggagtgttc agcccttatc tgacatctcg tcttccttcc tgggcaggag tgcgtcagaa   2400
tgtagtgggc tccaccgtgg acggacgacc ggtcgcccct gcaaattccg ccaccctcac   2460
ctatgccacc gtgggatcat cgttggacac tgccgcggca gctgccgctt ctgctgccgc   2520
ttctactgct cgcggcatgg cggctgattt tggactgtat aaccaactgg ccactgcagc   2580
tgtggcgtct cggtctctgg ttcaagaaga tgccctgaat gtgatcctga ctcgcctgga   2640
gatcatgtca cgtcgcttgg acgaactggc tgcgcagata tcccaagcta accccgatac   2700
cacttcagaa tcctaaaata aagacaaaca aatatgttga aaagtaaaat ggctttattt   2760
gtttttttttg gctcggtagg ctcgggtcca cctgtctcgg tcgttaagaa ctttgtgtat  2820
gttttccaaa acacggtaca gatgggcttg gatgttcaag tacatgggca tgaggccatc   2880
tttggggtga agataggacc attgaagagc gtcatgctcc ggggtggtgt tgtaaattac   2940
ccagtcgtag cagggtttct gggcgtggaa ctggaagatg tcctttagga gtaggctgat   3000
ggccaagggc aggcccttag tgtaggtgtt tacaaagcgg ttaagctggg agggatgcat   3060
gcgggggag atgatatgca tcttggcttg gatcttgagg ttagctatgt taccacccag    3120
gtctctgcgg gggttcatgt tatgaaggac caccagcacg gtgtagccgg tgcatttggg   3180
gaacttgtca tgcagtttgg aggggaaggc gtggaagaat ttagagaccc ccttgtggcc   3240
```

-continued

```
ccctaggttt tccatgcact catccataat gatggcaatg ggacccctgg cggccgcttt   3300
ggcaaacacg ttttgggggt tggaaacatc atagttttgc tctagagtga gctcatcata   3360
ggccatctta acaaagcggg gtaggagggt gcccgactgg gggatgatag ttccatctgg   3420
gcctggggcg tagttaccct cacagatctg catctcccag gccttaattt ccgagggggg   3480
tatcatgtcc acctgggggg caataaagaa cacggtttct ggcgggggat tgatgagctg   3540
ggtggaaagc aagttacgca gcagttgaga tttgccacag ccggtggggc cgtagatgac   3600
cccgatgacg ggttgcagct ggtagttgag agaggaacag ctgccgtcgg ggcgcaggag   3660
gggggctacc tcattcatca tgcttctaac atgtttattt tcactcacta agttttgcaa   3720
gagcctctcc ccacccaggg ataagagttc ttccaggctg ttgaagtgtt tcagcggttt   3780
taggccgtcg gccatgggca tcttttcgag cgactgacga agcaagtaca gtcggtccca   3840
gagctcggtg acgtgctcta tggaatctcg atccagcaga cttcttggtt gcggggggttg   3900
ggtcgacttt cgctgtaggg caccagccgg tgggcgtcca gggccgcgag ggttctgtcc   3960
ttccagggtc tcagcgtccg ggtgagggtg gtctcggtga cggtgaaggg atgagccccg   4020
ggctgggcgc ttgcgagggt gcgcttcagg ctcatcctgc tggtgctgaa gcggacgtcg   4080
tctccctgtg agtcggccag atagcaacga agcatgaggt cgtagctgag ggactcggcc   4140
gcgtgtccct tggcgcgcag ctttcccttg gaaacgtgct gacatttggt gcagtgcaga   4200
cattggaggg cgtagagttt gggggccagg aagaccgact cgggcgagta ggcgtcggct   4260
ccgcactgag cgcagacggt ctcgcactcc actagccacg tgagctcggg tttagcggga   4320
tcaaaaacca agttgcctcc atttttttg atgcgtttct taccttgcgt ttccatgagt   4380
ttgtggcccg cttccgtgac aaaaaggctg tcggtgtctc cgtagacaga cttgaggggg   4440
cgatcttcca aaggtgttcc gaggtcttcc gcgtacagga actgggacca ctccgagacg   4500
aaggctctgg tccaggctaa cacgaaggag gcaatctgcg aggggtatct gtcgttttca   4560
atgagggggt ccaccttttc cagggtgtgc agacacaggt cgtcctcctc cgcgtccacg   4620
aaggtgattg gcttgtaagt gtaggtcacg tgatctgcac cccccaaagg ggtataaaag   4680
ggggcgtgcc caccctctcc gtcactttct tccgcatcgc tgtggaccag agccagctgt   4740
tcgggtgagt aggccctctc aaaagccggc atgatctcgg cgctcaagtt gtcagtttct   4800
acaaacgagg tggatttgat attcacgtgc cccgcggcga tgcttttgat ggtggagggg   4860
tccatctgat cagaaaacac gatctttttg ttgtcaagtt tggtggcgaa agacccgtag   4920
agggcgttgg aaagcaactt ggcgatggag cgcagggtct gatttttctc ccgatcggcc   4980
ctctccttgg cggcgatgtt gagttgcacg tactcccggg ccgcgcaccg ccactcgggg   5040
aacacggcgg tgcgctcgtc gggcaggatg cgcacgcgcc agccgcgatt gtgcagggtg   5100
atgaggtcca cgctggtagc cacctccccg cggagggggct cgttggtcca acacaatcgc   5160
ccccctttc tggagcagaa cggaggcagg ggatctagca agttggcggg cggggggtcg   5220
gcgtcgatgg tgaagatacc gggtagcagg atcttattaa aataatcgat ttcggtgtcc   5280
gtgtcttgca acgcgtcttc ccacttcttc accgccaggg ccctttcgta gggattcagg   5340
ggcggtcccc agggcatggg gtgggtcagg gccgaggcgt acatgccgca gatgtcatac   5400
acgtacaggg gttccctcaa caccccgatg taagtggggt aacagcgccc cccgcggatg   5460
ctggctcgca cgtagtcgta catctcgcgc gagggagcca tgaggccgtc tcccaagtgg   5520
gtcttgtggg gtttttcggc ccggtagagg atctgtctga agatggcgtg ggagttggaa   5580
gagatggtgg ggcgttggaa gacgttaaag ttggccccgg gtagtcccac ggagtcttgg   5640
```

-continued

```
atgaactggg cgtaggattc ccggagtttg tccaccaggg cggcggtcac cagcacgtcg   5700
agagcgcagt agtccaacgt ctcgcggacc aggttgtagg ccgtctcttg ttttttctcc   5760
cacagttcgc ggttgaggag gtattcctcg cggtctttcc agtactcttc ggcgggaaat   5820
ccttttttcgt ccgctcggta agaacctaac atgtaaaatt cgttcaccgc tttgtatgga   5880
caacagcctt tttctaccgg cagggcgtac gcttgagcgg cctttctgag agaggtgtgg   5940
gtgagggcga aggtgtcccg caccatcact ttcaggtact gatgtttgaa gtccgtgtcg   6000
tcgcaggcgc cctgttccca cagcgtgaag tcggtgcgct tttctgcct gggattgggg   6060
agggcgaagg tgacatcgtt aaagagtatt ttcccggcgc ggggcatgaa gttgcgagag   6120
atcctgaagg gcccgggcac gtccgagcgg ttgttgatga cctgcgccgc caggacgatc   6180
tcgtcgaagc cgttgatgtt gtgacccacg atgtaaagtt cgatgaagcg cggctgtccc   6240
ttgagggccg gcgctttttt caactcctcg taggtgagac agtccggcga ggagagaccc   6300
agctcagccc gggcccagtc ggagagttga ggattagccg caaggaagga gctccataga   6360
tccaaggcca ggagagtttg caagcggtcg cggaactcgc ggaacttttt ccccacggcc   6420
attttctccg gtgtcactac gtaaaaggtg ttggggcggt tgttccacac gtcccatcgg   6480
agctctaggg ccagctcgca ggcttggcga acgagggtct cctcgccaga gacgtgcatg   6540
accagcataa agggtaccaa ctgtttcccg aacgagccca tccatgtgta ggtttctacg   6600
tcgtaggtga caaagagccg ctgggtgcgc gcgtgggagc cgatcggaaa gaagctgatc   6660
tcctgccacc agctggagga atgggtgtta atgtggtgga agtagaagtc ccgccggcgc   6720
acagagcatt cgtgctgatg tttgtaaaag cgaccgcagt agtcgcagcg ctgcacgctc   6780
tgtatctcct gaacgagatg cgcttttcgc ccgcgcacca gaaaccggag ggggaagttg   6840
agacgggggg ctggtggggc gacatcccct tcgccttggc ggtgggagtc tgcgtctgcg   6900
tcctccttct ctgggtggac gacggtgggg acgacgacgc cccgggtgcc gcaagtccag   6960
atctccgcca cggaggggtg caggcgctgc aggaggggac gcagctgccc gctgtccagg   7020
gagtcgaggg aagtcgcgct gaggtcggcg ggaagcgttt gcaagttcac tttcagaaga   7080
ccggtaagag cgtgagccag gtgcagatgg tacttgattt ccaggggggt gttggatgaa   7140
gcgtccacgg cgtagaggag tccgtgtccg cgcggggcca ccaccgtgcc ccgaggaggt   7200
tttatctcac tcgtcgaggg cgagcgccgg ggggtagagg cggctctgcg ccgggggggca   7260
gcggaggcag aggcacgttt tcgtgaggat tcggcagcgg ttgatgacga gcccggagac   7320
tgctggcgtg ggcgacgacg cggcggttga ggtcctggat gtgccgtctc tgcgtgaaga   7380
ccaccggccc ccgggtcctg aacctaaaga gagttccaca gaatcaatgt ctgcatcgtt   7440
aacggcggcc tgcctgagga tctcctgcac gtcgcccgag ttgtcctgat aggcgatctc   7500
ggccatgaac tgttccactt cttcctcgcg gaggtcaccg tggcccgctc gctccacggt   7560
ggcggccagg tcgttggaga tgcggcgcat gagttgagag aaggcgttga ggccgttctc   7620
gttccacacg cggctgtaca ccacgtttcc gaaggagtcg cgcgctcgca tgaccacctg   7680
ggccacgttg agttccacgt ggcgggcgaa gacggcgtag tttctgaggc gctggaagag   7740
gtagttgagc gtggtggcga tgtgctcgca gacgaagaag tacataatcc agcgccgcag   7800
ggtcatctcg ttgatgtctc cgatggcttc gagacgctcc atggcctcgt agaagtcgac   7860
ggcgaagttg aaaaattggg agttgcgggc ggccaccgtg agttcttctt gcaggaggcg   7920
gatgagatcg gcgaccgtgt cgcgcacctc ctgttcgaaa gcgccccgag gcgcctctgc   7980
```

-continued

```
ttcttcctcc ggctcctcct cttccagggg ctcgggttcc tccggcagct ctgcgacggg   8040
gacggggcgg cgacgtcgtc gtctgaccgg caggcggtcc acgaagcgct cgatcatttc   8100
gccgcgccgg cgacgcatgg tctcggtgac ggcgcgtccg ttttcgcgag gtcgcagttc   8160
gaagacgccg ccgcgcagag cgccccccgtg cagggagggt aagtggttag ggccgtcggg   8220
cagggacacg gcgctgacga tgcattttat caattgctgc gtaggcactc cgtgcaggga   8280
tctgagaacg tcgaggtcga cgggatccga gaacttctct aggaaagcgt ctatccaatc   8340
gcaatcgcaa ggtaagctga gaacggtggg tcgctggggg gcgttcgcgg gcagttggga   8400
ggtgatgctg ctgatgatgt aattaaagta ggcggtcttc aggcggcgga tggtggcgag   8460
gaggaccacg tctttgggcc cggcctgttg aatgcgcagg cgctcggcca tgccccaggc   8520
ctcgctctga cagcgacgca ggtctttgta gaagtcttgc atcagtctct ccaccggaac   8580
ctctgcttct cccctgtctg ccatgcgagt cgagccgaac cccgcagggg gctgcagcaa   8640
cgctaggtcg gccacgaccc tttcggccag cacggcctgt tgaatctgcg tgagggtggc   8700
ctggaagtcg tccaggtcca cgaagcggtg ataggccccc gtgttgatgg tgtaggtgca   8760
gttggccatg acggaccagt tgacgacttg catgccgggt tgggtgatct ccgtgtactt   8820
gaggcgcgag taggccctgg actcgaacac gtagtcgttg catgtgcgca ccagatactg   8880
gtagccgacc aggaagtgag gaggcggctc tcggtacagg ggccagccaa cggtggcggg   8940
ggcgccgggg gacaggtcgt ccagcatgag gcggtggtag tggtagatgt agcgggagag   9000
ccaggtgatg ccggccgagg tggttgcggc cctggtgaat tcgcggacgc ggttccagat   9060
gttgcgcagg ggaccaaagc gctccatggt gggcacgctc tgccccgtga ggcgggcgca   9120
atcttgtacg ctctagatgg aaaaaagaca gggcggtcat cgactccttt ccgtagcttg   9180
gggggtaaag tcgcaagggt gcggcggcgg ggaaccccgg ttcgagaccg gccggatccg   9240
ccgctcccga tgcgcctggc cccgcatcca cgacgtccgc gccgagaccc agccgcgacg   9300
ctccgcccca atacggaggg gagtcttttg gtgtttttttc gtagatgcat ccggtgctgc   9360
ggcagatgcg accccagacg cccactacca ccgccgtggc ggcagtaaac ctgagcggag   9420
gcggtgacag ggaggaggaa gagctggctt tagacctgga agagggagag gggctggccc   9480
ggctgggagc gccatcccca gagagacacc ctagggttca gctcgtgagg gacgccaggc   9540
aggcttttgt gccgaagcag aacctgttta gggaccgcag cggtcaggag gcggaggaga   9600
tgcgcgattg caggtttcgg gcgggcagag agctcagggc gggcttcgat cgggagcggc   9660
tcctgagggc ggaggatttc gagcccgacg agcgttctgg ggtgagcccg gcccgcgctc   9720
acgtatcggc ggccaacctg gtgagcgcgt acgagcagac ggtgaacgag gagcgcaact   9780
tccaaaagag ctttaacaat cacgtgagga ccctgatcgc gagggaggag gtgaccatcg   9840
ggctgatgca tctgtgggac ttcgtggagg cctacgtgca gaacccggct agcaaacccc   9900
tgacggccca gctgttcctg atcgtgcagc acagccgcga caacgagacg ttccgcgacg   9960
ccatgttgaa catcgcggag cccgagggtc gctggctctt ggatctgatt aacatcctgc  10020
agagcatcgt ggtgcaggag aggggcctga gtttagcgga caaggtggcg gccattaact  10080
attcgatgca gagcctgggg aagttctacg ctcgcaagat ctacaagagc ccttacgtgc  10140
ccatagacaa ggaggtgaag atagacagct tttacatgcg catggcgctg aaggtgctga  10200
cgctgagcga cgacctcggc gtgtaccgta acgacaagat ccacaaggcg gtgagcgcca  10260
gccgccggcg ggagctgagc gacagggagc tgatgcacag cctgcagagg gcgctggcgg  10320
gcgccgggga cgaggagcgc gaggcttact tcgacatggg agccgatctg cagtggcgtc  10380
```

-continued

```
ccagcgcgcg cgccttggag gcggcgggtt atcccgacga ggaggatcgg gacgatttgg  10440

aggaggcagg cgagtacgag gacgaagcct gaccgggcag gtgttgtttt agatgcagcg  10500

gccggcggac gggaccaccg cggatcccgc acttttggca tccatgcaga gtcaaccttc  10560

gggcgtgacc gcctccgatg actgggcggc ggccatggac cgcatcatgg cgctgaccac  10620

ccgcaacccc gaggctttta ggcagcaacc ccaggccaac cgtttttcgg ccatcttgga  10680

agcggtggtg ccgtcgcgca ccaacccgac gcacgagaaa gtcctgacta tcgtgaacgc  10740

cctggtagac agcaaggcca tccgccgtga cgaggcgggc ttgatttaca acgctctttt  10800

ggaacgcgtg gcgcgctaca acagcactaa cgtgcagacc aatctggacc gcctcaccac  10860

cgacgtgaag gaggcgctgg cgcagaagga gcggtttctg agggacagta atctgggctc  10920

tctggtggca ctgaacgcct tcctgagctc acagccggcc aacgtgcccc gcgggcagga  10980

ggattacgtg agcttcatca gcgctctgag actgctggtg tccgaggtgc cccagagcga  11040

ggtgtaccag tctgggccgg attacttttt ccagacgtcc cgacagggct tgcaaacggt  11100

gaacctgact caggccttta aaaacttgca aggcatgtgg ggggtcaagg ccccggtggg  11160

cgatcgcgcc actatctcca gtctgctgac ccccaacact cgcctgctgc tgctcttgat  11220

cgcaccgttt accaacagta gcactatcag ccgtgactcg tacctgggtc atctcatcac  11280

tctgtaccgc gaggccatcg gccaggctca gatcgacgag catacgtatc aggagattac  11340

taacgtgagc cgtgccctgg gtcaggaaga taccggcagc ctggaagcca cgttgaactt  11400

tttgctaacc aaccggaggc aaaaaatacc ctcccagttc acgttaagcg ccgaggagga  11460

gaggattctg cgatacgtgc agcagtccgt gagcctgtac ttgatgcgcg agggcgccac  11520

cgcttccacg gctttagaca tgacggctcg gaacatggaa ccgtcctttt actccgccca  11580

ccggccgttc attaaccgtc tgatggacta cttccatcgc gcggccgcca tgaacgggga  11640

gtacttcacc aatgccatcc tgaatccgca ttggatgccc ccgtccggct tctacaccgg  11700

ggagtttgac ctgcccgaag ccgacgacgg ctttctgtgg gacgacgtgt ccgatagcat  11760

tttcacgccg gctaatcgcc gattccagaa gaaggagggc ggagacgagc tcccccctctc  11820

cagcgtggaa gcggcctcaa ggggagagag tccctttcca agtctgtctt ccgccagtag  11880

cggtcgggta acgcgtccac ggttgccggg ggagagcgac tacctgaacg accccttgct  11940

gcgaccggct agaaagaaaa attttcccaa taacggggtg gaaagcttgg tggataaaat  12000

gaatcgttgg aagacgtacg cccaggagca gcgggagtgg gaggacagtc agccgcggcc  12060

gctggtaccg ccgcattggc gtcgccagag agaagacccg gacgactccg cagacgatag  12120

tagcgtgttg gacctgggag ggagcggagc caacccccttt gctcacttgc aacccaaggg  12180

gcgctcgagt cgcctgtatt aataaaaaag acgcggaaac ttaccagagc catggccaca  12240

gcgtgtgtgc tttcttcctc tctttcttcc tcggcgcggc aga atg aga aga gcg    12295
                                             Met Arg Arg Ala
                                             1

gtg aga gtc acg ccg gcg gcg tat gag ggc ccg ccc cct tct tac gaa    12343
Val Arg Val Thr Pro Ala Ala Tyr Glu Gly Pro Pro Pro Ser Tyr Glu
5                   10                  15                  20

agc gtg atg gga tca gcg aac gtg ccg gcc acg ctg gag gcg cct tac    12391
Ser Val Met Gly Ser Ala Asn Val Pro Ala Thr Leu Glu Ala Pro Tyr
                25                  30                  35

gtt cct ccc aga tac ctg gga cct acg gag ggc aga aac agc atc cgt    12439
Val Pro Pro Arg Tyr Leu Gly Pro Thr Glu Gly Arg Asn Ser Ile Arg
            40                  45                  50
```

-continued

```
tac tcc gag ctg gcg ccc ctg tac gat acc acc aag gtg tac ctg gtg     12487
Tyr Ser Glu Leu Ala Pro Leu Tyr Asp Thr Thr Lys Val Tyr Leu Val
        55                  60                  65

gac aac aag tcg gcg gac atc gcc tcc ctg aat tac caa aac gat cac     12535
Asp Asn Lys Ser Ala Asp Ile Ala Ser Leu Asn Tyr Gln Asn Asp His
    70                  75                  80

agt aac ttt ctg act acc gtg gtg cag aac aat gac ttc acc ccg acg     12583
Ser Asn Phe Leu Thr Thr Val Val Gln Asn Asn Asp Phe Thr Pro Thr
85                  90                  95                  100

gag gcg ggc acg cag acc att aac ttt gac gag cgt tcc cgc tgg ggc     12631
Glu Ala Gly Thr Gln Thr Ile Asn Phe Asp Glu Arg Ser Arg Trp Gly
                105                 110                 115

ggt cag ctg aaa acc atc ctg cac acc aac atg ccc aac atc aac gag     12679
Gly Gln Leu Lys Thr Ile Leu His Thr Asn Met Pro Asn Ile Asn Glu
            120                 125                 130

ttc atg tcc acc aac aag ttc agg gct aag ctg atg gta gaa aaa agt     12727
Phe Met Ser Thr Asn Lys Phe Arg Ala Lys Leu Met Val Glu Lys Ser
        135                 140                 145

aat gcg gaa act cgg cag ccc cga tac gag tgg ttc gag ttt acc att     12775
Asn Ala Glu Thr Arg Gln Pro Arg Tyr Glu Trp Phe Glu Phe Thr Ile
    150                 155                 160

cca gag ggc aac tat tcc gaa act atg act atc gat ctc atg aat aac     12823
Pro Glu Gly Asn Tyr Ser Glu Thr Met Thr Ile Asp Leu Met Asn Asn
165                 170                 175                 180

gcg atc gtg gac aat tac ctg caa gtg ggg aga cag aac ggg gtg ctg     12871
Ala Ile Val Asp Asn Tyr Leu Gln Val Gly Arg Gln Asn Gly Val Leu
                185                 190                 195

gaa agc gat atc ggc gtg aaa ttc gat acc aga aac ttc cga ctg ggg     12919
Glu Ser Asp Ile Gly Val Lys Phe Asp Thr Arg Asn Phe Arg Leu Gly
            200                 205                 210

tgg gat ccc gtg acc aag ctg gtg atg cca ggc gtg tac acc aac gag     12967
Trp Asp Pro Val Thr Lys Leu Val Met Pro Gly Val Tyr Thr Asn Glu
        215                 220                 225

gct ttt cac ccg gac atc gtg ctg ctg ccg ggg tgc ggt gtg gac ttc     13015
Ala Phe His Pro Asp Ile Val Leu Leu Pro Gly Cys Gly Val Asp Phe
    230                 235                 240

act cag agc cgt ttg agt aac ctg tta gga att aga aag cgc cgc ccc     13063
Thr Gln Ser Arg Leu Ser Asn Leu Leu Gly Ile Arg Lys Arg Arg Pro
245                 250                 255                 260

ttc caa gag ggc ttt caa atc atg tat gag gac ctg gag gga ggt aat     13111
Phe Gln Glu Gly Phe Gln Ile Met Tyr Glu Asp Leu Glu Gly Gly Asn
                265                 270                 275

ata ccc gcc tta ctg gac gtg tcg aag tac gaa gct agc ata caa cgc     13159
Ile Pro Ala Leu Leu Asp Val Ser Lys Tyr Glu Ala Ser Ile Gln Arg
            280                 285                 290

gcc aaa gcg gag ggt aga gag att cgg gga gac acc ttt gcg gta gct     13207
Ala Lys Ala Glu Gly Arg Glu Ile Arg Gly Asp Thr Phe Ala Val Ala
        295                 300                 305

ccc cag gac ctg gaa ata gtg cct tta act aaa gac agc aaa gac aga     13255
Pro Gln Asp Leu Glu Ile Val Pro Leu Thr Lys Asp Ser Lys Asp Arg
    310                 315                 320

agc tac aat att ata aac aac acg acg gac acc ctg tat cgg agc tgg     13303
Ser Tyr Asn Ile Ile Asn Asn Thr Thr Asp Thr Leu Tyr Arg Ser Trp
325                 330                 335                 340

ttt ctg gct tac aac tac gga gac ccc gag aaa gga gtg aga tca tgg     13351
Phe Leu Ala Tyr Asn Tyr Gly Asp Pro Glu Lys Gly Val Arg Ser Trp
                345                 350                 355

acc ata ctc acc acc acg gac gtg acc tgt ggc tcg cag caa gtg tac     13399
Thr Ile Leu Thr Thr Thr Asp Val Thr Cys Gly Ser Gln Gln Val Tyr
            360                 365                 370
```

-continued

```
tgg tcc ctg ccg gat atg atg caa gac ccg gtc acc ttc cgc ccc tcc    13447
Trp Ser Leu Pro Asp Met Met Gln Asp Pro Val Thr Phe Arg Pro Ser
        375                 380                 385

acc caa gtc agc aac ttc ccg gtg gtg ggc acc gag ctg ctg ccc gtc    13495
Thr Gln Val Ser Asn Phe Pro Val Val Gly Thr Glu Leu Leu Pro Val
    390                 395                 400

cat gcc aag agc ttc tac aac gag cag gcc gtc tac tcg caa ctt att    13543
His Ala Lys Ser Phe Tyr Asn Glu Gln Ala Val Tyr Ser Gln Leu Ile
405                 410                 415                 420

cgc cag tcc acc gcg ctt acc cac gtg ttc aat cgc ttt ccc gag aac    13591
Arg Gln Ser Thr Ala Leu Thr His Val Phe Asn Arg Phe Pro Glu Asn
                425                 430                 435

cag att ctg gtg cgc cct ccc gct cct acc att acc acc gtc agt gaa    13639
Gln Ile Leu Val Arg Pro Pro Ala Pro Thr Ile Thr Thr Val Ser Glu
            440                 445                 450

aac gtt ccc gcc ctc aca gat cac gga acc ctg ccg ctg cgc agc agt    13687
Asn Val Pro Ala Leu Thr Asp His Gly Thr Leu Pro Leu Arg Ser Ser
        455                 460                 465

atc agt gga gtt cag cgc gtg acc atc acc gac gcc aga cgt cga acc    13735
Ile Ser Gly Val Gln Arg Val Thr Ile Thr Asp Ala Arg Arg Arg Thr
    470                 475                 480

tgc ccc tac gtt tac aaa gcg ctt ggc gtg gtg gct cct aaa gtt ctt    13783
Cys Pro Tyr Val Tyr Lys Ala Leu Gly Val Val Ala Pro Lys Val Leu
485                 490                 495                 500

tct agt cgc acc ttc taa aaacatgtcc atcctcatct ctcccgataa          13831
Ser Ser Arg Thr Phe
                505

caacaccggc tggggactgg gctccggcaa gatgtacggc ggagccaaaa ggcgctccag  13891

tcagcaccca gttcgagttc ggggccactt ccgcgctcct tggggagctt acaagcgagg  13951

actctcgggt cgaacggctg tagacgatac catagatgcc gtgattgccg acgcccgccg  14011

gtacaacccc ggaccggtcg ctagcgccgc ctccaccgtg gattccgtga tcgacagcgt  14071

ggtagccggc gctcgggcct atgctcgccg caagaggcgg ctgcatcgga gacgtcgccc  14131

caccgccgcc atgctggcag ccagggccgt gctgaggcgg gcccggaggg caggcagaag  14191

ggctatgcgc cgcgctgccg ccaacgccgc cgccgggagg gcccgccgac aggctgcccg  14251

ccaggctgcc gctgccatcg ctagcatggc cagacccagg agagggaacg tgtactgggt  14311

gcgtgattct gtgacgggag tccgagtgcc ggtgcgcagc cgacctcccc gaagttagaa  14371

gatccaagct gcgaagacgg cggtactgag tctccctgtt gttatcagcc caacatgagc  14431

aagcgcaagt ttaaagaaga actgctgcag acgctggtgc ctgagatcta tggccctccg  14491

gacgtgaagc cagacattaa gccccgcgat atcaagcgtg ttaaaaagcg ggaaaagaaa  14551

gaggaactcg cggtggtaga cgatggcgga gtggaattta ttaggagttt cgccccgcga  14611

cgcagggttc aatggaaagg gcggcgggta caacgcgttt tgaggccggg caccgcggta  14671

gtttttaccc cgggagagcg gtcggccgtt aggggtttca aaaggcagta cgacgaggtg  14731

tacggcgacg aggacatatt ggaacaggcg gctcaacaga tcggagaatt tgcctacgga  14791

aagcgttcgc gtcgcgaaga cctggccatc gccttagaca gcggcaaccc cacgcccagc  14851

ctcaaacccg tgacgctgca gcaggtgctt cccgtgagcg ccagcacgga cagcaagagg  14911

gggattaaga gagaaatgga agatctgcat cccaccatcc aactcatggt ccctaaacgg  14971

cagaggctgg aagaggtcct ggagaagatg aaagtggacc ccagcataga gccggatgta  15031

aaagtcagac ctattaagga agtggccccc ggtcttgggg tgcaaacggt ggacattcaa  15091
```

-continued

```
atccccgtca ccaccgcttc aaccgccgtg gaagctatgg aaacgcaaac ggagacccct  15151

gccgcgatcg gtaccaggga agtggcgttg caaacggagc cttggtacga atacgcagcc  15211

cctcggcgtc agaggcgttc cgctcgttac ggccccgcca acgccatcat gccagaatat  15271

gcgctgcatc cgtctattct gcccactccc ggataccggg gtgtgacgta tcgcccgtct  15331

ggaacccgcc gccgaacccg tcgccgccgc cgctcccgtc gcgctctggc ccccgtgtcg  15391

gtgcggcgtg tgacccgccg gggaaagaca gtcgtcattc ccaacccgcg ttaccaccct  15451

agcatccttt aataactctg ccgttttgca gatggctctg acttgccgcg tgcgccttcc  15511

cgttccgcac tatcgaggaa gatctcgtcg taggagaggc atgacgggca gtggtcgccg  15571

gcgggctttg cgcaggcgca tgaaaggcgg aattttaccc gccctgatac ccataattgc  15631

cgccgccatc ggtgccatac ccggcgttgc ttcagtggcg ttgcaagcag ctcgtaataa  15691

ataaacaaag gcttttgcac ttatgacctg gtcctgacta ttttatgcag aaagagcatg  15751

gaagacatca attttacgtc gctggctccg cggcacggct cgcggccgct catgggcacc  15811

tggaacgaca tcggcaccag tcagctcaac gggggcgctt tcaattgggg gagcctttgg  15871

agcggcatta aaaactttgg ctccacgatt aaatcctacg gcagcaaagc ctggaacagt  15931

agtgctggtc agatgctccg agataaactg aaggacacca acttccaaga aaaagtggtc  15991

aatggggtgg tgaccggcat ccacggcgcg gtagatctcg ccaaccaagc ggtgcagaaa  16051

gagattgaca ggcgtttgga aagctcgcgg gtgccgccgc agagagggga tgaggtggag  16111

gtcgaggaag tagaagtaga ggaaaagctg cccccgctgg agaaagttcc cggtgcgcct  16171

ccgagaccgc agaagcggcc caggccagaa ctagaagaga ctctggtgac ggagagcaag  16231

gagcctccct cgtacgagca agccttgaaa gagggcgcct ctccaccctc ctacccgatg  16291

actaagccga tcgcacccat ggctcgaccg gtgtacggca aggattacaa gcccgtcacg  16351

ctagagctgc ccccaccgcc ccccacgcgc ccgaccgtcc ccccccctgcc gactccgtcg  16411

gcggccgcgg cgggacccgt gtccgcacca tccgctgtgc ctctgccagc cgcccgtcca  16471

gtggccgtgg ccactgccag aaaccccaga ggccagagag gagccaactg gcaaagcacg  16531

ctgaacagca tcgtgggcct gggagtgaaa agcctgaaac gccgccgttg ctattattaa  16591

aaaagtgtag ctaaaaagtc tcccgttgta tacgcctcct atgttaccgc cagagacgag  16651

tgactgtcgc cgcgagcgcc gctttcaag atg gcc acc cca tcg atg atg ccg   16704
                                Met Ala Thr Pro Ser Met Met Pro
                                                510

cag tgg tct tac atg cac atc gcc ggc cag gac gcc tcg gag tac ctg   16752
Gln Trp Ser Tyr Met His Ile Ala Gly Gln Asp Ala Ser Glu Tyr Leu
    515                 520                 525

agt ccc ggc ctc gtg cag ttt gcc cgc gcc acc gac acc tac ttc agc   16800
Ser Pro Gly Leu Val Gln Phe Ala Arg Ala Thr Asp Thr Tyr Phe Ser
530                 535                 540                 545

ttg gga aac aag ttt aga aac ccc acc gtg gcc ccc acc cac gat gtg   16848
Leu Gly Asn Lys Phe Arg Asn Pro Thr Val Ala Pro Thr His Asp Val
                550                 555                 560

acc acg gac cgc tcg cag agg ctg acc ctg cgc ttt gtg ccc gta gac   16896
Thr Thr Asp Arg Ser Gln Arg Leu Thr Leu Arg Phe Val Pro Val Asp
            565                 570                 575

cgg gag gac acc gcg tac tct tac aaa gtg cgc tac acg ttg gcc gta   16944
Arg Glu Asp Thr Ala Tyr Ser Tyr Lys Val Arg Tyr Thr Leu Ala Val
        580                 585                 590

ggg gac aac cga gtg ctg gac atg gcc agc acc tac ttt gac atc cgg   16992
Gly Asp Asn Arg Val Leu Asp Met Ala Ser Thr Tyr Phe Asp Ile Arg
    595                 600                 605
```

-continued

```
ggg gtg ctg gat cgg ggt ccc agc ttc aag ccc tat tcc ggc acc gct    17040
Gly Val Leu Asp Arg Gly Pro Ser Phe Lys Pro Tyr Ser Gly Thr Ala
610                 615                 620                 625

tac aac tcc ctg gcc ccc aag gga gct ccc aac ccc tcg gaa tgg acg    17088
Tyr Asn Ser Leu Ala Pro Lys Gly Ala Pro Asn Pro Ser Glu Trp Thr
                630                 635                 640

gac act tcc gac aac aaa ctt aaa gca tat gct cag gct ccc tac cag    17136
Asp Thr Ser Asp Asn Lys Leu Lys Ala Tyr Ala Gln Ala Pro Tyr Gln
            645                 650                 655

agt caa gga ctt aca aag gat ggt att cag gtt ggg cta gtt gtg aca    17184
Ser Gln Gly Leu Thr Lys Asp Gly Ile Gln Val Gly Leu Val Val Thr
        660                 665                 670

gag tca gga caa aca ccc caa tat gca aac aaa gtg tac caa ccc gag    17232
Glu Ser Gly Gln Thr Pro Gln Tyr Ala Asn Lys Val Tyr Gln Pro Glu
    675                 680                 685

cca caa att ggg gaa aac caa tgg aat tta gaa caa gaa gat aaa gcg    17280
Pro Gln Ile Gly Glu Asn Gln Trp Asn Leu Glu Gln Glu Asp Lys Ala
690                 695                 700                 705

gcg gga aga gtc cta aag aaa gat acc cct atg ttt ccc tgc tat ggg    17328
Ala Gly Arg Val Leu Lys Lys Asp Thr Pro Met Phe Pro Cys Tyr Gly
                710                 715                 720

tca tat gcc agg ccc aca aac gaa caa gga ggg cag gca aaa aac caa    17376
Ser Tyr Ala Arg Pro Thr Asn Glu Gln Gly Gly Gln Ala Lys Asn Gln
            725                 730                 735

gaa gta gat tta cag ttt ttt gcc act ccg ggc gac acc cag aac acg    17424
Glu Val Asp Leu Gln Phe Phe Ala Thr Pro Gly Asp Thr Gln Asn Thr
        740                 745                 750

gct aaa gtg gta ctt tat gct gaa aat gtc aac ctg gaa act cca gat    17472
Ala Lys Val Val Leu Tyr Ala Glu Asn Val Asn Leu Glu Thr Pro Asp
    755                 760                 765

act cac tta gtg ttt aaa ccc gat gac gac agc acc agt tca aaa ctt    17520
Thr His Leu Val Phe Lys Pro Asp Asp Asp Ser Thr Ser Ser Lys Leu
770                 775                 780                 785

ctt ctt ggg cag cag gct gca cct aac aga ccc aac tac ata ggt ttt    17568
Leu Leu Gly Gln Gln Ala Ala Pro Asn Arg Pro Asn Tyr Ile Gly Phe
                790                 795                 800

aga gat aat ttt att ggt tta atg tac tac aat agc act gga aac atg    17616
Arg Asp Asn Phe Ile Gly Leu Met Tyr Tyr Asn Ser Thr Gly Asn Met
            805                 810                 815

ggc gtg ctg gcc gga cag gct tct caa ttg aat gcc gta gtc gac ttg    17664
Gly Val Leu Ala Gly Gln Ala Ser Gln Leu Asn Ala Val Val Asp Leu
        820                 825                 830

cag gac aga aac acc gag ttg tcc tac cag ctg atg ctg gac gca ctg    17712
Gln Asp Arg Asn Thr Glu Leu Ser Tyr Gln Leu Met Leu Asp Ala Leu
    835                 840                 845

ggg gat cgc agc cga tat ttt tca atg tgg aat cag gca gta gac agc    17760
Gly Asp Arg Ser Arg Tyr Phe Ser Met Trp Asn Gln Ala Val Asp Ser
850                 855                 860                 865

tat gac cca gac gtt aga att ata gaa aac cac gga gtg gaa gac gaa    17808
Tyr Asp Pro Asp Val Arg Ile Ile Glu Asn His Gly Val Glu Asp Glu
                870                 875                 880

ctg cca aac tat tgt ttt cct ctg gga gga atg gtg gtg act gac aat    17856
Leu Pro Asn Tyr Cys Phe Pro Leu Gly Gly Met Val Val Thr Asp Asn
            885                 890                 895

tac aac tct gtg acg cct caa aat gga ggc agt gga aat aca tgg cag    17904
Tyr Asn Ser Val Thr Pro Gln Asn Gly Gly Ser Gly Asn Thr Trp Gln
        900                 905                 910

gca gac aat act aca ttt agt caa aga gga gcg cag att ggc tcc gga    17952
Ala Asp Asn Thr Thr Phe Ser Gln Arg Gly Ala Gln Ile Gly Ser Gly
```

-continued

```
    915                 920                 925

aac atg ttt gcc ctg gaa att aac cta cag gcc aac ctc tgg cgc ggc     18000
Asn Met Phe Ala Leu Glu Ile Asn Leu Gln Ala Asn Leu Trp Arg Gly
930                 935                 940                 945

ttc ttg tat tcc aat att ggg ttg tat ctt cca gac tct ctg aaa atc     18048
Phe Leu Tyr Ser Asn Ile Gly Leu Tyr Leu Pro Asp Ser Leu Lys Ile
                950                 955                 960

acc ccc gac aac atc acg ctg cca gaa aac aaa aac act tat cag tac     18096
Thr Pro Asp Asn Ile Thr Leu Pro Glu Asn Lys Asn Thr Tyr Gln Tyr
            965                 970                 975

atg aac ggt cgc gta acg cca ccc ggg ctc ata gac acc tat gta aac     18144
Met Asn Gly Arg Val Thr Pro Pro Gly Leu Ile Asp Thr Tyr Val Asn
        980                 985                 990

gtg ggc gcg cgc tgg tcc ccc  gat gtc atg gac agc  att aac ccc ttc   18192
Val Gly Ala Arg Trp Ser Pro  Asp Val Met Asp Ser  Ile Asn Pro Phe
    995                 1000                1005

aac  cac cac cgt aac gcg  ggc ttg cgc tac cgc  tcc atg ctc ttg     18237
Asn  His His Arg Asn Ala  Gly Leu Arg Tyr Arg  Ser Met Leu Leu
1010                 1015                 1020

ggc  aac ggc cgt tat gtg  cct ttt cac att cag  gtg ccc caa aaa     18282
Gly  Asn Gly Arg Tyr Val  Pro Phe His Ile Gln  Val Pro Gln Lys
1025                 1030                 1035

ttc  ttt gcc att aaa aac  ctg ctg ctt ctc ccc  ggt tcc tat acc     18327
Phe  Phe Ala Ile Lys Asn  Leu Leu Leu Leu Pro  Gly Ser Tyr Thr
1040                 1045                 1050

tat  gag tgg aac ttc cgc  aag gat gtc aac atg  atc ctg cag agc     18372
Tyr  Glu Trp Asn Phe Arg  Lys Asp Val Asn Met  Ile Leu Gln Ser
1055                 1060                 1065

tcg  ctg ggt aat gac ctg  cga gtg gac ggg gcc  agc ata cgc ttt     18417
Ser  Leu Gly Asn Asp Leu  Arg Val Asp Gly Ala  Ser Ile Arg Phe
1070                 1075                 1080

gac  agc att aac ctg tat  gcc aac ttt ttt ccc  atg gcc cac aac     18462
Asp  Ser Ile Asn Leu Tyr  Ala Asn Phe Phe Pro  Met Ala His Asn
1085                 1090                 1095

acg  gcc tct acc ctg gaa  gcc atg ctg cgc aac  gac acc aat gac     18507
Thr  Ala Ser Thr Leu Glu  Ala Met Leu Arg Asn  Asp Thr Asn Asp
1100                 1105                 1110

cag  tcc ttc aac gac tac  ctg tgc gcg gct aac  atg ctg tac ccc     18552
Gln  Ser Phe Asn Asp Tyr  Leu Cys Ala Ala Asn  Met Leu Tyr Pro
1115                 1120                 1125

atc  ccc gcc aac gcc acc  agc gtg ccc att tct  att cct tct cgg     18597
Ile  Pro Ala Asn Ala Thr  Ser Val Pro Ile Ser  Ile Pro Ser Arg
1130                 1135                 1140

aac  tgg gct gcc ttc agg  ggc tgg agt ttt act  cgc ctc aaa acc     18642
Asn  Trp Ala Ala Phe Arg  Gly Trp Ser Phe Thr  Arg Leu Lys Thr
1145                 1150                 1155

aag  gag act ccc tcg ctg  ggc tcc ggt ttt gac  ccc tac ttt gtt     18687
Lys  Glu Thr Pro Ser Leu  Gly Ser Gly Phe Asp  Pro Tyr Phe Val
1160                 1165                 1170

tac  tcc ggc tcc att ccc  tac cta gat ggc acc  ttt tac ctc aac     18732
Tyr  Ser Gly Ser Ile Pro  Tyr Leu Asp Gly Thr  Phe Tyr Leu Asn
1175                 1180                 1185

cac  act ttc aaa aag gtg  tct att atg ttt gac  tcc tcg gtt agc     18777
His  Thr Phe Lys Lys Val  Ser Ile Met Phe Asp  Ser Ser Val Ser
1190                 1195                 1200

tgg  ccc ggc aac gac cgc  ctg cta acg ccc aac  gag ttc gaa att     18822
Trp  Pro Gly Asn Asp Arg  Leu Leu Thr Pro Asn  Glu Phe Glu Ile
1205                 1210                 1215

aag  cgt tcc gtg gac ggt  gaa ggg tac aac gtg  gcc cag agc aac     18867
```

-continued

```
Lys  Arg Ser Val Asp Gly  Glu Gly Tyr Asn Val  Ala Gln Ser Asn
1220                 1225                 1230

atg  acc aag gac tgg ttt  cta att caa atg ctc  agt cac tat aat     18912
Met  Thr Lys Asp Trp Phe  Leu Ile Gln Met Leu  Ser His Tyr Asn
1235                 1240                 1245

ata  ggt tac cag ggc ttc  tat gtg ccc gag aac  tac aag gac cgc     18957
Ile  Gly Tyr Gln Gly Phe  Tyr Val Pro Glu Asn  Tyr Lys Asp Arg
1250                 1255                 1260

atg  tac tcc ttc ttc cgc  aac ttc caa cca atg  agc cgg cag gtg     19002
Met  Tyr Ser Phe Phe Arg  Asn Phe Gln Pro Met  Ser Arg Gln Val
1265                 1270                 1275

gta  gat acc gtg act tat  aca gac tac aaa gat  gtc aag ctc ccc     19047
Val  Asp Thr Val Thr Tyr  Thr Asp Tyr Lys Asp  Val Lys Leu Pro
1280                 1285                 1290

tac  caa cac aac aac tca  ggg ttc gtg ggc tac  atg gga ccc acc     19092
Tyr  Gln His Asn Asn Ser  Gly Phe Val Gly Tyr  Met Gly Pro Thr
1295                 1300                 1305

atg  cga gag gga cag gcc  tac ccg gcc aac tat  ccc tac ccc ctg     19137
Met  Arg Glu Gly Gln Ala  Tyr Pro Ala Asn Tyr  Pro Tyr Pro Leu
1310                 1315                 1320

atc  gga gag act gcc gta  ccc agc ctc acg cag  aaa aag ttc ctc     19182
Ile  Gly Glu Thr Ala Val  Pro Ser Leu Thr Gln  Lys Lys Phe Leu
1325                 1330                 1335

tgc  gac cgg gtg atg tgg  agg ata ccc ttc tct  agc aac ttt atg     19227
Cys  Asp Arg Val Met Trp  Arg Ile Pro Phe Ser  Ser Asn Phe Met
1340                 1345                 1350

tcg  atg ggc tcc ctc acc  gac ctg ggg cag aac  atg ctg tac gcc     19272
Ser  Met Gly Ser Leu Thr  Asp Leu Gly Gln Asn  Met Leu Tyr Ala
1355                 1360                 1365

aac  tcc gct cac gcc ttg  gac atg act ttt gag  gtg gat ccc atg     19317
Asn  Ser Ala His Ala Leu  Asp Met Thr Phe Glu  Val Asp Pro Met
1370                 1375                 1380

gat  gag ccc acg ctt ctc  tat gtt ctg ttt gaa  gtc ttc gac gtg     19362
Asp  Glu Pro Thr Leu Leu  Tyr Val Leu Phe Glu  Val Phe Asp Val
1385                 1390                 1395

gtg  cgc atc cac cag ccg  cac cgc ggc gtc atc  gag gcc gtc tac     19407
Val  Arg Ile His Gln Pro  His Arg Gly Val Ile  Glu Ala Val Tyr
1400                 1405                 1410

ctg  cgc aca cct ttc tct  gcc ggt aac gcc acc  acc taa agaagctgat  19456
Leu  Arg Thr Pro Phe Ser  Ala Gly Asn Ala Thr  Thr
1415                 1420                 1425

gggttccagc gaacaggagt tgcaggccat tgttcgcgac ctgggctgcg ggccctgctt  19516

tttgggcacc ttcgacaagc gttttcccgg attcatgtcc ccccacaagc cggcctgcgc  19576

catcgttaac acggccggac gggagacagg gggggtgcac tggctcgcct tcgcctggaa  19636

cccgcgcaac cgcacctgct acctgttcga cccttttggt ttctccgacg aaaggctgaa  19696

gcagatctac caattcgagt acgaggggct cctcaagcgc agcgctctgg cctccacgcc  19756

cgaccactgc gtcaccctgg aaaagtccac ccagacggtc caggggcccc tctcggccgc  19816

ctgcgggctt ttctgttgca tgtttttgca cgccttcgtg cactggcctc acaccccat   19876

ggagcgcaac cccaccatgg atctgctcac cggagtgccc aacagcatgc ttcacagtcc  19936

ccaggtcgcc cccaccctgc gtcgcaatca ggaccacctg tatcgctttc tggggaaaca  19996

ctctgcctat ttccgccgcc accggcagcg catcgaacag gccacggcct tcgaaagcat  20056

gagccaaaga gtgtaatcaa taaaaaccgt ttttatttga catgatacgc gcttctggcg  20116

tttttattaa aaatcgaagg gttcgaggga ggggtcctcg tgcccgctgg ggagggacac  20176
```

-continued

```
gttgcggtac tggaatcggg cgctccaacg aaactcgggg atcaccagcc gcggcagggc  20236
cacgtcttcc atgttctgct tccaaaactg tcgcaccagc tgcagggctc ccatcacgtc  20296
gggcgctgag atcttgaagt cgcagttagg gccggagccc ccgcggctgt tgcggaacac  20356
ggggttggca cactggaaca ccaacacgct ggggttgtgg atactagcca gggccgtcgg  20416
gtcggtcacc tccgatgcat ccagatcctc ggcattgctc agggcgaacg gggtcagctt  20476
gcacatctgc cgcccgatct ggggtaccag gtcgcgcttg ttgaggcagt cgcagcgcag  20536
agggatgagg atgcgacgct gcccgcgttg catgatgggg taactcgccg ccaggaactc  20596
ctctatctga cggaaggcca tctgggcctt gacgccctcg gtgaaaaata gcccacagga  20656
cttgctggaa aacacgttat tgccacagtt gatgtcttcc gcgcagcagc gcgcatcttc  20716
gttcttcagc tgaaccacgt tgcgacccca gcggttctga accaccttgg ctttcgtggg  20776
atgctccttc agcgcccgct gtccgttctc gctggtcaca tccatttcca ccacgtgctc  20836
cttgcagacc atctccactc cgtggaaaca gaacagaatg ccctcctgtt gggtattgcg  20896
atgctcccac acggcgcacc cggtggactc ccagctcttg tgtttcaccc ccgcgtaggc  20956
ttccatgtaa gccattagaa atctgcccat cagctcagtg aaggtcttct ggttggtgaa  21016
ggttagcggc aggccgcggt gttcctcgtt caaccaagtt tgacagatct tgcggtacac  21076
ggctccctgg tcgggcagaa acttaaaagt cgttctgctc tcgttgtcca cgtggaactt  21136
ctccatcaac atcgtcatga cttccatgcc cttctcccag gcagtcacca gcggcgcgct  21196
ctcggggttc ttcaccaaca cggcggtgga ggggccctcg ccggccccga cgtccttcat  21256
ggacattttt tgaaactcca cggtgccgtc cgcgcggcgt actctgcgca tcggagggta  21316
gctgaagccc acctccatga cggtgctttc gccctcgctg tcggagacga tctccgggga  21376
gggcggcgga acgggggcag acttgcgagc cttcttcttg ggagggagcg gaggcacctc  21436
ctgctcgcgc tcgggactca tctcccgcaa gtagggggtg atggagcttc ctggttggtt  21496
ctgacggttg gccattgtat cctaggcaga aagacatgga gcttatgcgc gaggaaactt  21556
taaccgcccc gtcccccgtc agcgacgaag aggtcatcgt cgaacaggac ccgggctacg  21616
ttacgccgcc cgaggatctg gaggggccct tagacgaccg gcgcgacgct agtgagcggc  21676
aggaaaatga gaaagaggag gaggagggct gctacctcct ggaaggcgac gttttgctaa  21736
agcatttcgc caggcagagc accatactca aggaggcctt gcaagaccgc tccgaggtgc  21796
ccttggacgt cgccgcgctc tcccaggcct acgaggcgaa cctttttctcg ccccgagtgc  21856
ctccgaagag acagcccaac ggcacctgcg agcccaaccc gcgactcaac ttctaccccg  21916
tgttcgccgt gcccgaggcg ctggccacct accacatctt tttcaaaaac cagcgcattc  21976
ccctttcctg ccgggccaac cgcaccgcgg ccgataggaa gctaacactc agaaacggag  22036
tcagcatacc tgatatcacg tcactggagg aagtgcctaa gatcttcgag ggtctgggtc  22096
gagatgagaa gcgggcggcg aacgctctgc agaaagaaca gaaagagagt cagaacgtgc  22156
tggtggagct ggagggggac aacgcgcgtc tgaccgtcct caaacgttgc atagaagttt  22216
cccacttcgc ctacccggcc ctcaacctgc cgcccaaagt tatgaaatcg gtcatggacc  22276
agctactcat caagagagct gagcccctga atcccgacca ccctgaggcg gaaaactcag  22336
aggacggaaa gcccgtcgtc agcgacgagg agctcgagcg gtggctggaa accagggacc  22396
cccagcagtt gcaagagagg cgcaagatga tgatggcggc cgtgctggtc acggtggagc  22456
tagaatgcct gcaacggttt ttcagcgacg tggagacgct acgcaaaatc ggggagtccc  22516
tgcactacac cttccgccag ggctacgttc gccaggcctg caaaatctcc aacgtagagc  22576
```

-continued

```
tcagcaacct ggtttcctac atgggcatcc tccacgagaa ccggctgggg cagagcgtgc  22636
tgcactgcac cttgcaaggc gaggcgcgaa gggactacgt ccgagactgc gtctacctct  22696
tcctcaccct cacctggcag accgccatgg gcgtgtggca gcagtgcttg gaagagagaa  22756
acctcaaaga gctggacaaa ctcctctgcc gccagcggcg ggccctctgg accggcttca  22816
gcgagcgcac ggtcgcctgc gccctggcag acatcatttt cccagaacgc ctgatgaaaa  22876
ccttgcagaa cggcctgccg gatttcatca gtcagagcat cttgcaaaac ttccgctcct  22936
tcgtcctgga gcgctccggg atcttgcccg ccatgagctg cgcgctgcct tctgactttg  22996
tcccccttc ctaccgcgag tgccctcccc cactgtggag ccactgctac ctcttccaac  23056
tggccaactt tctggcctac cactccgacc tcatggaaga cgtgagcgga gaggggctgc  23116
tcgagtgcca ctgccgctgc aacctctgca ccccccacag atcgctggcc tgcaacaccg  23176
agctgctcag cgaaacccag gtcataggta ccttcgagat ccaggggccc cagcagcaag  23236
agggtgcttc cggcttgaag ctcactccgg cgctgtggac ctcggcttac ttacgcaaat  23296
ttgtagccga ggactaccac gcccacaaaa ttcagtttta cgaagaccaa tctcgaccac  23356
cgaaagcccc cctcacggcc tgcgtcatca cccagagcaa aatcctggcc caattgcaat  23416
ccatcaacca agcgcgccga gatttccttt tgaaaaaggg tcggggggtg tacctggacc  23476
cccagaccgg cgaggaactc aacccgtcca cactttccgt cgaagcagcc cccccgagac  23536
atgccaccca agggaaccgc caagcagctg atcgctcggc agagagcgaa gaagcaagag  23596
ctgctccagc agcaggtgga ggacgaggaa gagctgtggg acagccaggc agaggaggtg  23656
tcagaggacg aggaggagat ggaaagctgg gacagcctag acgaggagga cgagctttca  23716
gaggaagagg cgaccgaaga aaaaccacct gcatccagcg cgccttctct gagccgacag  23776
ccgaagcccc ggcccccgac gcccccggcc ggctcactca aagccagccg taggtgggac  23836
gccaccggat ctccagcggc agcggcaacg gcagcgggta aggccaaacg cgagcggcgg  23896
gggtattgct cctggcggac ccacaaaagc agtatcgtga actgcttgca acactgcggg  23956
ggaaacatct cctttgcccg acgctacctc ctcttccatc acggtgtggc cttccctcgc  24016
aacgttctct attattaccg tcatctctac agcccctacg aaacgctcgg agaaaaaagc  24076
taaggcctcc tctgccgcga ggaaaaactc cgccgccgct gccgccaagg atccgccggc  24136
caccgaggag ctgagaaagc gcatctttcc cactctgtat gctatctttc agcaaagccg  24196
cgggcagcac cctcagcgcg aactgaaaat aaaaaaccgc tccttccgct cactcacccg  24256
cagctgtctg taccacaaga gagaagacca gctgcagcgc accctggacg acgccgaagc  24316
actgttcagc aaatactgct cagcgtctct taaagactaa aagacccgcg ctttttcccc  24376
ctcgggcgcc aaaacccacg tcatcgccag catgagcaag gagattccca ccccttacat  24436
gtggagctat cagccccaga tgggcctggc cgcgggggcc gcccaggact actccagcaa  24496
aatgaactgg ctcagcgccg gcccccacat gatctcacga gttaacggca tccgagccca  24556
ccgaaaccag atcctcttag aacaggcggc aatcaccgcc acaccccggc gccaactcaa  24616
cccgcccagt tggcccgccg cccaggtgta tcaggaaact ccccgcccga ccacagtcct  24676
cctgccacgc gacgcggagg ccgaagtcct catgactaac tctggggtac aattagcggg  24736
cgggtccagg tacgccaggt acagaggtcg ggccgctcct tactctcccg ggagtataaa  24796
gagggtgatc attcgaggcc gaggtatcca gctcaacgac gaggcggtga gctcctcaac  24856
cggtctcaga cctgacggag tcttccagct cggaggagcg ggccgctctt ccttcaccac  24916
```

-continued

```
tcgccaggcc tacctgaccc tgcagagctc ttcctcgcag ccgcgctccg ggggaatcgg  24976

cactctccag ttcgtggaag agttcgtccc ctccgtctac ttcaacccgt tttccggctc  25036

acctggacgc tacccggacg ccttcattcc caactttgac gcagtgagtg aatccgtgga  25096

cggctacgac tgatgacaga tggtgcggcc gtgagagctc ggctgcgaca tctgcatcac  25156

tgccgccagc ctcgctgcta cgctcgggag gcgatcgtgt tcagctactt tgagctgccg  25216

gacgagcacc ctcagggacc ggctcacggg ttgaaactcg agattgagaa cgcgcttgag  25276

tctcacctca tcgacgcctt caccgcccgg cctctcctgg tagaaaccga acgcgggatc  25336

actaccatca ccctgttctg catctgcccc acgcccggat tac atg aag atc tgt   25391
                                                 Met Lys Ile Cys
                                                             1430

gtt gtc atc ttt gcg  ctc agt tta ata aaa  act gaa ctt ttt gcc      25436
Val Val Ile Phe Ala  Leu Ser Leu Ile Lys  Thr Glu Leu Phe Ala
                1435                 1440                 1445

gta cct tca acg cca  cgc gtt gtt tct cct  tgt gaa aaa acc cca      25481
Val Pro Ser Thr Pro  Arg Val Val Ser Pro  Cys Glu Lys Thr Pro
                1450                 1455                 1460

gga gtc ctt aac tta  cac ata gca aaa ccc  ttg tat ttt acc ata      25526
Gly Val Leu Asn Leu  His Ile Ala Lys Pro  Leu Tyr Phe Thr Ile
                1465                 1470                 1475

gaa aaa caa cta gcc  ctt tca att gga aaa  ggg tta aca att tct      25571
Glu Lys Gln Leu Ala  Leu Ser Ile Gly Lys  Gly Leu Thr Ile Ser
                1480                 1485                 1490

gct aca gga cag ttg  gaa agc aca gca agc  gta cag gac agc gct      25616
Ala Thr Gly Gln Leu  Glu Ser Thr Ala Ser  Val Gln Asp Ser Ala
                1495                 1500                 1505

aca cca ccc cta cgt  ggt att tcc cct tta  aag ctg aca gac aac      25661
Thr Pro Pro Leu Arg  Gly Ile Ser Pro Leu  Lys Leu Thr Asp Asn
                1510                 1515                 1520

ggt tta aca tta agc  tat tca gat ccc ctg  cgt gtg gta ggt gac      25706
Gly Leu Thr Leu Ser  Tyr Ser Asp Pro Leu  Arg Val Val Gly Asp
                1525                 1530                 1535

caa ctt acg ttt aat  ttt act tct cca cta  cgt tac gaa aat ggc      25751
Gln Leu Thr Phe Asn  Phe Thr Ser Pro Leu  Arg Tyr Glu Asn Gly
                1540                 1545                 1550

agt ctt aca ttc aac  tac act tct ccc atg  aca cta ata aac aac      25796
Ser Leu Thr Phe Asn  Tyr Thr Ser Pro Met  Thr Leu Ile Asn Asn
                1555                 1560                 1565

agt ctt gct att aac  gtc aat acc tcc aaa  ggc ctc agt agt gac      25841
Ser Leu Ala Ile Asn  Val Asn Thr Ser Lys  Gly Leu Ser Ser Asp
                1570                 1575                 1580

aac ggc aca ctc gct  gta aat gtt act cca  gat ttt aga ttt aac      25886
Asn Gly Thr Leu Ala  Val Asn Val Thr Pro  Asp Phe Arg Phe Asn
                1585                 1590                 1595

agc tct ggt gcc tta  act ttt ggc ata caa  agt cta tgg act ttt      25931
Ser Ser Gly Ala Leu  Thr Phe Gly Ile Gln  Ser Leu Trp Thr Phe
                1600                 1605                 1610

cca acc aaa act cct  aac tgt acc gtg ttt  acc gaa agt gac tcc      25976
Pro Thr Lys Thr Pro  Asn Cys Thr Val Phe  Thr Glu Ser Asp Ser
                1615                 1620                 1625

ctg ctg agt ctt tgc  ttg act aaa tgc gga  gct cac gta ctt gga      26021
Leu Leu Ser Leu Cys  Leu Thr Lys Cys Gly  Ala His Val Leu Gly
                1630                 1635                 1640

agc gtg agt tta agc  gga gtg gca gga acc  atg cta aaa atg acc      26066
Ser Val Ser Leu Ser  Gly Val Ala Gly Thr  Met Leu Lys Met Thr
                1645                 1650                 1655

cac act tct gtt acc  gtt cag ttt tcg ttt  gat gac agt ggt aaa      26111
```

-continued

```
His Thr Ser Val Thr  Val Gln Phe Ser Phe  Asp Asp Ser Gly Lys
                1660                 1665                 1670

cta ata ttc tct cca  ctt gcg aac aac act  tgg ggt gtt cga caa      26156
Leu Ile Phe Ser Pro  Leu Ala Asn Asn Thr  Trp Gly Val Arg Gln
                1675                 1680                 1685

agc gag agt ccg ttg  ccc aac cca tcc ttc  aac gct ctc acg ttt      26201
Ser Glu Ser Pro Leu  Pro Asn Pro Ser Phe  Asn Ala Leu Thr Phe
                1690                 1695                 1700

atg cca aac agt acc  att tat tct aga gga  gca agt aac gaa cct      26246
Met Pro Asn Ser Thr  Ile Tyr Ser Arg Gly  Ala Ser Asn Glu Pro
                1705                 1710                 1715

caa aac aat tat tat  gtc cag acg tat ctt  aga ggc aac gtg cga      26291
Gln Asn Asn Tyr Tyr  Val Gln Thr Tyr Leu  Arg Gly Asn Val Arg
                1720                 1725                 1730

aag cca att cta cta  act gtt acc tac aac  tca gtt aat tca gga      26336
Lys Pro Ile Leu Leu  Thr Val Thr Tyr Asn  Ser Val Asn Ser Gly
                1735                 1740                 1745

tat tcc tta act ttt  aaa tgg gat gct gtc  gcc aat gaa aaa ttt      26381
Tyr Ser Leu Thr Phe  Lys Trp Asp Ala Val  Ala Asn Glu Lys Phe
                1750                 1755                 1760

gcc act cct aca tct  tcg ttt tgc tat gtt  gca gag caa taa          26423
Ala Thr Pro Thr Ser  Ser Phe Cys Tyr Val  Ala Glu Gln
                1765                 1770

aaccctgtta ccccaccgtc tcgttttttt cag atg aaa  cga gcg aga gtt      26474
                                     Met Lys  Arg Ala Arg Val
                                         1775

gat  gaa gac ttc aac cca  gtg tac cct tat gac  ccc cca tac gct     26519
Asp  Glu Asp Phe Asn Pro  Val Tyr Pro Tyr Asp  Pro Pro Tyr Ala
1780                 1785                 1790

ccc  gtc atg ccc ttc att  act ccg cct ttt acc  tcc tcg gat ggg     26564
Pro  Val Met Pro Phe Ile  Thr Pro Pro Phe Thr  Ser Ser Asp Gly
1795                 1800                 1805

ttg  cag gaa aaa cca ctt  gga gtg tta agt tta  aac tac agg gat     26609
Leu  Gln Glu Lys Pro Leu  Gly Val Leu Ser Leu  Asn Tyr Arg Asp
1810                 1815                 1820

ccc  att act aca caa aat  ggg tct ctc acg tta  aaa cta gga aac     26654
Pro  Ile Thr Thr Gln Asn  Gly Ser Leu Thr Leu  Lys Leu Gly Asn
1825                 1830                 1835

ggc  ctc act cta aac aac  cag gga cag tta aca  tca act gct ggc     26699
Gly  Leu Thr Leu Asn Asn  Gln Gly Gln Leu Thr  Ser Thr Ala Gly
1840                 1845                 1850

gaa  gtg gag cct ccg ctc  act aat gct aac aac  aaa ctt gca cta     26744
Glu  Val Glu Pro Pro Leu  Thr Asn Ala Asn Asn  Lys Leu Ala Leu
1855                 1860                 1865

gcc  tat agc gaa cca tta  gca gta aaa agc aac  cgc cta act cta     26789
Ala  Tyr Ser Glu Pro Leu  Ala Val Lys Ser Asn  Arg Leu Thr Leu
1870                 1875                 1880

tca  cac acc gct ccc ctt  gtc atc gct aat aat  tct tta gcg ttg     26834
Ser  His Thr Ala Pro Leu  Val Ile Ala Asn Asn  Ser Leu Ala Leu
1885                 1890                 1895

caa  gtt tca gag cct att  ttt gta aat gac gat  gac aag cta gcc     26879
Gln  Val Ser Glu Pro Ile  Phe Val Asn Asp Asp  Asp Lys Leu Ala
1900                 1905                 1910

ctg  cag aca gcc gcc ccc  ctt gta acc aac gct  ggc acc ctt cgc     26924
Leu  Gln Thr Ala Ala Pro  Leu Val Thr Asn Ala  Gly Thr Leu Arg
1915                 1920                 1925

tta  cag agc gct gcc cct  tta gga ttg gtt gaa  aat act ctt aaa     26969
Leu  Gln Ser Ala Ala Pro  Leu Gly Leu Val Glu  Asn Thr Leu Lys
1930                 1935                 1940
```

-continued

```
ctg  ctg ttt tct aaa ccc  ttg tat ttg caa aat  gat ttt ctt gca      27014
Leu  Leu Phe Ser Lys Pro  Leu Tyr Leu Gln Asn  Asp Phe Leu Ala
1945                1950                1955

tta  gcc att gaa cgc ccc  ctg gct gta gca gcc  gca ggt act ctg      27059
Leu  Ala Ile Glu Arg Pro  Leu Ala Val Ala Ala  Ala Gly Thr Leu
1960                1965                1970

acc  cta caa ctt act cct  cca tta aag act aac  gat gac ggg cta      27104
Thr  Leu Gln Leu Thr Pro  Pro Leu Lys Thr Asn  Asp Asp Gly Leu
1975                1980                1985

aca  cta tcc aca gtc gag  cca tta act gta aaa  aac gga aac cta      27149
Thr  Leu Ser Thr Val Glu  Pro Leu Thr Val Lys  Asn Gly Asn Leu
1990                1995                2000

ggc  ttg caa ata tcg cgc  cct tta gtt gtt caa  aac aac ggc ctt      27194
Gly  Leu Gln Ile Ser Arg  Pro Leu Val Val Gln  Asn Asn Gly Leu
2005                2010                2015

tcg  ctt gct att acc ccc  ccg ctg cgt ttg ttt  aac agc gac ccc      27239
Ser  Leu Ala Ile Thr Pro  Pro Leu Arg Leu Phe  Asn Ser Asp Pro
2020                2025                2030

gtt  ctt ggt ttg ggc ttc  act ttt ccc cta gct  gtc aca aac aac      27284
Val  Leu Gly Leu Gly Phe  Thr Phe Pro Leu Ala  Val Thr Asn Asn
2035                2040                2045

ctc  ctc tcc tta aac atg  gga gac gga gtt aaa  ctt acc tat aat      27329
Leu  Leu Ser Leu Asn Met  Gly Asp Gly Val Lys  Leu Thr Tyr Asn
2050                2055                2060

aaa  cta aca gcc aat ttg  ggt agg gat tta caa  ttt gaa aac ggt      27374
Lys  Leu Thr Ala Asn Leu  Gly Arg Asp Leu Gln  Phe Glu Asn Gly
2065                2070                2075

gcg  att gcc gta acg ctt  act gcc gaa tta cct  ttg caa tac act      27419
Ala  Ile Ala Val Thr Leu  Thr Ala Glu Leu Pro  Leu Gln Tyr Thr
2080                2085                2090

aac  aaa ctt caa ctg aat  att gga gct ggc ctt  cgt tac aat gga      27464
Asn  Lys Leu Gln Leu Asn  Ile Gly Ala Gly Leu  Arg Tyr Asn Gly
2095                2100                2105

gcc  agc aga aaa cta gat  gta aac att aac caa  aat aaa ggc tta      27509
Ala  Ser Arg Lys Leu Asp  Val Asn Ile Asn Gln  Asn Lys Gly Leu
2110                2115                2120

act  tgg gac aac gat gca  gtt att ccc aaa cta  gga tcg ggc tta      27554
Thr  Trp Asp Asn Asp Ala  Val Ile Pro Lys Leu  Gly Ser Gly Leu
2125                2130                2135

caa  ttt gac cct aat ggc  aac atc gct gtt atc  cct gaa acc gtg      27599
Gln  Phe Asp Pro Asn Gly  Asn Ile Ala Val Ile  Pro Glu Thr Val
2140                2145                2150

aag  ccg caa acg tta tgg  acg act gca gat ccc  tcg cct aac tgc      27644
Lys  Pro Gln Thr Leu Trp  Thr Thr Ala Asp Pro  Ser Pro Asn Cys
2155                2160                2165

tca  gtg tac cag gac ttg  gat gcc agg ctg tgg  ctc gct ctt gtt      27689
Ser  Val Tyr Gln Asp Leu  Asp Ala Arg Leu Trp  Leu Ala Leu Val
2170                2175                2180

aaa  agt ggc gac atg gtg  cat gga agc att gcc  cta aaa gcc cta      27734
Lys  Ser Gly Asp Met Val  His Gly Ser Ile Ala  Leu Lys Ala Leu
2185                2190                2195

aaa  ggg acg ttg cta aat  cct aca gcc agc tac  att tcc att gtg      27779
Lys  Gly Thr Leu Leu Asn  Pro Thr Ala Ser Tyr  Ile Ser Ile Val
2200                2205                2210

ata  tat ttt tac agc aac  gga gtc agg cgt acc  aac tat cca acg      27824
Ile  Tyr Phe Tyr Ser Asn  Gly Val Arg Arg Thr  Asn Tyr Pro Thr
2215                2220                2225

ttt  gac aac gaa ggc acc  tta gct aac agc gcc  act tgg gga tac      27869
Phe  Asp Asn Glu Gly Thr  Leu Ala Asn Ser Ala  Thr Trp Gly Tyr
2230                2235                2240
```

-continued

```
cga  cag ggg caa tct gct  aac act aat gtg acc  aat gcc act gaa     27914
Arg  Gln Gly Gln Ser Ala  Asn Thr Asn Val Thr  Asn Ala Thr Glu
2245                 2250                 2255

ttt  atg ccc agc tca agc  agg tac ccc gtg aat  aaa gga gac aac     27959
Phe  Met Pro Ser Ser Ser  Arg Tyr Pro Val Asn  Lys Gly Asp Asn
2260                 2265                 2270

att  caa aat caa tct ttt  tca tac acc tgt att  aaa gga gat ttt     28004
Ile  Gln Asn Gln Ser Phe  Ser Tyr Thr Cys Ile  Lys Gly Asp Phe
2275                 2280                 2285

gct  atg cct gtc ccg ttc  cgt gta aca tat aat  cac gcc ctg gaa     28049
Ala  Met Pro Val Pro Phe  Arg Val Thr Tyr Asn  His Ala Leu Glu
2290                 2295                 2300

ggg  tat tcc ctt aag ttc  acc tgg cgc gtt gta  gcc aat cag gcc     28094
Gly  Tyr Ser Leu Lys Phe  Thr Trp Arg Val Val  Ala Asn Gln Ala
2305                 2310                 2315

ttt  gat att cct tgc tgt  tca ttt tca tac atc  aca gaa taa         28136
Phe  Asp Ile Pro Cys Cys  Ser Phe Ser Tyr Ile  Thr Glu
2320                 2325                 2330

aaaaccactt tttcatttta atttcttttt attttacacg aacagtgaga cttcctccac  28196

ccttccattt gacagcatac accagcctct ccccccttcat agcagtaaac tgttgtgaat  28256

cagtccggta tttgggagtt aaaatccaaa cagtctcttt ggtgatgaaa cgtcgatcag  28316

taatggacac aaatccctgg gacaggtttt ccaacgtttc ggtgaaaaac tgcacaccgc  28376

cctacaaaac aaacaggttc aggctctcca cgggttatct ccccgatcaa actcagacag  28436

ggtaaaggtg cggtggtgtt ccactaaacc acgcaggtgg cgctgtctga acctctcggt  28496

gcgactcctg tgaggctggt aagaagttag attgtccagt agcctcacag catgtatcat  28556

cagtctacga gtgcgtctgg cgcagcagcg catctgaatc tcactgagat tccggcaaga  28616

atcgcacacc atcacaatca ggttgttcat gatcccatag ctgaacacgc tccagccaaa  28676

gctcattcgc tccaacagcg ccaccgcgtg tccgtccaac cttactttaa cataaatcag  28736

gtgtctgccg cgtacaaaca tgctacccac atacagaact tcccggggca ggcccctgtt  28796

caccacctgt ctgtaccagg gaaacctcac atttatcagg gagccataga tggccatttt  28856

aaaccaatta gctaataccg ccccaccagc tctacactga agagaaccgg gagagttaca  28916

atgacagtga ataatccatc tctcataacc cctgatggtc tgatgaaaat ctagatctaa  28976

cgtggcacaa caaatacaca ctttcatata cattttcata acatgttttt cccaggccgt  29036

taaaatacaa tcccaataca cgggccactc ctgcagtaca ataaagctaa tacaagatgg  29096

tatactcctc acctcactga cactgtgcat gttcatattt tcacattcta agtaccgaga  29156

gttctcctct acagcagcac tgctgcggtc ctcacaaggt ggtagctggt gatgattgta  29216

gggggccagt ctgcagcgat accgtctgtc gcgttgcatc gtagaccagg aaccgacgca  29276

cctcctcgta cttgtggtag cagaaccacg tccgctgcca gcacgtctcc acgtaacgcc  29336

ggtccctgcg tcgctcacgc tccctcctca atgcaaagtg caaccactct tgtaatccac  29396

acagatccct ctcggcctcc ggggtgatgc acacctcaaa cctacagatg tctcggtaca  29456

gttccaaaca cgtagtgagg gcgagttcca accaagacag acagcctgat ctatcccgac  29516

acactggagg tggaggaaga cacggaagag gcatgttatt ccaagcgatt caccaacggg  29576

tcgaaatgaa gatcccgaag atgacaacgg tcgcctccgg agccctgatg gaatttaaca  29636

gccagatcaa acgttatgcg attctccaag ctatcgatcg ccgcttccaa aagagcctgg  29696

acccgcactt ccacaaacac cagcaaagca aaagcactat tatcaaactc ttcaatcatc  29756
```

-continued

```
aagctgcagg actgtacaat gcctaagtaa ttttcgtttc tccactcgcg aatgatgtcg  29816

cggcagatag tctgaaggtt catcccgtgc agggtaaaaa gctccgaaag ggcgccctct  29876

acagccatgc gtagacacac catcatgact gcaagatatc gggctcctga gacacctgca  29936

gcagatttaa cagatcaagg tcaggttgct ctccgcgatc acgaatctcc atccgcaagg  29996

tcatttgcaa aaaattaaat aaatctatgc cgactagatc tgtcaactcc gcattaggaa  30056

ccaaatcagg tgtggctacg cagcacaaaa gttccaggga tggtgccaaa ctcactagaa  30116

ccgctcccga gtaacaaaac tgatgaatgg gagtaacaca gtgtaaaatg tgcaaccaaa  30176

aatcactaag gtgctccttt aaaaagtcca gtacttctat attcagtccg tgcaagtact  30236

gaagcaactg tgcgggaata tgcacaacaa aaaaaatagg gcggctcaga tacatgttga  30296

cctaaaataa aaagaatcat taaactaaag aagcttggcg aacggtggga taaatgacac  30356

gctccagcag cagacaggca accggctgtc cccgggaacc gcggtaaaat tcatccgaat  30416

gattaaaaag aacaacagaa acttcccacc atgtactcgg ttggatctcc tgagcacaca  30476

gcaatacccc cctcacattc atgtccgcca cagaaaaaaa acgtcccaga tacccagcgg  30536

ggatatccaa cgacagctgc aaagacagca aaacaatccc tctgggagcg atcacaaaat  30596

cctccggtga aaaaagcaca tacatattag aataaccctg ttgctggggc aaaaaggccc  30656

ggcgtcccag caaatgcaca taaatatgtt catcagccat tgccccgtct taccgcgtaa  30716

tcagccacga aaaaatcgag ctaaaattca cccaacagcc tatagctata tatacactcc  30776

gcccaatgac gctaataccg caccacccac gaccaaagtt cacccacacc cacaaaaccc  30836

gcgaaaatcc agcgccgtca gcacttccgc aatttcagtc tcacaacgtc acttccgcgc  30896

gccttttcac attcccacac acacccgcgc ccttcgcccc gccctcgcgc caccccgcgt  30956

caccgcacgt caccccggcc ccgcctcgct cctccccgct cattatcata ttggcacgtt  31016

tccagaataa ggtatattat tgatgatg                                     31044
```

<210> SEQ ID NO 30
<211> LENGTH: 505
<212> TYPE: PRT
<213> ORGANISM: simian adenovirus SV-25

<400> SEQUENCE: 30

```
Met Arg Arg Ala Val Arg Val Thr Pro Ala Ala Tyr Glu Gly Pro Pro
1               5                   10                  15

Pro Ser Tyr Glu Ser Val Met Gly Ser Ala Asn Val Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Thr Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
        115                 120                 125

Asn Ile Asn Glu Phe Met Ser Thr Asn Lys Phe Arg Ala Lys Leu Met
    130                 135                 140
```

-continued

```
Val Glu Lys Ser Asn Ala Glu Thr Arg Gln Pro Arg Tyr Glu Trp Phe
145                 150                 155                 160

Glu Phe Thr Ile Pro Glu Gly Asn Tyr Ser Glu Thr Met Thr Ile Asp
                165                 170                 175

Leu Met Asn Asn Ala Ile Val Asp Asn Tyr Leu Gln Val Gly Arg Gln
            180                 185                 190

Asn Gly Val Leu Glu Ser Asp Ile Gly Val Lys Phe Asp Thr Arg Asn
        195                 200                 205

Phe Arg Leu Gly Trp Asp Pro Val Thr Lys Leu Val Met Pro Gly Val
    210                 215                 220

Tyr Thr Asn Glu Ala Phe His Pro Asp Ile Val Leu Leu Pro Gly Cys
225                 230                 235                 240

Gly Val Asp Phe Thr Gln Ser Arg Leu Ser Asn Leu Leu Gly Ile Arg
                245                 250                 255

Lys Arg Arg Pro Phe Gln Glu Gly Phe Gln Ile Met Tyr Glu Asp Leu
            260                 265                 270

Glu Gly Gly Asn Ile Pro Ala Leu Leu Asp Val Ser Lys Tyr Glu Ala
        275                 280                 285

Ser Ile Gln Arg Ala Lys Ala Glu Gly Arg Glu Ile Arg Gly Asp Thr
    290                 295                 300

Phe Ala Val Ala Pro Gln Asp Leu Glu Ile Val Pro Leu Thr Lys Asp
305                 310                 315                 320

Ser Lys Asp Arg Ser Tyr Asn Ile Ile Asn Asn Thr Thr Asp Thr Leu
                325                 330                 335

Tyr Arg Ser Trp Phe Leu Ala Tyr Asn Tyr Gly Asp Pro Glu Lys Gly
            340                 345                 350

Val Arg Ser Trp Thr Ile Leu Thr Thr Thr Asp Val Thr Cys Gly Ser
        355                 360                 365

Gln Gln Val Tyr Trp Ser Leu Pro Asp Met Met Gln Asp Pro Val Thr
    370                 375                 380

Phe Arg Pro Ser Thr Gln Val Ser Asn Phe Pro Val Val Gly Thr Glu
385                 390                 395                 400

Leu Leu Pro Val His Ala Lys Ser Phe Tyr Asn Glu Gln Ala Val Tyr
                405                 410                 415

Ser Gln Leu Ile Arg Gln Ser Thr Ala Leu Thr His Val Phe Asn Arg
            420                 425                 430

Phe Pro Glu Asn Gln Ile Leu Val Arg Pro Pro Ala Pro Thr Ile Thr
        435                 440                 445

Thr Val Ser Glu Asn Val Pro Ala Leu Thr Asp His Gly Thr Leu Pro
    450                 455                 460

Leu Arg Ser Ser Ile Ser Gly Val Gln Arg Val Thr Ile Thr Asp Ala
465                 470                 475                 480

Arg Arg Arg Thr Cys Pro Tyr Val Tyr Lys Ala Leu Gly Val Val Ala
                485                 490                 495

Pro Lys Val Leu Ser Ser Arg Thr Phe
            500                 505


<210> SEQ ID NO 31
<211> LENGTH: 921
<212> TYPE: PRT
<213> ORGANISM: simian adenovirus SV-25

<400> SEQUENCE: 31

Met Ala Thr Pro Ser Met Met Pro Gln Trp Ser Tyr Met His Ile Ala
1               5                   10                  15
```

-continued

```
Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Tyr Thr Leu Ala Val Gly Asp Asn Arg Val Leu Asp Met
                85                  90                  95

Ala Ser Thr Tyr Phe Asp Ile Arg Gly Val Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ser Glu Trp Thr Asp Thr Ser Asp Asn Lys Leu Lys
    130                 135                 140

Ala Tyr Ala Gln Ala Pro Tyr Gln Ser Gln Gly Leu Thr Lys Asp Gly
145                 150                 155                 160

Ile Gln Val Gly Leu Val Val Thr Glu Ser Gly Gln Thr Pro Gln Tyr
                165                 170                 175

Ala Asn Lys Val Tyr Gln Pro Glu Pro Gln Ile Gly Glu Asn Gln Trp
            180                 185                 190

Asn Leu Glu Gln Glu Asp Lys Ala Ala Gly Arg Val Leu Lys Lys Asp
        195                 200                 205

Thr Pro Met Phe Pro Cys Tyr Gly Ser Tyr Ala Arg Pro Thr Asn Glu
    210                 215                 220

Gln Gly Gly Gln Ala Lys Asn Gln Glu Val Asp Leu Gln Phe Phe Ala
225                 230                 235                 240

Thr Pro Gly Asp Thr Gln Asn Thr Ala Lys Val Val Leu Tyr Ala Glu
                245                 250                 255

Asn Val Asn Leu Glu Thr Pro Asp Thr His Leu Val Phe Lys Pro Asp
            260                 265                 270

Asp Asp Ser Thr Ser Ser Lys Leu Leu Leu Gly Gln Gln Ala Ala Pro
        275                 280                 285

Asn Arg Pro Asn Tyr Ile Gly Phe Arg Asp Asn Phe Ile Gly Leu Met
    290                 295                 300

Tyr Tyr Asn Ser Thr Gly Asn Met Gly Val Leu Ala Gly Gln Ala Ser
305                 310                 315                 320

Gln Leu Asn Ala Val Val Asp Leu Gln Asp Arg Asn Thr Glu Leu Ser
                325                 330                 335

Tyr Gln Leu Met Leu Asp Ala Leu Gly Asp Arg Ser Arg Tyr Phe Ser
            340                 345                 350

Met Trp Asn Gln Ala Val Asp Ser Tyr Asp Pro Asp Val Arg Ile Ile
        355                 360                 365

Glu Asn His Gly Val Glu Asp Glu Leu Pro Asn Tyr Cys Phe Pro Leu
    370                 375                 380

Gly Gly Met Val Val Thr Asp Asn Tyr Asn Ser Val Thr Pro Gln Asn
385                 390                 395                 400

Gly Gly Ser Gly Asn Thr Trp Gln Ala Asp Asn Thr Thr Phe Ser Gln
                405                 410                 415

Arg Gly Ala Gln Ile Gly Ser Gly Asn Met Phe Ala Leu Glu Ile Asn
            420                 425                 430
```

-continued

```
Leu Gln Ala Asn Leu Trp Arg Gly Phe Leu Tyr Ser Asn Ile Gly Leu
        435                 440                 445

Tyr Leu Pro Asp Ser Leu Lys Ile Thr Pro Asp Asn Ile Thr Leu Pro
    450                 455                 460

Glu Asn Lys Asn Thr Tyr Gln Tyr Met Asn Gly Arg Val Thr Pro Pro
465                 470                 475                 480

Gly Leu Ile Asp Thr Tyr Val Asn Val Gly Ala Arg Trp Ser Pro Asp
                485                 490                 495

Val Met Asp Ser Ile Asn Pro Phe Asn His His Arg Asn Ala Gly Leu
            500                 505                 510

Arg Tyr Arg Ser Met Leu Leu Gly Asn Gly Arg Tyr Val Pro Phe His
        515                 520                 525

Ile Gln Val Pro Gln Lys Phe Phe Ala Ile Lys Asn Leu Leu Leu Leu
    530                 535                 540

Pro Gly Ser Tyr Thr Tyr Glu Trp Asn Phe Arg Lys Asp Val Asn Met
545                 550                 555                 560

Ile Leu Gln Ser Ser Leu Gly Asn Asp Leu Arg Val Asp Gly Ala Ser
                565                 570                 575

Ile Arg Phe Asp Ser Ile Asn Leu Tyr Ala Asn Phe Phe Pro Met Ala
            580                 585                 590

His Asn Thr Ala Ser Thr Leu Glu Ala Met Leu Arg Asn Asp Thr Asn
        595                 600                 605

Asp Gln Ser Phe Asn Asp Tyr Leu Cys Ala Ala Asn Met Leu Tyr Pro
    610                 615                 620

Ile Pro Ala Asn Ala Thr Ser Val Pro Ile Ser Ile Pro Ser Arg Asn
625                 630                 635                 640

Trp Ala Ala Phe Arg Gly Trp Ser Phe Thr Arg Leu Lys Thr Lys Glu
                645                 650                 655

Thr Pro Ser Leu Gly Ser Gly Phe Asp Pro Tyr Phe Val Tyr Ser Gly
            660                 665                 670

Ser Ile Pro Tyr Leu Asp Gly Thr Phe Tyr Leu Asn His Thr Phe Lys
        675                 680                 685

Lys Val Ser Ile Met Phe Asp Ser Ser Val Ser Trp Pro Gly Asn Asp
    690                 695                 700

Arg Leu Leu Thr Pro Asn Glu Phe Glu Ile Lys Arg Ser Val Asp Gly
705                 710                 715                 720

Glu Gly Tyr Asn Val Ala Gln Ser Asn Met Thr Lys Asp Trp Phe Leu
                725                 730                 735

Ile Gln Met Leu Ser His Tyr Asn Ile Gly Tyr Gln Gly Phe Tyr Val
            740                 745                 750

Pro Glu Asn Tyr Lys Asp Arg Met Tyr Ser Phe Phe Arg Asn Phe Gln
        755                 760                 765

Pro Met Ser Arg Gln Val Val Asp Thr Val Thr Tyr Thr Asp Tyr Lys
    770                 775                 780

Asp Val Lys Leu Pro Tyr Gln His Asn Asn Ser Gly Phe Val Gly Tyr
785                 790                 795                 800

Met Gly Pro Thr Met Arg Glu Gly Gln Ala Tyr Pro Ala Asn Tyr Pro
                805                 810                 815

Tyr Pro Leu Ile Gly Glu Thr Ala Val Pro Ser Leu Thr Gln Lys Lys
            820                 825                 830

Phe Leu Cys Asp Arg Val Met Trp Arg Ile Pro Phe Ser Ser Asn Phe
        835                 840                 845

Met Ser Met Gly Ser Leu Thr Asp Leu Gly Gln Asn Met Leu Tyr Ala
```

-continued

```
    850                 855                 860

Asn Ser Ala His Ala Leu Asp Met Thr Phe Glu Val Asp Pro Met Asp
865                 870                 875                 880

Glu Pro Thr Leu Leu Tyr Val Leu Phe Glu Val Phe Asp Val Val Arg
                885                 890                 895

Ile His Gln Pro His Arg Gly Val Ile Glu Ala Val Tyr Leu Arg Thr
            900                 905                 910

Pro Phe Ser Ala Gly Asn Ala Thr Thr
        915                 920


<210> SEQ ID NO 32
<211> LENGTH: 347
<212> TYPE: PRT
<213> ORGANISM: simian adenovirus SV-25

<400> SEQUENCE: 32

Met Lys Ile Cys Val Val Ile Phe Ala Leu Ser Leu Ile Lys Thr Glu
1               5                   10                  15

Leu Phe Ala Val Pro Ser Thr Pro Arg Val Val Ser Pro Cys Glu Lys
            20                  25                  30

Thr Pro Gly Val Leu Asn Leu His Ile Ala Lys Pro Leu Tyr Phe Thr
        35                  40                  45

Ile Glu Lys Gln Leu Ala Leu Ser Ile Gly Lys Gly Leu Thr Ile Ser
    50                  55                  60

Ala Thr Gly Gln Leu Glu Ser Thr Ala Ser Val Gln Asp Ser Ala Thr
65                  70                  75                  80

Pro Pro Leu Arg Gly Ile Ser Pro Leu Lys Leu Thr Asp Asn Gly Leu
                85                  90                  95

Thr Leu Ser Tyr Ser Asp Pro Leu Arg Val Val Gly Asp Gln Leu Thr
            100                 105                 110

Phe Asn Phe Thr Ser Pro Leu Arg Tyr Glu Asn Gly Ser Leu Thr Phe
        115                 120                 125

Asn Tyr Thr Ser Pro Met Thr Leu Ile Asn Asn Ser Leu Ala Ile Asn
    130                 135                 140

Val Asn Thr Ser Lys Gly Leu Ser Ser Asp Asn Gly Thr Leu Ala Val
145                 150                 155                 160

Asn Val Thr Pro Asp Phe Arg Phe Asn Ser Ser Gly Ala Leu Thr Phe
                165                 170                 175

Gly Ile Gln Ser Leu Trp Thr Phe Pro Thr Lys Thr Pro Asn Cys Thr
            180                 185                 190

Val Phe Thr Glu Ser Asp Ser Leu Leu Ser Leu Cys Leu Thr Lys Cys
        195                 200                 205

Gly Ala His Val Leu Gly Ser Val Ser Leu Ser Gly Val Ala Gly Thr
    210                 215                 220

Met Leu Lys Met Thr His Thr Ser Val Thr Val Gln Phe Ser Phe Asp
225                 230                 235                 240

Asp Ser Gly Lys Leu Ile Phe Ser Pro Leu Ala Asn Asn Thr Trp Gly
                245                 250                 255

Val Arg Gln Ser Glu Ser Pro Leu Pro Asn Pro Ser Phe Asn Ala Leu
            260                 265                 270

Thr Phe Met Pro Asn Ser Thr Ile Tyr Ser Arg Gly Ala Ser Asn Glu
        275                 280                 285

Pro Gln Asn Asn Tyr Tyr Val Gln Thr Tyr Leu Arg Gly Asn Val Arg
    290                 295                 300
```

-continued

```
Lys Pro Ile Leu Leu Thr Val Thr Tyr Asn Ser Val Asn Ser Gly Tyr
305                 310                 315                 320

Ser Leu Thr Phe Lys Trp Asp Ala Val Ala Asn Glu Lys Phe Ala Thr
                325                 330                 335

Pro Thr Ser Ser Phe Cys Tyr Val Ala Glu Gln
            340                 345


<210> SEQ ID NO 33
<211> LENGTH: 559
<212> TYPE: PRT
<213> ORGANISM: simian adenovirus SV-25

<400> SEQUENCE: 33

Met Lys Arg Ala Arg Val Asp Glu Asp Phe Asn Pro Val Tyr Pro Tyr
1               5                   10                  15

Asp Pro Pro Tyr Ala Pro Val Met Pro Phe Ile Thr Pro Pro Phe Thr
            20                  25                  30

Ser Ser Asp Gly Leu Gln Glu Lys Pro Leu Gly Val Leu Ser Leu Asn
        35                  40                  45

Tyr Arg Asp Pro Ile Thr Thr Gln Asn Gly Ser Leu Thr Leu Lys Leu
    50                  55                  60

Gly Asn Gly Leu Thr Leu Asn Asn Gln Gly Gln Leu Thr Ser Thr Ala
65                  70                  75                  80

Gly Glu Val Glu Pro Pro Leu Thr Asn Ala Asn Asn Lys Leu Ala Leu
                85                  90                  95

Ala Tyr Ser Glu Pro Leu Ala Val Lys Ser Asn Arg Leu Thr Leu Ser
            100                 105                 110

His Thr Ala Pro Leu Val Ile Ala Asn Asn Ser Leu Ala Leu Gln Val
        115                 120                 125

Ser Glu Pro Ile Phe Val Asn Asp Asp Asp Lys Leu Ala Leu Gln Thr
    130                 135                 140

Ala Ala Pro Leu Val Thr Asn Ala Gly Thr Leu Arg Leu Gln Ser Ala
145                 150                 155                 160

Ala Pro Leu Gly Leu Val Glu Asn Thr Leu Lys Leu Leu Phe Ser Lys
                165                 170                 175

Pro Leu Tyr Leu Gln Asn Asp Phe Leu Ala Leu Ala Ile Glu Arg Pro
            180                 185                 190

Leu Ala Val Ala Ala Ala Gly Thr Leu Thr Leu Gln Leu Thr Pro Pro
        195                 200                 205

Leu Lys Thr Asn Asp Asp Gly Leu Thr Leu Ser Thr Val Glu Pro Leu
    210                 215                 220

Thr Val Lys Asn Gly Asn Leu Gly Leu Gln Ile Ser Arg Pro Leu Val
225                 230                 235                 240

Val Gln Asn Asn Gly Leu Ser Leu Ala Ile Thr Pro Pro Leu Arg Leu
                245                 250                 255

Phe Asn Ser Asp Pro Val Leu Gly Leu Gly Phe Thr Phe Pro Leu Ala
            260                 265                 270

Val Thr Asn Asn Leu Leu Ser Leu Asn Met Gly Asp Gly Val Lys Leu
        275                 280                 285

Thr Tyr Asn Lys Leu Thr Ala Asn Leu Gly Arg Asp Leu Gln Phe Glu
    290                 295                 300

Asn Gly Ala Ile Ala Val Thr Leu Thr Ala Glu Leu Pro Leu Gln Tyr
305                 310                 315                 320

Thr Asn Lys Leu Gln Leu Asn Ile Gly Ala Gly Leu Arg Tyr Asn Gly
                325                 330                 335
```

-continued

```
Ala Ser Arg Lys Leu Asp Val Asn Ile Asn Gln Asn Lys Gly Leu Thr
            340                 345                 350

Trp Asp Asn Asp Ala Val Ile Pro Lys Leu Gly Ser Gly Leu Gln Phe
        355                 360                 365

Asp Pro Asn Gly Asn Ile Ala Val Ile Pro Glu Thr Val Lys Pro Gln
    370                 375                 380

Thr Leu Trp Thr Thr Ala Asp Pro Ser Pro Asn Cys Ser Val Tyr Gln
385                 390                 395                 400

Asp Leu Asp Ala Arg Leu Trp Leu Ala Leu Val Lys Ser Gly Asp Met
                405                 410                 415

Val His Gly Ser Ile Ala Leu Lys Ala Leu Lys Gly Thr Leu Leu Asn
            420                 425                 430

Pro Thr Ala Ser Tyr Ile Ser Ile Val Ile Tyr Phe Tyr Ser Asn Gly
        435                 440                 445

Val Arg Arg Thr Asn Tyr Pro Thr Phe Asp Asn Glu Gly Thr Leu Ala
    450                 455                 460

Asn Ser Ala Thr Trp Gly Tyr Arg Gln Gly Gln Ser Ala Asn Thr Asn
465                 470                 475                 480

Val Thr Asn Ala Thr Glu Phe Met Pro Ser Ser Ser Arg Tyr Pro Val
                485                 490                 495

Asn Lys Gly Asp Asn Ile Gln Asn Gln Ser Phe Ser Tyr Thr Cys Ile
            500                 505                 510

Lys Gly Asp Phe Ala Met Pro Val Pro Phe Arg Val Thr Tyr Asn His
        515                 520                 525

Ala Leu Glu Gly Tyr Ser Leu Lys Phe Thr Trp Arg Val Val Ala Asn
    530                 535                 540

Gln Ala Phe Asp Ile Pro Cys Cys Ser Phe Ser Tyr Ile Thr Glu
545                 550                 555
```

<210> SEQ ID NO 34
<211> LENGTH: 34115
<212> TYPE: DNA
<213> ORGANISM: simian adenovirus SV-39
<220> FEATURE:
<221> NAME/KEY: CDS
<222> LOCATION: (13448)..(14959)
<223> OTHER INFORMATION: L2 Penton
<220> FEATURE:
<221> NAME/KEY: CDS
<222> LOCATION: (17785)..(20538)
<223> OTHER INFORMATION: L3 Hexon
<220> FEATURE:
<221> NAME/KEY: CDS
<222> LOCATION: (29515)..(31116)
<223> OTHER INFORMATION: L5 Fiber #1

<400> SEQUENCE: 34

```
catcatcaat ataacaccgc aagatggcga ccgagttaac atgcaaatga ggtgggcgga      60

gttacgcgac ctttgtcttg ggaacgcgga agtgggcgcg gcgggtttcg gggaggagcg     120

cggggcgggg cgggcgtgtc gcgcggcggt gacgcgccgg ggacccggaa attgagtagt     180

ttttattcat tttgcaagtt tttctgtaca ttttggcgcg aaaactgaaa cgaggaagtg     240

aaaagtgaaa aatgccgagg tagtcaccgg gtggagatct gacctttgcc gtgtggagtt     300

tacccgctga cgtgtgggtt tcggtctcta ttttttcact gtggttttcc gggtacggtc     360

aaaggtcccc attttatgac tccacgtcag ctgatcgcta gggtatttaa tgcgcctcag     420

accgtcaaga ggccactctt gagtgccggc gagaagagtt ttctcctccg cgttccgcca     480
```

-continued

```
actgtgaaaa aatgaggaac ttcttgctat ctccggggct gccagcgacc gtagccgccg    540
agctgttgga ggacattgtt accggagctc tgggagacga tcctcaggtg atttctcact    600
tttgtgaaga ttttagtctt catgatctct atgatattga tccgggtgtt gaggggcaag    660
aggatgaatg gctggagtct gtggatgggt tttttccgga cgctatgctg ctagaggctg    720
atttgccacc acctcacaac tctcacactg agcccgagtc agctgctatt cctgaattgt    780
catcaggtga acttgacttg gcttgttacg agactatgcc tccggagtcg gatgaggagg    840
acagcgggat cagcgatccc acggctttta tggtctctaa ggcgattgct atactaaaag    900
aagatgatga tggcgatgat ggatttcgac tggacgctcc ggcggtgccg gggagagact    960
gtaagtcctg tgaataccac cgggatcgta ccggagaccc gtctatgttg tgttctctgt   1020
gttatctccg tcttaacgct gcttttgtct acagtaagtg ttttgtgctt ttttaccctg   1080
tggctttgtt gagtttattt ttttctgtgt ctcatagggt gttgtttatt ataggtcctg   1140
tttcagatgt ggaggaacct gatagtacta ctggaaatga ggaggaaaag ccctccccgc   1200
cgaaactaac tcagcgctgc agacctaata ttttgagacc ctcggcccag cgtgtgtcat   1260
cccggaaacg tgctgctgtt aattgcatag aagatttatt ggaagagccc actgaacctt   1320
tggacttgtc cttaaagcga ccccgcccgc agtagggcgc ggtgccagtt ttttctctct   1380
agcttccggg tgactcagtg caataaaaat tttcttggca acaggtgtat gtgtttactt   1440
tacgggcggg aagggattag gggagtataa agctggaggg gaaaaatctg aggctgtcag   1500
atcgagtgag aagttccatg gacttgtacg agagcctaga gaatctaagt tctttgcgac   1560
gtttgctgga ggaggcctcc gacagaacct cttacatttg gaggtttctg ttcggttccc   1620
ctctgagtcg ctttttgcac cgggtgaagc gagagcacct gacggaattt gatgggcttt   1680
tagagcagct gcctggactg tttgattctt tgaatctcgg ccaccggacg ctgctagagg   1740
agaggctttt tccacaattg gacttttcct ctccaggccg tctgtgttca gcgcttgctt   1800
ttgctgtaca tctgttggac agatggaacg agcagacgca gctcagcccg ggttacactc   1860
tggacttcct gacgctatgc ctatggaagt tcggaatcag gagggggagg aagctgtacg   1920
ggcgcttggt ggagaggcat ccgtctctgc gccagcagcg tctgcaagct caagtgctgc   1980
tgaggcggga ggatctggaa gccatttcgg aggaggagag cggcatggaa gagaagaatc   2040
cgagagcggg gctggaccct ccggcggagg agtagggggg ataccggacc cttttcctga   2100
gttggctttg gggcggtgg ggggcgcttc tgtggtacgt gaggatgaag aggggcgcca   2160
acgcggtcag aagagggagc attttgagtc ctcgactttc ttggctgatg taaccgtggc   2220
cctgatggcg aaaaacaggc tggaggtggt gtggtacccg gaagtatggg aggactttga   2280
gaagggggac ttgcacctgc tggaaaaata taactttgag caggtgaaaa catactggat   2340
gaacccggat gaggactggg aggtggtttt gaaccgatac ggcaaggtag ctctgcgtcc   2400
cgactgtcgc taccaggttc gcgacaaggt ggtcctgcga cgcaacgtgt acctgttggg   2460
caacggcgcc accgtggaga tggtggaccc cagaaggggt ggttttgtgg ccaatatgca   2520
agaaatgtgc cctggggtgg tgggcttgtc tggggtgact tttcatagtg tgaggtttag   2580
cggtagcaat tttgggggtg tggttattac cgcgaacact cctgtggtcc tgcataattg   2640
ctactttttt ggcttcagca acacctgtgt ggaaatgagg gtgggaggca aagtgcgcgg   2700
gtgttccttt tacgcttgct ggaagggggt ggtgagccag ggtaaggcta aagtgtctgt   2760
tcacaagtgt atgttggaga gatgcacctt gggcatttcc agtgagggct tcctccacgc   2820
cagcgacaac gtggcttctg acaacggctg cgcctttctt atcaagggag ggggtcgcat   2880
```

-continued

```
ctgtcacaac atgatatgcg gccctgggga tgtcccccca aagccttacc agatggttac   2940
ctgcacagat ggcaaggtgc gcatgctcaa gcctgtgcac attgtgggcc accggcgcca   3000
ccgctggcca gagtttgaac acaatgtgat gacccgctgt agcttgtacc tgggaggcag   3060
gcgaggagtt ttcttgccca gacagtgtaa cctggcccac tgcaacgtga tcatggaaca   3120
atccgccgct acccaggttt gctttggagg aatatttgat ataagcatgg tggtgtataa   3180
gatcctgcgc tacgacgact gtcgggctcg tactcgaacc tgcgactgcg gagcctctca   3240
cctgtgtaac ctgactgtga tggggatggt gactgaggag gtgcgactgg accactgtca   3300
gcactcttgc ctgcgggagg agttttcttc ctcggacgag gaggactagg taggtggttg   3360
gggcgtggcc agcgagaggg tgggctataa aggggaggtg tcggctgacg ctgtcttctg   3420
tttttcaggt accatgagcg gatcaagcag ccagaccgcg ctgagcttcg acggggccgt   3480
gtacagcccc tttctgacgg ggcgcttgcc tgcctgggcc ggagtgcgtc agaatgttac   3540
cggttcgacc gtggacggac gtcccgtgga tccatctaac gctgcttcta tgcgctacgc   3600
tactatcagc acatctactc tggacagcgc cgctgccgcc gcagccgcca cctcagccgc   3660
tctctccgcc gccaagatca tggctattaa cccaagcctt tacagccctg tatccgtgga   3720
cacctcagcc ctggagcttt accggcgaga tctagctcaa gtggtggacc aactcgcagc   3780
cgtgagccaa cagttgcagc tggtgtcgac ccgagtggag caactttccc gccctcccca   3840
gtaaccgcaa aaattcaata aacagaattt aataaacagc acttgagaaa agtttaaact   3900
tgtggttgac tttattcctg gatagctggg gggagggaac ggcgggaacg gtaagacctg   3960
gtccatcgtt cccggtcgtt gagaacacgg tggatttttt ccaagacccg atagaggtgg   4020
gtctgaacgt tgagatacat gggcatgagc ccgtctcggg ggtggaggta ggcccactgc   4080
agggcctcgt tttcaggggt ggtgttgtaa atgatccagt cgtaggcccc ccgctgggcg   4140
tggtgctgga agatgtcctt cagcagcaag ctgatggcaa cgggaagacc cttggtgtag   4200
gtgttgacaa agcggttgag ttgggagggg tgcatgcggg gactgatgag gtgcattttg   4260
gcctggatct tgaggttggc tatgttgccg cccagatcgc gcctgggatt catgttatgc   4320
aagaccacca gcaccgagta accggtgcag cgggggaatt tgtcgtgcag cttggaaggg   4380
aaagcgtgga agaatttgga gacccctcgg tgcccgccta ggttttccat gcactcatcc   4440
atgatgatgg cgatgggccc ccgggaggca gcctgggcaa aaacgttgcg gggggtccgtg   4500
acatcgtagt tgtggtcctg ggtgagttca tcataggaca ttttgacaaa gcgcgggcag   4560
agggtcccag actggggaat gatggttcca tccggtccgg gggcgtagtt gccctcgcag   4620
atttgcattt cccaggcttt gatttcagag ggagggatca tgtcaacctg gggggcgatg   4680
aaaaaaatgg tctctggggc gggggtgatg agctgggtgg aaagcaggtt gcgcaagagc   4740
tgtgacttgc cgcagccggt gggcccgtag atgacagcta tgacgggttg cagggtgtag   4800
tttagagagc tacaactgcc atcatccttc aaaagcgggg ccacactgtt taaaagttct   4860
ctaacatgta agttttcccg cactaagtcc tgcaggagac gtgaccctcc tagggagaga   4920
agttcaggaa gcgaagcaaa gtttttaagt ggcttgaggc catcggccaa gggcaagttc   4980
ctgagagttt gactgagcag ttccagccgg tcccagagct cggttacgtg ctctacggca   5040
tctcgatcca gcagacctcc tcgtttcggg ggttggggcg gctctggctg tagggaatga   5100
ggcggtgggc gtccagctgg gccatggtgc ggtccctcca tgggcgcagg gttctcttca   5160
gggtggtctc ggtcacggtg aatgggtggg ccccgggctg ggcgctggcc agggtgcgct   5220
```

-continued

```
tgaggctgag gcggctggtg gcgaaccgtt gcttttcgtc tccctgcaag tcagccaaat   5280
agcaacggac catgagctca tagtccaggc tctctgcggc atgtcctttg gcgcgaagct   5340
tgcctttgga aacgtgcccg cagtttgagc agagcaagca ttttagcgcg tagagttttg   5400
gcgccaagaa cacggattcc ggggaataag catccccacc gcagttggag caaacggttt   5460
cgcattccac cagccaggtc agctgaggat cttttgggtc aaaaaccaag cgcccgccgt   5520
tttttttgat gcgcttccta cctcgggtct ccatgaggcg gtgcccgcgt tcggtgacga   5580
agaggctgtc ggtgtctccg tagacggagg tcagggcgcg ctcctccagg ggggtcccgc   5640
ggtcctcggc gtagagaaac tcgcaccact ctgacataaa cgcccgggtc caggctagga   5700
cgaatgaggc gatgtgggaa gggtaccggt cgttatcgat gagggggtcg gtttttttcca   5760
aggtgtgcag gcacatgtcc ccctcgtccg cttccaaaaa tgtgattggc ttgtaggtgt   5820
aagtcacgtg atcctgtcct tccgcggggg tataaaaggg ggcgtttccc ccctcctcgt   5880
cactctcttc cggttcgctg tcgccaaagg ccagctgttg gggtacgtaa acgcgggtga   5940
aggcgggcat gacctgtgcg ctgaggttgt cagtttctat atacgaggaa gatttgatgg   6000
cgagcgcccc cgtggagatg cccttgaggt gctcggggcc catttggtca gaaaacacaa   6060
tctgtcggtt atcaagcttg gtggcaaaag acccgtagag ggcgttggag agcaacttgg   6120
cgatggagcg ctgggtttgg tttttttccc ggtcggcttt ttccttggcc gcgatgttga   6180
gctggacgta ctccctggcc acgcacttcc agccgggaaa aacggccgtg cgctcgtccg   6240
gcaccagcct cacgctccat ccgcggttgt gcagggtgat gacgtcgatg ctggtggcca   6300
cctctccgcg caggggctcg ttggtccagc agaggcgacc gcccttgcga gagcagaagg   6360
ggggcagggg gtcaagcagg cgctcgtccg gggggtcggc gtcgatggta aagatggcgg   6420
gcagcaggtg tttgtcaaag taatcgatct gatgcccggg gcaacgcagg gcggtttccc   6480
agtcccgcac cgccaaggcg cgctcgtatg gactgagggg ggcgccccag ggcatgggat   6540
gcgtcagggc cgaggcgtac atgccgcaga tgtcatagac gtaaaggggc tcctccagga   6600
cgccgaggta ggtggggtag cagcgccccc cgcggatgct ggcccgtacg tagtcgtaga   6660
gctcgtgcga gggggccaga aggtggcggc tgaggtgagc gcgctggggc ttttcatctc   6720
ggaagaggat ctgcctgaag atggcgtggg agttggagga gatggtgggc cgctgaaaaa   6780
tgttgaagcg ggcgtcgggc agacccacgg cctcgccgat aaagtgggcg taggactctt   6840
gcagcttttc caccagggag gcggtgacca gcacgtccag agcgcagtag tccagggttt   6900
cccgcacgat gtcataatgc tcttcctttt tttccttcca gaggtctcgg ttgaagagat   6960
actcttcgcg gtctttccag tactcttgga gaggaaaccc gttttcgtct ccacggtaag   7020
agcccaacat gtaaaactgg ttgacggcct gatagggaca gcatcccttc tccacgggca   7080
gcgagtaggc cagggcggcc ttgcgcaggg aggtgtgagt cagggcaaag gtgtcgcgga   7140
ccataacttt tacaaactgg tacttaaagt cccggtcgtc gcacatgcct cgctcccagt   7200
ctgagtagtc tgtgcgcttt ttgtgcttgg ggttaggcag ggagtaggtg acgtcgttaa   7260
agaggatttt gccacatctg ggcataaagt tgcgagagat tctgaagggg ccgggcacct   7320
ccgagcggtt gttgatgact tgggcagcca ggagaatttc gtcgaagccg ttgatgttgt   7380
gccccacgac gtagaactct atgaaacgcg gagcgccgcg cagcaggggg cacttttcaa   7440
gttgctggaa agtaagttcc cgcggctcga cgccgtgttc cgtgcggctc cagtcctcca   7500
ccgggtttcg ctccacaaaa tcctgccaga tgtggtcgac tagcaagagc tgcagtcggt   7560
cgcgaaattc gcggaatttt ctgccgatgg cttgcttctg gggttcaag caaaaaaagg   7620
```

-continued

```
tgtctgcgtg gtcgcgccag gcgtcccagc cgagctcgcg agccagattc agggccagca   7680
gcaccagagc cggctcaccg gtgattttca tgacgaggag aaagggcacc agctgttttc   7740
cgaacgcgcc catccaggtg taggtctcca cgtcgtaggt gagaaacaga cgttcggtcc   7800
gcgggtgcga tcccaggggg aaaaacttga tgggctgcca ccattgggag ctctgggcgt   7860
ggatgtgatg gaagtaaaag tcccggcggc gcgtggaaca ttcgtgctgg tttttgtaaa   7920
agcggccgca gtggtcgcag cgcgagacgg agtgaaggct gtgaatcagg tgaatcttgc   7980
gtcgctgagg gggccccaga gccaaaaagc ggagcgggaa cgaccgcgcg gccacttcgg   8040
cgtccgcagg caagatggat gagggttcca ccgttccccg cccgcggacc gaccagactt   8100
ccgccagctg cggcttcagt tcttgcacca gctctcgcag cgtttcgtcg ctgggcgaat   8160
cgtgaatacg gaagttgtcg ggtagaggcg ggaggcggtg gacttccagg aggtgtgtga   8220
gggccggcag gagatgcagg tggtacttga tttcccacgg atgacggtcg cgggcgtcca   8280
aggcgaagag atgaccgtgg ggccgcggcg ccaccagcgt tccgcggggg gtctttatcg   8340
gcggcgggga cgggctcccg gcggcagcgg cggctcggga cccgcgggca agtcgggcag   8400
cggcacgtcg gcgtggagct cgggcagggg ctggtgctgc gcgcggagct gactggcaaa   8460
ggctatcacc cggcgattga cgtcctggat ccggcggcgc tgcgtgaaga ccaccggacc   8520
cgtggtcttg aacctgaaag agagttcgac agaatcaatc tcggcatcgt taaccgcggc   8580
ctggcgcagg atttcggcca cgtccccgga gttgtcttga tacgcgattt ctgccatgaa   8640
ctggtcgatt tcctcttcct gcaagtctcc gtgaccggcg cgttcgacgg tggccgcgag   8700
atcgttggag atgcggccca tgagctggga aaaggcattg atgccgacct cgttccacac   8760
tcggctgtac accacctctc cgtgaacgtc gcgggcgcgc atcaccacct gggcgagatt   8820
gagttccacg tggcgggcga aaaccggata gtttcggagg cgctgataca gatagttgag   8880
ggtggtggcg gcgtgctcgg ccacaaaaaa atacatgatc cagcggcgga gggtcagctc   8940
gttgatgtcg cccagcgcct ccaggcgttc catggcctcg taaaagtcca cggcaaagtt   9000
gaaaaattgg ctgttcctgg ccgagaccgt gagctcttct tccaagagcc gaatgagatc   9060
cgccacggtg gccctgactt cgcgttcgaa agccccgggt gcctcctcca cctcttcctc   9120
ctcgacttct tcgaccgctt cgggcacctc ctcttcctcg accaccacct caggcggggc   9180
tcggcggcgc cggcggcgga cgggcaggcg gtcgacgaaa cgctcgatca tttcccccct   9240
ccgtcgacgc atggtctcgg tgacggcgcg accctgttcg cgaggacgca gggtgaaggc   9300
gccgccgccg agcggaggta acagggagat cgggggcgg tcgtggggga gactgacggc   9360
gctaactatg catctgatca atgtttgcgt agtgacctcg ggtcggagcg agctcagcgc   9420
ttgaaaatcc acgggatcgg aaaaccgttc caggaacgcg tctagccaat cacagtcgca   9480
aggtaagctg aggaccgtct cgggggcttg tctgttctgt cttcccgcgg tggtgctgct   9540
gatgaggtag ttgaagtagg cgctcttgag gcggcggatg gtggacagga gaaccacgtc   9600
tttgcgccca gcttgctgta tccgcaggcg gtcggccatg ccccacactt ctccttgaca   9660
gcggcggagg tccttgtagt attcttgcat cagcctttcc acgggcacct cgtcttcttc   9720
ttccgctcgg ccggacgaga gccgcgtcag gccgtacccg cgctgcccct gtggttggag   9780
cagggccagg tcggccacga cgcgctcggc cagcacggcc tgctggatgc gggtgagggt   9840
gtcctgaaag tcgtcgagat ccacaaagcg gtggtacgcg ccagtgttga tggtgtaggt   9900
gcagttgctc atgacggacc agtttacggt ctgggtgcca tggcccacgg tttccaggta   9960
```

-continued gcggagacgc gagtaggccc gcgtctcgaa gatgtagtcg ttgcaggtcc gcagcaggta 10020
ctggtagccc accagcagat gcggcggcgg ctggcggtag aggggccacc gctgggtggc 10080
gggggcgttg gggcgagat cttccaacat gaggcggtga tagccgtaga tgtagcgcga 10140
catccaagtg atgccgctgg ccgtggtgct ggcgcgggcg tagtcgcgaa cgcggttcca 10200
gatgtttcgc agcggctgga agtactcgat ggtggggcga ctctgccccg tgaggcgggc 10260
gcagtcggcg atgctctacg gggaaaaaga agggccagtg aacaaccgcc ttccgtagcc 10320
ggaggagaac gcaagggggt caaagaccac cgaggctcgg gttcgaaacc cgggtggcgg 10380
cccgaatacg gagggcggtt ttttgctttt ttctcagatg catcccgtgc tgcggcagat 10440
gcgtccgaac gcggggtccc agtccccggc ggtgcctgcg gccgtgacgg cggcttctac 10500
ggccacgtcg cgctccaccc cgcctaccac ggcccaggcg gcggtggctc tgcgcggcgc 10560
aggggaaccc gaagcagagg cggtgttgga cgtggaggag ggccaggggt tggctcggct 10620
gggggccctg agtcccgagc ggcacccgcg cgtggctctg aagcgcgacg cggcggaggc 10680
gtacgtgccg cggagcaatc tgtttcgcga ccgcagcggc gaggaggccg aggagatgcg 10740
agacttgcgt tttcgggcgg ggagggagtt gcgtcacggg ctggaccggc agagggttct 10800
gagagaggag gactttgagg cggacgagcg cacgggggtg agtcccgcgc gggctcacgt 10860
ggcggccgcc aacctggtga gcgcgtacga gcagacggtc aaggaggaga tgaacttcca 10920
gaagagcttc aatcatcacg tgcgcacgct gattgcgcgc gaagaggtgg ccatcggcct 10980
catgcatctg tgggattttg tggaggcgta cgttcagaac cccagcagca agccgctgac 11040
ggctcagctg ttcctcatcg tgcaacatag tcgagacaac gaaacgttca gggaggccat 11100
gctgaacatt gcagagcctg aggggcgctg gctcttggat ctcattaaca tcttgcagag 11160
tatcgtagtg caggagcgct cgctgagcct ggccgacaag gtggctgcca tcaactacag 11220
catgctgtcg ctgggcaaat tttacgcccg caagatctac aagtctccgt tcgtccccat 11280
agacaaggag gtgaagatag acagctttta catgcgcatg gcgctcaagg tgctgactct 11340
aagcgacgac ctggggggtgt accgcaacga ccgcatacac aaggcggtga gcgccagccg 11400
ccggcgcgag ctgagcgacc gcgagctttt gcacagcctg catcgggcgt tgactggtgc 11460
cggcagcgcc gaggcggccg agtactttga cgcccggagcg gacttgcgct ggcagccatc 11520
ccgacgcgcg ctggaggcgg ctggcgtcgg ggagtacggg gtcgaggacg acgatgaagc 11580
ggacgacgag ttgggcattg acttgtagcc gtttttcgtt agatatgtcg gcgaacgagc 11640
cgtctgcggc cgccatggtg acggcggcgg gcgcgcccca ggacccggcc acgcgcgcgg 11700
cgctgcagag tcagccttcc ggagtgacgc ccgcggacga ctggtccgag gccatgcgtc 11760
gcatcctggc gctgacggcg cgcaaccccg aggcttttcg gcagcagccg caggcaaacc 11820
ggtttgcggc cattttggaa gcggtggtgc cctccagacc caaccccacc cacgaaaagg 11880
tgctggccat cgtcaacgcc ctggcggaga ccaaggccat ccgcccagac gaggccgggc 11940
aggtttacaa cgcgctgcta gaaagggtgg gacgctacaa cagctccaac gtgcagacca 12000
atctggaccg cttggtgacg gacgtgaagg aggccgtagc ccagcgagag cggtttttca 12060
aggaagccaa tctgggctcg ctggtggccc tcaacgcctt cctgagcacg ctgccggcga 12120
acgtgccccg cggtcaggag gactacgtga actttctgag cgccctccgc ctgatggtgg 12180
ccgaggtgcc gcagagcgag gtgtaccagt ctggccccaa ctactacttc cagacctccc 12240
ggcagggcct gcagacggta aacctgacgc aggcctttca gaacctgcag ggcctttggg 12300
gggtgcgcgc tccgctgggc gaccgcagca cggtgtccag cctgctgacc cccaatgccc 12360

-continued

```
ggctgctctt gcttctcatt gctccgttca ccgacagcgg ttccatcagc cgcgactctt  12420

acctgggaca cctgctcacc ctgtaccggg aggccatcgg gcaggcgcgg gtggacgagc  12480

agacgtacca ggaaatcacc agcgtgagcc gcgcgctggg gcaggaggac acgggcagct  12540

tggaggcgac tctgaacttc ctgctgacca accggcggca gcgcctacct ccccagtacg  12600

cgctgaacgc ggaggaggag cgcatcctgc gtttcgtgca gcagagcacc gcgctgtact  12660

tgatgcggga aggcgcctct cccagcgctt cgctggacat gacggcggcc aacatggagc  12720

catcgttcta cgccgccaac cgtcccttcg tcaaccggct aatggactat ttgcatcggg  12780

cggcggccct gaacccggaa tactttacta acgtcatcct gaacgaccgt tggctgccac  12840

ctcccggctt ctacacgggg gagttcgacc tcccggaggc caacgacggt ttcatgtggg  12900

acgacgtgga cagcgtgttc ctgcccggca agaaggaggc gggtgactct cagagccacc  12960

gcgcgagcct cgcagacctg ggggcgaccg ggcccgcgtc tccgctgcct cgcctgccga  13020

gcgccagcag cgccagcgtg gggcgggtga gccgtccgcg cctcagcggt gaggaggact  13080

ggtggaacga tccgctgctc cgtccggccc gcaacaaaaa cttccccaac aacgggatag  13140

aggatttggt agacaaaatg aaccgttgga agacgtatgc ccaggagcat cgggagtggc  13200

aggcgaggca acccatgggc cctgttctgc cgccctctcg gcgcccgcgc agggacgaag  13260

acgccgacga ttcagccgat gacagcagcg tgttggatct gggcgggagc gggaacccct  13320

ttgcccacct gcaacctcgc ggcgtgggtc ggcggtggcg ctaggaaaaa aaattattaa  13380

aagcacttac cagagccatg gtaagaagag caacaaaggt gtgtcctgct ttcttcccgg  13440

tagcaaa atg cgt cgg gcg gtg gca gtt ccc tcc gcg gca atg gcg tta    13489
        Met Arg Arg Ala Val Ala Val Pro Ser Ala Ala Met Ala Leu
        1               5                   10

ggc ccg ccc cct tct tac gaa agc gtg atg gca gcg gcc acc ctg caa    13537
Gly Pro Pro Pro Ser Tyr Glu Ser Val Met Ala Ala Ala Thr Leu Gln
15                  20                  25                  30

gcg ccg ttg gag aat cct tac gtg ccg ccg cga tac ctg gag cct acg    13585
Ala Pro Leu Glu Asn Pro Tyr Val Pro Pro Arg Tyr Leu Glu Pro Thr
                35                  40                  45

ggc ggg aga aac agc att cgt tac tcg gag ctg acg ccc ctg tac gac    13633
Gly Gly Arg Asn Ser Ile Arg Tyr Ser Glu Leu Thr Pro Leu Tyr Asp
            50                  55                  60

acc acc cgc ctg tac ctg gtg gac aac aag tca gca gat atc gcc acc    13681
Thr Thr Arg Leu Tyr Leu Val Asp Asn Lys Ser Ala Asp Ile Ala Thr
        65                  70                  75

ttg aac tac cag aac gac cac agc aac ttt ctc acg tcc gtg gtg cag    13729
Leu Asn Tyr Gln Asn Asp His Ser Asn Phe Leu Thr Ser Val Val Gln
    80                  85                  90

aac agc gac tac acg ccc gcc gaa gcg agc acg cag acc att aac ttg    13777
Asn Ser Asp Tyr Thr Pro Ala Glu Ala Ser Thr Gln Thr Ile Asn Leu
95                  100                 105                 110

gac gac cgc tcg cgc tgg ggc ggg gac ttg aaa acc att ctg cac act    13825
Asp Asp Arg Ser Arg Trp Gly Gly Asp Leu Lys Thr Ile Leu His Thr
                115                 120                 125

aac atg ccc aac gtg aac gag ttc atg ttt acc aac tcg ttc agg gct    13873
Asn Met Pro Asn Val Asn Glu Phe Met Phe Thr Asn Ser Phe Arg Ala
            130                 135                 140

aaa ctt atg gtg gcg cac gag gcc gac aag gac ccg gtt tat gag tgg    13921
Lys Leu Met Val Ala His Glu Ala Asp Lys Asp Pro Val Tyr Glu Trp
        145                 150                 155

gtg cag ctg acg ctg ccg gag ggg aac ttt tca gag att atg acc ata    13969
Val Gln Leu Thr Leu Pro Glu Gly Asn Phe Ser Glu Ile Met Thr Ile
```

-continued

```
    160                 165                 170

gac ctg atg aac aac gcc att atc gac cac tac ctg gcg gta gcc aga     14017
Asp Leu Met Asn Asn Ala Ile Ile Asp His Tyr Leu Ala Val Ala Arg
175                 180                 185                 190

cag cag ggg gtg aaa gaa agc gag atc ggc gtc aag ttt gac acg cgc     14065
Gln Gln Gly Val Lys Glu Ser Glu Ile Gly Val Lys Phe Asp Thr Arg
                195                 200                 205

aac ttt cgt ctg ggc tgg gac ccg gag acg ggg ctt gtg atg ccg ggg     14113
Asn Phe Arg Leu Gly Trp Asp Pro Glu Thr Gly Leu Val Met Pro Gly
            210                 215                 220

gtg tac acg aac gaa gct ttc cat ccc gac gtg gtc ctc ttg ccg ggc     14161
Val Tyr Thr Asn Glu Ala Phe His Pro Asp Val Val Leu Leu Pro Gly
        225                 230                 235

tgc ggg gtg gac ttt acc tac agc cgg tta aac aac ctg cta ggc ata     14209
Cys Gly Val Asp Phe Thr Tyr Ser Arg Leu Asn Asn Leu Leu Gly Ile
    240                 245                 250

cgc aag aga atg ccc ttt cag gaa ggg ttt cag atc ctg tac gag gac     14257
Arg Lys Arg Met Pro Phe Gln Glu Gly Phe Gln Ile Leu Tyr Glu Asp
255                 260                 265                 270

ctg gag ggc ggt aac atc ccg gcc ctg ctg gac gtg ccg gcg tac gag     14305
Leu Glu Gly Gly Asn Ile Pro Ala Leu Leu Asp Val Pro Ala Tyr Glu
                275                 280                 285

gag agc atc gcc aac gca agg gag gcg gcg atc agg ggc gat aat ttc     14353
Glu Ser Ile Ala Asn Ala Arg Glu Ala Ala Ile Arg Gly Asp Asn Phe
            290                 295                 300

gcg gcg cag ccc cag gcg gct cca acc ata aaa ccc gtt ttg gaa gac     14401
Ala Ala Gln Pro Gln Ala Ala Pro Thr Ile Lys Pro Val Leu Glu Asp
        305                 310                 315

tcc aaa ggg cgg agc tac aac gta ata gcc aac acc aac aac acg gct     14449
Ser Lys Gly Arg Ser Tyr Asn Val Ile Ala Asn Thr Asn Asn Thr Ala
    320                 325                 330

tac agg agc tgg tat ctg gct tat aac tac ggc gac ccg gag aag ggg     14497
Tyr Arg Ser Trp Tyr Leu Ala Tyr Asn Tyr Gly Asp Pro Glu Lys Gly
335                 340                 345                 350

gtt agg gcc tgg acc ctg ctc acc act ccg gac gtg acg tgc ggt tca     14545
Val Arg Ala Trp Thr Leu Leu Thr Thr Pro Asp Val Thr Cys Gly Ser
                355                 360                 365

gag cag gtc tac tgg tcg ctg cct gac atg tac gtg gac cct gtg acg     14593
Glu Gln Val Tyr Trp Ser Leu Pro Asp Met Tyr Val Asp Pro Val Thr
            370                 375                 380

ttt cgc tcc acg cag caa gtt agc aac tac cca gtg gtg gga gcg gag     14641
Phe Arg Ser Thr Gln Gln Val Ser Asn Tyr Pro Val Val Gly Ala Glu
        385                 390                 395

ctt atg ccg att cac agc aag agc ttt tac aac gag cag gcc gtc tac     14689
Leu Met Pro Ile His Ser Lys Ser Phe Tyr Asn Glu Gln Ala Val Tyr
    400                 405                 410

tca cag ctc att cgt cag acc acc gcc cta acg cac gtt ttc aac cgc     14737
Ser Gln Leu Ile Arg Gln Thr Thr Ala Leu Thr His Val Phe Asn Arg
415                 420                 425                 430

ttc ccc gag aac caa atc cta gtg cga cct cca gcg ccc acc atc acc     14785
Phe Pro Glu Asn Gln Ile Leu Val Arg Pro Pro Ala Pro Thr Ile Thr
                435                 440                 445

acc gtc agc gag aac gtg ccc gct cta acc gat cac ggg acg ctg cct     14833
Thr Val Ser Glu Asn Val Pro Ala Leu Thr Asp His Gly Thr Leu Pro
            450                 455                 460

ttg cag aac agc atc cgc gga gtt cag cga gtt acc atc acg gac gcc     14881
Leu Gln Asn Ser Ile Arg Gly Val Gln Arg Val Thr Ile Thr Asp Ala
        465                 470                 475

cgt cgt cgg acc tgt ccc tac gtc tac aaa gcc ttg gga atc gtg gcc     14929
```

-continued

```
Arg Arg Arg Thr Cys Pro Tyr Val Tyr Lys Ala Leu Gly Ile Val Ala
    480                 485                 490

ccg cgc gtc ctg tcg agt cgc act ttc tag atgtccatcc tcatctctcc      14979
Pro Arg Val Leu Ser Ser Arg Thr Phe
495                 500

cagcaacaat accggttggg gtctgggcgt gaccaaaatg tacggaggcg ccaaacgacg  15039

gtccccacaa catcccgtgc gagtgcgcgg gcactttaga gccccatggg ggtcgcacac  15099

gcgcgggcgc accggccgaa ccaccgtcga cgacgtgatc gatagcgtgg tggccgacgc  15159

ccgcaactac cagcccgctc gatccacggt ggacgaagtc atcgacggcg tggtggccga  15219

cgccagggcc tacgcccgca gaaagtctcg tctgcgccgc cgccgttcgc taaagcgccc  15279

cacggccgcc atgaaagccg ctcgctctct gctgcgtcgc gcacgtatcg tgggtcgccg  15339

cgccgccaga cgcgcagccg ccaacgccgc cgccggccga gtgcgccgcc gggccgccca  15399

gcaggccgcc gccgccatct ccagtctatc cgcccccccga cgcgggaatg tgtactgggt  15459

cagggactcg gccaccggcg tgcgagttcc cgtgagaacc cgtcctcctc gtccctgaat  15519

aaaaagttct aagcccaatc ggtgttccgt tgtgtgttca gctcgtcatg accaaacgca  15579

agtttaaaga ggagctgctg caagcgctgg tccccgaaat ctatgcgccg gcgccggacg  15639

tgaaaccgcg tcgcgtgaaa cgcgtgaaga agcaggaaaa gctagagaca aaagaggagg  15699

cggtggcgtt gggagacggg gaggtggagt ttgtgcgctc gttcgcgccg cgtcggcgag  15759

tgaattggaa ggggcgcaag gtgcaacggg tgctgcgtcc cggcacggtg gtgtctttca  15819

ccccgggtga aaaatccgcc tggaagggca taaagcgcgt gtacgatgag gtgtacgggg  15879

acgaagacat tctggagcag gcgctggata gaagcgggga gtttgcttac ggcaagaggg  15939

cgaggacggg cgagatcgcc atcccgctgg acacttccaa ccccaccccc agtctgaaac  15999

ccgtgacgct gcaacaggtg ttgccggtga gcgccccctc gcgacgcggc ataaaacgcg  16059

agggcggcga gctgcagccc accatgcagc tcctggttcc caagaggcag aaactagagg  16119

acgtactgga catgataaaa atggagcccg acgtgcagcc cgatattaaa atccgtccca  16179

tcaaagaagt ggcgccggga atgggcgtgc agaccgtgga catccagatt cccatgacca  16239

gcgccgcaca ggcggtagag gccatgcaga ccgacgtggg gatgatgacg gacctgcccg  16299

cagctgctgc cgccgtggcc agcgccgcga cgcaaacgga agccggcatg cagaccgacc  16359

cgtggacgga ggcgcccgtg cagccggcca gaagacgcgt cagacggacg tacggccccg  16419

tttctggcat aatgccggag tacgcgctgc atccttccat catccccacc cccggctacc  16479

gggggcgcac ctaccgtccg cgacgcagca ccactcgccg ccgtcgccgc acggcacgag  16539

tcgccaccgc cagagtgaga cgcgtaacga cacgtcgcgg ccgccgcttg accctgcccg  16599

tggtgcgcta ccatcccagc attctttaaa aaaccgctcc tacgttgcag atgggcaagc  16659

ttacttgtcg actccgtatg gccgtgcccg gctaccgagg aagatcccgc cgacgacgga  16719

ctttgggagg cagcggtttg cgccgccgtc gggcggttca ccggcgcctc aagggaggca  16779

ttctgccggc cctgatcccc ataatcgccg cagccatcgg ggccattccc ggaatcgcca  16839

gcgtagcggt gcaggctagc cagcgccact gattttacta accctgtcgg tcgcgccgtc  16899

tctttcggca gactcaacgc ccagcatgga agacatcaat ttctcctctc tggccccgcg  16959

gcacggcacg cggccgtata tggggacgtg gagcgagatc ggcacgaacc agatgaacgg  17019

gggcgctttc aattggagcg gtgtgtggag cggcttgaaa aatttcggtt ccactctgaa  17079

aacttacggc aaccgggtgt ggaactccag cacggggcag atgctgaggg acaagctaaa  17139
```

-continued

```
ggacacgcag tttcagcaaa aggtggtgga cggcatcgct tcgggcctca acggcgccgt  17199

cgacctggcc aaccaggcca ttcaaaagga aattaacagc cgcctggagc cgcggccgca  17259

ggtggaggag aacctgcccc ctctggaggc gctgcccccc aagggagaga agcgcccgcg  17319

gcccgacatg gaggagacgc tagttactaa gagcgaggag ccgccatcat acgaggaggc  17379

ggtgggtagc tcgcagctgc cgtccctcac gctgaagccc accacctatc ccatgaccaa  17439

gcccatcgcc tccatggcgc gccccgtggg agtcgacccg cccatcgacg cggtggccac  17499

tttggacctg ccgcgccccg aacccggcaa ccgcgtgcct cccgtcccca tcgctccgcc  17559

ggtttctcgc cccgccatcc gccccgtcgc cgtggccact ccccgctatc cgagccgcaa  17619

cgccaactgg cagaccaccc tcaacagtat tgtcggactg gggggtgaagt ctctgaagcg  17679

ccgtcgctgt ttttaaagca caatttatta aacgagtagc cctgtcttaa tccatcgttg  17739

tatgtgtgcc tatatcacgc gttcagagcc tgaccgtccg tcaag atg gcc act ccg  17796
                                                  Met Ala Thr Pro
                                                      505

tcg atg atg ccg cag tgg tcg tac atg cac atc gcc ggg cag gac gcc    17844
Ser Met Met Pro Gln Trp Ser Tyr Met His Ile Ala Gly Gln Asp Ala
        510                 515                 520

tcg gag tac ctg agc ccg ggt ctg gtg cag ttt gcc cgt gcg acg gaa    17892
Ser Glu Tyr Leu Ser Pro Gly Leu Val Gln Phe Ala Arg Ala Thr Glu
    525                 530                 535

acc tac ttc tca ctg ggc aac aag ttc agg aac ccc acc gtg gcg ccc    17940
Thr Tyr Phe Ser Leu Gly Asn Lys Phe Arg Asn Pro Thr Val Ala Pro
540                 545                 550                 555

acc cac gac gtc acc acc gat cgg tcc cag cga ctg aca atc cgc ttc    17988
Thr His Asp Val Thr Thr Asp Arg Ser Gln Arg Leu Thr Ile Arg Phe
                560                 565                 570

gtc ccc gtg gac aag gaa gac acc gct tac tcc tac aaa acc cgc ttc    18036
Val Pro Val Asp Lys Glu Asp Thr Ala Tyr Ser Tyr Lys Thr Arg Phe
            575                 580                 585

acg ctg gcc gtg ggc gac aac cgg gtg cta gac atg gcc agt acc tac    18084
Thr Leu Ala Val Gly Asp Asn Arg Val Leu Asp Met Ala Ser Thr Tyr
        590                 595                 600

ttt gac atc cgc ggc gtg atc gac cgc gga cct agc ttc aag cct tac    18132
Phe Asp Ile Arg Gly Val Ile Asp Arg Gly Pro Ser Phe Lys Pro Tyr
    605                 610                 615

tcc ggc acg gct tac aac tca ctg gct ccc aaa ggg gcg ccc aac aac    18180
Ser Gly Thr Ala Tyr Asn Ser Leu Ala Pro Lys Gly Ala Pro Asn Asn
620                 625                 630                 635

agc caa tgg aac gcc aca gat aac ggg aac aag cca gtg tgt ttt gct    18228
Ser Gln Trp Asn Ala Thr Asp Asn Gly Asn Lys Pro Val Cys Phe Ala
                640                 645                 650

cag gca gct ttt ata ggt caa agc att aca aaa gac gga gtg caa ata    18276
Gln Ala Ala Phe Ile Gly Gln Ser Ile Thr Lys Asp Gly Val Gln Ile
            655                 660                 665

cag aac tca gaa aat caa cag gct gct gcc gac aaa act tac caa cca    18324
Gln Asn Ser Glu Asn Gln Gln Ala Ala Ala Asp Lys Thr Tyr Gln Pro
        670                 675                 680

gag cct caa att gga gtt tcc acc tgg gat acc aac gtt acc agt aac    18372
Glu Pro Gln Ile Gly Val Ser Thr Trp Asp Thr Asn Val Thr Ser Asn
    685                 690                 695

gct gcc gga cga gtg tta aaa gcc acc act ccc atg ctg cca tgt tac    18420
Ala Ala Gly Arg Val Leu Lys Ala Thr Thr Pro Met Leu Pro Cys Tyr
700                 705                 710                 715

ggt tca tat gcc aat ccc act aat cca aac ggg ggt cag gca aaa aca    18468
Gly Ser Tyr Ala Asn Pro Thr Asn Pro Asn Gly Gly Gln Ala Lys Thr
                720                 725                 730
```

-continued

```
gaa gga gac att tcg cta aac ttt ttc aca aca act gcg gca gca gac    18516
Glu Gly Asp Ile Ser Leu Asn Phe Phe Thr Thr Thr Ala Ala Ala Asp
            735                 740                 745

aat aat ccc aaa gtg gtt ctt tac agc gaa gat gta aac ctt caa gcc    18564
Asn Asn Pro Lys Val Val Leu Tyr Ser Glu Asp Val Asn Leu Gln Ala
        750                 755                 760

ccc gat act cac tta gta tat aag cca acg gtg gga gaa aac gtt atc    18612
Pro Asp Thr His Leu Val Tyr Lys Pro Thr Val Gly Glu Asn Val Ile
    765                 770                 775

gcc gca gaa gcc ctg cta acg cag cag gcg tgt ccc aac aga gca aac    18660
Ala Ala Glu Ala Leu Leu Thr Gln Gln Ala Cys Pro Asn Arg Ala Asn
780                 785                 790                 795

tac ata ggt ttc cga gat aac ttt atc ggt tta atg tat tat aac agc    18708
Tyr Ile Gly Phe Arg Asp Asn Phe Ile Gly Leu Met Tyr Tyr Asn Ser
                800                 805                 810

aca ggg aac atg gga gtt ctg gca ggt cag gcc tcg cag tta aac gca    18756
Thr Gly Asn Met Gly Val Leu Ala Gly Gln Ala Ser Gln Leu Asn Ala
            815                 820                 825

gtt gta gac ctg caa gat cga aac acg gaa ctg tcc tat cag cta atg    18804
Val Val Asp Leu Gln Asp Arg Asn Thr Glu Leu Ser Tyr Gln Leu Met
        830                 835                 840

cta gat gct ctg ggt gac aga act cga tat ttc tca atg tgg aat cag    18852
Leu Asp Ala Leu Gly Asp Arg Thr Arg Tyr Phe Ser Met Trp Asn Gln
    845                 850                 855

gcc gtg gac agc tac gat cca gac gtt agg att atc gag aac cat ggg    18900
Ala Val Asp Ser Tyr Asp Pro Asp Val Arg Ile Ile Glu Asn His Gly
860                 865                 870                 875

gtg gaa gac gag ctg ccc aat tac tgt ttt cca ctc cca ggc atg ggt    18948
Val Glu Asp Glu Leu Pro Asn Tyr Cys Phe Pro Leu Pro Gly Met Gly
                880                 885                 890

att ttt aac tcc tac aag ggg gta aaa cca caa aat ggc ggt aat ggt    18996
Ile Phe Asn Ser Tyr Lys Gly Val Lys Pro Gln Asn Gly Gly Asn Gly
            895                 900                 905

aac tgg gaa gca aac ggg gac cta tca aat gcc aat gag atc gct tta    19044
Asn Trp Glu Ala Asn Gly Asp Leu Ser Asn Ala Asn Glu Ile Ala Leu
        910                 915                 920

gga aac att ttt gcc atg gaa att aac ctc cac gca aac ctg tgg cgc    19092
Gly Asn Ile Phe Ala Met Glu Ile Asn Leu His Ala Asn Leu Trp Arg
    925                 930                 935

agc ttc ttg tac agc aat gtg gcg ctg tac ctg cca gac agc tat aaa    19140
Ser Phe Leu Tyr Ser Asn Val Ala Leu Tyr Leu Pro Asp Ser Tyr Lys
940                 945                 950                 955

ttc act ccc gct aac atc act ctg ccc gcc aac caa aac acc tac gag    19188
Phe Thr Pro Ala Asn Ile Thr Leu Pro Ala Asn Gln Asn Thr Tyr Glu
                960                 965                 970

tat atc aac ggg cgc gtc act tct cca acc ctg gtg gac acc ttt gtt    19236
Tyr Ile Asn Gly Arg Val Thr Ser Pro Thr Leu Val Asp Thr Phe Val
            975                 980                 985

aac att gga gcc cga tgg tcg ccg gat ccc atg gac aac  gtc aac ccc    19284
Asn Ile Gly Ala Arg Trp Ser Pro Asp Pro Met Asp Asn  Val Asn Pro
        990                 995                 1000

ttt aac  cat cac cgg aac gcg  ggc ctc cgt tac cgc  tcc atg ctg     19329
Phe Asn  His His Arg Asn Ala  Gly Leu Arg Tyr Arg  Ser Met Leu
    1005                 1010                 1015

ctg gga  aat gga cgc gtg gtg  cct ttc cac ata caa  gtg ccg caa     19374
Leu Gly  Asn Gly Arg Val Val  Pro Phe His Ile Gln  Val Pro Gln
    1020                 1025                 1030

aaa ttt  ttc gcg att aag aac  ctc ctg ctt ttg ccc  ggc tcc tac     19419
Lys Phe  Phe Ala Ile Lys Asn  Leu Leu Leu Leu Pro  Gly Ser Tyr
```

-continued

```
    1035                1040                1045

act tac  gag tgg agc ttc aga  aaa gac gtg aac atg  att ctg cag     19464
Thr Tyr  Glu Trp Ser Phe Arg  Lys Asp Val Asn Met  Ile Leu Gln
    1050                1055                1060

agc acc  ctg ggc aat gat ctt  cga gtg gac ggg gcc  agc gtc cgc     19509
Ser Thr  Leu Gly Asn Asp Leu  Arg Val Asp Gly Ala  Ser Val Arg
    1065                1070                1075

att gac  agc gtc aac ttg tac  gcc aac ttt ttc ccc  atg gcg cac     19554
Ile Asp  Ser Val Asn Leu Tyr  Ala Asn Phe Phe Pro  Met Ala His
    1080                1085                1090

aac acc  gct tct acc ttg gaa  gcc atg ctg cga aac  gac acc aac     19599
Asn Thr  Ala Ser Thr Leu Glu  Ala Met Leu Arg Asn  Asp Thr Asn
    1095                1100                1105

gac cag  tcg ttt aac gac tac  ctc agc gcg gcc aac  atg ctt tat     19644
Asp Gln  Ser Phe Asn Asp Tyr  Leu Ser Ala Ala Asn  Met Leu Tyr
    1110                1115                1120

ccc att  ccg gcc aac gcc acc  aac gtt ccc att tcc  att ccc tcc     19689
Pro Ile  Pro Ala Asn Ala Thr  Asn Val Pro Ile Ser  Ile Pro Ser
    1125                1130                1135

cgc aac  tgg gcg gcc ttc cgg  gga tgg agc ttc acc  cgc ctt aaa     19734
Arg Asn  Trp Ala Ala Phe Arg  Gly Trp Ser Phe Thr  Arg Leu Lys
    1140                1145                1150

gcc aag  gaa acg cct tcc ttg  ggc tcc ggc ttt gac  ccc tac ttt     19779
Ala Lys  Glu Thr Pro Ser Leu  Gly Ser Gly Phe Asp  Pro Tyr Phe
    1155                1160                1165

gtg tac  tca ggc acc att cct  tac ctg gac ggc agc  ttt tac ctc     19824
Val Tyr  Ser Gly Thr Ile Pro  Tyr Leu Asp Gly Ser  Phe Tyr Leu
    1170                1175                1180

aac cac  act ttc aaa cgt ctg  tcc atc atg ttc gat  tct tcc gta     19869
Asn His  Thr Phe Lys Arg Leu  Ser Ile Met Phe Asp  Ser Ser Val
    1185                1190                1195

agt tgg  ccg ggc aac gac cgc  ctc ctg acg ccg aac  gag ttc gaa     19914
Ser Trp  Pro Gly Asn Asp Arg  Leu Leu Thr Pro Asn  Glu Phe Glu
    1200                1205                1210

att aag  cgc att gtg gac ggg  gaa ggc tac aac gtg  gct caa agt     19959
Ile Lys  Arg Ile Val Asp Gly  Glu Gly Tyr Asn Val  Ala Gln Ser
    1215                1220                1225

aac atg  acc aaa gac tgg ttt  tta att caa atg ctc  agc cac tac     20004
Asn Met  Thr Lys Asp Trp Phe  Leu Ile Gln Met Leu  Ser His Tyr
    1230                1235                1240

aac atc  ggc tac caa ggc ttc  tat gtt ccc gag ggc  tac aag gat     20049
Asn Ile  Gly Tyr Gln Gly Phe  Tyr Val Pro Glu Gly  Tyr Lys Asp
    1245                1250                1255

cgg atg  tat tct ttc ttc cga  aac ttt cag ccc atg  agc cgc cag     20094
Arg Met  Tyr Ser Phe Phe Arg  Asn Phe Gln Pro Met  Ser Arg Gln
    1260                1265                1270

gtg ccg  gat ccc acc gct gcc  ggc tat caa gcc gtt  ccc ctg ccc     20139
Val Pro  Asp Pro Thr Ala Ala  Gly Tyr Gln Ala Val  Pro Leu Pro
    1275                1280                1285

aga caa  cac aac aac tcg ggc  ttt gtg ggg tac atg  ggc ccg acc     20184
Arg Gln  His Asn Asn Ser Gly  Phe Val Gly Tyr Met  Gly Pro Thr
    1290                1295                1300

atg cgc  gaa gga cag cca tac  ccg gcc aac tac ccc  tat ccc ctg     20229
Met Arg  Glu Gly Gln Pro Tyr  Pro Ala Asn Tyr Pro  Tyr Pro Leu
    1305                1310                1315

atc ggc  gct acc gcc gtc ccc  gcc att acc cag aaa  aag ttt ttg     20274
Ile Gly  Ala Thr Ala Val Pro  Ala Ile Thr Gln Lys  Lys Phe Leu
    1320                1325                1330

tgc gac  cgc gtc atg tgg cgc  ata cct ttt tcc agc  aac ttt atg     20319
```

-continued

```
Cys Asp  Arg Val Met Trp Arg  Ile Pro Phe Ser Ser  Asn Phe Met
    1335                 1340                 1345

tca atg  ggg gcc ctg acc gac  ctc gga cag aac atg  ctt tac gct     20364
Ser Met  Gly Ala Leu Thr Asp  Leu Gly Gln Asn Met  Leu Tyr Ala
    1350                 1355                 1360

aac tcc  gcc cat gcc ctg gat  atg act ttt gag gtg  gac ccc atg     20409
Asn Ser  Ala His Ala Leu Asp  Met Thr Phe Glu Val  Asp Pro Met
    1365                 1370                 1375

aac gag  ccc acg ttg ctg tac  atg ctt ttt gag gtg  ttc gac gtg     20454
Asn Glu  Pro Thr Leu Leu Tyr  Met Leu Phe Glu Val  Phe Asp Val
    1380                 1385                 1390

gtc aga  gtg cac cag ccg cac  cgc ggt att atc gag  gcc gtg tac     20499
Val Arg  Val His Gln Pro His  Arg Gly Ile Ile Glu  Ala Val Tyr
    1395                 1400                 1405

ctg cgc  acc ccc ttc tct gcg  ggc aat gcc acc aca  taa gccgctgaac  20548
Leu Arg  Thr Pro Phe Ser Ala  Gly Asn Ala Thr Thr
    1410                 1415                 1420

tagctggttt ttaccccaga tcccatgggc tccacggaag acgaactgcg ggccattgtg  20608

cgagacctgg gctgcggacc ctacttcctg ggcacctttg acaagcggtt tcccgggttc  20668

gtgtctcctc gcaaactcgc gtgcgcgatc gtgaataccg ccggccgaga gaccggagga  20728

gagcattggc tagctctggg ctggaacccc cgctcgtcca cgtttttcct gttcgacccc  20788

tttggctttt cagaccaacg cttgaagcag atctatgcat ttgaatatga gggtctactc  20848

aagcgaagcg cgctggcctc ctccgccgat cactgtctaa ccctggtaaa gagcactcag  20908

acggttcagg gccctcacag cgccgcctgt ggcctttttt gttgcatgtt tttgcacgcc  20968

tttgtgaact ggccggacac ccccatggaa aacaacccca ccatggacct cctgactggc  21028

gttcccaact ccatgctcca aagccccagc gtgcagacca ccctcctcca aaaccagaaa  21088

aatctgtacg cctttctgca caagcactct ccctactttc gccgccatcg ggaacaaata  21148

gaaaatgcaa ccgcgtttaa caaaactctg taacgtttaa taaatgaact ttttattgaa  21208

ctggaaaacg ggtttgtgat ttttaaaaat caaaggggtt gagctggaca tccatgtggg  21268

aggccggaag ggtggtgttc ttgtactggt acttgggcag ccacttaaac tctggaatca  21328

caaacttggg cagcggtatt tctgggaagt tgtcgtgcca cagctggcgg gtcagctgaa  21388

gtgcctgcag aacatcgggg gcggagatct tgaagtcgca gtttatctgg ttcacggcac  21448

gcgcgttgcg gtacatggga ttggcacact gaaacaccag caggctggga ttcttgatgc  21508

tagccagggc cacggcgtcg gtcacgtcac cggtgtcttc tatgttggac agcgaaaaag  21568

gcgtgacttt gcaaagctgg cgtcccgcgc gaggcacgca atctcccagg tagttgcact  21628

cacagcggat gggcagaaga agatgcttgt ggccgcgggt catgtaggga taggccgctg  21688

ccataaaagc ttcgatctgc ctgaaagcct gcttggcctt gtgcccttcg gtataaaaaa  21748

caccgcagga cttgttggaa aaggtattac tggcgcaagc ggcatcgtga aagcaagcgc  21808

gtgcgtcttc gtttcgtaac tgcaccacgc tgcggcccca ccggttctga atcaccttgg  21868

ccctgccggg gttttccttg agagcgcgct ggccggcttc gctgcccaca tccatttcca  21928

cgacatgctc cttgttaatc atggccagac cgtggaggca gcgcagctcc tcgtcatcgt  21988

cggtgcagtg atgctcccac acgacgcagc cagtgggctc ccacttgggc ttggaggcct  22048

cggcaatgcc agaatacagg agaacgtagt ggtgcagaaa acgtcccatc atggtgccaa  22108

aggttttctg gctgctgaag gtcatcgggc agtacctcca gtcctcgtta agccaagtgt  22168

tgcagatctt cctgaagacc gtgtactgat cgggcataaa gtggaactca ttgcgctcgg  22228
```

-continued

```
tcttgtcgat cttatacttt tccatcagac tatgcataat ctccatgccc ttttcccagg  22288

cgcaaacaat cttggtgcta cacgggttag gtatggccaa agtggttggc ctctgaggcg  22348

gcgcttgttc ttcctcttga gccctctccc gactgacggg ggttgaaaga gggtgcccct  22408

tggggaacgg cttgaacacg gtctggcccg aggcgtcccg aagaatctgc atcgggggat  22468

tgctggccgt catggcgatg atctgacccc ggggctcctc cacttcgtcc tcctcgggac  22528

tttcctcgtg cttttcgggg gacggtacgg gagtaggggg aagagcgcgg cgcgccttct  22588

tcttgggcgg cagttccgga gcctgctctt gacgactggc cattgtcttc tcctaggcaa  22648

gaaaaacaag atggaagact ctttctcctc ctcctcgtca acgtcagaaa gcgagtcttc  22708

caccttaagc gccgagaact cccagcgcat agaatccgat gtgggctacg agactccccc  22768

cgcgaacttt tcgccgcccc ccataaacac taacgggtgg acggactacc tggccctagg  22828

agacgtactg ctgaagcaca tcaggcggca gagcgttatc gtgcaagatg ctctcaccga  22888

gcgactcgcg gttccgctgg aagtggcgga acttagcgcc gcctacgagc gaaccctctt  22948

ctccccaaag actcccccca agaggcaggc taacggcacc tgcgagccta accctcgact  23008

caacttctac cctgcctttg ccgtgccaga ggtactggct acgtaccaca ttttttttcca  23068

aaaccacaaa atccctctct cgtgccgcgc caaccgcacc aaagccgatc gcgtgctgcg  23128

actggaggaa ggggctcgca tacctgagat tgcgtgtctg gaggaagtcc caaaaatctt  23188

tgaaggtctg ggccgcgacg aaaagcgagc agcaaacgct ctggaagaga acgcagagag  23248

tcacaacagc gccttggtag aactcgaggg cgacaacgcc agactggccg tcctcaaacg  23308

gtccatagaa gtcacgcact tcgcctaccc cgccgttaac ctccctccaa aagttatgac  23368

agcggtcatg gactcgctgc tcataaagcg cgctcagccc ttagacccag agcacgaaaa  23428

caacagtgac gaaggaaaac cggtggtttc tgatgaggag ttgagcaagt ggctgtcctc  23488

caacgacccc gccacgttgg aggaacgaag aaaaaccatg atggccgtgg tgctagttac  23548

cgtgcaatta gaatgtctgc agaggttctt ttcccaccca gagaccctga gaaaagtgga  23608

ggaaacgctg cactacacat ttaggcacgg ctacgtgaag caagcctgca agatttccaa  23668

cgtagaactt agcaacctca tctcctacct ggggatcttg cacgaaaacc gcctcggaca  23728

aaacgtgctg cacagcacac tgaaaggaga agcccgccga gactatgtgc gagactgcgt  23788

gttcctagcg ctagtgtaca cctggcagag cggaatggga gtctggcagc agtgcctgga  23848

ggacgaaaac ctcaaagagc ttgaaaagct gctggtgcgc tccagaaggg cactgtggac  23908

cagttttgac gagcgcaccg ccgcgcgaga cctagctgat attatttttc ctcccaagct  23968

ggtgcagact ctccgggaag gactgccaga ttttatgagt caaagcatct tgcaaaactt  24028

ccgctctttc atcttggaac gctcgggaat cttgcccgcc actagctgcg ccctacccac  24088

agattttgtg cctctccact accgcgaatg cccaccgccg ctgtggccgt acacttactt  24148

gcttaaactg gccaactttc taatgttcca ctctgacctg gcagaagacg ttagcggcga  24208

ggggctgcta gaatgccact gccgctgcaa cctgtgcacc ccccaccgct ctctagtatg  24268

caacactccc ctgctcaatg agacccagat catcggtacc tttgaaatcc agggaccctc  24328

cgacgcggaa aacggcaagc aggggtctgg gctaaaactc acagccggac tgtggacctc  24388

cgcctacttg cgcaaatttg taccagaaga ctatcacgcc caccaaatta aattttacga  24448

aaaccaatca aaaccaccca aaagcgagtt aacggcttgc gtcattacgc agagcagcat  24508

agttgggcag ttgcaagcca ttaacaaagc gcggcaagag tttctcctaa aaaaaggaaa  24568

aggggtctac ttggaccccc agaccggcga ggaactcaac ggaccctcct cagtcgcagg  24628
```

-continued

```
ttgtgtgccc catgccgccc aaaaagaaca cctcgcagtg gaacatgcca gagacggagg  24688
aagaggagtg gagcagtgtg agcaacagcg aaacggagga agagccgtgg cccgaggggt  24748
gcaacgggga agaggacacg gagggacggc gaagtcttcg ccgaagaact ctcgccgctg  24808
cccccgaagt cccagccggc cgcctcggcc caagatcccg cacacacccg tagatgggat  24868
agcaagacca aaaagccggg taagagaaac gctcgccccc gccagggcta ccgctcgtgg  24928
agaaagcaca aaaactgcat cttatcgtgc ttgctccagt gcggcggaga cgtttcgttc  24988
acccgtagat acttgctttt taacaaaggg gtggccgtcc cccgtaacgt cctccactac  25048
taccgtcact cttacagctc cgaagcggac ggctaagaaa acgcagcagt tgccggcggg  25108
aggactgcgt ctcagcgccc gagaaccccc agccaccagg gagctccgaa accgcatatt  25168
tcccaccctc tacgctatct ttcagcaaag ccgggggcag cagcaagaac tgaaaataaa  25228
aaaccgcacg ctgaggtcgc ttacccgaag ctgcctctat cacaagagcg aagagcagct  25288
gcagcgaacc ctggaggacg cagaagcgct gttccagaag tactgcgcga ccaccctaaa  25348
taactaaaaa agcccgcgcg cgggacttca aaccgtctga cgtcaccagc cgcgcgccaa  25408
aatgagcaaa gagattccca cgccttacat gtggagttac cagccgcaga tgggattagc  25468
cgccggcgcc gcccaggatt actccacgaa aatgaactgg ctcagcgccg ggccccacat  25528
gatttcccgc gtaaacgaca ttcgcgccca ccgcaatcag ctattgttag aacaggctgc  25588
tctgaccgcc acgccccgta ataacctgaa ccctcccagc tggccagctg ccctggtgta  25648
ccaggaaacg cctccaccca ccagcgtact tttgccccgt gacgcccagg cggaagtcca  25708
gatgactaac gcgggcgcgc aattagcggg cggatcccgg tttcggtaca gagttcacgg  25768
cgccgcaccc tatagcccag gtataaagag gctgatcatt cgaggcagag gtgtccagct  25828
caacgacgag acagtgagct cttcgcttgg tctacgacca gacggagtgt tccagctcgc  25888
gggctcgggc cgctcttcgt tcacgcctcg ccaggcatac ctgactctgc agagctctgc  25948
ctctcagcct cgctcgggag gaatcggacc ccttcagttt gtggaggagt ttgtgccctc  26008
ggtctacttt cagcctttct ccggatcgcc cggccagtac ccggacgagt tcatccccaa  26068
cttcgacgcg gtgagtgact ctgtggacgg ttatgactga tgtcgagccc gcttcagtgc  26128
tagtggaaca agcgcggctc aatcacctgg ttcgttgccg ccgccgctgc tgcgtggctc  26188
gcgacttgag cttagctctc aagtttgtaa aaaacccgtc cgaaaccggg agcgctgtgc  26248
acgggttgga gctagtgggt cctgagaagg ccaccatcca cgttctcaga aactttgtgg  26308
aaaaacccat tttggttaaa cgagatcagg ggccttttgt aatcagctta ctctgcacct  26368
gtaaccatgt tgaccttcac gactatttta tggatcattt gtgcgctgaa ttcaataagt  26428
aaagcgaatt cttaccaaga ttatgatgtc catgactgtt cctcgccact atacgatgtt  26488
gtgccagtaa actctcttgt cgacatctat ctgaactgtt ccttttggtc cgcacagctt  26548
acttggtact acggtgacac cgtcctttct ggctcactgg gcagctcaca cggaataaca  26608
cttcacctct tttcgccgtt tcgatacgga aactacagct gtcgtgccgg tacctgcctc  26668
cacgttttca atcttcagcc ctgtccaccg accaaacttg tatttgtcga ctctaagcac  26728
ttacagctca actgcagcat tctaggcccc agtatcttgt ggacatacaa taaaatcagg  26788
ttggtggaat ttgtctacta cccacccagc gcccgcggtt ttggggaaat tcctttccag  26848
atctactaca actatcttgc cacacattat gcaagtcaac agcaactaaa cttgcaagca  26908
cccttcacgc caggagagta ctcctgtcac gtaggctcct gcacagaaac ttttattctc  26968
```

-continued ttcaacagat cttctgccat tgaacgcttc actactaact actttagaaa ccaagttgtg 27028 cttttcactg acgaaacccc taacgtcacc ctggactgtg catgtttttc tcatgacacc 27088 gtaacttgga ctcttaacaa tactctctgg ctcgcgttcg ataaccaaag cttgattgtt 27148 aaaaattttg atttaacctt tactaaaccc tctcctcgcg aaatagttat ctttgctcct 27208 tttaatccaa aaactacctt agcctgtcag gttttgttta agccttgcca aacaaacttt 27268 aagtttgttt atttgcctcc gcaatctgtc aaactcatag aaaaatacaa caaagcgccc 27328 gtcttggctc ctaaaacctt ctaccactgg ctaacctaca cggggctgtt tgcactaatt 27388 gtttttttcc taattaacat ttttatatgt ttcttgcctt cctccttctt ttcgcgaaca 27448 ccgttgccgc agaaagacct ctccttatta ctgtagcgct tgctatacaa aaccaagagt 27508 ggtcaaccgt gctctcaatc tattttcaat tttcatttt gtccttaata ctttctctta 27568 ttgtcgttaa caatgatctg gagcattggt ctcgcctttt tttggctgct tagtgcaaaa 27628 gccactattt ttcacaggta tgtggaagaa ggaactagca ccctctttac gatacctgaa 27688 acaattaagg cggctgatga agtttcttgg tacaaaggct cgctctcaga cggcaaccac 27748 tcattctcag gacagaccct ttgcatccaa gaaacttatt ttaaatcaga actacaatac 27808 agctgcataa aaaacttttt ccatctctac aacatctcaa aaccctatga gggtatttac 27868 aatgccaagg tttcagacaa ctccagcaca cggaactttt actttaatct gacagttatt 27928 aaagcaattt ccattcctat ctgtgagttt agctcccagt ttctttctga aacctactgt 27988 ttaattacta taaactgcac taaaaatcgc cttcacacca ccataatcta caatcacaca 28048 caatcacctt gggttttaaa cctaaaattt tctccacaca tgccttcgca atttctcacg 28108 caagttaccg tctctaacat aagcaagcag tttggctttt actatccttt ccacgaactg 28168 tgcgaaataa ttgaagccga atatgaacca gactacttta cttacattgc cattggtgta 28228 atcgttgttt gcctttgctt tgttattggg gggtgtgttt atttgtacat tcagagaaaa 28288 atattgctct cgctgtgctc ctgcggttac aaagcagaag aaagaattaa aatctctaca 28348 ctttattaat gttttccaga aatggcaaaa ctaacgctcc tacttttgct tctcacgccg 28408 gtgacgcttt ttaccatcac tttttctgcc gccgccacac tcgaacctca atgtttgcca 28468 ccggttgaag tctactttgt ctacgtgttg ctgtgctgcg ttagcgtttg cagtataaca 28528 tgttttacct ttgtttttct tcagtgcatt gactacttct gggtcagact ctactaccgc 28588 agacacgcgc ctcagtatca aaatcaacaa attgccagac tactcggtct gccatgattg 28648 tcttgtattt taccctgatt ttttttcacc ttacttgcgc ttgtgatttt cacttcactc 28708 aattttggaa aacgcaatgc ttcgacccgc gcctctccaa cgactggatg atggctcttg 28768 caattgccac gcttggggcg tttggacttt ttagtggttt tgctttgcat tacaaattta 28828 agactccatg gacacatggc tttctttcag attttccagt tacacctact ccgccgcctc 28888 ccccggccat cgacgtgcct caggttccct caccttctcc atctgtctgc agctactttc 28948 atctgtaatg gccgacctag aatttgacgg agtgcaatct gagcaaaggg ctatacactt 29008 ccaacgccag tcggaccgcg aacgcaaaaa cagagagctg caaaccatac aaaacaccca 29068 ccaatgtaaa cgcgggatat tttgtattgt aaaacaagct aagctccact acgagcttct 29128 atctggcaac gaccacgagc tccaatacgt ggtcgatcag cagcgtcaaa cctgtgtatt 29188 cttaattgga gtttccccca ttaaagttac tcaaaccaag ggtgaaacca agggaaccat 29248 aaggtgctca tgtcacctgt cagaatgcct ttacactcta gttaaaaccc tatgtggctt 29308 acatgattct atccccttta attaaataaa cttactttaa atctgcaatc acttcttcgt 29368

-continued

```
ccttgttttt gtcgccatcc agcagcacca ccttcccctc ttcccaactt tcatagcata  29428

ttttccgaaa agaggcgtac tttcgccaca ccttaaaggg aacgtttact tcgctttcaa  29488

gctctcccac gattttcatt gcagat atg aaa cgc gcc aaa  gtg gaa gaa gga  29541
                             Met Lys Arg Ala Lys  Val Glu Glu Gly
                                             1425

ttt  aac ccc gtt tat ccc  tat gga tat tct act  ccg act gac gtg     29586
Phe  Asn Pro Val Tyr Pro  Tyr Gly Tyr Ser Thr  Pro Thr Asp Val
1430                 1435                 1440

gct  cct ccc ttt gta gcc  tct gac ggt ctt caa  gaa aac cca cct     29631
Ala  Pro Pro Phe Val Ala  Ser Asp Gly Leu Gln  Glu Asn Pro Pro
1445                 1450                 1455

ggg  gtc ttg tcc cta aaa  ata tcc aaa cct tta  act ttt aat gcc     29676
Gly  Val Leu Ser Leu Lys  Ile Ser Lys Pro Leu  Thr Phe Asn Ala
1460                 1465                 1470

tcc  aag gct cta agc ctg  gct att ggt cca gga  tta aaa att caa     29721
Ser  Lys Ala Leu Ser Leu  Ala Ile Gly Pro Gly  Leu Lys Ile Gln
1475                 1480                 1485

gat  ggt aaa cta gtg ggg  gag gga caa gca att  ctt gca aac ctg     29766
Asp  Gly Lys Leu Val Gly  Glu Gly Gln Ala Ile  Leu Ala Asn Leu
1490                 1495                 1500

ccg  ctt caa atc acc aac  aac aca att tca cta  cgt ttt ggg aac     29811
Pro  Leu Gln Ile Thr Asn  Asn Thr Ile Ser Leu  Arg Phe Gly Asn
1505                 1510                 1515

aca  ctt gcc ttg aat gac  aat aat gaa ctc caa  acc aca cta aaa     29856
Thr  Leu Ala Leu Asn Asp  Asn Asn Glu Leu Gln  Thr Thr Leu Lys
1520                 1525                 1530

tct  tca tcg ccc ctt aaa  atc aca gac cag act  ctg tcc ctt aac     29901
Ser  Ser Ser Pro Leu Lys  Ile Thr Asp Gln Thr  Leu Ser Leu Asn
1535                 1540                 1545

ata  ggg gac agc ctt gca  att aaa gat gac aaa  cta gaa agc gct     29946
Ile  Gly Asp Ser Leu Ala  Ile Lys Asp Asp Lys  Leu Glu Ser Ala
1550                 1555                 1560

ctt  caa gcg acc ctc cca  ctc tcc att agc aac  aac acc atc agc     29991
Leu  Gln Ala Thr Leu Pro  Leu Ser Ile Ser Asn  Asn Thr Ile Ser
1565                 1570                 1575

ctc  aac gtg ggc acc gga  ctc acc ata aat gga  aac gtt tta caa     30036
Leu  Asn Val Gly Thr Gly  Leu Thr Ile Asn Gly  Asn Val Leu Gln
1580                 1585                 1590

gct  gtt ccc tta aat gct  cta agt ccc cta act  att tcc aac aat     30081
Ala  Val Pro Leu Asn Ala  Leu Ser Pro Leu Thr  Ile Ser Asn Asn
1595                 1600                 1605

aac  atc agc ctg cgc tat  ggc agt tcc ctg acg  gtg ctt aac aat     30126
Asn  Ile Ser Leu Arg Tyr  Gly Ser Ser Leu Thr  Val Leu Asn Asn
1610                 1615                 1620

gaa  ctg caa agc aac ctc  aca gtt cac tcc cct  tta aaa ctc aac     30171
Glu  Leu Gln Ser Asn Leu  Thr Val His Ser Pro  Leu Lys Leu Asn
1625                 1630                 1635

tcc  aac aac tca att tct  ctc aac act cta tct  ccg ttt aga atc     30216
Ser  Asn Asn Ser Ile Ser  Leu Asn Thr Leu Ser  Pro Phe Arg Ile
1640                 1645                 1650

gag  aat ggt ttc ctc acg  ctc tat ttg gga aca  aaa tct ggc ttg     30261
Glu  Asn Gly Phe Leu Thr  Leu Tyr Leu Gly Thr  Lys Ser Gly Leu
1655                 1660                 1665

cta  gtt caa aac agt ggc  tta aaa gtt caa gcg  ggc tac ggc ctg     30306
Leu  Val Gln Asn Ser Gly  Leu Lys Val Gln Ala  Gly Tyr Gly Leu
1670                 1675                 1680

caa  gta aca gac acc aat  gct ctc aca tta aga  tat ctc gct cca     30351
Gln  Val Thr Asp Thr Asn  Ala Leu Thr Leu Arg  Tyr Leu Ala Pro
```

-continued

```
1685                1690                1695

ctg  acc att cca gac tcg  ggc tca gaa caa ggc  att ctt aaa gta     30396
Leu  Thr Ile Pro Asp Ser  Gly Ser Glu Gln Gly  Ile Leu Lys Val
1700                1705                1710

aac  act gga cag ggc cta  agt gtg aac caa gct  gga gcg ctt gaa     30441
Asn  Thr Gly Gln Gly Leu  Ser Val Asn Gln Ala  Gly Ala Leu Glu
1715                1720                1725

aca  tcc cta gga ggt gga  tta aaa tat gct gat  aac aaa ata acc     30486
Thr  Ser Leu Gly Gly Gly  Leu Lys Tyr Ala Asp  Asn Lys Ile Thr
1730                1735                1740

ttt  gat aca gga aac gga  ctg aca tta tct gaa  aat aaa ctt gca     30531
Phe  Asp Thr Gly Asn Gly  Leu Thr Leu Ser Glu  Asn Lys Leu Ala
1745                1750                1755

gta  gct gca ggt agt ggt  cta act ttt aga gat  ggt gcc ttg gta     30576
Val  Ala Ala Gly Ser Gly  Leu Thr Phe Arg Asp  Gly Ala Leu Val
1760                1765                1770

gcc  acg gga acc gca ttt  acg caa aca ctg tgg  act acg gct gat     30621
Ala  Thr Gly Thr Ala Phe  Thr Gln Thr Leu Trp  Thr Thr Ala Asp
1775                1780                1785

ccg  tct ccc aac tgc aca  att ata cag gac cgc  gac aca aaa ttt     30666
Pro  Ser Pro Asn Cys Thr  Ile Ile Gln Asp Arg  Asp Thr Lys Phe
1790                1795                1800

act  ttg gcg ctt acc att  agt ggg agc caa gtg  ctg ggg acg gtt     30711
Thr  Leu Ala Leu Thr Ile  Ser Gly Ser Gln Val  Leu Gly Thr Val
1805                1810                1815

tcc  att att gga gta aaa  ggc ccc ctt tca agt  agc ata ccg tca     30756
Ser  Ile Ile Gly Val Lys  Gly Pro Leu Ser Ser  Ser Ile Pro Ser
1820                1825                1830

gct  acc gtt aca gta caa  ctt aac ttt gat tcc  aac gga gcc cta     30801
Ala  Thr Val Thr Val Gln  Leu Asn Phe Asp Ser  Asn Gly Ala Leu
1835                1840                1845

ttg  agc tcc tct tca ctt  aaa ggt tac tgg ggg  tat cgc caa ggt     30846
Leu  Ser Ser Ser Ser Leu  Lys Gly Tyr Trp Gly  Tyr Arg Gln Gly
1850                1855                1860

ccc  tca att gac cct tac  ccc ata att aat gcc  tta aac ttt atg     30891
Pro  Ser Ile Asp Pro Tyr  Pro Ile Ile Asn Ala  Leu Asn Phe Met
1865                1870                1875

cca  aac tca ctg gct tat  ccc ccg gga caa gaa  atc caa gca aaa     30936
Pro  Asn Ser Leu Ala Tyr  Pro Pro Gly Gln Glu  Ile Gln Ala Lys
1880                1885                1890

tgt  aac atg tac gtt tct  act ttt tta cga gga  aat cca caa aga     30981
Cys  Asn Met Tyr Val Ser  Thr Phe Leu Arg Gly  Asn Pro Gln Arg
1895                1900                1905

cca  ata gtt tta aac atc  act ttt aat aat caa  acc agc ggg ttt     31026
Pro  Ile Val Leu Asn Ile  Thr Phe Asn Asn Gln  Thr Ser Gly Phe
1910                1915                1920

tcc  att aga ttt aca tgg  aca aat tta acc aca  gga gaa gca ttt     31071
Ser  Ile Arg Phe Thr Trp  Thr Asn Leu Thr Thr  Gly Glu Ala Phe
1925                1930                1935

gca  atg ccc cca tgc act  ttt tcc tac att gct  gaa caa caa taa     31116
Ala  Met Pro Pro Cys Thr  Phe Ser Tyr Ile Ala  Glu Gln Gln
1940                1945                1950

actatgtaac cctcaccgtt aacccgcctc cgcccttcca ttttatttta taaaccaccc  31176

gatccacctt ttcagcagta aacaattgca tgtcagtagg ggcagtaaaa cttttgggag  31236

ttaaaatcca cacaggttct tcacaagcta agcgaaaatc agttacactt ataaaaccat  31296

cgctaacatc ggacaaagac aagcatgagt ccaaagcttc cggttctgga tcagattttt  31356

gttcattaac agcgggagaa acagcttctg gaggattttc catctccatc tccttcatca  31416
```

-continued

```
gttccaccat gtccaccgtg gtcatctggg acgagaacga cagttgtcat acacctcata  31476
agtcaccggt cgatgacgaa cgtacagatc tcgaagaatg tcctgtcgcc gcctttcggc  31536
agcactgggc cgaaggcgaa agcgcccatg tttaacaatg gccagcaccg cccgcttcat  31596
caggcgccta gttcttttag cgcaacagcg catgcgcagc tcgctaagac tggcgcaaga  31656
aacacagcac agaaccacca gattgttcat gatcccataa gcgtgctgac accagcccat  31716
actaacaaat tgtttcacta ttctagcatg aatgtcatat ctgatgttca agtaaattaa  31776
atggcgcccc cttatgtaaa cacttcccac gtacaacacc tcctttggca tctgataatt  31836
aaccacctcc cgataccaaa tacatctctg attaatagtc gccccgtaca ctacccgatt  31896
aaaccaagtt gccaacataa tccccccctgc catacactgc aaagaacctg gacggctaca  31956
atgacagtgc aaagtccaca cctcgttgcc atggataact gaggaacgcc ttaagtcaat  32016
agtggcacaa ctaatacaaa catgtaaata gtgtttcaac aagtgccact cgtatgaggt  32076
gagtatcatg tcccagggaa cgggccactc cataaacact gcaaaaccaa cacatcctac  32136
catcccccgc acggcactca catcgtgcat ggtgttcata tcacagtccg gaagctgagg  32196
acaaggaaaa gtctcgggag cattttcata gggcggtagt gggtactcct tgtaggggtt  32256
cagtcggcac cggtatctcc tcaccttctg ggccataaca cacaagttga gatctgattt  32316
caaggtactt tctgaatgaa aaccaagtgc tttcccaaca atgtatccga tgtcttcggt  32376
ccccgcgtcg gtagcgctcc ttgcagtaca cacggaacaa ccactcacgc aggcccagaa  32436
gacagttttc cgcggacggt gacaagttaa tccccctcag tctcagagcc aatatagttt  32496
cttccacagt agcataggcc aaacccaacc aggaaacaca agctggcacg tcccgttcaa  32556
cgggaggaca aggaagcaga ggcagaggca taggcaaagc aacagaattt ttattccaac  32616
tggtcacgta gcacttcaaa caccaggtca cgtaaatggc agcgatcttg ggtttcctga  32676
tggaacataa cagcaagatc aaacatgaga cgattctcaa ggtgattaac cacagctgga  32736
attaaatcct ccacgcgcac atttagaaac accagcaata caaaagcccg gttttctccg  32796
ggatctatca tagcagcaca gtcatcaatt agtcccaagt aattttcccg tttccaatct  32856
gttataattt gcagaataat gccctgtaaa tccaagccgg ccatggcgaa aagctcagat  32916
aatgcacttt ccacgtgcat tcgtaaacac accctcatct tgtcaatcca aaaagtcttc  32976
ttcttgagaa acctgtagta aattaagaat cgccaggtta ggctcgatgc ctacatcccg  33036
gagcttcatt ctcagcatgc actgcaaatg atccagcaga tcagaacagc aattagcagc  33096
cagctcatcc ccggtttcca gttccggagt tcccacggca attatcactc gaaacgtggg  33156
acaaatcgaa ataacatgag ctcccacgtg agcaaaagcc gtagggccag tgcaataatc  33216
acagaaccag cggaaaaaag attgcagctc atgtttcaaa aagctctgca gatcaaaatt  33276
cagctcatgc aaataacaca gtaaagtttg cggtatagta accgaaaacc acacgggtcg  33336
acgttcaaac atctcggctt acctaaaaaa gaagcacatt tttaaaccac agtcgcttcc  33396
tgaacaggag gaaatatggt gcggcgtaaa accagacgcg ccaccggatc tccggcagag  33456
ccctgataat acagccagct gtggttaaac agcaaaacct ttaattcggc aacggttgag  33516
gtctccacat aatcagcgcc cacaaaaatc ccatctcgaa cttgctcgcg tagggagcta  33576
aaatggccag tatagcccca tggcacccga acgctaatct gcaagtatat gagagccacc  33636
ccattcggcg ggatcacaaa atcagtcgga gaaaacaacg tatacacccc ggactgcaaa  33696
agctgttcag gcaaacgccc ctgcggtccc tctcggtaca ccagcaaagc ctcgggtaaa  33756
```

-continued

```
gcagccatgc caagcgctta ccgtgccaag agcgactcag acgaaaaagt gtactgaggc  33816

gctcagagca gcggctatat actctacctg tgacgtcaag aaccgaaagt caaaagttca  33876

cccggcgcgc ccgaaaaaac ccgcgaaaat ccacccaaaa agcccgcgaa aaacacttcc  33936

gtataaaatt tccgggttac cggcgcgtca ccgccgcgcg acacgcccgc cccgccccgc  33996

gctcctcccc gaaacccgcc gcgcccactt ccgcgttccc aagacaaagg tcgcgtaact  34056

ccgcccacct catttgcatg ttaactcggt cgccatcttg cggtgttata ttgatgatg   34115
```

<210> SEQ ID NO 35
<211> LENGTH: 503
<212> TYPE: PRT
<213> ORGANISM: simian adenovirus SV-39

<400> SEQUENCE: 35

```
Met Arg Arg Ala Val Ala Val Pro Ser Ala Ala Met Ala Leu Gly Pro
1               5                   10                  15

Pro Pro Ser Tyr Glu Ser Val Met Ala Ala Ala Thr Leu Gln Ala Pro
            20                  25                  30

Leu Glu Asn Pro Tyr Val Pro Pro Arg Tyr Leu Glu Pro Thr Gly Gly
        35                  40                  45

Arg Asn Ser Ile Arg Tyr Ser Glu Leu Thr Pro Leu Tyr Asp Thr Thr
    50                  55                  60

Arg Leu Tyr Leu Val Asp Asn Lys Ser Ala Asp Ile Ala Thr Leu Asn
65                  70                  75                  80

Tyr Gln Asn Asp His Ser Asn Phe Leu Thr Ser Val Val Gln Asn Ser
                85                  90                  95

Asp Tyr Thr Pro Ala Glu Ala Ser Thr Gln Thr Ile Asn Leu Asp Asp
            100                 105                 110

Arg Ser Arg Trp Gly Gly Asp Leu Lys Thr Ile Leu His Thr Asn Met
        115                 120                 125

Pro Asn Val Asn Glu Phe Met Phe Thr Asn Ser Phe Arg Ala Lys Leu
    130                 135                 140

Met Val Ala His Glu Ala Asp Lys Asp Pro Val Tyr Glu Trp Val Gln
145                 150                 155                 160

Leu Thr Leu Pro Glu Gly Asn Phe Ser Glu Ile Met Thr Ile Asp Leu
                165                 170                 175

Met Asn Asn Ala Ile Ile Asp His Tyr Leu Ala Val Ala Arg Gln Gln
            180                 185                 190

Gly Val Lys Glu Ser Glu Ile Gly Val Lys Phe Asp Thr Arg Asn Phe
        195                 200                 205

Arg Leu Gly Trp Asp Pro Glu Thr Gly Leu Val Met Pro Gly Val Tyr
    210                 215                 220

Thr Asn Glu Ala Phe His Pro Asp Val Val Leu Leu Pro Gly Cys Gly
225                 230                 235                 240

Val Asp Phe Thr Tyr Ser Arg Leu Asn Asn Leu Leu Gly Ile Arg Lys
                245                 250                 255

Arg Met Pro Phe Gln Glu Gly Phe Gln Ile Leu Tyr Glu Asp Leu Glu
            260                 265                 270

Gly Gly Asn Ile Pro Ala Leu Leu Asp Val Pro Ala Tyr Glu Glu Ser
        275                 280                 285

Ile Ala Asn Ala Arg Glu Ala Ala Ile Arg Gly Asp Asn Phe Ala Ala
    290                 295                 300

Gln Pro Gln Ala Ala Pro Thr Ile Lys Pro Val Leu Glu Asp Ser Lys
305                 310                 315                 320
```

-continued

Gly Arg Ser Tyr Asn Val Ile Ala Asn Thr Asn Asn Thr Ala Tyr Arg
325 330 335

Ser Trp Tyr Leu Ala Tyr Asn Tyr Gly Asp Pro Glu Lys Gly Val Arg
340 345 350

Ala Trp Thr Leu Leu Thr Thr Pro Asp Val Thr Cys Gly Ser Glu Gln
355 360 365

Val Tyr Trp Ser Leu Pro Asp Met Tyr Val Asp Pro Val Thr Phe Arg
370 375 380

Ser Thr Gln Gln Val Ser Asn Tyr Pro Val Val Gly Ala Glu Leu Met
385 390 395 400

Pro Ile His Ser Lys Ser Phe Tyr Asn Glu Gln Ala Val Tyr Ser Gln
405 410 415

Leu Ile Arg Gln Thr Thr Ala Leu Thr His Val Phe Asn Arg Phe Pro
420 425 430

Glu Asn Gln Ile Leu Val Arg Pro Pro Ala Pro Thr Ile Thr Thr Val
435 440 445

Ser Glu Asn Val Pro Ala Leu Thr Asp His Gly Thr Leu Pro Leu Gln
450 455 460

Asn Ser Ile Arg Gly Val Gln Arg Val Thr Ile Thr Asp Ala Arg Arg
465 470 475 480

Arg Thr Cys Pro Tyr Val Tyr Lys Ala Leu Gly Ile Val Ala Pro Arg
485 490 495

Val Leu Ser Ser Arg Thr Phe
500

<210> SEQ ID NO 36
<211> LENGTH: 917
<212> TYPE: PRT
<213> ORGANISM: simian adenovirus SV-39

<400> SEQUENCE: 36

Met Ala Thr Pro Ser Met Met Pro Gln Trp Ser Tyr Met His Ile Ala
1 5 10 15

Gly Gln Asp Ala Ser Glu Tyr Leu Ser Pro Gly Leu Val Gln Phe Ala
20 25 30

Arg Ala Thr Glu Thr Tyr Phe Ser Leu Gly Asn Lys Phe Arg Asn Pro
35 40 45

Thr Val Ala Pro Thr His Asp Val Thr Thr Asp Arg Ser Gln Arg Leu
50 55 60

Thr Ile Arg Phe Val Pro Val Asp Lys Glu Asp Thr Ala Tyr Ser Tyr
65 70 75 80

Lys Thr Arg Phe Thr Leu Ala Val Gly Asp Asn Arg Val Leu Asp Met
85 90 95

Ala Ser Thr Tyr Phe Asp Ile Arg Gly Val Ile Asp Arg Gly Pro Ser
100 105 110

Phe Lys Pro Tyr Ser Gly Thr Ala Tyr Asn Ser Leu Ala Pro Lys Gly
115 120 125

Ala Pro Asn Asn Ser Gln Trp Asn Ala Thr Asp Asn Gly Asn Lys Pro
130 135 140

Val Cys Phe Ala Gln Ala Ala Phe Ile Gly Gln Ser Ile Thr Lys Asp
145 150 155 160

Gly Val Gln Ile Gln Asn Ser Glu Asn Gln Gln Ala Ala Ala Asp Lys
165 170 175

Thr Tyr Gln Pro Glu Pro Gln Ile Gly Val Ser Thr Trp Asp Thr Asn

-continued

```
            180                 185                 190

Val Thr Ser Asn Ala Ala Gly Arg Val Leu Lys Ala Thr Thr Pro Met
        195                 200                 205

Leu Pro Cys Tyr Gly Ser Tyr Ala Asn Pro Thr Asn Pro Asn Gly Gly
    210                 215                 220

Gln Ala Lys Thr Glu Gly Asp Ile Ser Leu Asn Phe Phe Thr Thr Thr
225                 230                 235                 240

Ala Ala Ala Asp Asn Asn Pro Lys Val Val Leu Tyr Ser Glu Asp Val
                245                 250                 255

Asn Leu Gln Ala Pro Asp Thr His Leu Val Tyr Lys Pro Thr Val Gly
            260                 265                 270

Glu Asn Val Ile Ala Ala Glu Ala Leu Leu Thr Gln Gln Ala Cys Pro
        275                 280                 285

Asn Arg Ala Asn Tyr Ile Gly Phe Arg Asp Asn Phe Ile Gly Leu Met
    290                 295                 300

Tyr Tyr Asn Ser Thr Gly Asn Met Gly Val Leu Ala Gly Gln Ala Ser
305                 310                 315                 320

Gln Leu Asn Ala Val Val Asp Leu Gln Asp Arg Asn Thr Glu Leu Ser
                325                 330                 335

Tyr Gln Leu Met Leu Asp Ala Leu Gly Asp Arg Thr Arg Tyr Phe Ser
            340                 345                 350

Met Trp Asn Gln Ala Val Asp Ser Tyr Asp Pro Asp Val Arg Ile Ile
        355                 360                 365

Glu Asn His Gly Val Glu Asp Glu Leu Pro Asn Tyr Cys Phe Pro Leu
    370                 375                 380

Pro Gly Met Gly Ile Phe Asn Ser Tyr Lys Gly Val Lys Pro Gln Asn
385                 390                 395                 400

Gly Gly Asn Gly Asn Trp Glu Ala Asn Gly Asp Leu Ser Asn Ala Asn
                405                 410                 415

Glu Ile Ala Leu Gly Asn Ile Phe Ala Met Glu Ile Asn Leu His Ala
            420                 425                 430

Asn Leu Trp Arg Ser Phe Leu Tyr Ser Asn Val Ala Leu Tyr Leu Pro
        435                 440                 445

Asp Ser Tyr Lys Phe Thr Pro Ala Asn Ile Thr Leu Pro Ala Asn Gln
    450                 455                 460

Asn Thr Tyr Glu Tyr Ile Asn Gly Arg Val Thr Ser Pro Thr Leu Val
465                 470                 475                 480

Asp Thr Phe Val Asn Ile Gly Ala Arg Trp Ser Pro Asp Pro Met Asp
                485                 490                 495

Asn Val Asn Pro Phe Asn His His Arg Asn Ala Gly Leu Arg Tyr Arg
            500                 505                 510

Ser Met Leu Leu Gly Asn Gly Arg Val Val Pro Phe His Ile Gln Val
        515                 520                 525

Pro Gln Lys Phe Phe Ala Ile Lys Asn Leu Leu Leu Leu Pro Gly Ser
    530                 535                 540

Tyr Thr Tyr Glu Trp Ser Phe Arg Lys Asp Val Asn Met Ile Leu Gln
545                 550                 555                 560

Ser Thr Leu Gly Asn Asp Leu Arg Val Asp Gly Ala Ser Val Arg Ile
                565                 570                 575

Asp Ser Val Asn Leu Tyr Ala Asn Phe Phe Pro Met Ala His Asn Thr
            580                 585                 590

Ala Ser Thr Leu Glu Ala Met Leu Arg Asn Asp Thr Asn Asp Gln Ser
        595                 600                 605
```

-continued

```
Phe Asn Asp Tyr Leu Ser Ala Ala Asn Met Leu Tyr Pro Ile Pro Ala
    610                 615                 620

Asn Ala Thr Asn Val Pro Ile Ser Ile Pro Ser Arg Asn Trp Ala Ala
625                 630                 635                 640

Phe Arg Gly Trp Ser Phe Thr Arg Leu Lys Ala Lys Glu Thr Pro Ser
                645                 650                 655

Leu Gly Ser Gly Phe Asp Pro Tyr Phe Val Tyr Ser Gly Thr Ile Pro
            660                 665                 670

Tyr Leu Asp Gly Ser Phe Tyr Leu Asn His Thr Phe Lys Arg Leu Ser
        675                 680                 685

Ile Met Phe Asp Ser Ser Val Ser Trp Pro Gly Asn Asp Arg Leu Leu
    690                 695                 700

Thr Pro Asn Glu Phe Glu Ile Lys Arg Ile Val Asp Gly Glu Gly Tyr
705                 710                 715                 720

Asn Val Ala Gln Ser Asn Met Thr Lys Asp Trp Phe Leu Ile Gln Met
                725                 730                 735

Leu Ser His Tyr Asn Ile Gly Tyr Gln Gly Phe Tyr Val Pro Glu Gly
            740                 745                 750

Tyr Lys Asp Arg Met Tyr Ser Phe Phe Arg Asn Phe Gln Pro Met Ser
        755                 760                 765

Arg Gln Val Pro Asp Pro Thr Ala Ala Gly Tyr Gln Ala Val Pro Leu
    770                 775                 780

Pro Arg Gln His Asn Asn Ser Gly Phe Val Gly Tyr Met Gly Pro Thr
785                 790                 795                 800

Met Arg Glu Gly Gln Pro Tyr Pro Ala Asn Tyr Pro Tyr Pro Leu Ile
                805                 810                 815

Gly Ala Thr Ala Val Pro Ala Ile Thr Gln Lys Lys Phe Leu Cys Asp
            820                 825                 830

Arg Val Met Trp Arg Ile Pro Phe Ser Ser Asn Phe Met Ser Met Gly
        835                 840                 845

Ala Leu Thr Asp Leu Gly Gln Asn Met Leu Tyr Ala Asn Ser Ala His
    850                 855                 860

Ala Leu Asp Met Thr Phe Glu Val Asp Pro Met Asn Glu Pro Thr Leu
865                 870                 875                 880

Leu Tyr Met Leu Phe Glu Val Phe Asp Val Val Arg Val His Gln Pro
                885                 890                 895

His Arg Gly Ile Ile Glu Ala Val Tyr Leu Arg Thr Pro Phe Ser Ala
            900                 905                 910

Gly Asn Ala Thr Thr
        915
```

<210> SEQ ID NO 37
<211> LENGTH: 533
<212> TYPE: PRT
<213> ORGANISM: simian adenovirus SV-39

<400> SEQUENCE: 37

```
Met Lys Arg Ala Lys Val Glu Glu Gly Phe Asn Pro Val Tyr Pro Tyr
1               5                   10                  15

Gly Tyr Ser Thr Pro Thr Asp Val Ala Pro Pro Phe Val Ala Ser Asp
            20                  25                  30

Gly Leu Gln Glu Asn Pro Pro Gly Val Leu Ser Leu Lys Ile Ser Lys
        35                  40                  45

Pro Leu Thr Phe Asn Ala Ser Lys Ala Leu Ser Leu Ala Ile Gly Pro
```

-continued

```
    50                  55                  60

Gly Leu Lys Ile Gln Asp Gly Lys Leu Val Gly Glu Gly Gln Ala Ile
65                  70                  75                  80

Leu Ala Asn Leu Pro Leu Gln Ile Thr Asn Asn Thr Ile Ser Leu Arg
                85                  90                  95

Phe Gly Asn Thr Leu Ala Leu Asn Asp Asn Asn Glu Leu Gln Thr Thr
            100                 105                 110

Leu Lys Ser Ser Ser Pro Leu Lys Ile Thr Asp Gln Thr Leu Ser Leu
        115                 120                 125

Asn Ile Gly Asp Ser Leu Ala Ile Lys Asp Asp Lys Leu Glu Ser Ala
    130                 135                 140

Leu Gln Ala Thr Leu Pro Leu Ser Ile Ser Asn Asn Thr Ile Ser Leu
145                 150                 155                 160

Asn Val Gly Thr Gly Leu Thr Ile Asn Gly Asn Val Leu Gln Ala Val
                165                 170                 175

Pro Leu Asn Ala Leu Ser Pro Leu Thr Ile Ser Asn Asn Asn Ile Ser
            180                 185                 190

Leu Arg Tyr Gly Ser Ser Leu Thr Val Leu Asn Asn Glu Leu Gln Ser
        195                 200                 205

Asn Leu Thr Val His Ser Pro Leu Lys Leu Asn Ser Asn Asn Ser Ile
    210                 215                 220

Ser Leu Asn Thr Leu Ser Pro Phe Arg Ile Glu Asn Gly Phe Leu Thr
225                 230                 235                 240

Leu Tyr Leu Gly Thr Lys Ser Gly Leu Leu Val Gln Asn Ser Gly Leu
                245                 250                 255

Lys Val Gln Ala Gly Tyr Gly Leu Gln Val Thr Asp Thr Asn Ala Leu
            260                 265                 270

Thr Leu Arg Tyr Leu Ala Pro Leu Thr Ile Pro Asp Ser Gly Ser Glu
        275                 280                 285

Gln Gly Ile Leu Lys Val Asn Thr Gly Gln Gly Leu Ser Val Asn Gln
    290                 295                 300

Ala Gly Ala Leu Glu Thr Ser Leu Gly Gly Gly Leu Lys Tyr Ala Asp
305                 310                 315                 320

Asn Lys Ile Thr Phe Asp Thr Gly Asn Gly Leu Thr Leu Ser Glu Asn
                325                 330                 335

Lys Leu Ala Val Ala Ala Gly Ser Gly Leu Thr Phe Arg Asp Gly Ala
            340                 345                 350

Leu Val Ala Thr Gly Thr Ala Phe Thr Gln Thr Leu Trp Thr Thr Ala
        355                 360                 365

Asp Pro Ser Pro Asn Cys Thr Ile Ile Gln Asp Arg Asp Thr Lys Phe
    370                 375                 380

Thr Leu Ala Leu Thr Ile Ser Gly Ser Gln Val Leu Gly Thr Val Ser
385                 390                 395                 400

Ile Ile Gly Val Lys Gly Pro Leu Ser Ser Ser Ile Pro Ser Ala Thr
                405                 410                 415

Val Thr Val Gln Leu Asn Phe Asp Ser Asn Gly Ala Leu Leu Ser Ser
            420                 425                 430

Ser Ser Leu Lys Gly Tyr Trp Gly Tyr Arg Gln Gly Pro Ser Ile Asp
        435                 440                 445

Pro Tyr Pro Ile Ile Asn Ala Leu Asn Phe Met Pro Asn Ser Leu Ala
    450                 455                 460

Tyr Pro Pro Gly Gln Glu Ile Gln Ala Lys Cys Asn Met Tyr Val Ser
465                 470                 475                 480
```

-continued

```
Thr Phe Leu Arg Gly Asn Pro Gln Arg Pro Ile Val Leu Asn Ile Thr
                485                 490                 495

Phe Asn Asn Gln Thr Ser Gly Phe Ser Ile Arg Phe Thr Trp Thr Asn
            500                 505                 510

Leu Thr Thr Gly Glu Ala Phe Ala Met Pro Pro Cys Thr Phe Ser Tyr
        515                 520                 525

Ile Ala Glu Gln Gln
    530


<210> SEQ ID NO 38
<211> LENGTH: 50
<212> TYPE: DNA
<213> ORGANISM: Artificial sequence
<220> FEATURE:
<223> OTHER INFORMATION: oligomer SV25T

<400> SEQUENCE: 38

aatttaaata cgtagcgcac tagtcgcgct aagcgcggat atcatttaaa              50


<210> SEQ ID NO 39
<211> LENGTH: 49
<212> TYPE: DNA
<213> ORGANISM: Artificial sequence
<220> FEATURE:
<223> OTHER INFORMATION: oligomer SV25B

<400> SEQUENCE: 39

tatttaaatg atatccgcgc ttaagcgcga ctagtgcgct acgtattta               49
```